(12) United States Patent
Pringle et al.

(10) Patent No.: US 12,315,714 B2
(45) Date of Patent: May 27, 2025

(54) TISSUE ANALYSIS BY MASS SPECTROMETRY OR ION MOBILITY SPECTROMETRY

(71) Applicant: Micromass UK Limited, Wilmslow (GB)

(72) Inventors: Steven Derek Pringle, Darwen (GB); Tamas Karancsi, Budapest (HU); Emrys Jones, Manchester (GB); Michael Raymond Morris, Glossop (GB); Julia Balog, Solymar (HU); James Ian Langridge, Sale (GB); Zoltan Takats, Cambridge (GB); Frances Bolt, London (GB); Lajos Godorhazy, Erd (HU); Daniel Szalay, Budapest (HU); Daniel Simon, Morichida (HU); Keith Richardson, High Peak (GB)

(73) Assignee: Micromass UK Limited, Wilmslow (GB)

( * ) Notice: Subject to any disclaimer, the term of this patent is extended or adjusted under 35 U.S.C. 154(b) by 234 days.

(21) Appl. No.: 17/670,854

(22) Filed: Feb. 14, 2022

(65) Prior Publication Data

US 2022/0165558 A1    May 26, 2022

Related U.S. Application Data

(63) Continuation of application No. 15/555,998, filed as application No. PCT/GB2016/050619 on Mar. 7, 2016, now Pat. No. 11,289,320.

(30) Foreign Application Priority Data

Mar. 6, 2015  (GB) ..................................... 1503863
Mar. 6, 2015  (GB) ..................................... 1503864

(Continued)

(51) Int. Cl.
*H01J 49/04*  (2006.01)
*A61B 1/04*  (2006.01)
(Continued)

(52) U.S. Cl.
CPC ............ *H01J 49/049* (2013.01); *A61B 1/041* (2013.01); *A61B 1/2736* (2013.01);
(Continued)

(58) Field of Classification Search
None
See application file for complete search history.

(56) References Cited

U.S. PATENT DOCUMENTS

| 5,015,848 A | 5/1991 | Bomse et al. |
| 10,867,779 B2 | 12/2020 | Richardson et al. |

(Continued)

FOREIGN PATENT DOCUMENTS

| CA | 2167099 A1 | 7/1996 |
| CA | 2339552 A1 | 2/2000 |

(Continued)

OTHER PUBLICATIONS

Eberlin, L.S. et al. Desorption electrospray ionization mass spectrometry for lipid characterization and biological tissue imaging, Biochimica et Biophysica Acta, 1811, 946-960 (Year: 2011).*

(Continued)

*Primary Examiner* — Xiaoyun R Xu
(74) *Attorney, Agent, or Firm* — Goodwin Procter LLP

(57) ABSTRACT

A method of analysis using mass and/or ion mobility spectrometry or ion mobility spectrometry is disclosed comprising: using a first device to generate aerosol, smoke or vapour from one or more regions of a first target of biological material; and mass and/or ion mobility analysing and/or ion mobility analysing said aerosol, smoke, or vapour, or ions (Continued)

derived therefrom so as to obtain first spectrometric data. The method may use an ambient ionisation method.

17 Claims, 65 Drawing Sheets

(30) Foreign Application Priority Data

| | | | |
|---|---|---|---|
| Mar. 6, 2015 | (GB) | ..................................... | 1503867 |
| Mar. 6, 2015 | (GB) | ..................................... | 1503876 |
| Mar. 6, 2015 | (GB) | ..................................... | 1503877 |
| Mar. 6, 2015 | (GB) | ..................................... | 1503878 |
| Mar. 6, 2015 | (GB) | ..................................... | 1503879 |
| Sep. 9, 2015 | (GB) | ..................................... | 1516003 |
| Oct. 16, 2015 | (GB) | ..................................... | 1518369 |

(51) Int. Cl.

| | |
|---|---|
| A61B 1/273 | (2006.01) |
| A61B 5/00 | (2006.01) |
| A61B 5/01 | (2006.01) |
| A61B 5/0507 | (2021.01) |
| A61B 5/055 | (2006.01) |
| A61B 6/03 | (2006.01) |
| A61B 8/13 | (2006.01) |
| A61B 10/00 | (2006.01) |
| A61B 10/02 | (2006.01) |
| A61B 17/32 | (2006.01) |
| A61B 18/04 | (2006.01) |
| A61B 18/14 | (2006.01) |
| A61B 18/18 | (2006.01) |
| A61B 18/20 | (2006.01) |
| A61B 90/13 | (2016.01) |
| A61F 13/38 | (2006.01) |
| C12Q 1/02 | (2006.01) |
| C12Q 1/04 | (2006.01) |
| C12Q 1/18 | (2006.01) |
| C12Q 1/24 | (2006.01) |
| G01N 1/22 | (2006.01) |
| G01N 3/00 | (2006.01) |
| G01N 9/00 | (2006.01) |
| G01N 27/623 | (2021.01) |
| G01N 27/624 | (2021.01) |
| G01N 30/72 | (2006.01) |
| G01N 33/487 | (2006.01) |
| G01N 33/68 | (2006.01) |
| G01N 33/92 | (2006.01) |
| H01J 49/00 | (2006.01) |
| H01J 49/02 | (2006.01) |
| H01J 49/06 | (2006.01) |
| H01J 49/10 | (2006.01) |
| H01J 49/14 | (2006.01) |
| H01J 49/16 | (2006.01) |
| H01J 49/24 | (2006.01) |
| H01J 49/26 | (2006.01) |
| A61B 1/00 | (2006.01) |
| A61B 1/31 | (2006.01) |
| A61B 5/145 | (2006.01) |
| A61B 18/00 | (2006.01) |
| G16B 20/00 | (2019.01) |
| G16H 10/40 | (2018.01) |
| G16H 15/00 | (2018.01) |
| G16H 50/20 | (2018.01) |

(52) U.S. Cl.
CPC .......... *A61B 5/0066* (2013.01); *A61B 5/0075* (2013.01); *A61B 5/015* (2013.01); *A61B 5/0507* (2013.01); *A61B 5/055* (2013.01); *A61B 6/032* (2013.01); *A61B 6/037* (2013.01); *A61B 8/13* (2013.01); *A61B 10/0041* (2013.01); *A61B 10/0233* (2013.01); *A61B 10/0283* (2013.01); *A61B 17/320068* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/623* (2021.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/0404* (2013.01); *H01J 49/0409* (2013.01); *H01J 49/0422* (2013.01); *H01J 49/044* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 2001/2223* (2013.01); *G01N 33/48735* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G16B 20/00* (2019.02); *G16H 10/40* (2018.01); *G16H 15/00* (2018.01); *G16H 50/20* (2018.01)

(56) References Cited

U.S. PATENT DOCUMENTS

| | | |
|---|---|---|
| 11,031,222 B2 | 6/2021 | Pringle et al. |
| 2005/0230611 A1 | 10/2005 | Denny et al. |
| 2005/0255606 A1 | 11/2005 | Ahmed et al. |
| 2006/0027744 A1 | 2/2006 | Stults et al. |
| 2006/0038120 A1 | 2/2006 | Lean et al. |
| 2008/0315087 A1 | 12/2008 | Wollnik et al. |
| 2010/0120085 A1 | 5/2010 | Hyman et al. |
| 2010/0291704 A1 | 11/2010 | Cody |
| 2011/0012016 A1 | 1/2011 | Maier et al. |
| 2012/0141789 A1 | 6/2012 | Wyndham et al. |
| 2012/0190055 A1 | 7/2012 | Cezar et al. |
| 2012/0286155 A1 | 11/2012 | Mulligan |
| 2013/0306856 A1 | 11/2013 | Trimpin et al. |
| 2014/0127734 A1 | 5/2014 | Charretier et al. |
| 2014/0264004 A1 | 9/2014 | Cooks et al. |

(56) References Cited

U.S. PATENT DOCUMENTS

| | | | |
|---|---|---|---|
| 2016/0254130 A1 | 9/2016 | Brown | |
| 2020/0144044 A1 | 5/2020 | Zarrine-Afsar et al. | |

FOREIGN PATENT DOCUMENTS

| | | | | |
|---|---|---|---|---|
| CN | 1774627 | A | 5/2006 | |
| CN | 101113970 | A | 1/2008 | |
| CN | 101173914 | A | 5/2008 | |
| CN | 101201335 | A | 6/2008 | |
| CN | 101978269 | A | 2/2011 | |
| CN | 102969217 | A | 3/2013 | |
| CN | 103293141 | A | 9/2013 | |
| CN | 103620413 | A | 3/2014 | |
| EP | 1225616 | A2 | 7/2002 | |
| EP | 1530721 | A2 | 5/2005 | |
| EP | 1650549 | A2 | 4/2006 | |
| EP | 2592420 | A1 | 5/2013 | |
| EP | 2660590 | A1 | 11/2013 | |
| GB | 2278952 | A | 12/1994 | |
| GB | 2462190 | A | 2/2010 | |
| GB | 2491484 | A | 12/2012 | |
| GB | 2507298 | A | 4/2014 | |
| JP | 2000149866 | A | 5/2000 | |
| JP | 2008249563 | A | 10/2008 | |
| WO | 2008131362 | A2 | 10/2008 | |
| WO | 2009070555 | A1 | 6/2009 | |
| WO | WO 2010/136887 | * | 12/2010 | G01N 1/02 |
| WO | 2012155090 | A2 | 11/2012 | |
| WO | 2014167828 | A1 | 10/2014 | |
| WO | 2017109563 | A1 | 6/2017 | |

OTHER PUBLICATIONS

Zhang, J.I. et al. Rapid direct lipid profiling of bacteria using desorption electrospray ionization mass spectrometry, International Journal of Mass Spectrometry, 301,37-44 (Year: 2011).*

Klein, L.L. et al. Shotgun Proteomic Analysis of Vaginal Fluid From Women in Late Pregnancy, Reproductive Sciences vol. 15 No. Mar. 3, 2008 263-273 (Year: 2008).*

Gonzalez-Dominguez, R., et al. "Development of a metabolomic approach based on urine samples and direct infusion mass spectrometry", Analytical Biochemistry, 465:20-27, Jul. 23, 2014.

Djidja, M-C., et al., "Novel molecular tumour classification using MALDI-mass spectrometry imaging of tissue micro-array", Analytical and Bioanalytical Chemistry, 397(2): 587-601, Mar. 4, 2010.

Chen, H., et al., "Neutral desorption sampling coupled to extractive electrospray ionization mass spectrometry for rapid differentiation of biosamples by metabolomic fingerprinting", Journal of Mass Spectrometry, 42(9):1123-1135, Sep. 1, 2007.

Gao, L., et al., "Design and Characterization of a Multisource Hand-Held Tandem Mass Spectrometer", Analytical Chemistry, 80(19):7198-7205, Oct. 1, 2008.

Ouyang, Z., et al., "Handheld Miniature Ion Trap Mass Spectrometers", Analytical Chemistry, 81(7):2421-2425 Apr. 1, 2009.

Chen, H., et al., "Surface desorption atmospheric pressure chemical ionization mass spectrometry for direct ambient sample analysis without toxic chemical contamination", Journal of Mass Spectrometry, 42(8):1045-1056, Jan. 1, 2007.

Cooks, R.G., et al., "Ambient Mass Spectrometry", Science, 311(5767):1566-1570, Mar. 17, 2006.

Hanson, et al., "Polymer-coated reversed-phase packings in high-performance liquid chromatography", J Chromat. A656:369-380 (1993). Abstract.

Dixit, et al., "Development of a High Sensitivity Rapid Sandwich ELISA Procedure and Its Comparison with the Conventional Approach", Anal Chem 82(16):7049-7052 (2010).

Weinstein, J.N., "Integromic analysis of the NCI-60 cancer cell lines", Breast Dis 19:11-22 (2004).Abstract.

Gholami, A.M., et al., "Global Proteome Analysis of the NCI-60 Cell Line Panel", Cell Reports 4(3):609-620 (2013).

Shamir, E. R., et al., "Three-dimensional organotypic culture: experimental models of mammalian biology and disease", Nature Reviews Molecular Cell Biology 15:47-664 (2014).

Kind, et al., "LipidBlast—in-silico tandem mass spectrometry database for lipid identification", Nat Methods 10(8):755-758 (2013).

Herzog, et al., "LipidXplorer: A Software for Consensual Cross-Platform Lipidomics" Plos ONE 7(1): e29851, (2012).

Lipid Maps®[online] [retrieved on Jun. 25, 2021]. Retrieved from URL: http://www.lipidmaps.org , 3 pages.

White, D.C., et al., "Fatty Acid Composition of the Complex Lipids of *Staphylococcus aureus* During the Formation of Membrane-bound Electron Transport System", Journal of Bacteriology 95:2198-2209 (1968).

Krishtalik, Lev I., "The mechanism of the proton transfer: an outline", Biochimica et Biophysica Acta (BBA)—Bioenergetics 1458(1):6-27 (2000).

Knockenmuss, R., "Ion formation mechanisms in UV-MALDI" Analyst 131:9660986 (2006). Abstract.

Kuppusami, S., et al., "Metabolite profiling of Clostridium difficile ribotypes using small molecular weight volatile organic compounds", Metabolomics, 11(2):251-260, Jul. 17, 2014.

Griffin, P.M., et al., "Use of Matrix-Assisted Laser Desorption Ionization.Time of Flight Mass Spectrometry To Identify Vancomycin-Resistant Enterococci and Investigate the Epidemiology of an Outbreak", Journal of Clinical Microbiology, 50(9):2918-2931, Jun. 27, 2012.

Nakano, S., et al., "Development and evaluation of MALDI-TOF MS-based serotyping for *Streptococcus pneumoniae*", European Journal of Clinical Microbiology & Infectious Diseases, 34(11):2191-2198, Aug. 19, 2015.

* cited by examiner

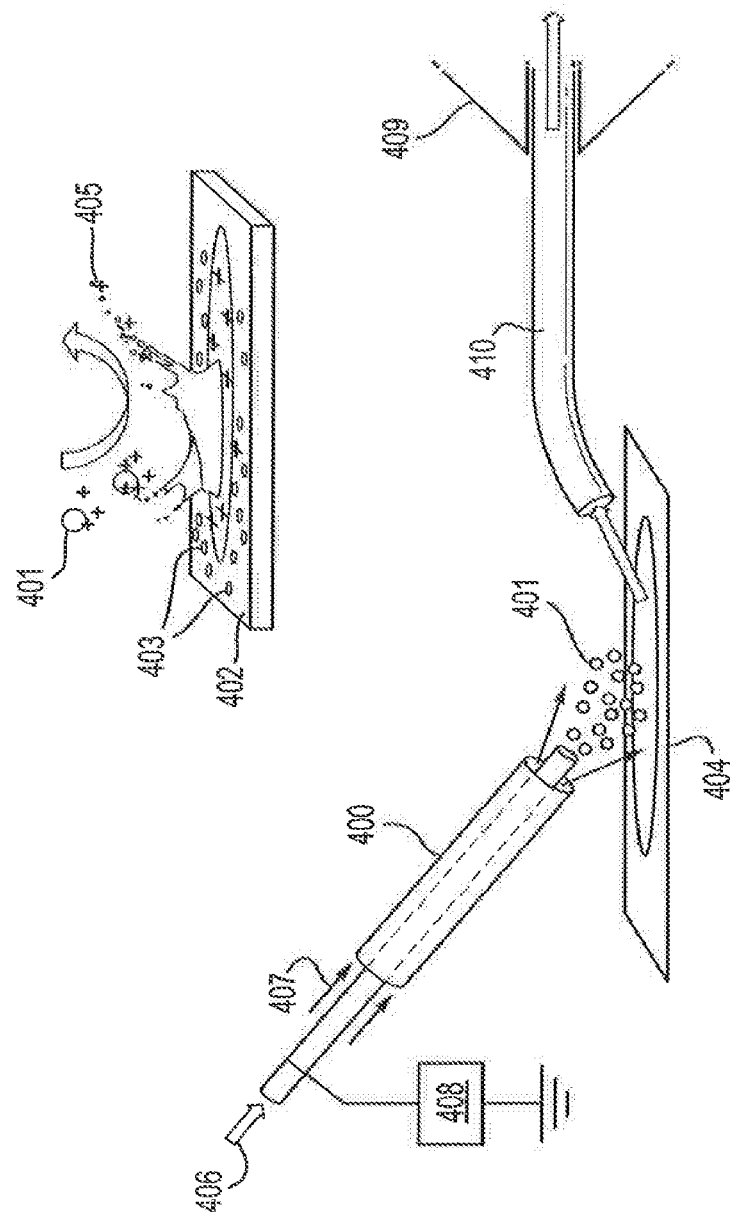

⊗ Malignant tissue
⊘ Tumor section fibrous section
⊚ Tumor section adipose tissue
⊜ Tumor section glandular tissue
○ Necrotic ⊗ Malignant tissue
⊘ Tumor section fibrous section
⊚ Tumor section adipose tissue
⊜ Tumor section glandular tissue ⊘ Serous carcinoma
◉ Serous carcinoma associated stroma
⊗ Normal stroma from ovary
⊜ Background Fig. 15
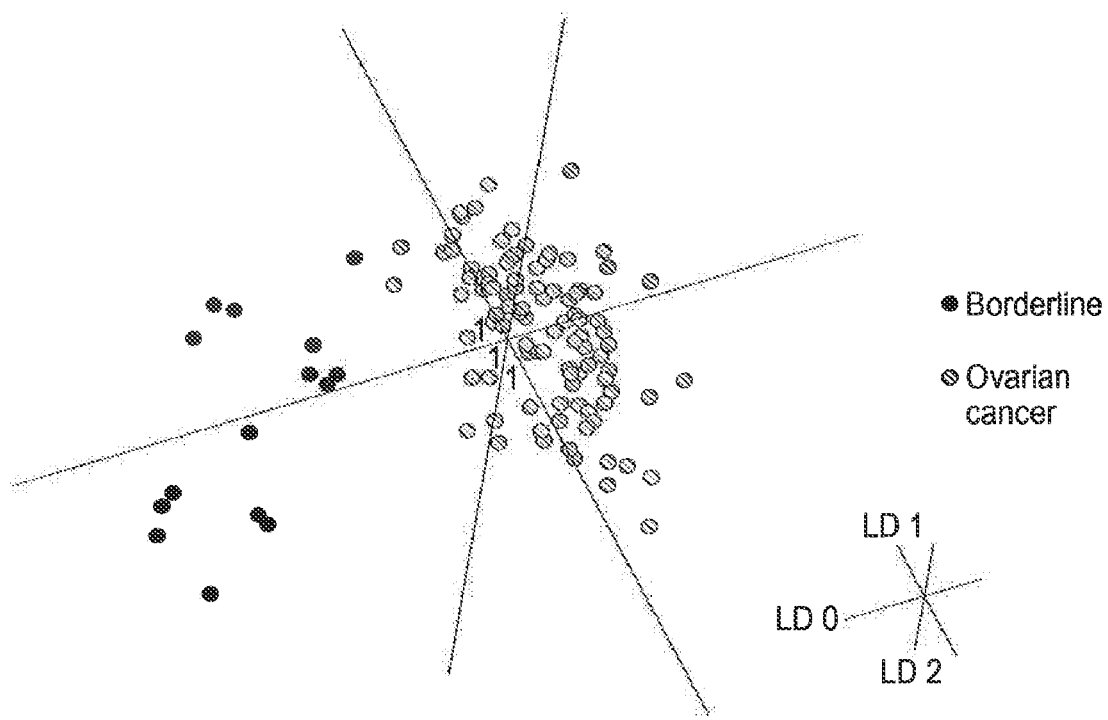
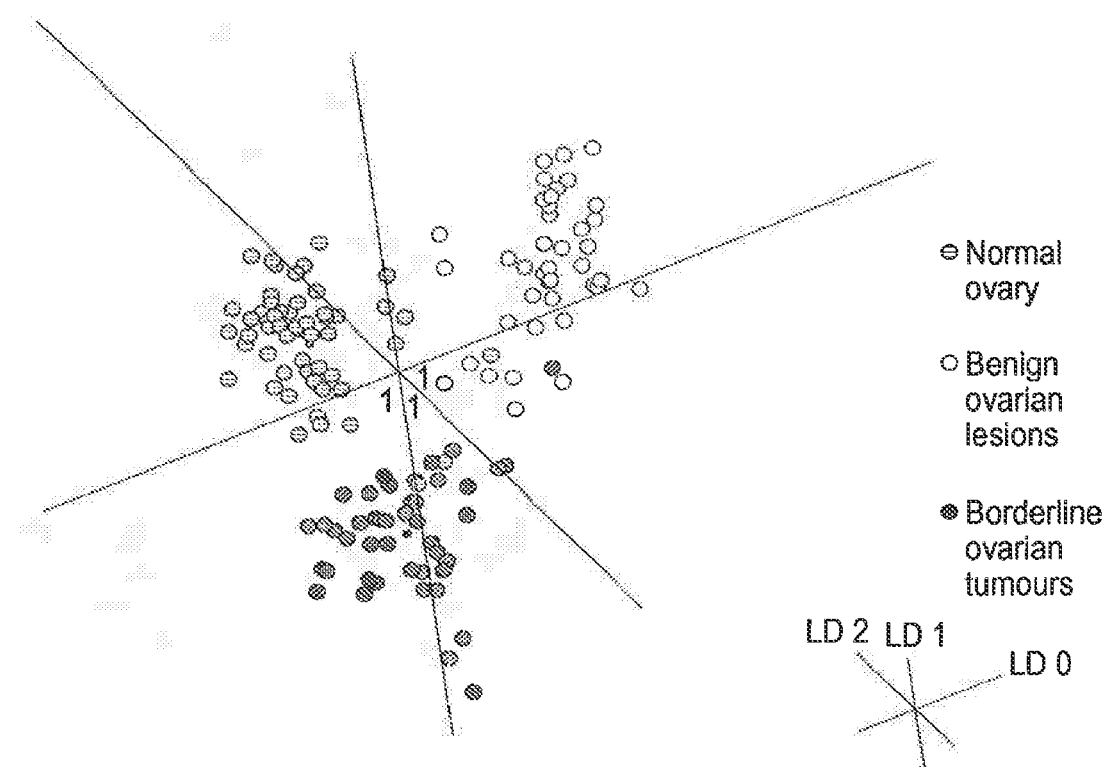

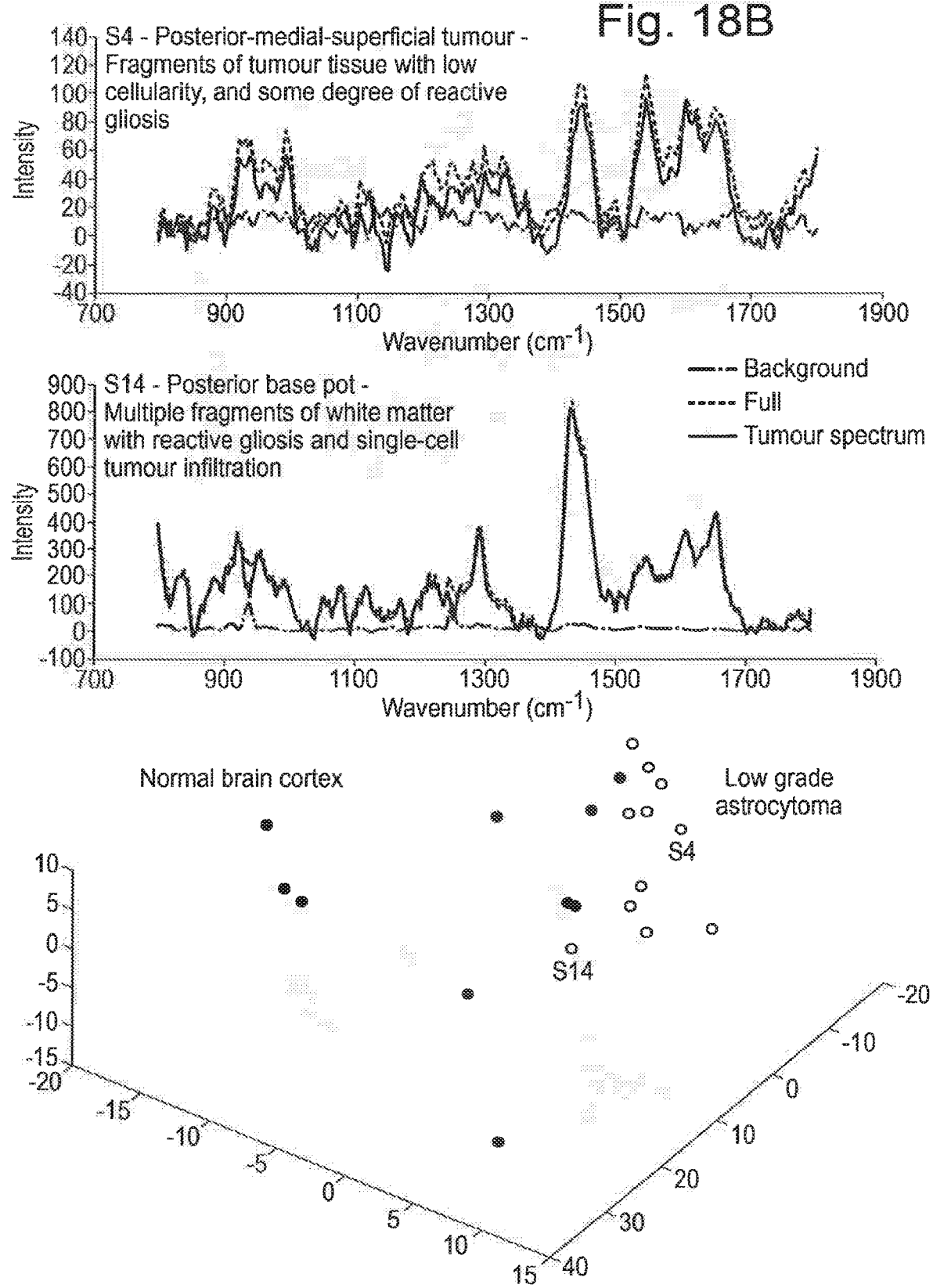

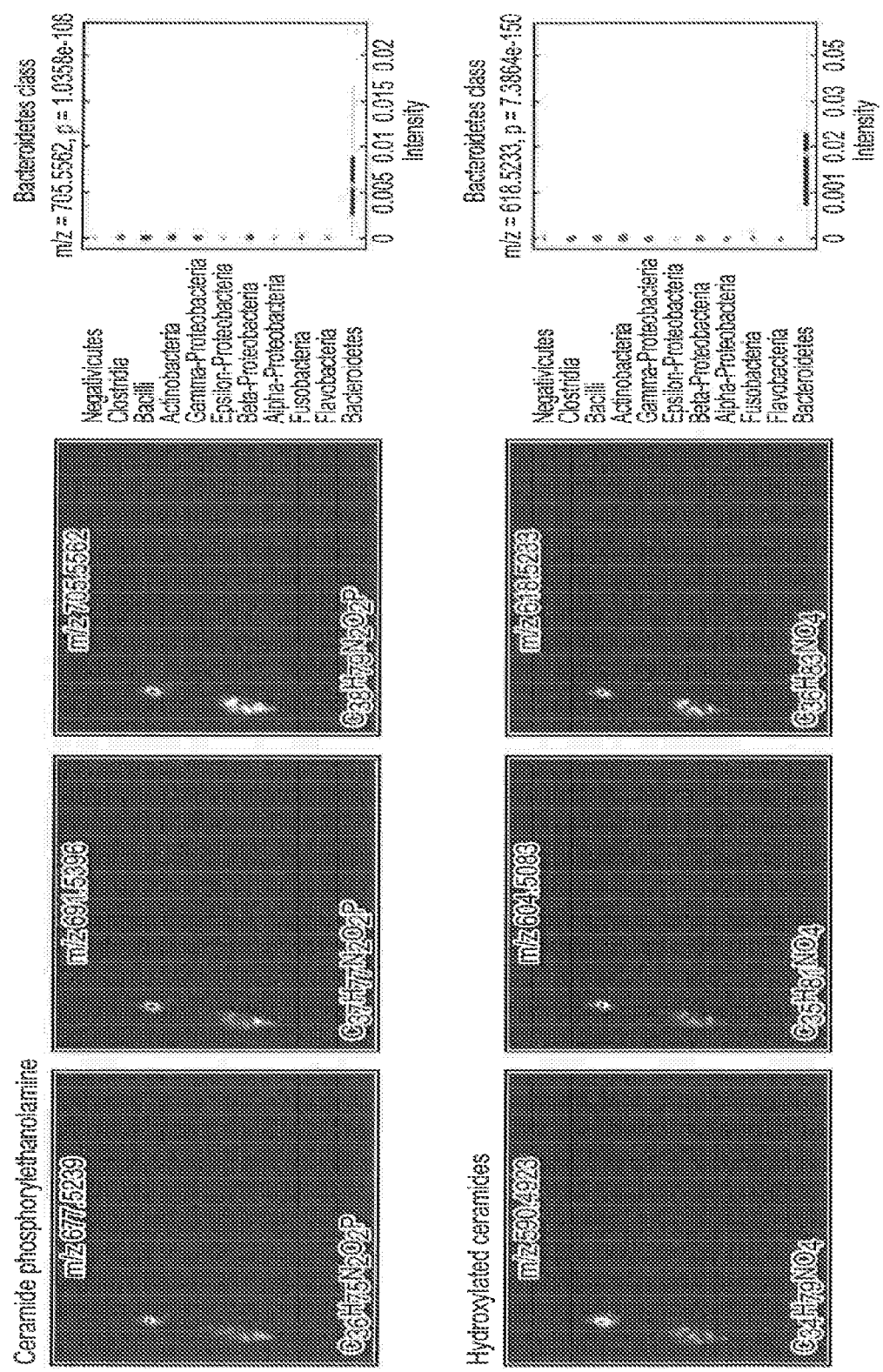

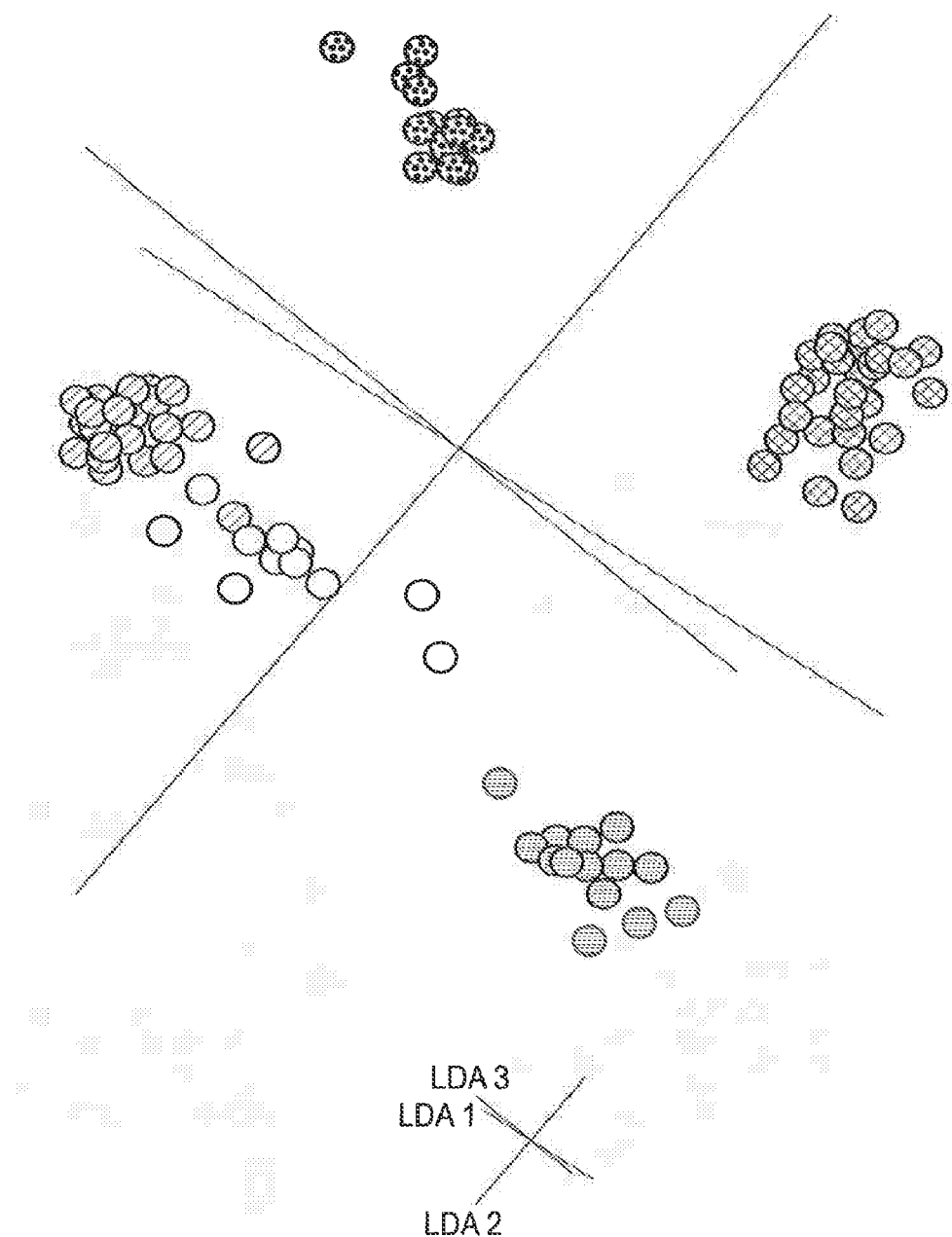

Score plot

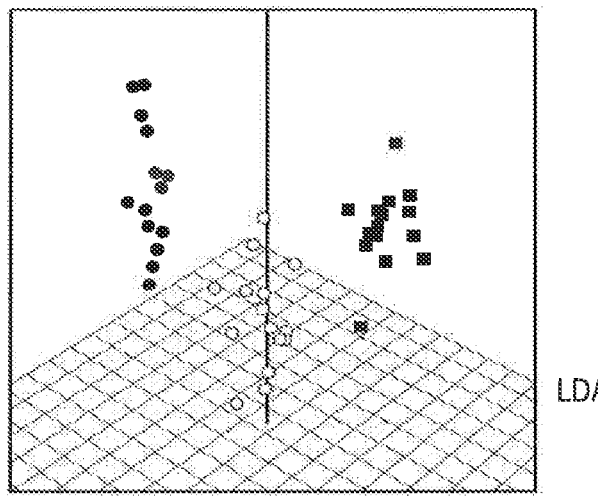

Fig. 24

| Overall correct classification 97.7% | Predicted class | | |
|---|---|---|---|
| | Normal fallopian | Normal ovary | Normal peritoneum |
| Actual class — Normal fallopian | 100% (15) | 0% (0) | 0% (0) |
| Actual class — Normal ovary | 6.7% (1) | 93.3% (14) | 0% (0) |
| Actual class — Normal peritoneum | 0% (0) | 0% (0) | 100% (14) |

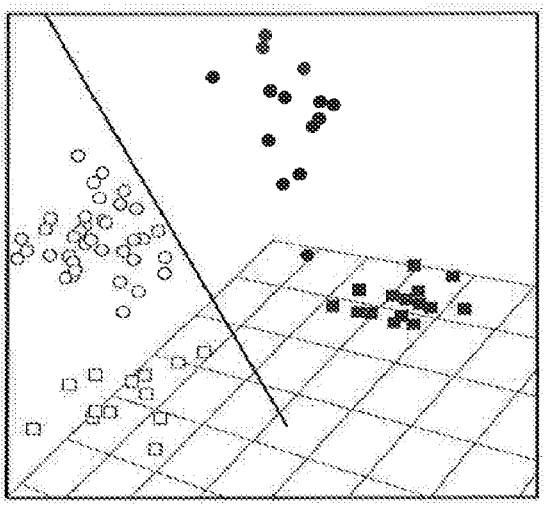

| Overall correct classification 97.6% | Predicted class | | | |
|---|---|---|---|---|
| | Normal fallopian | Normal ovary | Normal peritoneum | Ovarian cancer |
| Actual class — Normal fallopian | 93.3% (14) | 6.7% (1) | 0% (0) | 0% (0) |
| Actual class — Normal ovary | 0% (0) | 100% (15) | 0% (0) | 0% (0) |
| Actual class — Normal peritoneum | 0% (0) | 0% (0) | 100% (14) | 0% (0) |
| Actual class — Ovarian cancer | 0% (0) | 0% (0) | 2.6% (1) | 97.4% (38) |

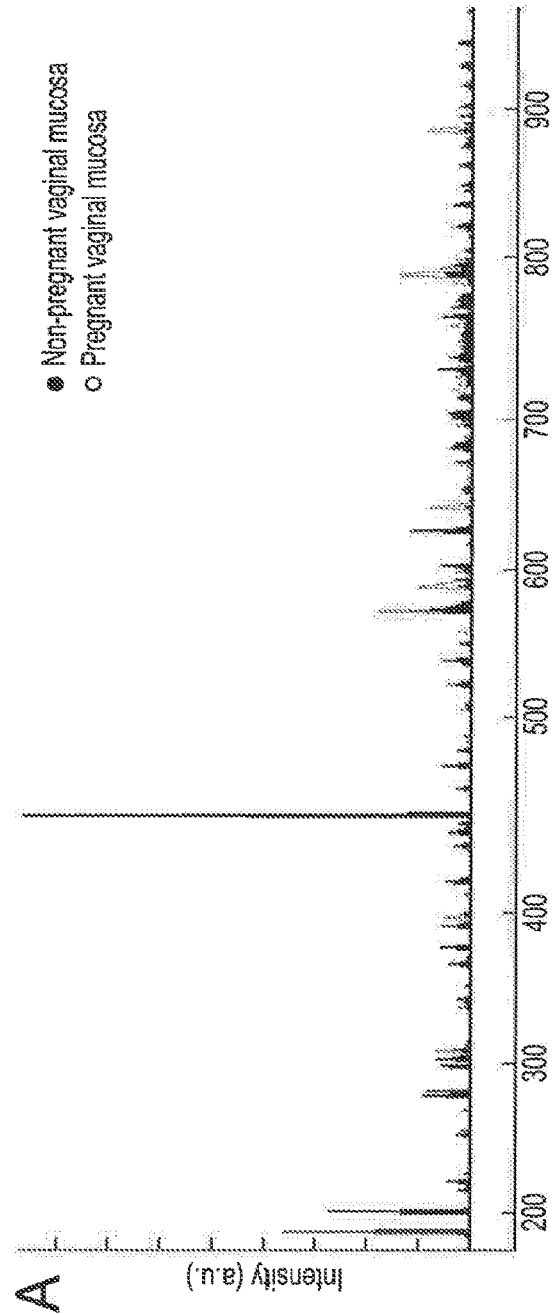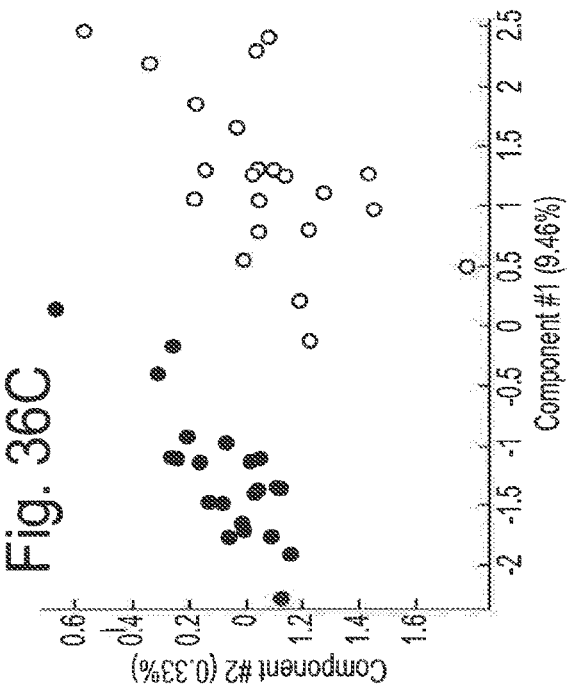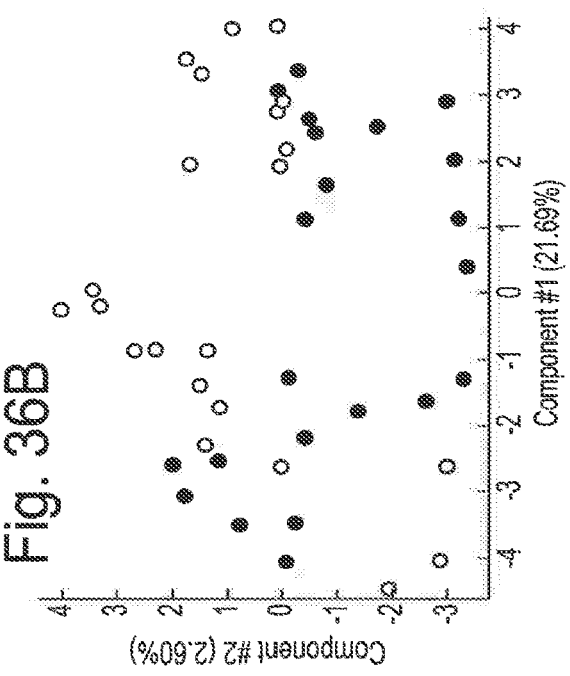

Fig. 37A
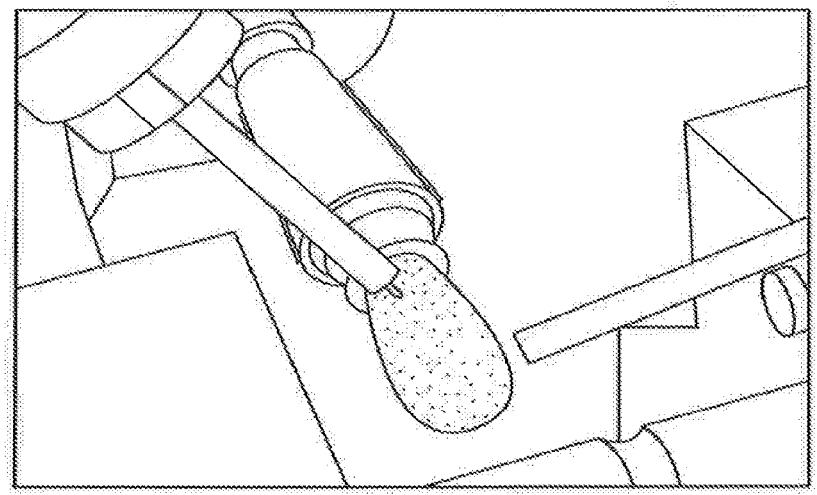
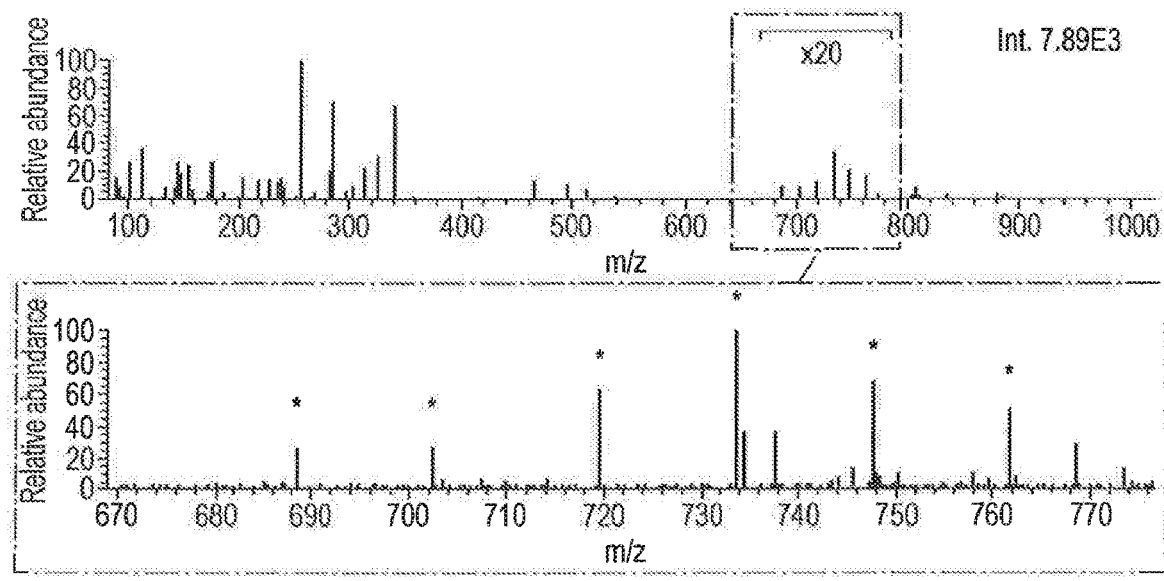

Fig. 37B
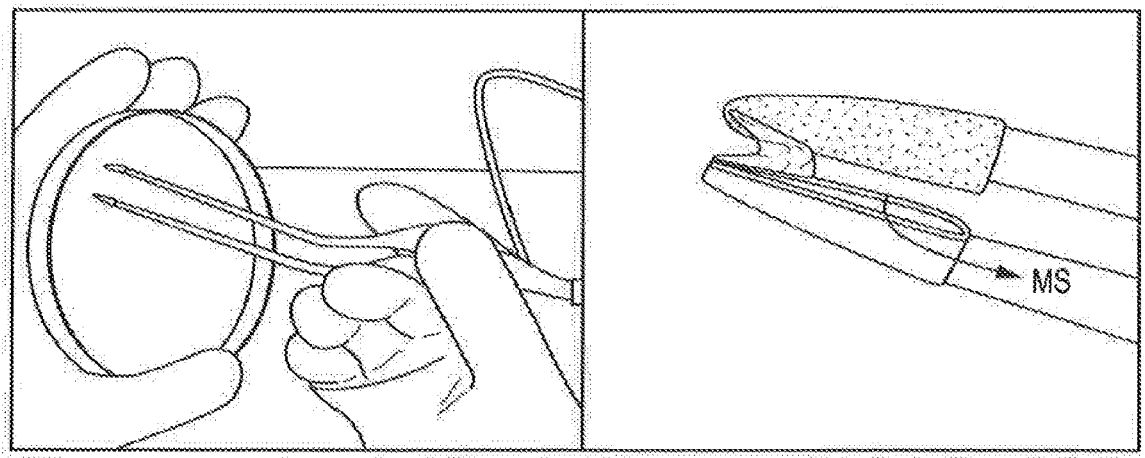
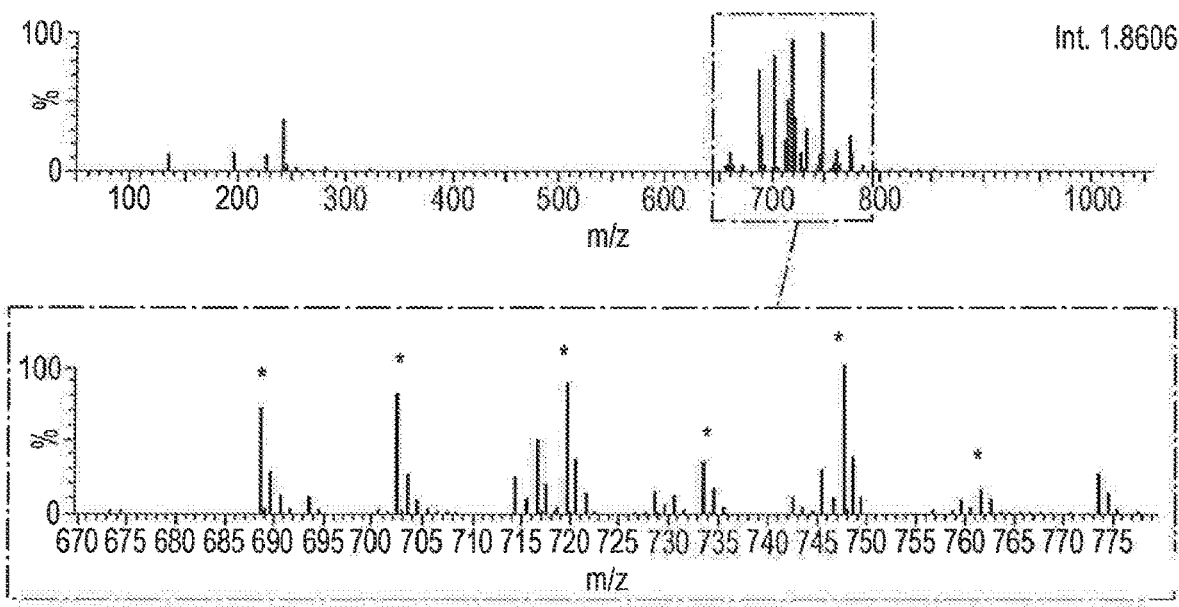

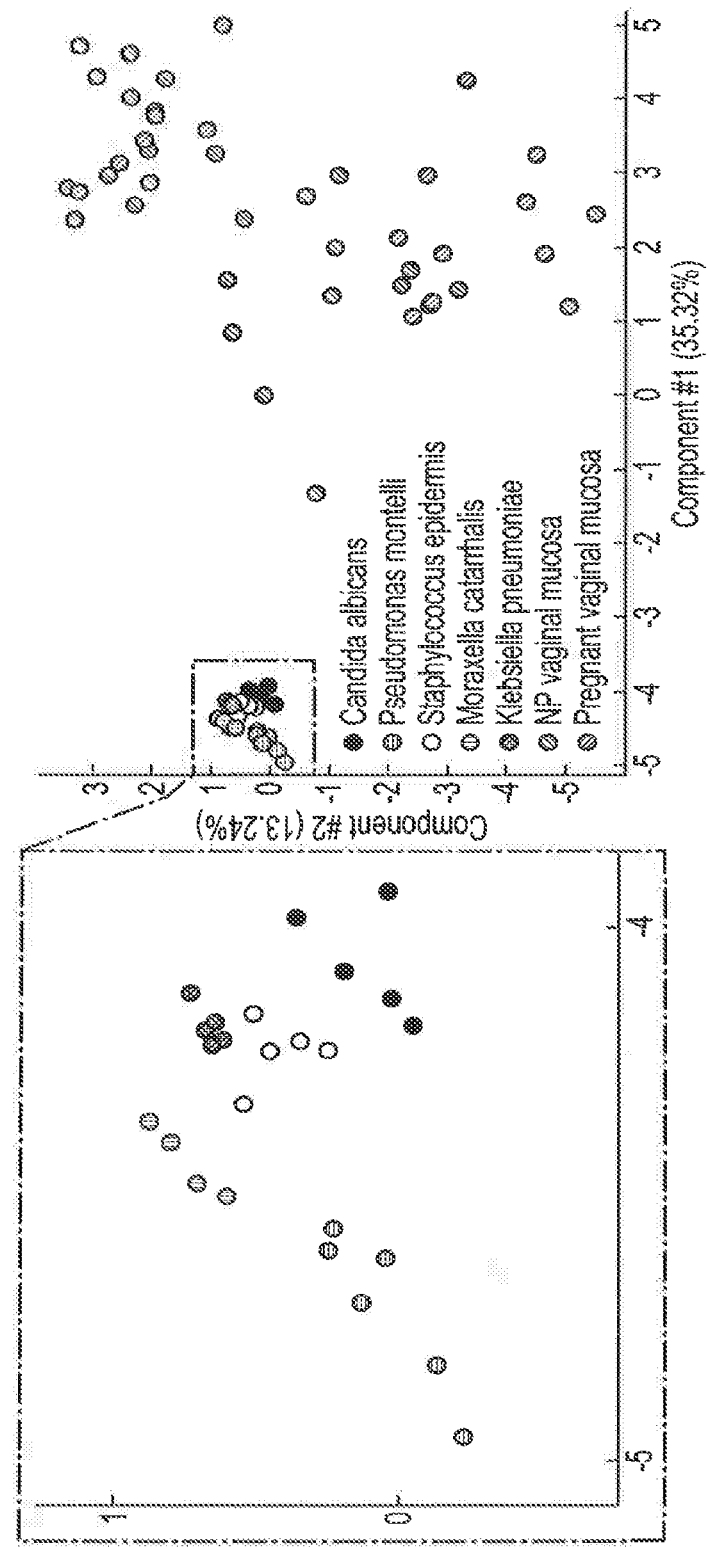

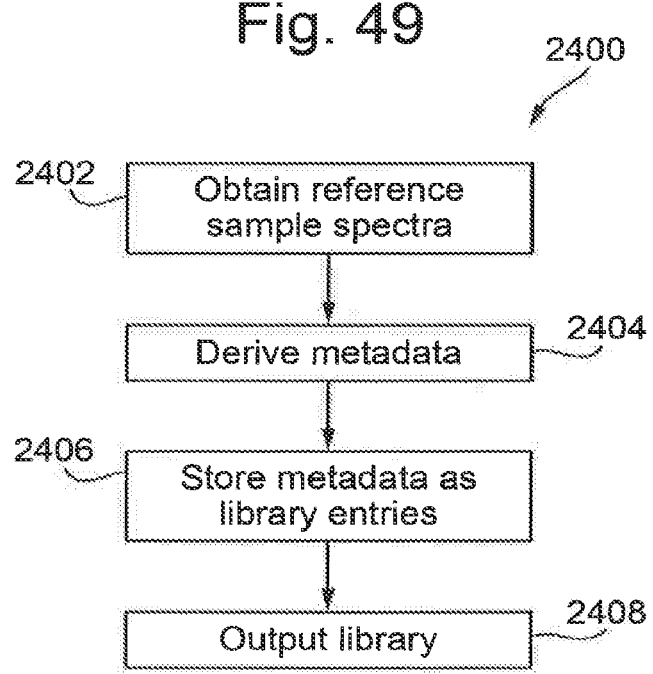
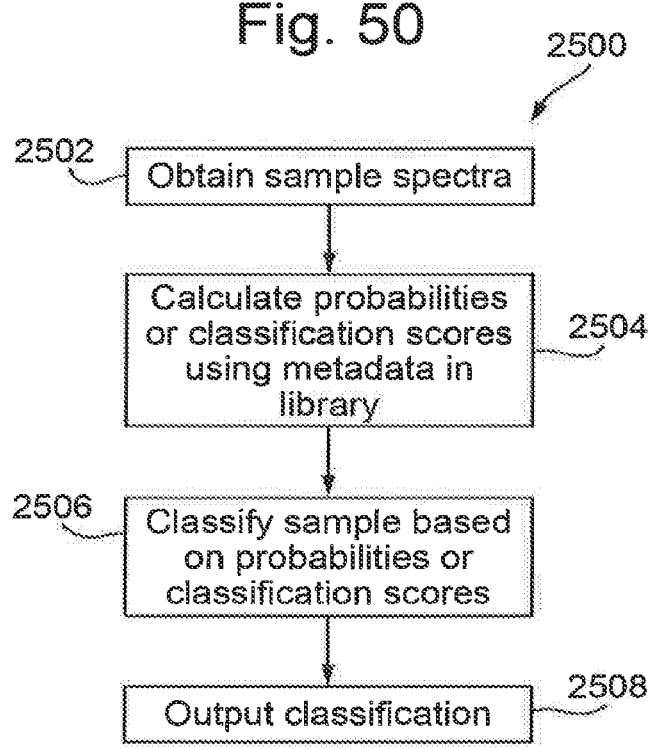

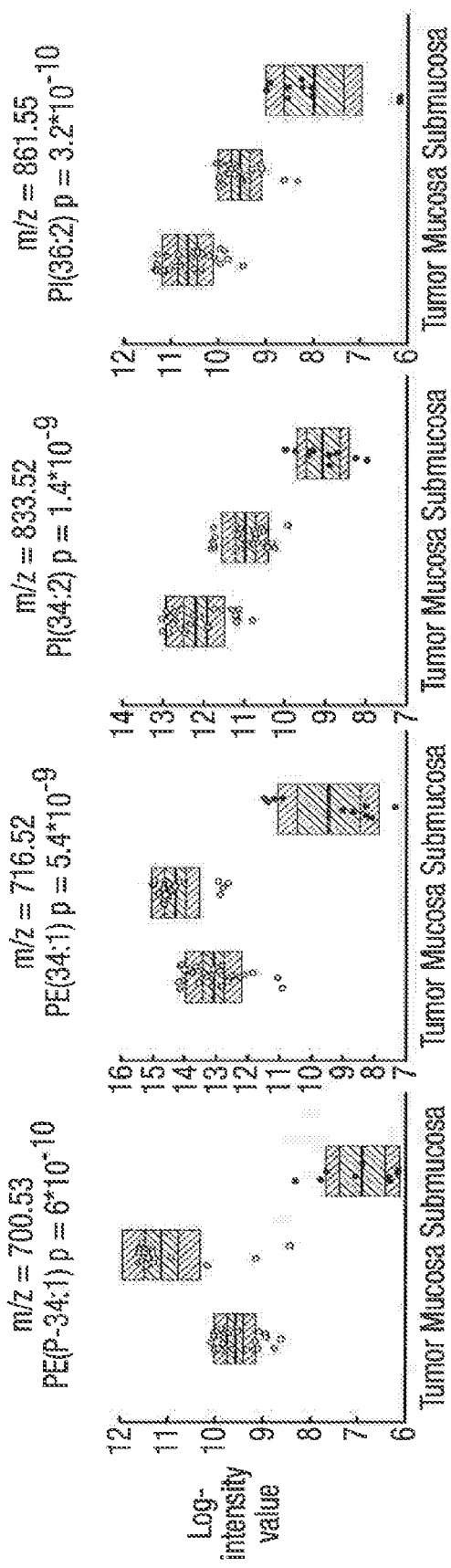

□ Colonic adenocarcinoma
○ Healthy colon mucosa
△ Adenomatous polyp

□ Stomach adenocarcinoma
○ Healthy stomach mucosa
△ Healthy stomach submucosa

TISSUE ANALYSIS BY MASS SPECTROMETRY OR ION MOBILITY SPECTROMETRY

CROSS-REFERENCE TO RELATED APPLICATIONS

This application is a continuation application of U.S. patent application Ser. No. 15/555,998, filed Sep. 6, 2017, which is a U.S. National Phase of International Application number PCT/GB2016/050619, filed Mar. 7, 2016, which claims priority from and the benefit of United Kingdom patent application No. 1503876.3 filed on 6 Mar. 2015, United Kingdom patent application No. 1503864.9 filed on 6 Mar. 2015, United Kingdom patent application No. 1518369.2 filed on 16 Oct. 2015, United Kingdom patent application No. 1503877.1 filed on 6 Mar. 2015, United Kingdom patent application No. 1503867.2 filed on 6 Mar. 2015, United Kingdom patent application No. 1503863.1 filed on 6 Mar. 2015, United Kingdom patent application No. 1503878.9 filed on 6 Mar. 2015, United Kingdom patent application No. 1503879.7 filed on 6 Mar. 2015 and United Kingdom patent application No. 1516003.9 filed on 9 Sep. 2015. The entire contents of these applications are incorporated herein by reference.

FIELD OF THE INVENTION

The present invention generally relates to mass spectrometry and/or ion mobility spectrometry, and in particular to methods of in vivo, ex vivo or in vitro specimen and/or tissue analysis.

BACKGROUND

Cancers figure among the leading causes of morbidity and mortality worldwide, with approximately 14 million new cases and 8.2 million cancer related deaths in 2012. According to the World Health Organisation, the number of new cases is expected to rise by about 70% over the next 2 decades.

Gastro-intestinal cancers are a leading cause of mortality and account for 23% of cancer-related deaths worldwide.

Mamma carcinoma is a carcinoma of breast tissue. Worldwide it is the most common form of cancer in women, affecting approximately 10% of all females at some stage of their life (in the Western world). Although significant efforts have been made to achieve early detection and effective treatment, about 20% of all women with breast cancer still die from the disease. Mamma carcinoma is the second most common cause of cancer deaths in women.

In order to improve outcomes from cancers and other diseases, novel tissue characterisation methods are needed in order to facilitate accurate diagnosis.

A common treatment option is surgery. Current surgical methods rely on the trained eye of the surgeon, sometimes with the help of an operating microscope and/or imaging from scans performed before the surgery.

The main goal of tumour surgery is to maximize tumour resection while preserving as much of the healthy tissue, and its function, as possible. However, using existing techniques it can be difficult or impossible to delineate tumour boundaries. Similar considerations apply to surgery of necrotic tissue.

Surgical resection therefore typically involves the removal of apparently normal tissue as a "safety margin", but this can increase morbidity and risk of complications. Moreover, there is a risk of the "safety margin" being too small, leaving cancerous or necrotic tissue behind. For example, up to 40 percent of subjects undergoing breast cancer surgery require additional operations because surgeons may fail to remove all the cancerous tissue in the initial operation.

There is therefore a need for a tool that will help surgeons better distinguish cancerous tissue from normal tissue, thereby decreasing the risk of the need for repeat operations.

There is also a need for novel methods to facilitate accurate diagnosis and/or treatment of further diseases such as necrosis, or inflammatory conditions.

There is also a need for novel methods to detect infections and/or to analyse microbial interactions with one another and/or with a host.

Mass spectrometry imaging ("MSI") analysis of biological samples is known and allows simultaneous and spatially resolved detection of metabolites, proteins and lipids directly from biological tissue sections.

The technique has gained significant momentum during the course of the last two decades with the introduction of new techniques such as matrix assisted laser desorption/ionization ("MALDI"), secondary ion mass spectrometry ("SIMS") and desorption electrospray ionization ("DESI"). The spatially resolved nature of the resulting data allows its use as a supplemental layer of information for histopathological characterization and classification of tissues including the possibility of cancer biomarker discovery.

Rapid evaporative ionization mass spectrometry ("REIMS") is a technology which has recently been developed for the real time identification of tissues during surgical interventions. Coupling of REIMS technology with handheld sampling devices has resulted in iKnife sampling technology, which can provide intra-operative tissue identification. The iKnife sampling technology allows surgeons to more efficiently resect tumours intra-operatively through minimizing the amount of healthy tissue removed whilst ensuring that all the cancerous tissue is removed.

REIMS analysis of biological tissue has been shown to yield phospholipid profiles showing high histological and histopathological specificity—similar to Matrix Assisted Laser Desorption Ionisation ("MALDI"), Secondary Ion Mass Spectrometry ("SIMS") and Desorption Electrospray Ionisation ("DESI") imaging. A mass spectrometric signal is obtained by subjecting the cellular biomass to alternating electric current at radiofrequency which causes localized Joule-heating and the disruption of cells along with desorption of charged and neutral particles. The resulting aerosol or surgical smoke is then transported to a mass spectrometer for on-line mass spectrometric analysis.

In this process, cellular biomass is held between the tips of the forceps and an electric current is applied causing the cells to undergo thermal disintegration and release a partially charged aerosol that is transported to a mass spectrometer.

REIMS profiling applications typically require a spectral library of reference mass spectra in order to build multivariate classification models which are necessary for pattern-based identification.

The collection of reference mass spectra using iKnife sampling technology is carried out by manual electrosurgical sampling of ex-vivo tissue specimens followed by the histopathological examination of the remaining material. Although the workflow provides satisfactory data, there is a degree of uncertainty involved at the validation step since the tissue part producing the spectral data cannot be investigated since it is evaporated during the course of the analysis. Hence, conventionally all identifications are based on interpolation of the histological environment of the evaporated tissue.

SUMMARY

The invention provides a method of mass and/or ion mobility spectrometry comprising;
using a first device to generate aerosol, smoke or vapour from one or more regions of a target; and
mass analysing and/or ion mobility analysing said aerosol, smoke or vapour or ions derived therefrom.

The invention also provides a method of analysis using mass and/or ion mobility spectrometry comprising;
(a) using a first device to generate to generate aerosol, smoke or vapour from one or more regions of a target;
(b) mass analysing and/or ion mobility analysing said aerosol, smoke or vapour or ions derived therefrom in order to obtain spectrometric data; and
(c) analysing said spectrometric data in order to analyse said target.

Embodiments of the invention also provide methods of analysis, diagnosis, prognosis, monitoring, stratification, treatment, and/or surgery.

Details of embodiments of the methods are discussed in the detailed description.

Optional features of any of these methods are discussed below. Thus, unless otherwise stated, any reference to "a method" or "the method" is intended to be a reference to any of the methods of the invention listed herein. It is explicitly intended that any of these features may be present in any combination in any of these methods.

Various embodiments are contemplated wherein analyte ions are generated from the target, aerosol, smoke or vapour, e.g., by an ambient ionisation ion source. The analyte ions, or ions derived therefrom, may be subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

Obtaining the spectrometric data may comprise recording the ion signal intensity of the ions derived from the smoke, aerosol or vapour as a function of one or more physicochemical property (or as a function of a property related thereto). For example, the ion signal intensity may be recorded as a function of mass to charge ratio and/or ion mobility. The location and/or size and/or pattern of peaks in this recorded ion signal may then be used to characterise or identify one or more analytes present in the smoke, aerosol or vapour.

Tandem mass spectrometry may be used to assign an analyte/compound to each of the peaks. For example, parent ions having a physicochemical property (e.g., mass to charge ratio) corresponding to that of a peak may be isolated (e.g., using a mass filter) and then fragmented or reacted so as to produce fragment or product ions. These fragment or product ions may then be analysed (e.g., by mass analysis) and their determined properties used to identify the parent ion giving rise to the peak in the ion signal. Such tandem mass spectrometry may be used, for example, to identify biomarkers in the spectrometric data.

The mass and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated. Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

BRIEF DESCRIPTION OF THE DRAWINGS

Various embodiments will now be described, by way of example only, and with reference to the accompanying drawings in which:

FIG. 4 illustrates the technique of Desorption Electrospray Ionisation ("DESI") according to various embodiments;

FIG. 15 shows data from Example 6. Linear discriminant analysis showing separation of tissue that is borderline margin between normal and cancer, and between normal, borderline and ovarian lesions;

FIG. 36A shows averaged desorption electrospray ionisation ("DESI") mass spectra from a pregnant and a non-pregnant group acquired in negative ion mode in the mass range m/z 150-1000, FIG. 36B shows principal component analysis and discriminatory analysis using recursive maximum margin criterion ("RMMC"), FIG. 36C shows analysis with leave-one-out cross-validation for enhanced separation of group classes with highly accurate identification (>80%) based on chemical signatures in the vaginal mucosal membrane.

FIG. 37A shows desorption electrospray ionisation ("DESI") spectrometric analysis of a bacteria sample on a swab in accordance with various embodiments and shows that bacterial samples can be detected using DESI, and FIG. 37B shows a comparison with rapid evaporative ionisation mass spectrometry ("REIMS") analysis in conjunction with a Time of Flight mass analysis of a bacterial sample directly from an agar plate;

FIGS. 38B and 38C show PCA plots showing a separation between the vaginal mucosa (pregnant and non-pregnant group) from the microorganism species within the first two components, and a separation between the different bacteria and fungi species;

FIG. 49 shows a method of analysis that comprises building a classification library according to various embodiments;

FIG. 50 shows a method of analysis that comprises using a classification library according to various embodiments;

FIG. 54B shows a comparison of the abundance of selected peaks showing significant differences between cancerous and healthy tissue in the 600-900 m/z range using Kruskal-Wallis ANOVA wherein all peaks above m/z 800 are significantly different when comparing submucosa to the other two tissue types;

DETAILED DESCRIPTION

Figure 1B:
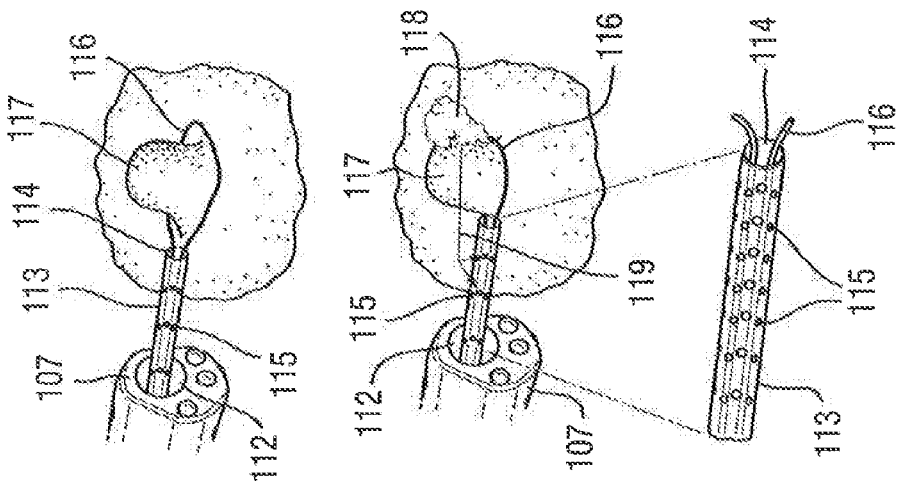
FIG. 1B shows a resection of a GI polyp according to an embodiment of the invention.

Although the present invention has been described with reference to preferred embodiments, it will be understood by those skilled in the art that various changes in form and detail may be made without departing from the scope of the invention as set forth in the accompanying claims.

The skilled person will understand that any of the features listed herein may be combined in any combination.

Mass spectrometry ("MS") based identification of tissues is known using imaging techniques, sampling probe/electrospray systems and the direct ambient ionization mass spectrometry investigation of tissues. Direct ambient ionization mass spectrometry, such as REIMS technology, has emerged as a technology allowing in-situ real-time analysis by the utilization of electrosurgical tools as a mass spectrometry ion source. The REIMS fingerprint of human tissues shows high histological specificity with 90-100% concordance with standard histology.

The embodiments of the invention described herein may, for example, be used in or with a real-time, robust tissue characterisation tool which utilises ambient ionisation technologies, such as REIMS technology. Optionally, the tool may be an endoscopic tool.

As will become further apparent, embodiments described herein enables accurate real time spectrometric data to be obtained and utilised, e.g., in order to reduce mis-diagnosis rates and improve complete resection rates.

Various embodiments will now be described in more detail below which in general relate to generating an aerosol, surgical smoke or vapour from one or more regions of a target (details of which are provided elsewhere herein, e.g., in vivo tissue) using an ambient ionisation ion source. The aerosol, surgical smoke or vapour may then be mixed with a matrix and aspirated into a vacuum chamber of a mass and/or ion mobility spectrometer. The mixture may be caused to impact upon a collision surface causing the aerosol, smoke or vapour to be ionised by impact ionisation which results in the generation of analyte ions. The resulting analyte ions (or fragment or product ions derived from the analyte ions) may then be mass and/or ion mobility analysed and the resulting mass and/or ion mobility spectrometric data may be subjected to multivariate analysis or other mathematical treatment in order to determine one or more properties of the target in real time. For example, the multivariate analysis may enable a determination to be made as to whether or not a portion of tissue which is currently being resected is cancerous or not.

Ambient Ionisation Ion Sources

In any of the methods of the invention a device may be used to generate an aerosol, smoke or vapour from one or more regions of a target (details of which are provided elsewhere herein, e.g., in vivo tissue). The device may comprise an ambient ionisation ion source which is characterised by the ability to generate analyte aerosol, smoke or vapour from target (details of which are provided elsewhere herein), which may, e.g., be a native or unmodified target. By contrast, other types of ionisation ion sources such as Matrix Assisted Laser Desorption Ionisation ("MALDI") ion sources require a matrix or reagent to be added to the sample prior to ionisation.

It will be apparent that the requirement to add a matrix or a reagent directly to a sample may prevent the ability to perform in vivo analysis of tissue and also, more generally, prevents the ability to provide a rapid simple analysis of target material.

Ambient ionisation techniques are particularly useful since firstly they do not require the addition of a matrix or a reagent to the sample (and hence are suitable for the analysis of in vivo tissue) and since secondly they enable a rapid simple analysis of target material to be performed. Whilst there is no requirement to add a matrix or reagent to a sample in order to perform ambient ionization techniques, the method may optionally include a step of adding a matrix or reagent to the target (e.g., directly to the target) prior to analysis. The matrix or reagent may be added to the target, e.g., to lyse the cells of the target or to enhance the signal therefrom during the analysis.

A number of different ambient ionisation techniques are known and are intended to fall within the scope of the present invention. As a matter of historical record, Desorption Electrospray Ionisation ("DESI") was the first ambient ionisation technique to be developed and was disclosed in 2004. Since 2004, a number of other ambient ionisation techniques have been developed. These ambient ionisation techniques differ in their precise ionisation method but they share the same general capability of generating gas-phase ions directly from (e.g., native, untreated or unmodified) samples. The various ambient ionisation techniques which are intended to fall within the scope of the present invention may not require any prior sample preparation. As a result, the various ambient ionisation techniques enable both in vivo tissue and ex vivo tissue samples to be analysed without the time, expense and problems associated with adding a matrix or reagent to the tissue sample or other target material.

A list of ambient ionisation techniques which are intended to fall within the scope of the present invention are given in the following table:

| Acronym | Ionisation technique |
| --- | --- |
| DESI | Desorption electrospray ionization |
| DeSSI | Desorption sonic spray ionization |
| DAPPI | Desorption atmospheric pressure photoionization |
| EASI | Easy ambient sonic-spray ionization |
| JeDI | Jet desorption electrospray ionization |
| TM-DESI | Transmission mode desorption electrospray ionization |
| LMJ-SSP | Liquid microjunction-surface sampling probe |
| DICE | Desorption ionization by charge exchange |
| Nano-DESI | Nanospray desorption electrospray ionization |
| EADESI | Electrode-assisted desorption electrospray ionization |
| APTDCI | Atmospheric pressure thermal desorption chemical ionization |
| V-EASI | Venturi easy ambient sonic-spray ionization |
| AFAI | Air flow-assisted ionization |
| LESA | Liquid extraction surface analysis |
| PTC-ESI | Pipette tip column electrospray ionization |
| AFADESI | Air flow-assisted desorption electrospray ionization |
| DEFFI | Desorption electro-flow focusing ionization |
| ESTASI | Electrostatic spray ionization |
| PASIT | Plasma-based ambient sampling ionization transmission |
| DAPCI | Desorption atmospheric pressure chemical ionization |
| DART | Direct analysis in real time |
| ASAP | Atmospheric pressure solid analysis probe |
| APTDI | Atmospheric pressure thermal desorption ionization |
| PADI | Plasma assisted desorption ionization |
| DBDI | Dielectric barrier discharge ionization |
| FAPA | Flowing atmospheric pressure afterglow |
| HAPGDI | Helium atmospheric pressure glow discharge ionization |
| APGDDI | Atmospheric pressure glow discharge desorption ionization |
| LTP | Low temperature plasma |
| LS-APGD | Liquid sampling-atmospheric pressure glow discharge |
| MIPDI | Microwave induced plasma desorption ionization |
| MFGDP | Microfabricated glow discharge plasma |
| RoPPI | Robotic plasma probe ionization |
| PLASI | Plasma spray ionization |
| MALDESI | Matrix assisted laser desorption electrospray ionization |
| ELDI | Electrospray laser desorption ionization |
| LDTD | Laser diode thermal desorption |
| LAESI | Laser ablation electrospray ionization |
| CALDI | Charge assisted laser desorption ionization |
| LA-FAPA | Laser ablation flowing atmospheric pressure afterglow |

-continued

| Acronym | Ionisation technique |
|---|---|
| LADESI | Laser assisted desorption electrospray ionization |
| LDESI | Laser desorption electrospray ionization |
| LEMS | Laser electrospray mass spectrometry |
| LSI | Laser spray ionization |
| IR-LAMICI | Infrared laser ablation metastable induced chemical ionization |
| LDSPI | Laser desorption spray post-ionization |
| PAMLDI | Plasma assisted multiwavelength laser desorption ionization |
| HALDI | High voltage-assisted laser desorption ionization |
| PALDI | Plasma assisted laser desorption ionization |
| ESSI | Extractive electrospray ionization |
| PESI | Probe electrospray ionization |
| ND-ESSI | Neutral desorption extractive electrospray ionization |
| PS | Paper spray |
| DIP-APCI | Direct inlet probe-atmospheric pressure chemical ionization |
| TS | Touch spray |
| Wooden-tip | Wooden-tip electrospray |
| CBS-SPME | Coated blade spray solid phase microextraction |
| TSI | Tissue spray ionization |
| RADIO | Radiofrequency acoustic desorption ionization |
| LIAD-ESI | Laser induced acoustic desorption electrospray ionization |
| SAWN | Surface acoustic wave nebulization |
| UASI | Ultrasonication-assisted spray ionization |
| SPA-nanoESI | Solid probe assisted nanoelectrospray ionization |
| PAUSI | Paper assisted ultrasonic spray ionization |
| DPESI | Direct probe electrospray ionization |
| ESA-Py | Electrospray assisted pyrolysis ionization |
| APPIS | Ambient pressure pyroelectric ion source |
| RASTIR | Remote analyte sampling transport and ionization relay |
| SACI | Surface activated chemical ionization |
| DEMI | Desorption electrospray metastable-induced ionization |
| REIMS | Rapid evaporative ionization mass spectrometry |
| SPAM | Single particle aerosol mass spectrometry |
| TDAMS | Thermal desorption-based ambient mass spectrometry |
| MAII | Matrix assisted inlet ionization |
| SAII | Solvent assisted inlet ionization |
| SwiFERR | Switched ferroelectric plasma ionizer |
| LPTD | Leidenfrost phenomenon assisted thermal desorption |

According to an embodiment the ambient ionisation ion source may comprise a rapid evaporative ionisation mass spectrometry ("REIMS") ion source wherein a RF voltage is applied to one or more electrodes in order to generate smoke, aerosol or vapour by Joule heating.

However, it will be appreciated that other ambient ion sources including those referred to above may also be utilised. For example, according to another embodiment the ambient ionisation ion source may comprise a laser ionisation ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionisation ion source may comprise a laser ablation ion source having a wavelength close to 2.94 µm on the basis of the high absorption coefficient of water at 2.94 µm. According to an embodiment the laser ablation ion source may comprise a Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of e.g. 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a Co:MgF$_2$ laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a CO$_2$ laser having a wavelength of 10.6 µm may be used to generate the aerosol, smoke or vapour.

According to other embodiments the ambient ionisation ion source may comprise an ultrasonic ablation ion source, or a hybrid electrosurgical—ultrasonic ablation source that generates a liquid sample which is then aspirated as an aerosol. The ultrasonic ablation ion source may comprise a focused or unfocussed ultrasound.

According to an embodiment the first device for generating aerosol, smoke or vapour from one or more regions of a target may comprise an tool which utilises an RF voltage, such as continuous RF waveform. According to other embodiments a radiofrequency tissue dissection system may be used which is arranged to supply pulsed plasma RF energy to a tool. The tool may comprise, for example, a PlasmaBlade®. Pulsed plasma RF tools operate at lower temperatures than conventional electrosurgical tools (e.g. 40-170° C. c.f. 200-350° C.) thereby reducing thermal injury depth. Pulsed waveforms and duty cycles may be used for both cut and coagulation modes of operation by inducing electrical plasma along the cutting edge(s) of a thin insulated electrode.

According to an embodiment the first device comprises a surgical water/saline jet device such as a resection device, a hybrid of such device with any of the other devices herein, an electrosurgery argon plasma coagulation device, a hybrid argon plasma coagulation and water/saline jet device. According to an embodiment the first device comprises or forms part of an ambient ion or ionisation source; or said first device generates said aerosol, smoke or vapour from the target and contains ions and/or is subsequently ionised by an ambient ion or ionisation source, or other ionisation source.

Optionally, the first device comprises or forms part of a device, or an ion source, selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EASI") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focused or unfocussed ultrasonic ablation device; (xxiii) a hybrid focused or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

Optionally, the step of using said first device to generate aerosol, smoke or vapour comprises contacting said target with one or more electrodes.

Optionally, said one or more electrodes comprises either: (i) a monopolar device, wherein said method optionally further comprises providing a separate return electrode; (ii) a bipolar device; or (iii) a multi-phase RF device, wherein said method optionally further comprises providing a separate return electrode or electrodes.

Optionally, said one or more electrodes comprise or forms part of a rapid evaporation ionization mass spectrometry ("REIMS") device.

Optionally, said method further comprises applying an AC or RF voltage to said one or more electrodes in order to generate said aerosol, smoke or vapour.

Optionally, the step of applying said AC or RF voltage to said one or more electrodes further comprises applying one or more pulses of said AC or RF voltage to said one or more electrodes.

Optionally, said step of applying said AC or RF voltage to said one or more electrodes causes heat to be dissipated into said target.

Optionally, said step of using said first device to generate aerosol, smoke or vapour from one or more regions of the target further comprises irradiating the target with a laser.

Optionally, said first device generates aerosol from one or more regions of the target by direct evaporation or vaporisation of target material from said target by Joule heating or diathermy.

Optionally, said step of using said first device to generate aerosol, smoke or vapour from one or more regions of the target further comprises directing ultrasonic energy into said target.

Optionally, said aerosol comprises uncharged aqueous droplets, optionally comprising cellular material.

Optionally, at least 50%, 55%, 60%, 65%, 70%, 75%, 80%, 85%, 90% or 95% of the mass or matter generated by said first device and which forms said aerosol may be in the form of droplets.

The first device may be arranged and adapted to generate aerosol wherein the Sauter mean diameter ("SMD", d32) of said aerosol is in a range: (i) <5 µm; (ii) 5-10 µm; (iii) 10-15 µm; (iv) 15-20 µm; (v) 20-25 µm; or (vi) >25 µm.

The aerosol may traverse a flow region with a Reynolds number (Re) in the range: (i)<2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number (Sk) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i)<20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

Optionally, said aerosol comprises uncharged aqueous droplets, which may comprise cellular material.

Optionally, the method comprises ionising at least some of said aerosol, smoke or vapour, or analyte therein, so as to generate analyte ions; wherein said analyte ions are analysed to obtain said spectrometric data.

Optionally, the method comprises directing or aspirating at least some of said aerosol, smoke or vapour into a vacuum chamber of a mass and/or ion mobility spectrometer; and/or ionising at least some said aerosol, smoke or vapour, or the analyte therein, within a, or said, vacuum chamber of said spectrometer so as to generate a plurality of analyte ions.

Optionally, the method comprises causing said aerosol, smoke or vapour, or analyte therein, to impact upon a collision surface, optionally located within a, or the, vacuum chamber of said spectrometer, so as to generate the plurality of analyte ions.

Optionally, the collision surface may be heated. The collision surface may be heated to a temperature selected from the group consisting of: (i) about ≤100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

Optionally, the method comprises adding a matrix to said aerosol, smoke or vapour;

optionally wherein said matrix is selected from the group consisting of: (i) a solvent for said aerosol, smoke or vapour or analyte therein; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; an aldehyde; (xviii) a ketone; (xiv) non-polar molecules; (xx) hexane; (xxi) chloroform; and (xxii) propanol.

Rapid Evaporative Ionisation Mass Spectrometry ("REIMS") Technology

Figure 1A:
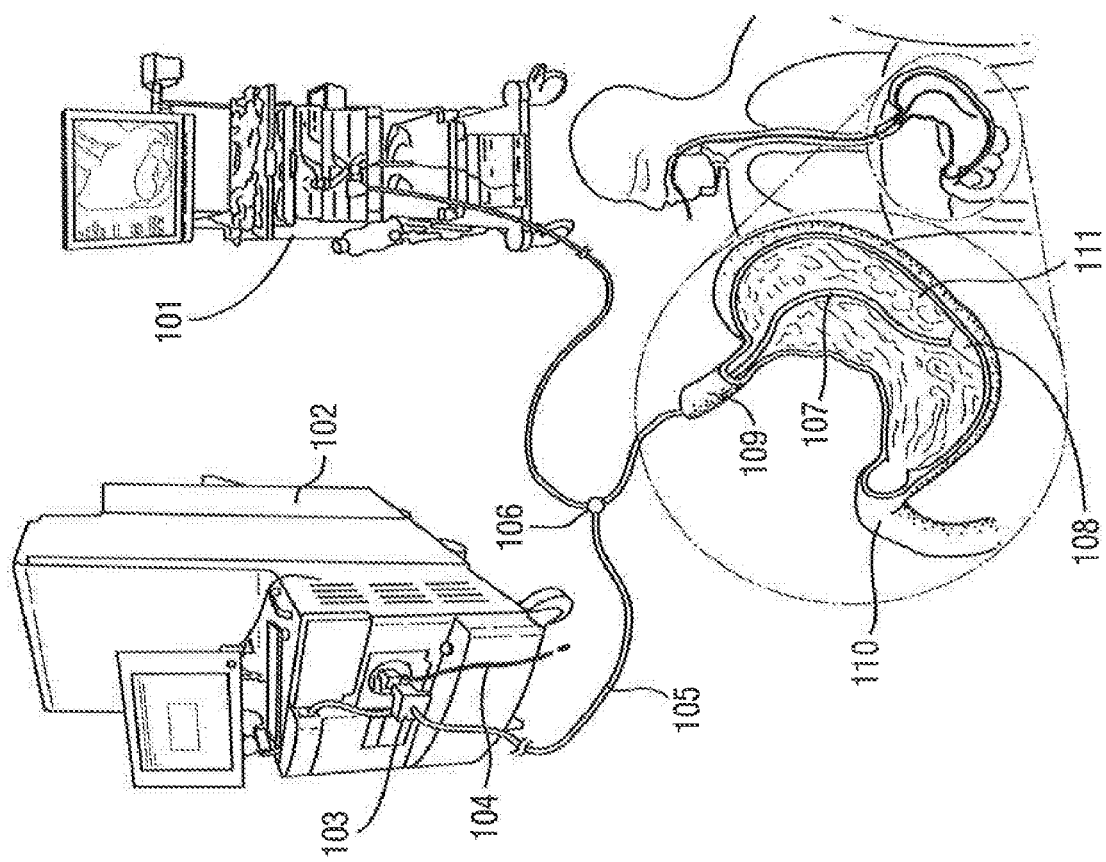
FIG. 1A shows an endoscopic experimental setup according to an embodiment wherein smoke, aerosol or vapour generated by an electrosurgical electrode tip is analysed by a mass and/or ion mobility spectrometer.

FIG. 1A and FIG. 1B show a REIMS technology endoscope and snare arrangement in accordance with an embodiment of the present invention. According to the embodiment a polypectomy snare may be provided. As shown in FIG. 1B, the snare 116 comprises a wire loop which runs through a length of tubing 113. The wire loop is attached to a manipulator which, as shown in FIG. 1A, may be operated by a user via an endoscopic stack 101. The manipulator allows a user to close the snare 116 around a polyp 117. The wire snare 116 is connected to an RF voltage generator (not shown). The wire snare 116 acts as an electrosurgical tool and may be deployed through a port 112 in an endoscope 107 and used to resect polyps 117 located e.g., in the stomach 111, pylorus 110 or colon etc., e.g., via the oesophagus 109. As the polypectomy snare 116 is deployed and tightened around a polyp 117, the polyp 117 effectively restricts or seals the open end 114 of the tubing 113 which houses the wire snare 116.

When an RF voltage is applied to the wire snare 116, the wire snare 116 acts as an electrosurgical tool and effectively cuts and removes the polyp 117. At the same time, surgical smoke or aerosol 118 is generated which is substantially unable to pass into the end 114 of the tubing 113 which houses the wire snare 116. The tubing 113 which houses the wire snare 116 is additionally provided with fenestrations or one or more aspiration ports 115 which enables the surgical smoke or aerosol 118 to be aspirated into the tubing 113 which houses the wire snare 116. The surgical smoke or aerosol 118 may be sucked towards the tubing by a pump (not shown) connected to the tubing and the direction of smoke suction may be as illustrated by arrow 119, i.e., the surgical smoke or aerosol 118 may be sucked towards the tubing 113 and through the fenestrations or one or more aspiration ports 115. The surgical smoke or aerosol 118 is then aspirated along the length of the tubing 113 and, as shown in FIG. 1A, via a connector 106 is passed to a vacuum chamber of a mass and/or ion mobility spectrometer 102 whereupon the surgical smoke or aerosol 118 is ionised, e.g., upon impacting a collision surface.

The resulting analyte ions are then mass and/or ion mobility analysed and real time information relating to the tissue which is being resected may be provided to a user (who may be, for example, a surgeon or a specialist nurse). In addition to cutting the polyp 117 away from the lining of the stomach 111 or colon, the snare 116 may be also be used to hold on to the polyp 117 so that the polyp 117 can be removed from the stomach 111 or colon, optionally analysed and then disposed of.

The endoscope may emit light 108 and comprise a camera such that a user may appropriately operate the apparatus.

According to other embodiments the electrosurgical tool and associated endoscope may be used in any other body cavities and organs, details of which are provided elsewhere herein, including the lung, nose and urethra.

The snare 116 may comprise a monopolar device and a relatively large pad acting as a return electrode may be placed underneath the patient so that electrical current flows from the snare electrode, through the patient, to the return electrode. Alternatively, the snare electrode may comprise a bipolar device such that electrical current does not flow through the patient's body. A bipolar device may be used, for example, in very sensitive operations such as brain surgery wherein it is clearly undesirable for an electrical current to flow through surrounding tissue.

Other embodiments are also contemplated wherein the electrosurgical tool may comprise a multi-phase or 3-phase device and may comprise, for example, three or more separate electrodes or probes.

Surgical smoke, aerosol or vapour 118 which is aspirated via the electrosurgical tool may be passed via a liquid separator or liquid trap (not shown) in order to remove or reduce the amount of liquid which is onwardly transmitted to the mass and/or ion mobility spectrometer 102.

A matrix may be added or mixed with the smoke, aerosol or vapour, optionally prior to the smoke, aerosol or vapour impacting upon a collision surface. The matrix may dissolve, dilute or form clusters with at least some of the analytes within the smoke, aerosol or vapour. This may assist in the ionisation of the analytes.

The matrix may be selected from the group consisting of: (i) a solvent for said aerosol, smoke or vapour or analyte therein; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; an aldehyde; (xviii) a ketone; (xiv) non-polar molecules; NO hexane; (xxi) chloroform; and (xxii) 1-propanol. Isopropanol is of particular interest, e.g., in the analyse of lipids and triglycerides.

The matrix and/or aerosol, smoke or vapour may be doped with one or more additives to, for example, enhance the solvation or dilution of analyte with the matrix, or for enhancing the ionisation of the analyte within the aerosol, smoke or vapour.

The doping compound may be an acidic or basic additive such as, for example, formic acid or diethylamine.

The matrix and/or doping compound may cause derivatisation of the analyte in the aerosol, smoke or vapour. For example, the matrix and/or doping compound may cause the derivatisation of cholesterol or steroids in the analyte. This may render the analyte more easily ionised.

The addition of a matrix is particularly advantageous in that diluting the sample to be analysed, dissolving analyte in the matrix or forming said clusters may reduce intermolecular bonding between the analyte molecules. This enhances the ionisation of the analyte. For example, if the analyte is then atomised, e.g., by being collided with a collision surface, the analyte will fragment into smaller droplets or clusters, wherein any given droplet or cluster is likely to contain fewer analyte molecules than it would if the matrix were not present. This in turn leads to a more efficient generation of ions when the matrix in each droplet is evaporated.

FIG. 1A also shows in more detail an embodiment wherein an endoscopic polypectomy snare which was equipped with an additional T-piece connector 106 in order to establish a transfer line between the tissue evaporation point and the atmospheric inlet 103 of a mass and/or ion mobility spectrometer 102. The atmospheric inlet 103 may comprise a grounding 104.

The REIMS endoscopic setup was initially optimized and its reproducibility was assessed using a porcine stomach model. Artificial polyps 117 were created within porcine stomach mucosa and resections were undertaken using a polypectomy snare 116 as shown in FIG. 1B. This set-up allowed for an exact simulation of a standard endoscopic resection. Since the polyp 117 completely blocks the opening or tool deployment opening 114 of the plastic sheath tubing 113 of the snare 116 during resection as can be seen from FIG. 1B, the aerosol 118 produced by the resection is aspirated through fenestrations 115 which are provided on the plastic sheath 113 of the snare 116.

The provision of fenestrations 115 on the plastic sheath 113 of the REIMS snare and which are distal from the tool deployment opening 114 of the snare is particularly advantageous since the fenestrations or aspiration ports 115 allow surgical smoke, aerosol or vapour 118 to be aspirated when the tool deployment opening 114 is at least partially or totally blocked.

The aerosol particles 118 which enter the tubing 113 housing the REIMS snare 116 via the fenestrations or aspiration ports 115 are then may transferred to a mass and/or ion mobility spectrometer 102 via PTFE tubing 105 which may be connected to a port of the snare. The snare 116 may be connected to the proximal end of a REIMS endoscope 107. The tubing may be connected directly to an inlet capillary or ion sampling orifice of the mass and/or ion mobility spectrometer 102. It will be understood that the mass and/or ion mobility spectrometer is distal to the point of evaporation.

Aspiration of the aerosols may be facilitated using a Venturi pump driven by standard medical air.

The mass and/or ion mobility spectrometer may include an atmospheric interface including the collision surface mentioned above, as will be described in relation to FIG. 2.

Figure 2:
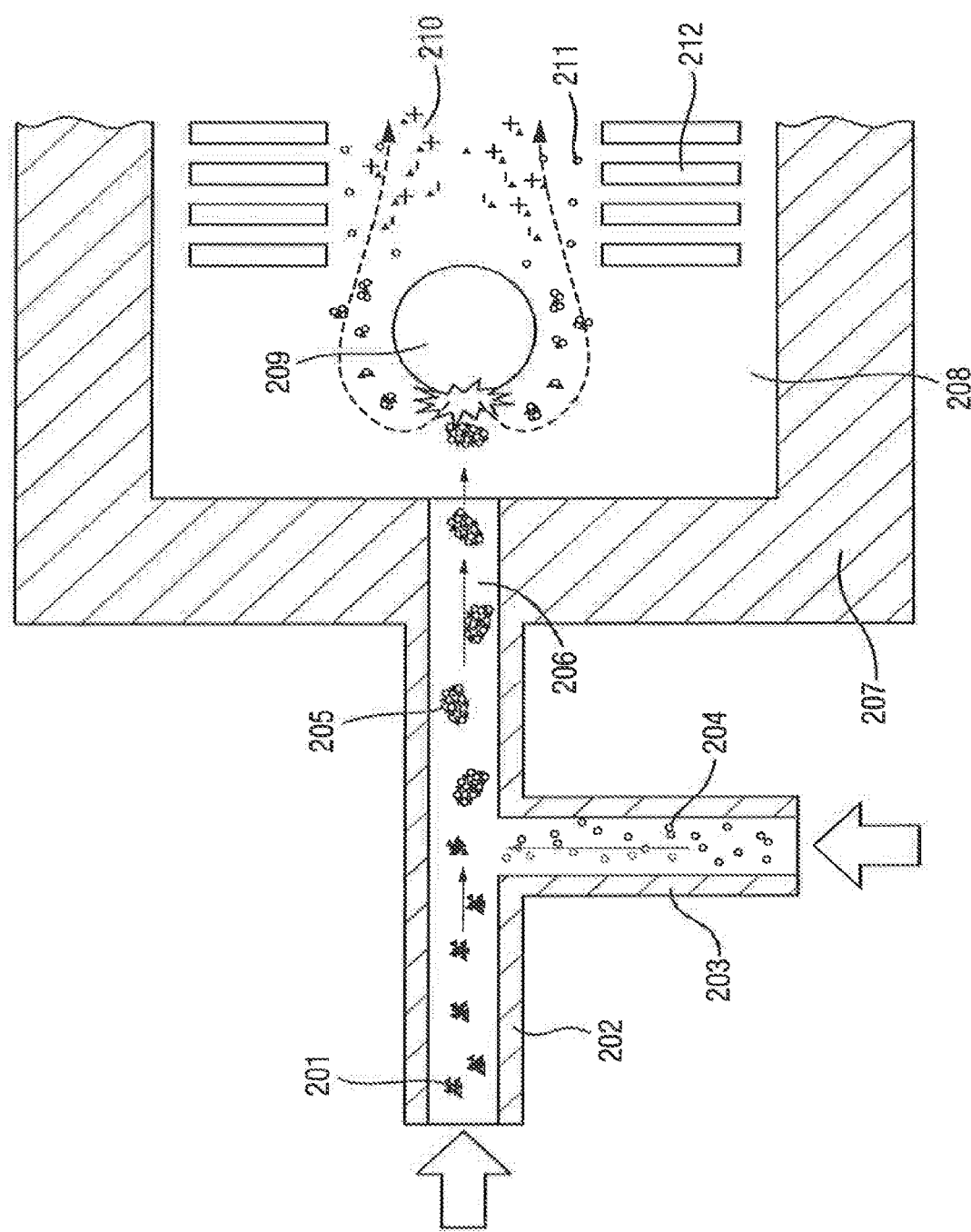
FIG. 2 shows an embodiment of the interface between the electrosurgical device and the mass and/or ion mobility spectrometer.

FIG. 2 shows a schematic of an embodiment of the interface between the electrosurgical tool and the mass and/or ion mobility spectrometer. The instrument may comprise an ion analyser 207 having an inlet 206, a vacuum region 208, said collision surface 209 and ion optics 212 (such as a Stepwave® ion guide) arranged within the vacuum region 208. The instrument also may comprise a sample transfer tube 202 and a matrix introduction conduit 203. The sample transfer tube 202 has an inlet for receiving the smoke, aerosol or vapour sample 201 (which may correspond to the plume 118 described in relation to FIG. 1) from a sample being investigated and an outlet that is connected to the inlet 206 of the ion analyser 207. The matrix introduction conduit 203 has an inlet for receiving a matrix compound and an outlet that intersects with the sample transfer tube 202 so as to allow the matrix 204 to be intermixed with the aerosol sample 201 in the sample transfer tube 202. A T-junction component may be provided at the junction between tubes 202, 203 and 206. The tubes 202, 203 and 206 may be removably inserted into the T-junction.

A method of operating the device of FIG. 2 will now be described. A sample, such as biological tissue, may be subjected to the REIMS technique. For example, a diathermic device may be used to evaporate biological tissue from the sample so as to form an aerosol, e.g., as described above in relation to FIG. 1. The aerosol particles 201 are then introduced into the inlet of the sample transfer tube 202. A matrix compound 204 is introduced into the inlet of the matrix introduction conduit 203. The aerosol particles 201 and matrix compound 204 are drawn towards the inlet 206 of the ion analyser 207 by a pressure differential caused by the vacuum chamber 208 being at a lower pressure than the inlets to the tubes 202, 203. The aerosol particles 201 may encounter the molecules of matrix compound 204 in, and downstream of, the region that the sample transfer tube 202 intersects with the matrix introduction conduit 203. The aerosol particles 201 intermix with the matrix 204 so as to form aerosol particles containing matrix molecules 205, in which both the molecular constituents of the aerosol sample 201 and the matrix compound 204 are present. The matrix molecules 204 may be in excess compared to the molecular constituents of aerosol sample 201.

The particles 205 may exit the sample transfer tube 202 and pass into the inlet 206 of the ion analyser 207. The particles 205 then enter into the decreased pressure region 208 and gain substantial linear velocity due to the adiabatic expansion of gas entering the vacuum region 208 from the sample transfer tube 202 and due to the associated free jet formation. The accelerated particles 205 may impact on the collision surface 209, where the impact event fragments the particles 205, leading to the eventual formation of gas phase ions 210 of the molecular constituents of the aerosol sample 201 and the formation of matrix molecules 211. The collision surface 209 may be controlled and maintained at a temperature that is substantially higher than the ambient temperature.

The matrix 204 includes a solvent for the analyte 201, such that the analyte 201 dissolves by the matrix 204, thereby eliminating intermolecular bonding between the analyte molecules 201. As such, when the dissolved analyte 205 is then collided with the collision surface 209, the dissolved analyte 205 will fragment into droplets and any given droplet is likely to contain fewer analyte molecules than it would if the matrix were not present. This in turn leads to a more efficient generation of analyte ions 210 when the matrix in each droplet is evaporated. The matrix may include an organic solvent and/or a volatile compound. The matrix may include polar molecules, water, one or more alcohols, methanol, ethanol, isopropanol, acetone or acetonitrile. Isopropanol is of particular interest.

The matrix molecules 211 may freely diffuse into the vacuum. In contrast, the gas phase ions 210 of the molecular constituents of the aerosol sample 201 may be transferred by the ion optics 212 to an analysis region (not shown) of the ion analyser 207. The ions 210 may be guided to the analysis region by applying voltages to the ion optics 212.

The ion optics 2012 may be a StepWave® ion guide. The collision surface may be positioned along and adjacent to the central axis of the large opening of a StepWave® ion guide. As will be understood by those skilled in the art, a StepWave® ion guide comprises two conjoined ion tunnel ion guides. Each ion guide comprises a plurality of ring or other electrodes wherein ions pass through the central aperture provided by the ring or other electrodes. Ions enter a first of the ion guides, along with any neutrals that may be present, and travel through the first ion guide. Ions are then directed orthogonally into a second of the ion guides and are transmitted therethrough. Transient DC voltages or potentials are applied to the electrodes to drive the ions through them. The StepWave® ion guide is based on stacked ring ion guide technology and is designed to maximise ion transmission from the source to the mass and/or ion mobility analyser. The device allows for the active removal of neutral contaminants, since the neutrals are not directed orthogonally into the second ion guide, thereby providing an enhancement to overall signal to noise. The design enables the efficient capture of the diffuse ion cloud entering a first lower stage which is then may focused into an upper ion guide for transfer to the ion analyser. The ions are then analysed by the ion analyser, which may comprise a mass spectrometer and/or an ion mobility spectrometer, or a combination of the two. As a result of the analysis, chemical information about the sample 201 may be obtained.

REIMS spectra recorded from the porcine stomach model in the m/z range of 600-1000 features predominantly phospholipids, which have been observed for all mammalian tissue types in previous REIMS experiments.

The REIMS endoscopic setup was tested on ex-vivo human samples including gastric adenocarcinoma, healthy gastric mucosa and healthy gastric submucosa. The samples were acquired from three individual patients, all of whom provided written informed consent. It was also tested on humans in vivo.

Real time and/or delayed information may be provided to a user of the electrosurgical tool that may comprise spectrometric information and/or tissue classification information. A feedback device and/or an alarm and/or an alert may also may be provided to provide a user of the electrosurgical tool with feedback and/or an alarm and/or an alert that analyte from an undesired target region or area is being analysed by the analyser or that the electrosurgical tool is operating in and/or is located in an undesired target region or area.

Electrical power to the electrosurgical tool may be reduced and/or stopped in the event that analyte from an undesired target region or area is being analysed by the analyser and/or the electrosurgical tool is operating in and/or is located in an undesired target region or area.

A liquid trap or separator may be provided between the electrosurgical probe and the analyser which captures or discards undesired liquids that are aspirated by the probe whilst may allowing the aerosol or surgical smoke itself to pass relatively uninhibited to the mass and/or ion mobility spectrometer. This prevents undesired liquid from reaching the analyser without affecting the measurement of the aerosol or surgical smoke. The liquid trap or separator may be arranged to capture the liquid, may using a liquid collector, for later disposal.

Figure 3:
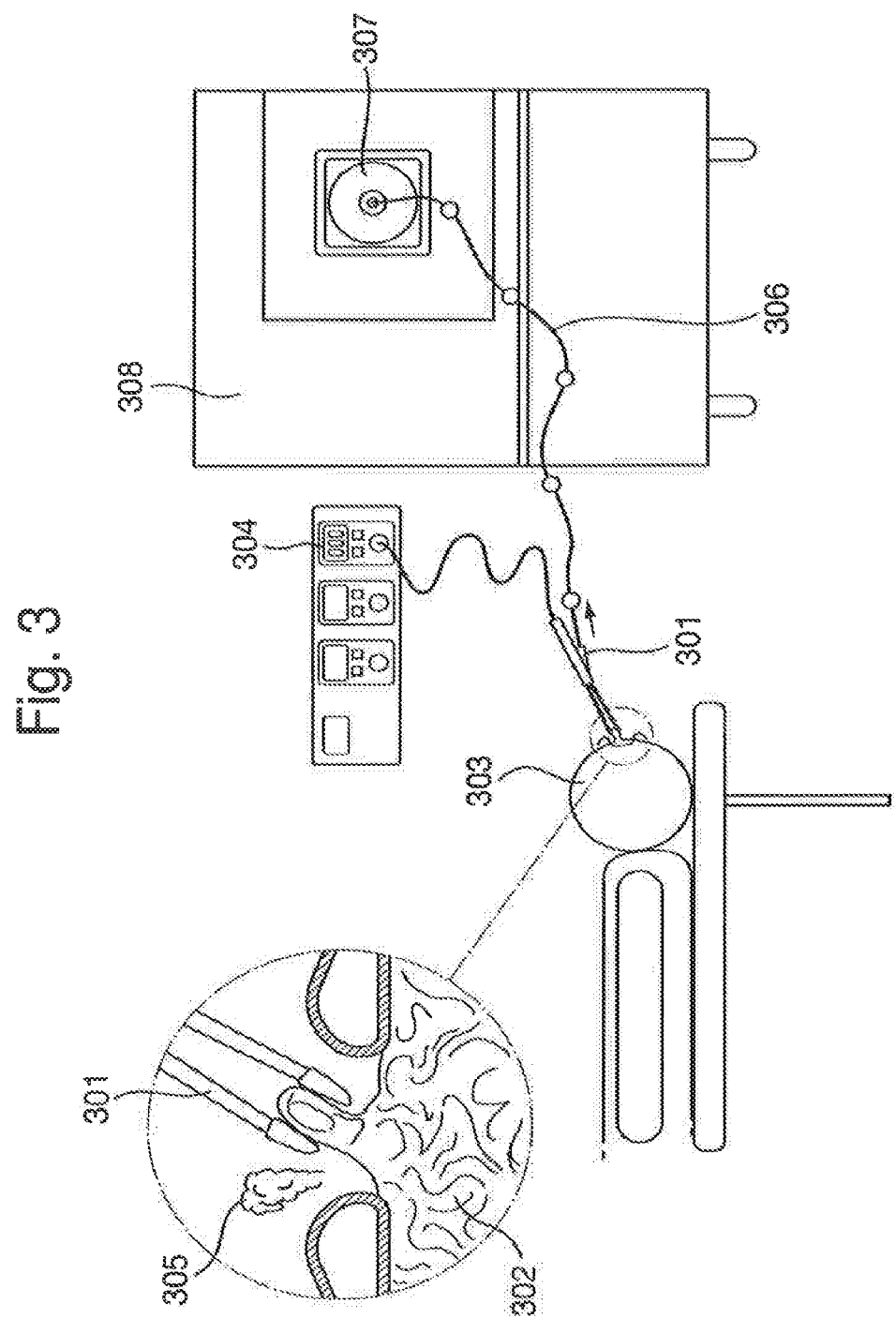
FIG. 3 illustrates a method of REIMS wherein an RF voltage is applied to bipolar forceps, resulting in the generation of smoke, aerosol or vapour, which is then analysed by a mass and/or ion mobility spectrometer.

FIG. 3 illustrates another REIMS embodiment of the invention wherein bipolar forceps 301 may be brought into contact with in vivo tissue 302 of a patient 303. In the example shown in FIG. 3, the bipolar forceps 301 may be brought into contact with brain tissue 302 of a patient 303 during the course of a surgical operation on the patient's brain. An RF voltage from an RF voltage generator 304 may be applied to the bipolar forceps 301 which causes localised Joule or diathermy heating of the tissue 302. As a result, smoke, aerosol or vapour 305 is generated. The smoke, aerosol or vapour 305 may then be captured or otherwise aspirated through an irrigation port of the bipolar forceps 301. The irrigation port of the bipolar forceps 301 is therefore reutilised as an aspiration port. The smoke, aerosol or vapour 305 may then be passed from the irrigation (aspiration) port of the bipolar forceps 301 to tubing 306 (e.g. ⅛" or 3.2 mm diameter Teflon® tubing). The tubing 306 is arranged to transfer the smoke, aerosol or vapour 305 to an atmospheric pressure interface 307 of a mass and/or ion mobility spectrometer 308.

Although embodiments have been described in which in vivo tissue is analysed, the invention extends to embodiments wherein ex vivo or in vitro specimens are analysed. Also, the invention extends to embodiments wherein non-tissue specimens are analysed, either in vivo, ex vivo or in vitro. For example, a body fluid sample or faecal sample may be analysed.

Although embodiments have been described in which REIMS is used to generate the smoke, aerosol or vapour for analysis, other ambient ionisation techniques may be used such as, for example, Desorption Electrospray Ionisation ("DESI").

Desorption Electrospray Ionisation ("DESI")

Desorption Electrospray Ionisation ("DESI") has also been found to be a particularly useful and convenient method for the real time rapid and direct analysis of biological material, such as tissues. DESI techniques allow direct and fast analysis of surfaces without the need for prior sample preparation. The technique will now be described in more detail with reference to FIG. 4.

As shown in FIG. 4, the DESI technique is an ambient ionisation method that involves directing a spray of (primary) electrically charged droplets 401 onto a target. The electrospray mist is pneumatically directed at the target by a sprayer 400 where subsequent splashed (secondary) droplets 405 carry desorbed ionised analytes (e.g. desorbed lipid ions). The sprayer 400 may be supplied with a solvent 406, a gas 407 (such as nitrogen) and a voltage from a high voltage source 408. After ionisation, the ions travel through air into an atmospheric pressure interface 409 of a mass and/or ion mobility spectrometer or mass and/or ion mobility analyser (not shown), e.g. via a transfer capillary 410. The transfer capillary 410 may be heated, e.g., to a temperature up to 500° C.

The ions may be analysed by the method described in relation to FIG. 2, or by other methods. The DESI technique allows, for example, direct analysis of biological compounds such as lipids, metabolites and peptides in their native state without requiring any advance sample preparation.

General Methods of the Invention

The invention provides a method of analysis using mass spectrometry and/or ion mobility spectrometry comprising:

a) using a first device to generate aerosol, smoke or vapour from one or more regions of a first target of biological material; and b) mass analysing and/or ion mobility analysing said aerosol, smoke, or vapour, or ions derived therefrom so as to obtain first spectrometric data, wherein said biological material is a human subject, a non-human animal subject, or a specimen derived from said human or non-human animal subject.

In one aspect, the method may be a method of analysing a disease, a diseased tissue, and/or a biomarker of a disease. Thus, the method may optionally comprise a step of analysing a disease, a diseased tissue, and/or a biomarker of a disease.

The method may be a method of, or of obtaining information relevant to, (i) diagnosing a disease; (ii) monitoring the progression or development of a disease; (iii) disease prognosis;

(iv) predicting the likelihood of a disease responding to treatment; (v) monitoring the response of a disease to treatment; (vi) stratifying subjects; (vii) determining the distribution of diseased tissue; and/or (viii) determining the margin between diseased and healthy tissue.

Thus, the method may optionally comprise a step of (i) diagnosing a disease; (ii) monitoring the progression or development of a disease; (iii) disease prognosis;

(iv) predicting the likelihood of a disease responding to treatment; (v) monitoring the response of a disease to treatment; (vi) stratifying subjects; (vii) determining the distribution of diseased tissue; and/or (viii) determining the margin between diseased and healthy tissue.

Details of suitable diseases are provided elsewhere herein.

In one aspect, the method may be a method of analysing a microbe, a microbial interaction, a microbial biomarker, and/or a microbiome. Thus, the method may optionally comprise a step of analysing a microbe, a microbial interaction, a microbial biomarker, and/or a microbiome.

In one aspect, the method may be a method of analysing the genotype and/or phenotype of a cell. Thus, the method may optionally comprise a step of analysing the genotype and/or phenotype of a cell.

In one aspect, the method may be a method of treatment. Thus, the method may optionally comprise a step of administering a therapeutically effective amount of a therapeutic agent to a subject in need thereof.

In one aspect, the method may be a method of surgery. Thus, the method may optionally comprise a surgical step of resecting tissue, optionally prior to, during, and/or after the method of analysis. The method may optionally be a method of surgery, comprising using the method to determine what tissue to resect, or comprising resecting tissue that was identified, characterised, and/or confirmed as being diseased by the method.

In one aspect, the method may be a method of analysing a faecal and/or body fluid specimen. Thus, the method may optionally comprise a step of analysing a faecal and/or body fluid specimen.

In one aspect, the method may be a method of analysing a compound. Thus, the method may optionally comprise a step of analysing a compound and/or a biomarker for a compound.

Optionally, the method may include 2 or more of the aspects disclosed herein, e.g., 3 or more, 4 or more 5, or more etc. For example, the method may optionally comprise a step of analysing a faecal and/or body fluid specimen, wherein a microbial biomarker and/or a compound biomarker is analysed.

Optional features of any of these methods are discussed below. Thus, unless otherwise stated, any reference to "a method" or "the method" is intended to be a reference to any of the methods of the invention listed herein. It is explicitly intended that any of these features may be present in any combination in any of these methods.

Targets and Analysis Thereof

The method may be carried out on a "target", which may optionally be a biological material, e.g., a subject or a specimen derived from a subject.

The "subject" may be a human or a non-human animal. The subject may be alive or dead. If the method is carried out on a living subject, then it may be referred to as an in vivo method. If the method is carried out on a specimen, then it may be referred to as an in vitro or ex vivo method.

Optionally, the animal may be a mammal, optionally selected, for example, from any livestock, domestic or laboratory animal, such as, mice, guinea pigs, hamsters, rats, goats, pigs, cats, dogs, sheep, rabbits, cows, horses, camels, donkeys, buffalos, lamas, chickens, ducks, geese, and/or monkeys. Optionally, it may be an insect, bird or fish, e.g. a fly or a worm. Thus, any veterinary applications of the method of the invention are contemplated.

The method may optionally be carried out on an in vivo target, i.e. on a living subject. For example, it may be carried out by using a thermal ablation method.

Alternatively or in addition, it may optionally be carried out on a dead subject, for example as part of an autopsy or a necropathy.

Alternatively or in addition, it may optionally be carried out on an ex vivo or in vitro target, e.g., on a specimen. The specimen may optionally be a provided specimen, i.e. a specimen that was previously obtained or removed from a subject. Optionally, the method may include a step of obtaining a specimen from a subject.

Thus, it may optionally be carried out on a specimen, which may optionally be selected, for example, from a surgical resection specimen, a biopsy specimen, a xenograft specimen, a swab, a smear, a body fluid specimen and/or a faecal specimen.

Resection is the surgical removal of part or all of a tissue.

A biopsy specimen may optionally be obtained, e.g., by using a needle to withdraw tissue and/or fluid comprising cells; by using an endoscope; and/or during surgery. A biopsy may optionally be incisional, excisional, or be retrieved from a surgical resection. A biopsy specimen comprises cells and may optionally be a tissue specimen, for example, comprising or consisting of diseased and/or non-diseased tissue.

A "xenograft specimen" is a tissue specimen derived from a xenograft. A "xenograft" refers to cellular material, such as tissue, that originated from a first subject and was inserted into a second subject. Optionally, the xenograft may comprise or consist of tumour cells. For example, cells or tissue obtained from a human tumour may be xenografted into a host animal.

Optionally, a xenograft may be analysed in vivo, in which case the target may be referred to as a subject comprising the xenograft. Thus, the target may optionally be a subject comprising a xenograft. Optionally, a specimen may be derived from a xenograft.

A "swab" is intended to be understood as comprising a "standard medical swab" i.e. a swab that is designed for sampling biological samples such as mucosal membranes. For example, the term "standard medical swab" should be understood as covering a "cotton bud" (British) or a "cotton swab" (American) i.e. a small wad of cotton wrapped around one or both ends of a tube. The tube may be made from plastic, rolled paper or wood.

A swab may optionally, for example, comprise a tissue or other cellular material, e.g., a mucosal sample.

A smear may, for example, optionally be a specimen that has been smeared onto a solid support, e.g. between two slides.

A body fluid may, for example, optionally be selected from blood, plasma, serum, sputum, lavage fluid, pus, urine, saliva, phlegm, vomit, faeces, amniotic fluid, cerebrospinal fluid, pleural fluid, semen, sputum, vaginal secretion, interstitial fluid, and/or lymph. Optionally, it may be dried, collected with a swab, and/or dispensed onto an absorbent carrier, e.g. a filter or paper. Optionally, it may be a pellet. A pellet may be prepared, e.g., by centrifuging the body fluid at a suitable force and for a suitable time to sediment any cells, large structures and/or macromolecules to form a pellet. The remainder of the fluid, i.e. the supernatant, may then be discarded, e.g. by tipping it out of via aspiration.

Optionally, the specimen may be sectioned and/or sequentially disassociated, e.g., mechanically and/or enzymatically, for example with trypsin, to obtain different layers of the specimen, and/or to derive cells from different layers of a specimen. For example, this may be of interest if the specimen is a tissue, e.g., a xenograft tissue. Different layers, or cells derived from different layers, of the specimen may then be analysed. During tissue growth and/or maintenance, different layers of a tissue may have been exposed to different environmental conditions, and/or been exposed to different concentrations of a substance, as substances may not penetrate each layer at the same rate. Thus, the method may optionally be used to analyse one or more different layers of a specimen, or cells derived therefrom.

The method may optionally involve the analysis of one or more different targets. Optionally, 2 or more targets from different subjects, and/or from different locations within a subject, may be analysed. Optionally, the targets may be at or from 2 or more different locations, e.g., specimens may be at or from 2 or more locations in/of a subject. For example, in the case of coeliac disease, it is recommended that more or more biopsy specimen be obtained from each of the second and third duodenal portion of the GI tract, and such a strategy may also be suitable for any of the other diseases discussed herein.

Optionally, a target may be at or from one or more locations known or suspected to be healthy; and one or more locations known or suspected to be diseased. In the case of cancer, for example, a target may optionally be at or from at least 1 location known or suspected to be healthy; at least 1 location known or suspected to be a tumour margin; at least 1 location known or suspected to be a tumour stroma; and/or at least 1 location known or suspected to be a neoplastic tumour.

Optionally, the method may involve the analysis one 2 or more locations of a target. Optionally, distinct locations of a target may be analysed, e.g., a series of points may be sampled, optionally with or without spatial encoding information for imaging purposes.

The analysis may optionally be made intra-operatively, i.e. whilst a surgical procedure is under way. Thus, the analysis may optionally be used to provide real-time analysis of a target. The analysis may optionally be used to identify disease margins. A disease margin may optionally be analysed, e.g., by analysing the concentration of a particular cell type, e.g. a diseased, cancerous, and/or necrotic cell in a target region. The analysis may optionally be made in vivo, e.g., during a surgical procedure. This may optionally involve using, e.g., a thermal ablation surgical method, e.g., REIMS technology, such as, the iKnife technology. For example, a tissue on which surgery is being performed may be analysed in vivo and the results of the analysis may be used to inform, influence or determine a further surgical step.

The surgery may optionally be surgery in relation to any of the diseases mentioned herein, such as, cancer surgery, neurosurgery, and the like. The surgery may optionally be laparoscopic, and/or endoscopic.

The analysis may optionally be made in vitro or ex vivo. This may optionally be, e.g., in parallel to a surgical procedure. For example, a specimen, such as, a biopsy, may be obtained during a surgical procedure. Such a provided specimen may then be analysed ex vivo and the results of the analysis may be used to inform, influence or determine a further surgical step.

The method may optionally be carried out on a target that is native. By "native" is meant that the target has not been modified prior to performing the method of the invention. In particular, the target may be native in that the tissue or cells present in the target are not subjected to a step of lysis or extraction, e.g., lipid extraction, prior to performance of the method of the invention. Thus, a target may be native in that it comprises or consists essentially of intact cells Thus, by native is meant that the target has not been chemically or physically modified and is thus chemically and physically native. Optionally, the target may be chemically native, i.e. it may be chemically unmodified, meaning that it has not been contacted with a chemical agent so as to change its chemistry. Contacting a target with a matrix is an example of a chemical modification.

Optionally, the target may be physically native, i.e. it may be physically unmodified, meaning that it has not been modified physically. Freezing, thawing, and/or sectioning are examples of physical modifications. The skilled person will appreciate that although physical actions, such as, freezing, may affect a specimen's chemistry, for the purpose of this invention such an action is not considered to be a chemical modification.

Thus, optionally the target may be chemically native, but not physically native, e.g. because it has been frozen and/or sectioned.

Optionally, the target may be frozen, previously frozen and then thawed, fixed, sectioned, and/or otherwise prepared, as discussed with regard to specimen preparation. Optionally, the method may be carried out on a target that has not undergone a step of preparation specifically for the purpose of mass and/or ion mobility spectrometry analysis.

The target may not have been contacted with a solvent, or a solvent other than water, prior to generating the smoke, aerosol or vapour from the target.

Additionally, or alternatively, the target may not be contacted with a matrix prior to generating the smoke, aerosol or vapour from the target. For example, the target may not be contacted with a MALDI matrix or other matrix for assisting ionisation of material in the target. A MALDI matrix may, e.g., comprise or consist of small organic acids such as α-cyano-4-hydroxycinnamic acid (CHCA) and/or 2,5-dihydroxybenzoic acid (DHB).

The method may optionally be carried out on a target that has been prepared for a particular mass and/or ion mobility spectrometry analysis; and/or that has been prepared for any of the analytical methods mentioned elsewhere herein.

Specimen preparation (for any of the methods of the invention and/or any of the analytical methods disclosed herein) may optionally involve one or more of the following.

The specimen or part thereof may optionally be deposited on a solid surface, such as, a glass or plastic slide.

The specimen may optionally be fixed chemically, or via a frozen section procedure, e.g., to preserve tissue from degradation, and to maintain the structure of the cell and of sub-cellular components such as cell organelles, e.g., nucleus, endoplasmic reticulum, and/or mitochondria. The fixative may, for example, be 10% neutral buffered formalin. The specimen may optionally be processed with e.g., epoxy resins or acrylic resins to allow or facilitate sections to be cut. The sample may optionally be embedded, for example, in paraffin. The specimen may optionally be cut into sections of, for example, 1 μm to 200 nm. For example, the specimen may optionally be about 5 μm thick for light microscopy, or about 80-100 nm thick for electron microscopy. Optionally, the specimen may be cut into sections of at least 1, 3, 5, 7, 9, 10, 12, 14, 16, 18, 20, 22, 24 or 25 μm and no more than 100, 90, 80, 70, 60, 50, 40, 35, 30, 28, or 26 μm, for example, 5-25 μm.

Frozen sections may optionally be prepared, e.g., by freezing and slicing the specimen. Prior to freezing, the specimen may optionally be embedded, e.g. as described above. Embedding medium helps conduct heat away from the specimen during freezing, helps protect the tissue from drying during storage, and supports the tissue during sectioning.

Freezing may optionally be performed, e.g., by contacting the specimen with a suitable cooling medium, such as, dry ice, liquid nitrogen, or an agent that has been cooled in dry ice or liquid nitrogen, e.g. isopentane (2-methyl butane). Frozen specimens may optionally be stored at, e.g., between about −80 and −4 degrees Celsius, e.g. at −70 or −20 degrees Celcius.

The specimen or sections thereof may be stained, for example, with Hematoxylin and eosin (H&E stain). Hematoxylin, a basic dye, stains nuclei blue due to an affinity to nucleic acids in the cell nucleus; eosin, an acidic dye, stains the cytoplasm pink.

Any of the methods may optionally include automatic sampling, which may optionally be carried out using a REIMS device. Any of the methods may optionally comprise using a disposable sampling tip.

Biomarkers

The method may optionally involve the analysis of one or more biomarkers. A biomarker may be an objective, quantifiable characteristic of, e.g., a cell type, disease status, microbe, compound, and/or biological process.

The term "biomarker" is sometimes used explicitly herein, but it should also be understood that any of the analyses mentioned herein may optionally be the analysis of a biomarker. Thus, e.g., any reference to analysing a "microbe" should be understood optionally to be "analysing a microbial biomarker"; any reference to analysing "bile" should be understood optionally to be "analysing a bile biomarker"; any reference to analysing a "compound"

should be understood optionally to be "analysing a biomarker for that compound"; and so on.

The biomarker may optionally be a spectrometric biomarker. The term "(mass-) spectral biomarker" is used herein to refer to spectrometric data that is characteristic of a cell type, disease status, microbe, compound, and/or biological process, but for simplicity, a spectrometric biomarker may simply be referred to as a "biomarker".

By "characteristic of a cell type" is meant that the biomarker may optionally be used to analyse, e.g., detect, identify and/or characterise said cell type. Optionally, the biomarker may be used to distinguish between cells originating from different tissues; between genotypically and/or phenotypically different cell types; between an animal cell and a microbial cell; between a normal and an abnormal cell; between a wild-type and a mutant cell; and/or between a diseased and a healthy cell.

By "characteristic of a disease status" is meant that the biomarker may optionally be used to analyse the disease status of a target. Optionally, the biomarker may be used to distinguish between healthy and diseased cells; and/or to analyse the severity, grade, and/or stage of a disease.

By "characteristic of a microbe" is meant that the biomarker may optionally be used to analyse, e.g., detect, identify and/or characterise said microbe. As discussed elsewhere herein, identification may be on any level, for example, on a taxonomic level. A biomarker that allows identification of a microbe as belonging to a particular taxonomic level may be referred to as a "taxonomic marker" or "taxonomic biomarker". Thus, a taxonomic marker may be specific for a Kingdom, Phylum, Class, Order, Family, Genus, Species and/or Strain.

By "characteristic of a compound" is meant that the biomarker may optionally be used to analyse, e.g., detect, identify and/or characterise said compound.

By "characteristic of a biological process" is meant that the biomarker may optionally be used to analyse a biological process. Optionally, the biomarker may be used to analyse the start, progression, speed, efficiency, specificity and/or end of a biological process.

Different cell types, disease states, compounds, microbes, biological progresses and the like may be characterised by the presence or absence, and/or relative abundance, of one or more compounds, which may serve as biomarkers. Any reference herein to a biomarker being a particular compound, or class of compounds, should be understood optionally to be the spectrometric data of that compound, or class of compounds.

For example, a reference to a "C24:1 sulfatide (C48H91NO11S)" biomarker should be understood to be a reference to the spectrometric data corresponding to C24:1 sulfatide (C48H91NO11S) which may, e.g., be a signal corresponding to m/z of about 888.6; whereas a reference to a "glycosylated ceramide" biomarker should be understood to be a reference to the spectrometric data corresponding to glycosylated ceramide, which may, e.g., be a signal corresponding to m/z of 842, 844 or 846.

As explained above, a biomarker may be indicative of a cell type, disease status, microbe, compound, and/or biological process. A biomarker which is indicative of cancer may therefore be referred to as a "cancer biomarker"; a biomarker which is indicative of *Pseudomonas aeruginosa* may be referred to as a "*Pseudomonas aeruginosa* biomarker" and so on.

Optionally, a spectrometric biomarker may be identified as being the spectrometric data of a particular compound, or class of compounds. Thus, a signal corresponding to a particular mass, charge state, m/z and/or ion mobility (e.g., due to cross-sectional shape or area) may optionally be identified as being indicative of the presence of a particular compound, or class of compounds.

Optionally, spectrometric signal may serve as a biomarker even if a determination has not been made as to which particular compound, or class of compounds gave rise to that signal. Optionally, a pattern of spectrometric signals may serve as a biomarker even if a determination has not been made as to which particular compounds, or class of compounds, gave rise to one or more signals in that pattern, or any of the signals in a pattern.

The work disclosed herein has led to the identification of a range of biomarkers, as well as allowing the identification of further biomarkers. Optionally, the biomarker may be selected from any of the biomarkers disclosed herein, including in any of the Examples and/or the Tables, particularly Tables 1-19. Optionally, the biomarker may be a biomarker of the substituted or unsubstituted form of any of the biomarkers mentioned herein; and or of an ether, ester, phosphorylated and/or glycosylated form, or other derivative, of any of the biomarkers mentioned herein.

Optionally, the biomarker may be a biomarker of a lipid; a protein; a carbohydrate; a DNA molecule; an RNA molecule; a polypeptide, such as, a ribosomal peptide or a non-ribosomal peptide; an oligopeptide; a lipoprotein; a lipopeptide; an amino acid; and/or a chemical compound, optionally an organic chemical molecule or an inorganic chemical molecule.

A biomarker may optionally be the clear-cut presence or absence of a particular compound, which may optionally manifest itself as the presence or absence of a spectrometric signal corresponding to a specific mass, charge state, m/z and/or ion mobility.

A biomarker may optionally be the relative abundance of a particular biomolecule or compound, which may optionally manifest itself as the relative intensity of a spectrometric signal corresponding to a specific mass, charge state, m/z and/or ion mobility.

A biomarker may optionally be the relative abundance of more or more compounds, which may optionally manifest itself as the relative intensity of two or more spectrometric signals corresponding to two or more specific mass, charge state, m/z and/or ion mobility.

Thus, a biomarker may optionally be an increased or decreased level of one or more compounds, e.g., a metabolite, a lipopeptide and/or lipid species, which may optionally manifest itself as an increase and/or decrease in the intensity of two or more spectrometric signals corresponding to two or more specific mass, charge state, m/z and/or ion mobility.

The presence, absence and relative abundance of a variety of compounds may be referred to as a molecular "fingerprint" or "profile". The totality of the lipids of a cell may be referred to as a lipidomic fingerprint/profile, whereas the totality of metabolites produced by a cell may be referred to as a metabolomic fingerprint/profile.

Thus, the biomarker may be a molecular fingerprint, e.g., a lipid fingerprint and/or a metabolomic fingerprint, more particularly e.g., a (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; or (viii) a phosphatidylinositol (PI) profile.

By way of example, phosphatidylglycerol may be found in almost all bacterial types, but it may be present in different bacteria in different relative amounts. Phosphatidylglycerol may be present at a level of only 1-2% in most animal tissues. It may therefore be a biomarker for bacteria in an animal specimen, and/or be a biomarker for specific types of bacteria.

The biomarker may optionally be a direct biomarker or an indirect biomarker. By "direct" biomarker is meant that the spectrometric data is produced directly from the biomarker. For example, if a particular compound has a specific spectrometric signal or signal pattern, then obtaining this signal or signal pattern from a sample provides direct information about the presence of that compound. This may be the case, for example, for a metabolite produced in significant amounts by a cell or microbe. Optionally, in such an example, the spectrometric data from the compound may alternatively or in addition serve as an indirect biomarker for the cell or microbe that produced this compound.

By "indirect" biomarker is meant that the spectrometric data is produced from one or more biomarkers that is/are indicative of a particular compound, biological process, and/or type of microbe or cell. Thus, an indirect biomarker is spectrometric data generated from one or more molecules that provides information about a different molecule. For example, a molecular fingerprint, such as, a lipid fingerprint, may be indicative of the expression of a particular protein, e.g. a receptor; or of a particular cell type or microbial type.

A lipid biomarker may optionally be selected from, e.g., fatty acids, glycerolipids, sterol lipids, sphingolipids, prenol lipids, saccharolipids and/or phospholipids. A brief overview of various lipids is provided below, but it must be appreciated that any particular lipid may fall into more than one of the groups mentioned herein.

A fatty acid is an aliphatic monocarboxylic acid. The fatty acid may optionally have a carbon chain comprising precisely or at least 4, 6, 8, 10, 12, 14, 16, 18, 20, 22, 24, 26, 28, 30, 32, 36, 38 or 40 carbons. It may optionally be monounsaturated, polyunsaturated, or saturated. It may optionally be an eicosanoid. It may, for example, be oleic acid, palmitic acid, arachidonic acid, a prostaglandin, a prostacyclin, a thromboxane, a leukotriene, or an epoxyeicosatrienoic acid.

The glycerolipid may optionally be selected from e.g., monoacylglycerol, diacylglycerol, and/or triacylglycerol.

The sterol may optionally be selected from free sterols, acylated sterols (sterol esters), alkylated sterols (steryl alkyl ethers), sulfated sterols (sterol sulfate), sterols linked to a glycoside moiety (steryl glycosides) and/or acylated sterols linked to a glycoside moiety (acylated sterol glycosides).

The sterol may optionally have an aliphatic side chain of precisely or at least 8, 9, 10, 11, 12, 13, 14, 15, 16, 17, 18, 19, 10, 21, 22, 23, 24, 25, 26, 27, 28, 29, 20, 35 or 40 carbon atoms. The number of carbon atoms in the aliphatic side chain may be expressed by the letter C followed by the number, e.g., C27 for cholesterol. It may, for example, be selected from cholesterol, cholesterol sulphate, ergosterol, lanosterol, dinosterol (4a,23,24-tri methyl-5a-cholest-22E-en-3b-ol), oxysterol and/or a derivative of any thereof.

A phospholipid may comprise two fatty acids, a glycerol unit, a phosphate group and a polar molecule. The Phospholipid may optionally comprise an ester, ether and/or other 0-derivative of glycerol. The phospholipid may optionally be selected from, e.g., Phosphatidylglycerol, diphosphatidylglycerol (cardiolipin), Acylphosphatidylglycerol (1,2-diacyl-sn-glycero-3-phospho-(3'-acyl)-1'-sn-glycerol), and/or plasmalogen.

The phosphatidylglycerol lipid may optionally be selected from phosphatidic acids (PAs), phosphatidylethanolamines (PEs), phosphatidylglycerols (PGs), phosphatidylcholines (PCs), phosphatidylinositols (PIs) and/or phosphatidylserines (PSs).

A sphingolipid is a lipid containing a sphingoid. It may optionally be selected from, e.g., a ceramide, i.e. an N-acylated sphingoid; sphingomyelin, i.e. a ceramide-1-phosphocholine; phosphoethanolamine dihidroceramide, and/or a glycosphingolipid, i.e. a lipid containing a sphingoid and one or more sugars. For example, it may optionally be a glycosylated ceramide.

The biomarker may optionally be a metabolite, such as, a primary or a secondary metabolite; an antibiotic; a quorum sensing molecule; a fatty acid synthase product; a pheromone; and/or a biopolymer.

A biomarker compound may optionally be characterised by one or more of the following functional groups: alcohol, ester, alkane, alkene, alkyne, ether, ketone, aldehyde, anhydride, amine, amide, nitrile, aromatic, carboxylic acid, alkyl halide, and/or carbonyl. Optionally, it may additionally be identified as being primary, secondary or tertiary, e.g., a primary alcohol, a secondary amine, or the like.

For example, it may optionally be a terpene; prenylquinone; sterol; terpenoid; alkaloid; glycoside; surfactin; lichenysin, 2-Heptyl-3-hydroxy-4(1H)-quinolone or 2-heptyl-3,4-dihydroxyquinoline ("PQS" or *Pseudomonas* quinolone signal); 4-hydroxy-2-heptylquinoline ("HHQ"); phenol, such as, a natural phenol; phenazine; biphenyl; dibenzofurans; beta-lactam; polyketide; rhamnolipid; mycolic acids; and/or polyhydroxyalkanoates;

The biomarker may optionally be selected from, e.g., Glycerophosphocholines, Sphingomyelins, Glycerophospholipids, Galactoceramides, Glycerophosphoinositols, Glycerophosphoserines, Glycerophosphoglycerols, Cholesterol sulphate, sulfatides, seminolipids, citric acid, Glycerophosphoethanolamines, Glycerophosphoethanolamines, 2-hydroxygluterate, glutamine, glutamate, succinate, fumarate, palmitoylglycine, ubiquinones, gadoteridol and/or any of the other biomarkers mentioned herein, including any of the Tables.

The inventors have identified inter alia the following biomarkers:

Mycolic acids for bacteria belonging to the Corynebacterineae suborder such as *Mycobacterium* spp., *Corynebacterium* spp. and *Rhodococcus* spp. In particular, the following mycolic acids have been detected from the corresponding genera:

*Mycobacterium* spp.: C77-C81 (even and odd numbered, 0-2 unsaturations); *Corynebacterium* spp.: C28-C36 (even numbered, 0-2 unsaturations);

*Nocardia* spp.: C48-056 (even numbered, 0-3 unsaturations);

*Rhodococcus* spp.: C28-C38 (even and odd numbered, 0-4 unsaturations).

A variety of sphingolipid species were found to be specific for members of the Bacteroidetes phylum. These sphingolipids include oxidized ceramides species, phosphoethanolamine dihydroceramides and C15:0-substituted phosphoglycerol dihydroceramides and dihydroceramide. Among those sphingolipid species, a series of galactosylated sphingolipids was found to be specific for *Bacteroides fragilis* (*Bacteroides fragilis* alpha-Galactosylceramides).

Among bacteria, plasmalogens are highly specific for anaerobic bacteria such as *Clostridium* spp. and *Fusobacterium* spp. This is due to the fact that aerobic bacteria lost the biochemical pathway required for plasmalogen synthesis. Humans are able to synthesize plasmalogens (although via a different biochemical pathway from anaerobes), although these were generally found to have longer chain lengths than bacterial plasmalogens.

Other biomarkers that are indicative of a certain group of bacteria include, for instance, lipopeptides that are produced specifically by certain *Bacillus* species, such as, surfactin for *B. subtilis* and lichenysin for *B. licheniformis*. Production of these two molecules also enables straightforward differentiation of these otherwise very closely related bacteria. A further example includes PQS-derived quorum-sensing molecules and mono- and di-rhamnolipid species found for *Pseudomonas aeruginosa*.

Quorum sensing is a form of cell-to-cell communication which relies on the principle that when a single microbe releases quorum sensing molecules into the environment, the concentration of such molecules is too low to be detected. However, when sufficient bacteria are present, quorum sensing molecule concentrations reach a threshold level that allows the microbes to sense a critical cell mass and, in response, to activate or repress particular genes. Quorum sensing molecules may therefore also be referred to as autoinducers. Pathogens may use quorum sensing molecules as virulence factors.

Some examples of quorum sensing molecules are listed above. Additional examples include N-acyl homoserine lactones (N-acyle HSLs), such as, 3-oxo-$C_8$-HSL, 3-oxo-$C_{10}$-HSL, or 3-oxo-$C_{12}$-HSL; diketopiperazines; 3-hydroxypalmitic acid methyl ester; and peptide-based quorum sensing molecules, such as, that of *Staphylococcus aureus*, which is an oligopeptide that has been termed the autoinducing peptide (AIP), encoded by the gene agrD. The active AIP is 7-9 amino acids, with a 5-membered thiolactone ring.

By way of example, sphingomyelin lipids may optionally be a biomarker, e.g. for cancer; ergosterol may optionally be a biomarker, e.g., for fungi; dinosterol may optionally be a biomarker, e.g. for dinoflagellates; cholesterol sulphate may optionally be a biomarker, e.g., for cancer; 2-hydroxyglu-terate may optionally be a biomarker, e.g., for cancer; and/or one or more sulfatides may optionally be a biomarker, e.g., for cancer, for example, astrocytoma. Optionally, the sulfatide may be selected from $C_{48}H_{91}NO_{11}S$, $C_{48}H_{92}NO_{12}S$, and/or $C_{50}H_{94}NO_{11}S$.

Iso-C15:0-substituted phosphoglycerol dihydroceramides may be specific for the Porphyromonadaceae family. m/z=566.4790 may be a biomarker for members of the Flavobacteria class.

The method of the invention may optionally involve the analysis of an exogenous compound, i.e. a compound that was administered to a subject and/or brought into contact with a subject or specimen. Thus, the biomarker may be an exogenous compound. The exogenous compound may optionally, e.g., be a contrast agent, e.g., a gadolinium-containing contrast agent, optionally selected from gadoterate, gadodiamide, gadobenate, gadopentetate, gadoteridol, gadoversetamide, gadoxetate, and/or gadobutrol.

Compounds

The method may optionally involve the analysis of one or more compounds. Unless otherwise stated, the terms "compound", "molecule" and "biomolecule" are used interchangeably herein.

The compound may optionally be intracellular and/or extracellular. It may optionally be endogenous, i.e. produced by the subject, and/or exogenous, i.e. added to the subject, tissue, cell, and/or microbe.

The compound may optionally comprise or consist of any of the compounds or classes of compounds mentioned herein, e.g. any of the biomarker compounds mentioned herein. Optionally, it may comprise or consist of, for example, a lipid, such as, a glycolipid or phospholipid; carbohydrate; DNA; RNA; protein; polypeptide, such as, a ribosomal peptide or a non-ribosomal peptide; oligopeptide; lipoprotein; lipopeptide; amino acid; and/or chemical molecule, optionally an organic chemical molecule.

The compound may optionally be linear, cyclic or branched.

The compound may optionally be a metabolite, such as, a primary or a secondary metabolite; an antibiotic; a quorum sensing molecule; a fatty acid synthase product; a pheromone; and/or a biopolymer.

The compound may optionally be characterised by one or more of the following functional groups: alcohol, ester, alkane, alkene, alkyne, ether, ketone, aldehyde, anhydride, amine, amide, nitrile, aromatic, carboxylic acid, alkyl halide, and/or carbonyl. Optionally, it may additionally be identified as being primary, secondary or tertiary, e.g., a primary alcohol, a secondary amine, or the like.

Analysis of Tissues

The term "tissue" is used herein to denote a structure of cells, which may optionally be, for example, a structure, an organ, or part of a structure of organ. The tissue may be in vivo or ex vivo. It may be in or from a human or a non-human animal.

Examples of tissues that may optionally be analysed are adrenal gland tissue, appendix tissue, bladder tissue, bone, bowel tissue, brain tissue, breast tissue, bronchi, ear tissue, oesophagus tissue, eye tissue, endometrioid tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue; (ii) grade I, grade II, grade III or grade IV cancerous tissue; (iii) metastatic cancerous tissue; (iv) mixed grade cancerous tissue; (v) a sub-grade cancerous tissue; (vi) healthy or normal tissue; or (vii) cancerous or abnormal tissue.

The analysis may optionally relate to a disease or condition, such as, any of the diseases or conditions listed in this section and/or elsewhere herein. The terms "disease" and "condition" are used interchangeably herein.

The condition may optionally be a skin condition selected, for example, from Acne, Alopecia, Boils, Bowen's Disease, Bullous pemphigoid (BP), Carbuncle, Cellulitis, Chilblains, Cysts, Dariers disease, Dermatitis, Dermatomyositis, Eczema, Erythema, Exanthema, Folliculitis, Frostbite, Herpes, Ichthyosis, Impetigo, Intertrigo, Keratosis, Lichen planus, Linear IgA disease, Melanoma, Moles, Onychomycosis, Papillioma, Petechiae, Prurigo, Psoriasis, Rosacea, Scabies, Scleroderma, Sebaceous Cyst, Shingles/Chickenpox, Telangiectasia, Urticaria (Hives), Warts and/or Xeroderma.

The condition may optionally be a liver condition selected from, for example, hepatitis, fatty liver disease, alcoholic hepatitis, liver sclerosis and/or cirrhosis.

Lung conditions may optionally be selected from, for example, Asthma, Atelectasis, Bronchitis, Chronic obstructive pulmonary disease (COPD), Emphysema, Lung cancer, Pneumonia, Pulmonary edema, Pneumothorax, and/or Pulmonary embolus.

The thyroid gland is an endocrine gland which normally produces thyroxine (T4) and triiodothyronine (T3). The condition may optionally be a thyroid condition, e.g., hypothyroidism or hyperthyroidism.

Optionally, a lesion, optionally of any of the tissues mentioned herein, may be analysed. A lesion is region in a tissue which is abnormal as a consequence of, e.g., injury or disease. The lesion may, for example, be selected from a wound, an ulcer, an abscess, and/or a tumour. The lesion may, for example, be a diabetic lesion, such as, a diabetic limb or digit, or a diabetic ulcer.

Further examples of tissues that may be analysed are discussed elsewhere herein, e.g., tissue affected by, or in the vicinity of, cancer, necrosis, microbes and the like. For example, the tissue may optionally comprise or consist of mucosa, which is discussed elsewhere herein.

Optionally, the method may involve the analysis of the cellular composition of a tissue. For example, the proportion of one or more particular cell types may be analysed. The cell types may optionally be selected from any known cell types, e.g., any of the cell types mentioned herein.

Optionally, the method may comprise analysing an immune response to a disease, which may optionally be selected from any of the diseases listed elsewhere herein, e.g., to a cancer and/or an infection. Thus, optionally, cells that form part of a subject's immune response may be analysed. For example, the presence, location, spatial distribution, concentration and/or type of one or more cells that form part of a subject's immune response may be analysed, e.g., in a tissue.

Cancer and/or Tumour Analysis

The method of the invention may optionally involve the analysis of a cancer or tumour cell or tissue. The method of the invention may optionally involve the analysis of a cancer biomarker.

The uncontrolled growth and division of cells may give rise to cancer, such as, blood cancers or malignant tumours; or to benign tumours. Cells that grow and divide in an uncontrolled way may also be referred to as neoplastic cells. A cancer may therefore also be referred to as a "neoplasm" and a tumour may be referred to as comprising "neoplastic cells".

A "tumour" is a population of cells characterized by abnormal growth. Most tumours are solid, i.e. a mass of cells. Tumours are typically classed as either benign or malignant, based on the criteria of spread and invasion. Malignant tumours are capable of invading and destroying surrounding tissues. Their cells may also spread beyond the original site of the tumour. Benign tumours do not possess these characteristics, but benign tumours may progress to a malignant stage, so it can be useful to detect and potentially treat benign tumours. For example, in oral squamous carcinoma, neoplasia is not usually treated, but this condition can rapidly progress into a malignant stage where parts or the whole tongue has to be surgically removed. Moreover, benign tumours may still be per se undesirable, particularly if they are large and grow adjacent to vital organs, and so treatment of a benign tumour which thereby reduces subsequent similar benign tumours can be desirable.

Thus, "malignant" cells may be defined as cells that exhibit uncontrolled proliferation, evading growth suppressors, avoiding cell death, limitless proliferative capacity (i.e. immortality), metastatic capacity and/or genetic instability, or any combination thereof.

Optionally, a tumour may be benign or malignant, which may optionally be known before the method of the invention is performed. Optionally, a tumour may be analysed to determine whether it is benign or malignant. Thus, the method of the invention may optionally involve the characterisation of a tumour as being benign or malignant.

Metastasis is a complex series of biological steps in which cancerous cells leave an original site and migrate to another site in a subject via a number of different possible routes, such as via the bloodstream, the lymphatic system, or by direct extension. Metastatic cancer or "metastasis" is the spread of a cancer from one organ to another organ or another site in a subject. Thus, metastatic cancer gives rise to metastatic tumours, i.e. "metastases", at distal sites from a primary tumour site within a subject.

The method of the invention may optionally involve the characterisation of a tumour as being metastatic. Optionally, one or more metastases may be analysed.

Optionally, a pre-cancerous state may be analysed.

A great hurdle in the search for a way to treat cancer is that cancers develop from cells which originate from the subject's own body. The immune system struggles to recognise them as abnormal. Recognition of foreign or abnormal cells by the immune system typically involves the detection of molecules located at the cell surface, antigens. Most cancer cells possess at least one kind of antigen which distinguishes them from normal cells and in many cases the antigens are specific for a particular type of cancer. Some cancer cells may possess a variety of antigens, whilst others may only possess a single type of antigen. The type of antigen, the number of different antigens and the prominence of the antigens on the cell surface may all influence the chances that the immune system may recognise the cancer cells as abnormal. Many types of cancer possess very few antigens, or only antigens which are poorly recognised by the immune system as foreign and are thus capable of escaping recognition and destruction by the immune system. The type and quantity of antigens possessed by any particular cancer type thus plays a big part in determining how "immunogenic" a cancer is. By "immunogenic" is meant the ability to elicit an immune response, so the more immunogenic a cancer is, the more likely it is that it will be recognised and attacked by the immune system. The method of the invention may optionally involve analysing how immunogenic a cancer is.

Tumours comprise two distinct, but interdependent, compartments: the parenchyma consisting essentially of neoplastic cells; and the stroma. The stroma comprises a variety of non-neoplastic cell types, including, for example, fibroblasts, myofibroblasts, glial cells, epithelial cells, fat cells, immune-competent cells, vascular cells, and/or smooth muscle cells; as well as an extracellular matrix (ECM) and extracellular molecules, such as, inflammatory cytokines and/or chemokines. Macrophages may, for example, represent up to 50% of the tumour mass.

Although most cells in the stroma initially possess certain tumour-suppressing abilities, the stroma typically changes during malignancy and eventually promotes growth, invasion, and/or metastasis. Stromal changes may include the appearance of carcinoma-associated fibroblasts (CAFs) through the transdifferentiation of fibroblasts to CAFs, typically driven to a great extent by cancer-derived cytokines, such as, transforming growth factor-3. CAFs may constitute a major portion of the tumour stroma and play a crucial role in tumour progression.

The method of the invention may optionally involve the analysis of a tumour stroma.

The method may optionally involve the analysis of a tumour margin, for example, the margin between the parenchyma, the stroma, and/or healthy tissue.

"Tumour heterogeneity" is a term used to refer to differences between tumours of the same type in different subjects, and between neoplastic cells within a tumour. Both can lead to divergent responses to therapy. The differences may, for example, be genetic and/or epigenetic.

The method of the invention may optionally involve the analysis of tumour heterogeneity.

The cancer or tumour may optionally be selected from, for example, carcinomas, sarcomas, leukaemias, lymphomas and gliomas.

More particularly, it may optionally be selected from, for example, Acute Lymphoblastic Leukemia (ALL), Acute Myeloid Leukemia (AML), Adrenocortical Carcinoma, adenoma, Anal Cancer, Appendix Cancer, Astrocytomas, Basal Cell Carcinoma, Bile Duct Cancer, Birch-Hirschfield, Blastoma, Bladder Cancer, Bone Cancer, Ewing Sarcoma, Osteosarcoma, Malignant Fibrous Histiocytoma, Brain Stem Glioma, Brain cancer, glioblastoma multiforme ("GBM"), Astrocytomas, Spinal Cord cancer, Craniopharyngioma, Breast Cancer, Bronchial Tumour, Burkitt Lymphoma, Carcinoid Tumour, Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Childhood, Ductal Carcinoma In Situ (DCIS), Endometrial Cancer, Ependymoma, Esophageal Cancer, Esthesioneuroblastoma, Fibroadenoma, Intraocular Melanoma, Retinoblastoma, Fallopian Tube Cancer, Gallbladder Cancer, Gastric (Stomach) Cancer, Germinoma, Hairy Cell Leukemia, Head and Neck Cancer, Heart Cancer, Heptacarcinoma, Hodgkin Lymphoma, Hypopharyngeal Cancer, Kahler, Kaposi Sarcoma, Kidney cancer, Laryngeal Cancer, Leiomyoma, Lip and Oral Cavity Cancer, Liver Cancer, Lung Cancer (such as, Non-Small Cell or Small Cell), Lymphoma, Lymphoblastoma, Male Breast Cancer, Malignant Fibrous Histiocytoma of Bone, Melanoma, Melanocarcinoma, Medulloblastoma, Merkel Cell Carcinoma, Mesothelioma, Mouth Cancer, Myeloma, Multiple Myeloma, Mycosis Fungoides, Myeloproliferative disorder, Nasal Cavity and Paranasal Sinus Cancer, Nasopharyngeal Cancer, Neuroblastoma, Nephroblastoma, Non-Hodgkin Lymphoma, Oral Cancer, Oropharyngeal Cancer, Osteosarcoma, Ovarian Cancer, Pancreatic Cancer, Papillomatosis, Paraganglioma, Parathyroid Cancer, Penile Cancer, Peritoneal cancer, Pharyngeal Cancer, Pheochromocytoma, Pineoblastoma, Pituitary Tumour, Prostate Cancer, Rectal Cancer, Retinoblastoma, Rhabdomyosarcoma, Salivary Gland Cancer, Sézary Syndrome, Skin Cancer, Seminoma, Teratoma, Testicular Cancer, Throat Cancer, Thyroid Cancer, thoracic cancer, Urethral Cancer, Vaginal Cancer, Vulvar Cancer, Waldenstrom macroglobulinemia, and/or Wilm's tumour. In the above list, any reference to a "cancer" or a "tumour" should be understood to include a reference to a "cancer and/or a tumour" of that type.

Optionally, the brain cancer may be glioblastoma multiforme, glioblastoma, giant cell glioblastoma, recurrent gliobastoma, anaplastic astrocytoma, oligodendroglioma and/or diffuse astrocytoma.

If the cancer is breast cancer, it may optionally be selected from, for example, ductal carcinoma in situ (DCIS), lobular carcinoma in situ (LCIS), Invasive breast cancer (NST), Invasive lobular breast cancer, Inflammatory breast cancer, breast cancer associated with Paget's disease and angiosarcoma of the breast.

The cancer may be caused by, associated with, and/or characterised by a mutation or other genetic variation, which may optionally result in the altered expression of a molecule, e.g. a molecule comprising or consisting of a lipid, such as, a glycolipid or phospholipid; a carbohydrate; DNA; RNA; a protein; a polypeptide, such as, a ribosomal peptide or a non-ribosomal peptide; an oligopeptide; a lipoprotein; a lipopeptide; an amino acid; and/or a chemical compound, optionally an organic chemical compound. More particularly, a mutation may optionally result in the altered expression of a protein and/or metabolite.

A cancer may optionally express one or more metabolites that may serve as a biomarker for that cancer. For example, optionally a metabolite such as succinate, fumarate, 2-HG, and/or any of the other metabolites mentioned herein may accumulate in a cancer.

Subtypes of cancer may optionally be identified, e.g., based on such altered expression. For example, a cancer may optionally be identified as being of a particular subtype based on the expression, or lack thereof, of a receptor, e.g., selected from estrogen receptors (ER), progesterone receptors (PR) and human epidermal growth factor receptor 2 (HER2). A cancer may therefore, for example, be referred to as ER negative if it lacks expression of ER; or be referred to as triple-negative breast cancer (TNBC), if it is ER-, PR- and Her2-.

The mutation may optionally, e.g., be in a gene encoding isocitrate dehydrogenase 1 (IDH1) and/or 2 (IDH2) yielding mutant enzymes capable of converting alpha-ketoglutarate to 2-hydroxyglutarate (2-HG). Such a mutation may optionally be present, e.g., in a glioma, intrahepatic cholangiocarcinoma, acute myelogenous leukaemia (AML) and/or chondrosarcomas. 2-HG may thus be referred to as an oncometabolite. 2-HG may be present in very small amounts in normal tissues, whereas it may be present in high concentrations, e.g., several micromoles per gram of tumour, in mutant tumours.

Thus, a cancer subtype may have a specific biomarker. The method of the invention may optionally involve the analysis of a cancer subtype.

The method may optionally involve the analysis of the phenotype and/or genotype of a cancer, which may optionally involve an analysis of any of the mutations discussed above.

The grade of a tumour is a measure of the aggressive potential of the tumour. It is an indicator of how quickly a tumour is likely to grow and spread. Generally speaking, "low grade" cancers tend to be less aggressive than "high grade" cancers.

Tumour grade is the description of a tumour based inter alia on the differentiation stage of the tumour cells. The differentiation stage may be assessed microscopically. In layman's terms, it is a measure of how abnormal the tumour cells and the tumour tissue look under a microscope. If the cells of the tumour and the organization of the tumour's tissue are close to those of normal cells and tissue, the tumour may be called "well-differentiated." If the tumour comprises abnormal-looking cells and/or the tumour tissue lacks normal tissue structures, the tumour may be called "undifferentiated" or "poorly differentiated".

Based on these and other differences in microscopic appearance, a numerical "grade" may be assigned to most cancers. The factors used to determine tumour grade vary between different types of cancer. Thus, grading systems differ depending on the type of cancer.

In general, tumours may optionally be graded as 1, 2, 3, or 4, depending on the amount of abnormality. In Grade 1 tumours, the tumour cells and the organization of the tumour tissue appear close to normal. These tumours tend to grow and spread slowly. In contrast, the cells and tissue of Grade 3 and Grade 4 tumours do not look like normal cells and tissue. Grade 3 and Grade 4 tumours tend to grow rapidly and spread faster than tumours with a lower grade. If a grading system for a tumour type is not specified, the following system may optionally be used:
GX: Grade cannot be assessed (undetermined grade)
G1: Well differentiated (low grade)
G2: Moderately differentiated (intermediate grade)
G3: Poorly differentiated (high grade)
G4: Undifferentiated (high grade)

Breast and prostate cancers are the most common types of cancer that have their own grading systems.

The Nottingham grading system (also called the Elston-Ellis modification of the Scarff-Bloom-Richardson grading system) may optionally be used for breast cancer. This system grades breast tumours based on the following features: (i) Tubule formation: how much of the tumour tissue has normal breast (milk) duct structures; (ii) Nuclear grade: an evaluation of the size and shape of the nucleus in the tumour cells; and (iii) Mitotic rate: how many dividing cells are present, which is a measure of how fast the tumour cells are growing and dividing.

Each of the categories gets a score between 1 and 3; a score of "1" means the cells and tumour tissue look the most like normal cells and tissue, and a score of "3" means the cells and tissue look the most abnormal. The scores for the three categories are then added, yielding a total score of 3 to 9. Three grades are possible: (i) Total score=3-5: G1 (Low grade or well differentiated); (ii) Total score=6-7: G2 (Intermediate grade or moderately differentiated); (iii) Total score=8-9: G3 (High grade or poorly differentiated).

The Gleason scoring system may optionally be used to grade prostate cancer. The Gleason score is based on biopsy samples taken from the prostate. The pathologist checks the samples to see how similar the tumour tissue looks to normal prostate tissue. Both a primary and a secondary pattern of tissue organization are identified. The primary pattern represents the most common tissue pattern seen in the tumour, and the secondary pattern represents the next most common pattern. Each pattern is given a grade from 1 to 5, with 1 looking the most like normal prostate tissue and 5 looking the most abnormal. The two grades are then added to give a Gleason score. Based on a recommendation of the American Joint Committee on Cancer Gleason scores may be grouped into the following categories: (i) Gleason X: Gleason score cannot be determined; (ii) Gleason 2-6: The tumour tissue is well differentiated; (iii) Gleason 7: The tumour tissue is moderately differentiated; (iv) Gleason 8-10: The tumour tissue is poorly differentiated or undifferentiated.

With regard to bladder cancer, the term "high grade bladder cancer" (HGBC) means and includes a tumour that has invaded into the muscularis propria of the bladder: non-muscle invasive bladder cancer (NMIBC, Ta, TI) and muscleinvasive bladder cancer (MIBC, >T2) including bladder cancer metastases.

The method of the invention may optionally involve the analysis of a tumour grade.

In addition or instead of tumour grade, one or more other factors, such as cancer stage and/or a subject's age and general health, may be used to develop a treatment plan and to determine a subject's prognosis. Generally, a lower grade indicates a better prognosis. A higher-grade cancer may grow and spread more quickly and may require immediate or more aggressive treatment. The importance of tumour grade in planning treatment and determining a subject's prognosis is particularly important for cancers, such as, soft tissue sarcoma, primary brain tumours, and breast and/or prostate cancer.

Staging is a well-known way of describing the size of a (primary) tumour and how far it has grown. A cancer may optionally be stage 1, 2, 3 or 4; or, alternatively viewed, early stage, advanced stage and/or metastatic; or, alternatively viewed, non-invasive non-metastatic, non-invasive metastatic, invasive non-metastatic or invasive metastatic. Stage 1 may also be referred to as "early stage" cancer and is characterised by a tumour which is relatively small and contained within the organ it started in. Stage 2 typically means the cancer has not started to spread into surrounding tissue, but the tumour is larger than in stage 1. Cancer cells may or may not have spread into lymph nodes close to the tumour, depending on the particular type of cancer. Stage 3 may also be referred to as "advanced" cancer. It is characterised by a large tumour, which may have started to spread into surrounding tissues. It is also characterised by cancer cells in at least some of the lymph nodes. Stage 4 may also be referred to as "metastatic" cancer. The stages of a (primary) tumour may be referred to as T1, T2, T3 and/or T4.

The method may optionally be carried out on cancerous tissue in vivo, and/or on a specimen, such as, a biopsy. The specimen may optionally comprise tumour tissue, stroma tissue and/or healthy tissue. The specimen may optionally comprise part or all of a tumour. The specimen may optionally comprise tissue from a lymph node, e.g., a sentinel lymph node and/or a regional lymph node. A regional lymph node is a lymph node that drains lymph from the region around a tumour. A sentinel lymph node is defined as the first lymph node to which cancer cells are most likely to spread from a primary tumour. Sometimes, there can be more than one sentinel lymph node.

A cancer may alternatively or in addition be staged by reference to lymph nodes. The letter N followed by a number from 0 to 3 indicates whether the cancer has spread to lymph nodes near the primary tumour and, if so, how many lymph nodes are affected. These stages may be referred to as NX, N0, N1, N2 and/or N3.

NX: Nearby lymph nodes cannot be assessed (for example, if they were removed previously).

N0: Cancer has not spread to nearby lymph nodes. N1 to N3 indicate the severity of spread of the cancer to lymph nodes. The exact staging criteria vary from cancer to cancer, but as a general rule, N1 denotes a spread to at least 1 or a small number of lymph nodes; N2 denotes a spread to a greater number of lymph nodes; and N3 denotes a spread to an even greater number of lymph nodes.

A cancer may alternatively or in addition be staged by reference to Metastasis.

MX: Distant spread (metastasis) cannot be assessed; M0: No distant spread is found on x-rays (or other imaging procedures) or by physical exam; M1: Cancer has spread to distant organs.

The method may optionally involve the analysis of a cancer stage.

Optionally, the type, subtype, phenotype, grade and/or stage of a cancer or tumour may provide prognostic information. Thus, optionally, the method may be a prognostic method and/or involve a step of making a prognosis.

The method may optionally involve the analysis of a cancer in an animal model, e.g. in a xenograft model. For example, a tumour or specimen thereof may be obtained from a subject, and/or a tumour cell line may be used. The tumour cell may optionally be genetically manipulated, e.g. it may be transformed by introducing a transgene and/or by exposing it to a mutagen. The tumour cell may optionally be cultured ex vivo. The (optionally transformed) tumour cell may optionally be injected or xenografted into an animal model, which may optionally be selected from any of the animals mentioned herein. The animal model may optionally be treated with a known anti-cancer agent and/or a test agent. The tumour, its stroma, and/or the tissue in the vicinity of the tumour, e.g. the tumour microenvironment, may optionally be analysed. This method may optionally be used to analyse the effect of a transgene on a cancer; to analyse the effect of an anti-cancer agent on a cancer; and/or to analyse the effect of a test agent on a cancer.

Genetic manipulation of cells may optionally involve targeted mutagenesis and/or random mutagenesis, which may optionally, e.g., be the knock-out, alteration, and/or insertion of genetic information. A cell that has been manipulated via targeted mutation may be referred to as a "transformed" cell, particularly if a new gene or gene variant, i.e. a "transgene" has been inserted. A gene that has been knocked-out may also be referred to as a silenced gene.

The analysis of cancer will now be discussed in more detail with reference to ovarian cancer, but it should be understood that the information applies mutatis mutandis to any other cancer types, e.g., any of the other cancer types listed elsewhere herein.

Primary epithelial ovarian cancer (EOC) has a poor prognosis and remains the most lethal gynaecological malignancy. In greater than 80% of cases, EOC presents with late stage disease, once the disease has already left the realms of the pelvis. Disease burden at this stage can be extensive and involve metastatic dissemination to the upper abdomen, diaphragm, hepatic and splenic parenchyma as well as distant spread beyond the abdominal cavity. Five-year relative survival for EOC presenting at stage three and four is 18.6% and 3.5% respectively.

Cytoreductive surgery has proven prognostic benefit for progression-free and overall survival, especially in patients with stage III and IV disease. One study shows three-year overall survival in patients with zero residual disease to be 72.4% versus 45.2% in patients with >1 cm residual disease. Cytoreductive surgery may be the only treatment, but alternatively and/or in addition patients may receive, chemotherapy, e.g., platinum and/or taxane based chemotherapy. Maximal cytoreduction generally confers survival benefit.

Once disease has progressed beyond the ovaries and affects other peritoneal surfaces, it may be difficult to discriminate this identification from non-malignant disease. This identification may be more challenging in a delayed primary surgery setting after the administration of neo-adjuvant chemotherapy. Lesions may undergo morphological changes, which may include fibrosis, calcification and/or lymphocytic infiltration. The surgeon may rely, e.g., on pre-chemotherapy computed tomography imaging and/or experience to identify the location and malignant nature of lesions. The robust evidence that proves survival benefit from maximal surgical effort may promote a more radical surgical approach. Debulking operations for EOC may include, e.g., appendicectomy, splenectomy, peritonectomy, omentectomy, diaphragmatic stripping, and/or total hysterectomy with bilateral salpingo-oophorectomy. Until recently, there has been no technology to accurately guide the surgeon during the operation. Surgeons cannot be sure of complete resection of disease and healthy margins of tissue may be taken in excess.

Prior to surgery, the precise histopathological nature of the pelvic or ovarian tumour is often unknown. Only during surgery can an attempt at diagnosis be made. The only established technique for intraoperative diagnosis is histopathological frozen section, which is time consuming, costly, and its diagnostic accuracy varies. A meta-analysis of 18 studies showed diagnostic sensitivity for benign tumours to be 65-97% and 71-100% for malignant tumours at frozen section. Other studies have shown that borderline ovarian tumours are especially difficult to characterise at frozen section with diagnostic sensitivity ranging from 25-87%. Low stage borderline ovarian tumours can be treated more conservatively and younger women may wish to opt for unilateral oophorectomy to preserve their fertility. With frozen section diagnostic accuracy for borderline tumours being so low, it is likely that many women of child bearing age have radical cytoreductive surgery, which may be unnecessary.

During surgery, electrosurgical diathermy instruments may be used to cut tissue as they provide haemostasis. Surgical smoke is a by-product when cutting the tissue, which has been historically extracted from the surgical field. However, this smoke may be a rich source of biological information and mass spectrometry (MS) and/or ion mobility spectrometry may be used to measure its metabolomic composition.

This coupling of the surgical diathermy, which converts tissue components into gas-phase ionic species, with a mass spectrometer has been described as rapid evaporative ionisation mass spectrometry (REIMS) technology. Intra-operative direct sampling with MS was in the past not possible, as MS usually requires sample preparation, which is not possible in a surgical setting. REIMS functions at atmospheric pressure in ambient conditions, which makes it ideal for intra-operative use.

Coupling of REIMS technology with handheld sampling devices has resulted in iKnife sampling technology, which can provide intra-operative tissue identification. The iKnife sampling technology allows surgeons to more efficiently resect tumours intra-operatively through minimizing the amount of healthy tissue removed whilst ensuring that all the cancerous tissue is removed.

Statistical analysis of REIMS spectra with comparison to histologically authentic spectral libraries may optionally be used for the unambiguous in vivo or ex-vivo identification of major tissue types, optionally selected from any of the tissue types mentioned elsewhere herein, such as, liver, lung, and/or colon. It may optionally be used to identify the origin of metastatic lesions in an ex-vivo and/or in-vivo setting. It may optionally be used in an in-vivo endoscopic setting, e.g., to classify intestinal wall, cancer and/or polyps.

The present application presents the first use of the surgical diathermy with spectrometric analysis in gynaecological targets. As explained in the Examples, particularly Example 13, samples ranging from normal through to malignant were included to demonstrate the potential of the method as a real-time diagnostic surgical tool.

Analysis of Necrosis

"Necrosis" is unprogrammed cell death, which may be contrasted with apoptosis, which is a form of programmed cell death.

Necrosis typically involves damage to the cell membrane and/or damage to intracellular compartments, such as, lysosomes. Necrosis is typically accompanied by the release of intracellular molecules, such as, enzymes, organic chemical molecules and the like. For example, it may include the release of the lysosomal enzymes. The release of such molecules may cause inflammation and/or damage to neighbouring cells.

The necrosis may optionally be caused by, or associated with, for example, injury, infection, cancer, infarction, toxins, inflammation, lack of proper care to a wound site, frostbite, diabetes, and/or arteriosclerosis. Optionally, the necrosis may be necrosis of cancerous or non-cancerous tissue.

The necrosis may optionally, for example, be coagulative, liquefactive, caseous, fat necrosis, fibrinoid necrosis and/or gangrenous necrosis.

A visual and/or microscopic examination of a subject or tissue sample may optionally be carried out to determine the presence or absence of one or more characteristics of a type of necrosis optionally selected from coagulative, liquefactive, caseous, fat necrosis, fibrinoid necrosis and/or gangrenous necrosis. By visual examination is meant examination without the aid of a microscope, typically with the bare eye.

Coagulative necrosis may arise due to ischemia, i.e., lack of blood flow to the affected tissue. Visually, it may be characterised by firm tissue. Microscopically, it may be characterised by preserved cell outlines, i.e., cells of a ghostly appearance, and redness.

Liquefactive necrosis may arise due to infections, although it may alternatively occur due to a brain infarct. Visually, it may be characterised by liquified tissue and/or pus, which may be creamy yellow. Microscopically, it may be characterised by the presence of neutrophils and cell debris.

Caseous necrosis may arise due to an infection, such as, tuberculosis, in response to which the body tries to fight the infective microbe with macrophages. Visually, it may be characterised by white, soft, caseous material. Microscopically, it may be characterised by a granuloma, such as, fragmented cells and debris surrounded by a collar of lymphocytes and macrophages.

Fat necrosis may arise due to injury or trauma, e.g., from a seat belt, biopsy, or implant removal. Visually, it may be characterised by saponification, i.e. chalky, white areas from the combination of the newly-formed free fatty acids with calcium. Microscopically, it may be characterised by shadowy outlines of dead fat cells and/or a bluish cast from calcium deposits.

Fibrinoid necrosis may arise due to autoimmune disorders such as rheumatoid arthritis or polyarteritis nodosa. Visually, it may be characterised by the presence of an amorphous eosinophilic material reminiscent of fibrin. Microscopically, it may be characterised by thickened and pinkish-red vessel walls, typically called "fibrinoid".

Necrosis may also be referred to as "gangrene", which may be divided into "dry gangrene" and "wet gangrene".

Necrosis treatment may involve surgery, such as, debridement (the surgical removal of the dead and dying tissue) and/or amputation. A balance must be struck between the need remove the necrotic tissue, and the desire to maintain as much of the subject's affected area, such as a limb, digit, or organ, as possible.

The method may optionally involve the analysis of necrosis, e.g. the analysis of tissue to determine whether a particular tissue is necrotic or healthy. Thus, the margin between healthy and necrotic tissue may optionally be analysed. This analysis may be used to assist in deciding which tissue to remove surgically and which tissue may be viable enough to be retained by the subject.

Necrosis can arise through insufficient oxygenation of a tissue. It may therefore be desirable to analyse, e.g., the oxygenation status or ability of a tissue. Thus, optionally, the method may involve the analysis of tissue oxygenation. Optionally, the functional capacity of tissue to process oxygen may be analysed, which may optionally be used to determine the viability of tissue. For example, Oxy haemoglobin (OxyHb) and/or deoxyhaemoglobin (DeoxyHb) may be analysed. DeoxyHb is the form of haemoglobin without oxygen, whereas OxyHb is the form of haemoglobin with oxygen. For example, the relative amount of OxyHb versus DeoxyHb may be analysed.

Mucosal Analysis

The mucosa lines several passages and cavities of the body, particularly those with openings exposed to the external environment, including the oral-pharyngeal cavity, gastrointestinal (GI) tract, respiratory tract, urogenital tract, and exocrine glands. Thus, the mucosa may optionally be selected from Bronchial mucosa, Endometrium (mucosa of the uterus), Esophageal mucosa, Gastric mucosa, Intestinal mucosa (gut mucosa), Nasal mucosa, Olfactory mucosa, Oral mucosa, Penile mucosa and/or Vaginal mucosa.

Broadly speaking, the mucosa comprises a mucus layer (the inner mucus layer); an epithelium; a basement membrane, a Lamina propria (LP), which is a layer of connective tissue; and a Muscularis mucosae, which is a thin layer of smooth muscle. Thus, the term "mucosa" is used herein to refer to this entire complex, unless stated otherwise. The term "mucosal membrane" is used to refer to the mucosa without the mucus layer, i.e., the epithelium, basement membrane, LP and Muscularis mucosae. The mucosa may also be covered by a further, outer mucus layer, which is typically more loosely associated therewith. Any reference herein to a "mucosa" may include reference to this further, outer mucus layer. Adjacent to the mucosa is the submucosa.

The submucosa in the GI tract represents a connective tissue layer containing arterioles, venules and lymphatic vessels. It is made up of mostly collagenous and elastic fibres with varying amounts of adipose elements.

The inner mucus layer may be degraded by microbes. For example, mucin monosaccharides may be used by bacteria, e.g., commensal bacteria, as an energy source. Therefore, continuous renewal of the inner mucus layer is very important.

The epithelium is a single or multiple layer(s) of epithelial cells. The epithelium may comprise, for example, intraepithelial lymphocytes (IELs), endocrine cells, goblet cells, enterocytes and/or Paneth cells.

The basement membrane may comprise various proteins, particularly structural or adhesive proteins, such as, laminins, collagens, e.g., collagen IV, proteoglycans, and/or calcium binding proteins such as fibulin.

The Lamina propria is connective tissue which may comprise, for example, plasma cells, eosinophils, histiocytes, mast cells and/or lymphocytes. Neutrophils are generally absent in the Lamina propria of healthy humans.

As discussed below, the mucosa may also comprise, for example, antigen presenting cells (APCs) and microfold cells (M-cells). The mucosa may include one or more distinct types of regulatory immune cells, including intestinal intraepithelial lymphocytes (IELs), Foxp3(+) regulatory T cells, regulatory B cells, alternatively activated macrophages, dendritic cells, and/or innate lymphoid cells.

The mucosa typically secretes mucus, which forms a mucus layer between the mucosal epithelium and the lumen. The mucus layer may have a protective function. A major constituent of mucus are mucins, which are produced by specialized mucosal cells called goblet cells. Mucins are glycoproteins characterized mainly by a high level of O-linked oligosaccharides. The level to which the protein moiety is linked to the carbohydrate moieties, as well as the precise identity of the carbohydrates moieties, may vary significantly.

Mucosa establish a barrier between sometimes hostile external environments and the internal milieu. However, mucosae are also responsible for nutrient absorption and waste secretion, which require a selectively permeable barrier. These functions place the mucosal epithelium at the centre of interactions between the mucosal immune system and luminal contents, including dietary antigens and microbial products. Thus, many physiological and immunological stimuli trigger responses in the mucosa. Dysfunctional responses may contribute to disease.

The mucosal immune system is a localized and specific immune organisation. The mucosal immune system at different organs share similar anatomical organization and features. The GI mucosal immune system is best understood, and is discussed below for illustrative purposes. The GI mucosal immune system is composed of three major compartments: the epithelial layer; the lamina propria (LP); and the mucosal-associated lymphoid tissue (MALT), which, in the GI tract, may be referred to as gut-associated lymphoid tissue, and which comprises Peyer's patches and isolated lymphoid follicles.

Dendritic cells may project dendrites into the epithelium to uptake antigens and migrate to the LP, secondary lymphoid tissue and draining lymph nodes, where they prime naive T cells. Microfold cells (M-cells), located in the epithelium of Peyer's patches, may pass the antigens to dendritic cells, macrophages and other antigen presenting cells. Naive T cells in secondary lymphoid tissues may become activated after being primed by antigen presenting cell and home to LP (called LPLs) or infiltrate into inflamed epithelium.

The gastrointestinal (GI) tract can be divided into four concentric layers that surround the lumen in the following order: (i) Mucosa; (ii) Submucosa; (iii) Muscular layer; and (iv) Adventitia or serosa.

Thus, the GI mucosa is the innermost layer of the gastrointestinal tract. This layer comes in direct contact with digested food. In the GI mucosa, the epithelium is responsible for most digestive, absorptive and secretory processes, whereas the Muscularis mucosae aids the passing of material and enhances the interaction between the epithelial layer and the contents of the lumen by agitation and peristalsis. GI mucosae are highly specialized in each organ of the GI tract to deal with the different conditions. The most variation may occur in the epithelium.

Different types of mucosa differ from one another and the inventors have shown that the method of the invention may optionally be used, e.g., to distinguish between different types of mucosa, e.g. vaginal, nasal and oral.

Figure 26:
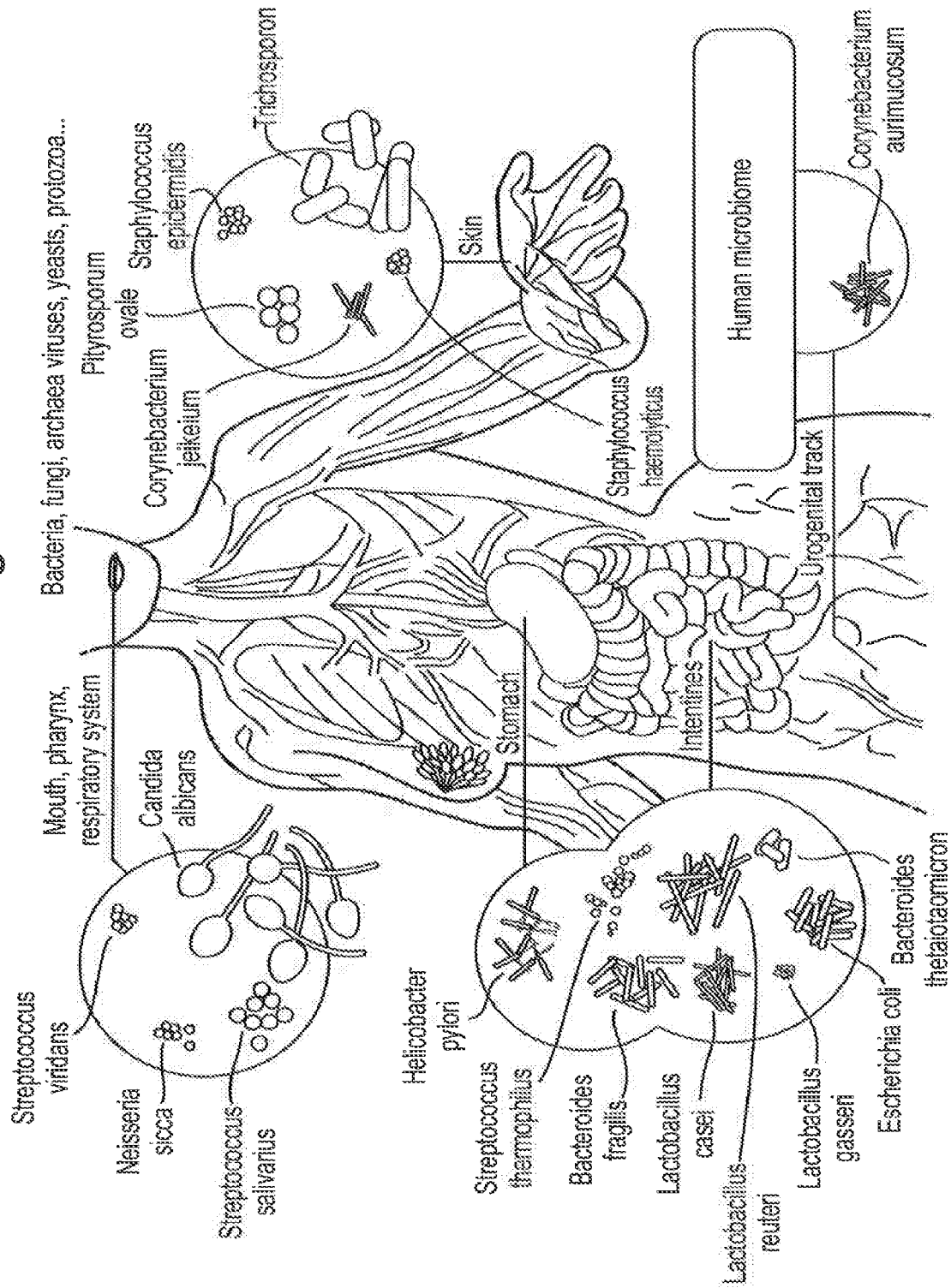
FIG. 26 shows schematically a variety of microbes that are present in the human microbiome.

FIG. 26 illustrates a variety of microbes that may be present in the human microbiome. As shown in FIG. 26, the human microbiome may include various bacteria, fungi, archaea, viruses, yeasts, protozoa, etc. which may be present, e.g., in the mouth, pharynx, respiratory system, skin, stomach, intestines, and/or urogenital tract, etc.

Figure 27:
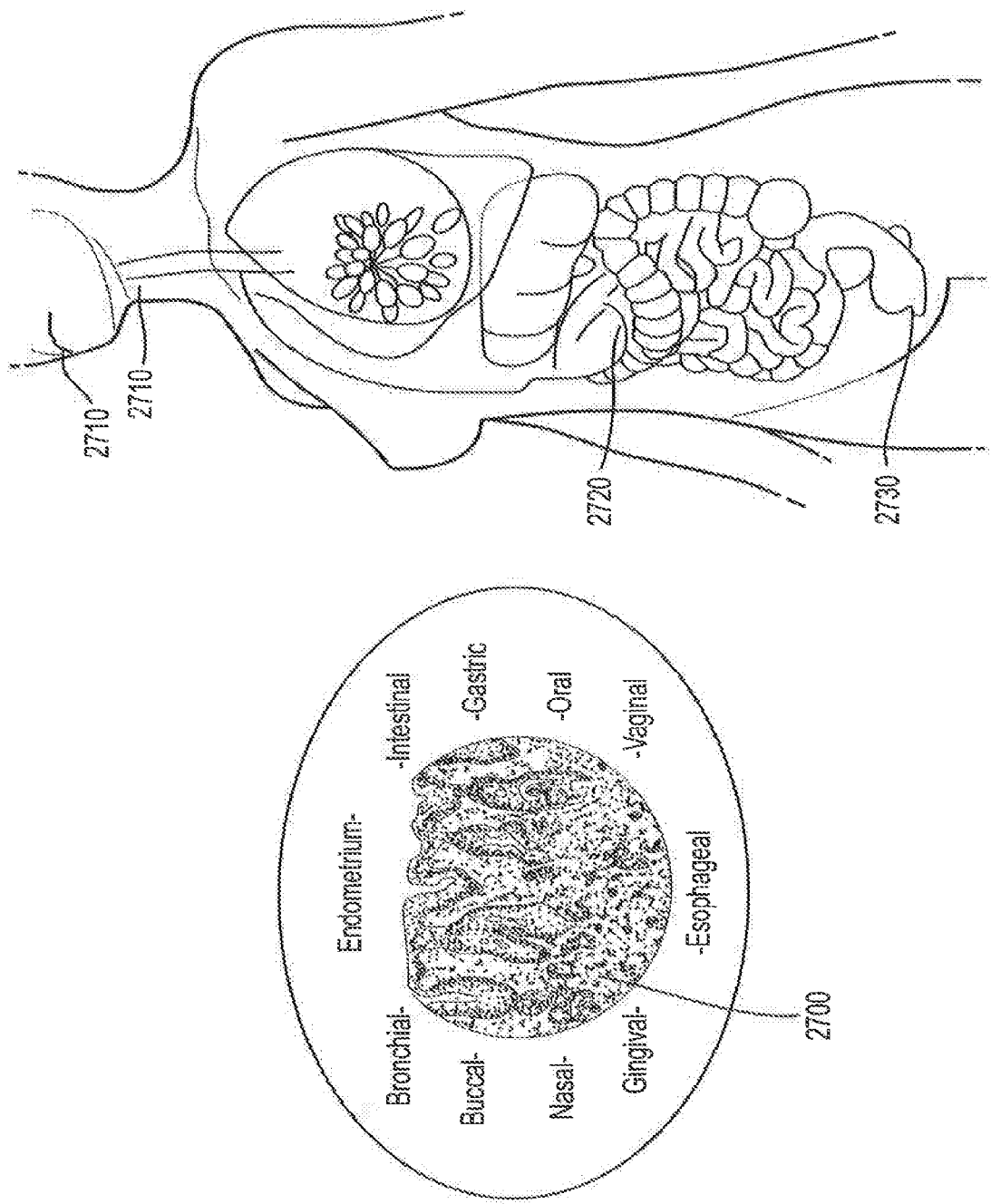
FIG. 27 shows schematically various mucosa or mucosal membranes which are present in the human body.

FIG. 27 illustrates various different mucosa or mucosal membranes which are present in the human body.

Mucosal membranes 2700 comprise a layer of epithelial tissue which lines all passages in the human body that are open to the external environments including the nose and parts of the digestive, urogenital and respiratory tracts. Mucosal membranes typically act as a protective barrier to trap pathogens such as bacteria, viruses and fungi. As shown in FIG. 27, mucosal membranes are present in the mouth, pharynx, and respiratory system 2710, as well as in the gastro-intestinal tract 2720 and the urogenital tract 2730, and include the endometrium, intestinal, gastric, oral, vaginal, esophageal, gingival, nasal, buccal and bronchial membranes.

Studies as part of the human microbiome project have revealed that colonization by different microbial species within the mucosa has an immense impact upon human health and disease. As discussed elsewhere herein, many diseases (e.g. cancer, infections, etc.) are associated with the mucosa. As such, the mucosal membrane is an easily accessible and highly clinically relevant sample to analyse, e.g., diagnose diseases, e.g., microbial and/or cancerous associated diseases.

Figure 28:
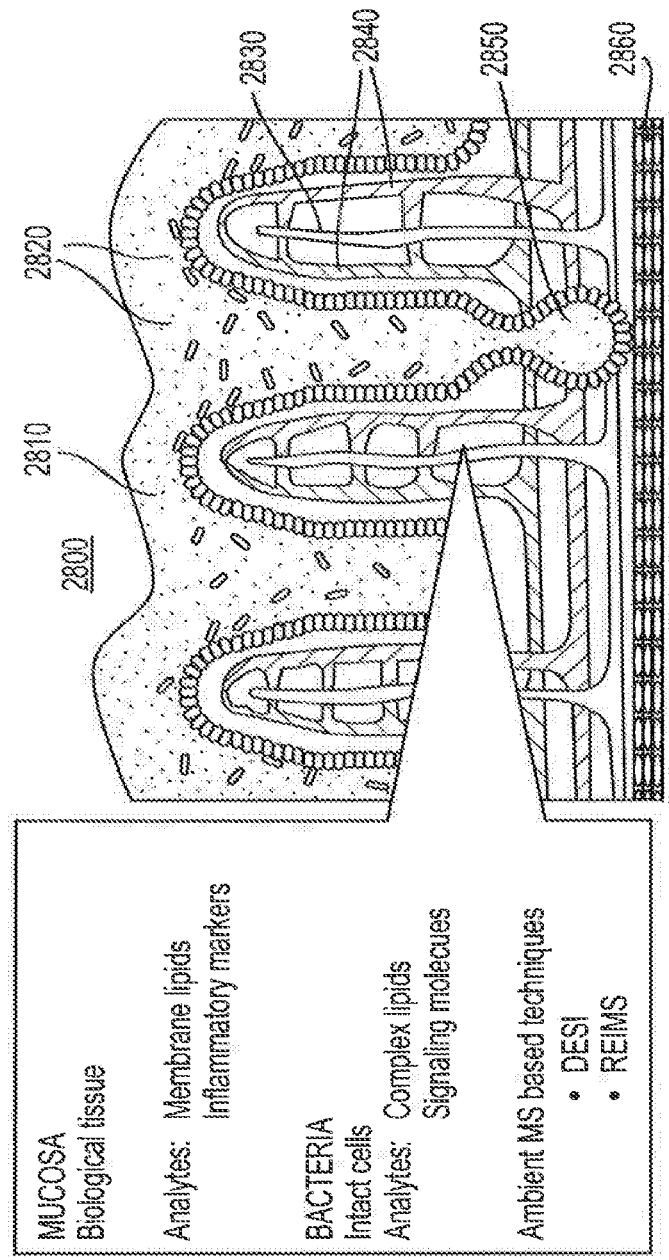
FIG. 28 shows schematically a mucosa or mucosal membrane comprising biological tissue and bacteria.

As shown in FIG. 28, a typical mucosal membrane may be present in a lumen 2800 and may include mucus 2810, bacteria 2820, lymphatic vessels 2830, blood vessels 2840, mucosal glands 2850, and submucosa 2860. As illustrated by FIG. 28, the biological tissue of the mucosa itself, e.g. mucus 2810, and/or bacteria 2820 present in or associated with the mucosa represent potential analytes/biomarkers. For example, membrane lipids, and/or inflammatory markers of the mucosa, and/or complex lipids and/or signalling molecules of intact bacteria cells represent potential analytes/biomarkers.

Mucosal Analysis

Optionally, the method may involve the analysis of a mucosal target, which may be in vivo, or a specimen comprising or consisting of mucosa. Optionally, the method may involve the analysis of a mucosal target to analyse the cellular composition of the mucosa; to analyse a disease; to analyse the response to a drug; to analyse the response to a particular food, diet, and/or a change in diet; to analyse a mucosal microbe; to analyse a microbial interaction with the mucosa, and/or to analyse the mucosal microbiome.

The analysis of the cellular composition of a mucosa, may, e.g., analyse the presence or absence and/or proportion of one or more cell types, which may optionally be selected from any of the cell types listed herein. Optionally, the method may involve the analysis of MALT and/or a Peyer's patch. Optionally, the method may involve the analysis of the phenotype and/or genotype of one or more cell types, which may optionally be selected from any of the cell types listed herein.

Optionally, the method may involve the analysis of a change in the mucosa, which may optionally be a change in, e.g., the cellular composition of the mucosa, the microbial interaction(s) with the mucosa, and/or the mucosal microbiome. By a "change" in the mucosa is meant that the mucosa is different from how it would typically present in a healthy subject; that it is different in one location compared to another location within the same subject; and/or that it is different from how it was when it was analysed at an earlier point in time. A change in the mucosa may optionally, for example, be caused by, or associated with, a disease, the response to a substance, such as a drug, and/or the response to a food, diet, and/or diet change.

A disease may optionally be selected from an autoimmune disorder, an inflammatory disease, tropical sprue, a food intolerance, an infection, a cancer, and/or any of the disorders mentioned herein.

More particularly, the disease may optionally be selected from, for example, asthma, Coeliac disease, gastritis, peptic duodenitis, Gluten-sensitive enteropathy; allergy and/or intolerance to an allergen, e.g. to milk, soy, tree nut(s), egg, wheat, meat, fish, shellfish, peanut, seed, such as sesame, sunflower, and/or poppy seeds, garlic, mustard, coriander, and/or onion; Hashimoto's thyroiditis; Irritable bowel syndrome; Graves's disease; reactive arthritis; psoriasis; multiple sclerosis; Systemic lupus erythematosus (SLE or lupus); ankylosing spondylitis; progressive systemic sclerosis (PSS); glomerulonephritis; autoimmune enteropathy;

IgA deficiency; common variable immunodeficiency; Crohn's disease; colitis, such as, lymphocytic colitis, collagenous colitis and/or ulcerative colitis; diffuse lymphocytic gastroenteritis; ulcer; intestinal T-cell lymphoma; infection, e.g., pharyngitis, bronchitis, and/or infection with a microbe selected, for example, from *Giardia, Cryptosporidium, Helicobacter* and/or any of the other microbes mentioned herein; and/or cancer, details of which are discussed elsewhere herein.

The method may, e.g., optionally involve the analysis of the interaction of the mucosa with microbes, or a change in the mucosa caused by, or associated with, such an interaction. Optionally, the interaction may, e.g., be the translocation of microbes into the mucosa, e.g., the translocation of commensal bacteria. The method may, e.g., optionally involve the analysis of the mucosal microbiome, or a change in the mucosa caused by, or associated with, the mucosal microbiome. The method may, e.g., optionally involve the analysis of an infection, or a change in the mucosa caused by, or associated with, an infection. The analysis of microbes, a microbial interaction, infections and/or the microbiome are also discussed elsewhere herein.

As mentioned above, IELs are a normal constituent of the small intestinal mucosa. They play a significant role in immune surveillance and activation. In healthy humans, the vast majority of IELs are of T-cell type and express an α/β T-cell receptor on their surface. It is generally accepted that healthy humans have no more than about 20 lymphocytes per 100 epithelial cells in the intestinal mucosa.

An increased number of lymphocytes in a mucosal specimen may optionally be indicative of a change, such as, a disease, the response to a drug, and/or a microbial change. The term "elevated" or "increased" levels of IELs is therefore used to refer to more than 20 IELs per 100 epithelial cells in the intestinal mucosa, optionally at least 22, 24, 25, 26, 28, 30, 32, 34, 36, 38, 40, 42, 44, 46, 48, 50, 52, 54, 56, 58, 60, 65, 70, 75, 80 20 IELs per 100 epithelial cells in the intestinal mucosa.

The gamma-delta receptor of T lymphocytes is not expressed by more than 2-3% of T lymphocytes in normal conditions. An increase in the percentage of T lymphocytes expressing this receptor may therefore be indicative of a change, such as, a disease, the response to a drug, and/or a microbial change. The method may therefore involve determining the presence or percentage of T lymphocyte gamma-delta receptor expression. For example, in coeliac disease 20-30% of mucosal T lymphocytes may express this receptor.

Thus, the method may optionally involve the analysis of lymphocytes in a target, which may optionally be T lymphocytes, e.g. gamma-delta receptor-positive T lymphocytes. Optionally, a target may be analysed for an increase or decrease in the number of lymphocytes. Optionally, the phenotype and/or genotype of the lymphocytes may be analysed.

Polymorphonuclear leukocytes (PMN), also called neutrophils, are the most abundant leukocyte population in the blood, comprising 50-60% of the circulating leukocytes ($25 \times 10^9$ cells). PMN are critical components of the innate immune response that are essential in protecting the host, e.g., from microbial pathogens, while also minimizing deleterious effects mediated by dying or injured cells.

PMN may perform a variety of antimicrobial functions such as degranulation and phagocytosis. They are uniquely capable of forming large amounts of reactive oxygen species and other toxic molecules that may weaken and/or destroy pathogens. Upon PMN contact with invading microbes, reactive oxygen species may be generated in an oxidative burst by an nicotinamide adenine dinucleotide phosphate (NADPH) oxidase PMN may also possess different pools of intracellular granules that contain antimicrobial peptides, such as, α-defensins and/or cathelicidins; myeloperoxidase; hydrolytic enzymes, such as, lysozyme, sialidase, and/or collagenase; proteases, such as, cathepsin G; azurocidin, and/or elastase; cationic phospholipase; and/or metal chelators such as lactoferrin. Such granules may be released upon contact with microbes.

PMN may also be capable of imprinting the tissue with neutrophil extracellular traps (NETs). NETs may be composed of nuclear contents (DNA and chromatin) mixed with toxic molecules from intracellular granules and the cytosol. Invading microorganisms may be sequestered in these NETs and effectively destroyed.

During intestinal inflammation, resident monocytes contribute to the recruitment of neutrophils through production of macrophage-derived chemokines. Neutrophils present in the blood sense the chemoattractant gradient and traverse the vascular endothelium to reach the intestinal lamina propria. In this manner, neutrophils are recruited to sites of infection or inflammatory stimuli within minutes. The response typically peaks by 24-48 hours. Under certain physiological or pathological conditions, neutrophils may cross the epithelium into the intestinal lumen.

At inflammatory sites, neutrophils may selectively release monocyte chemoattractants, such as CAP18, cathepsin G, and/or azurocidin. Thus, shortly after arrival of PMN to the mucosa, macrophages are recruited for a second-wave inflammatory response that ensues for the next several days.

Thus, the method may optionally involve the analysis of neutrophils in a target. Optionally, the presence of reactive oxygen species and/or neutrophils generating reactive oxygen species in a target may be analysed. Optionally, the presence of NETs and/or neutrophils generating NETs in a target may be analysed. Optionally, the presence of monocyte chemoattractants and/or neutrophils generating monocyte chemoattractants in a target may be analysed.

As described in the Examples, a total of n=85 mucosal membrane models were collected from three cohorts (urogenital tract, nasal and oral cavity). The mucosal membrane samples were subjected to desorption electrospray ionisation ("DESI") spectrometric analysis and the resulting spectrometric data was subjected to multivariate statistical analysis. Multivariate statistical analysis was able to separate different mucosa classes and biomarker changes that can be associated with a diverse microbiome within the mucosa.

According to various embodiments, microbial, e.g., bacterial, and/or animal, e.g., human mucosal membrane analytes may be characterised, e.g. using ambient mass and/or ion mobility spectrometry based techniques such as the desorption electrospray ionisation ("DESI") technique and the rapid evaporative ionisation mass spectrometry ("REIMS") technique.

Figure 29:
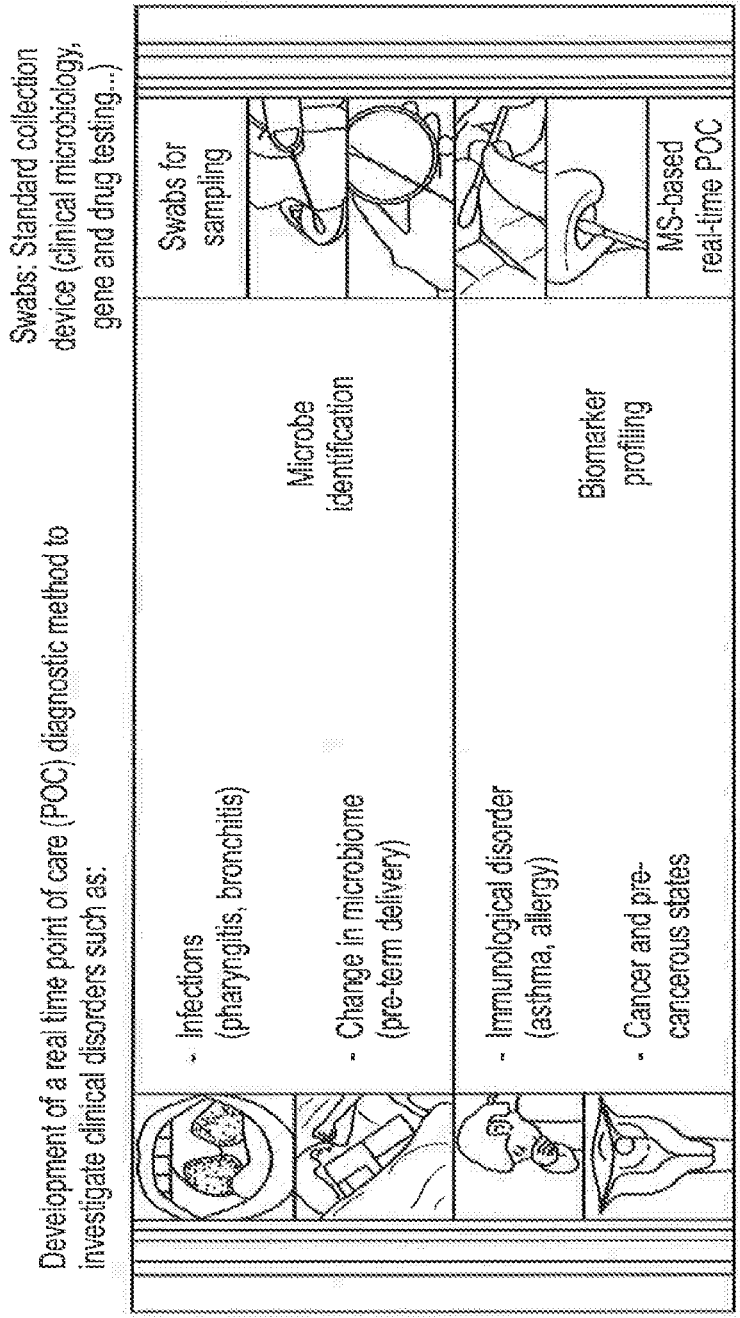
FIG. 29 shows schematically how analytes present in a mucosa may be useful in identifying a number of clinical disorders.

As illustrated by FIG. 29, these analytes (e.g., membrane lipids and inflammatory markers of the mucosa, and complex lipids and signalling molecules of intact bacteria cells) can be useful in identifying a number of clinical disorders.

Accordingly, various embodiments are directed to the development of a real time point of care ("POC") diagnostic method to investigate various clinical disorders. In particular, various embodiments are directed to mass spectrometry ("MS") and/or ion mobility spectrometry based real-time point of care ("POC") techniques.

For example, infections such as pharyngitis, bronchitis, and/or infections with any of the microbes mentioned herein can be identified e.g. by analysing, e.g., identifying microbes.

Changes in the microbiome can also be analysed, e.g., detected, e.g., by identifying microbes, and by way of example, determining a change in the microbiome of a pregnant patient can be used to identify those patients who are at an increased risk of having a pre-term or premature delivery during pregnancy.

Furthermore, the various analytes taken from mucosal membranes, e.g. biomarker profiling, can be used to identify various immunological disorders (e.g., asthma, allergies) as well as to identify cancer and/or pre-cancerous states.

Figure 30:
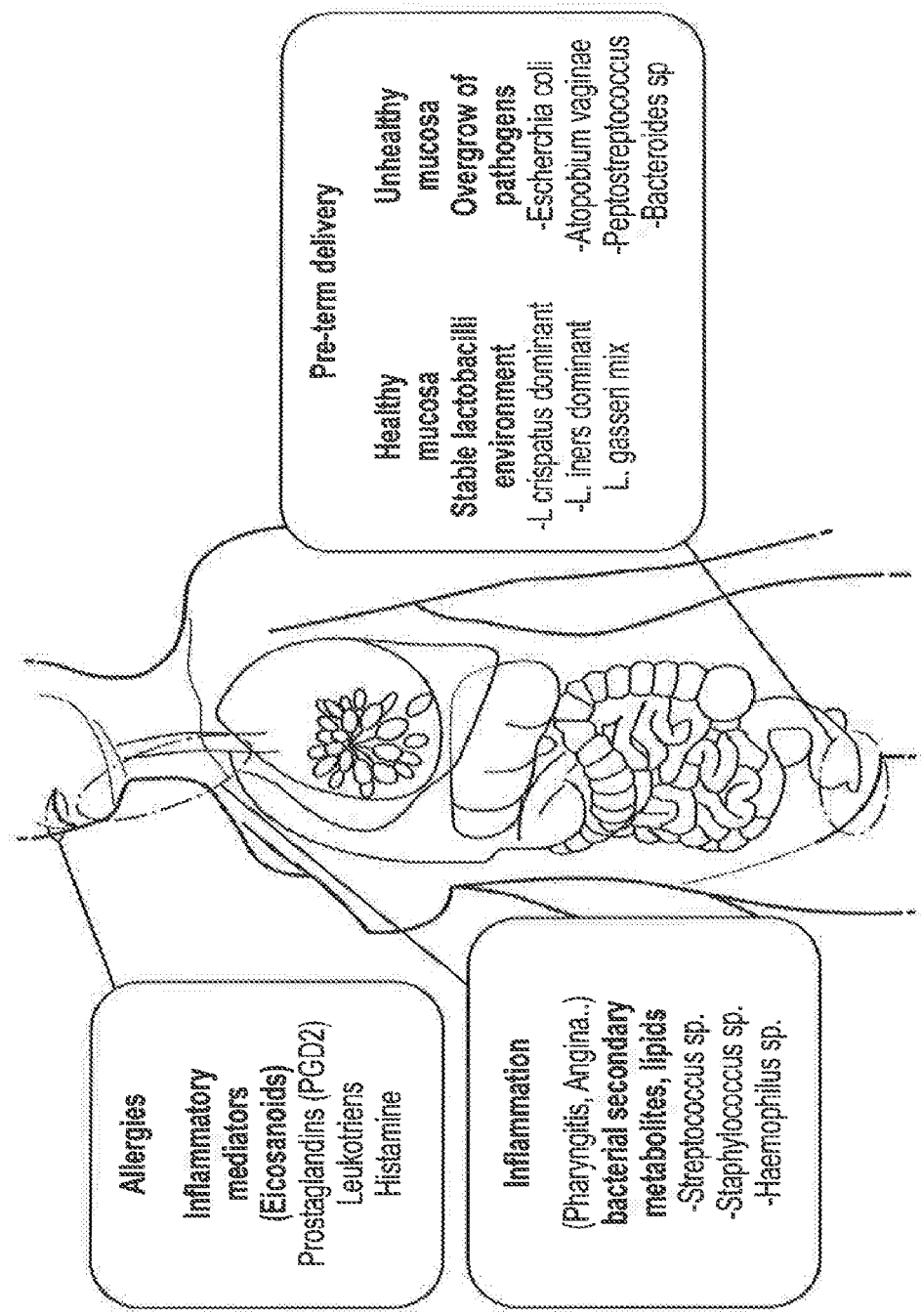
FIG. 30 shows schematically how metabolomic profiling of analytes from a mucosal membrane can be useful in identifying clinical disorders such as allergies, inflammation and pre-term delivery.

As further illustrated by FIG. 30, metabolomic profiling of analytes from various mucosal membranes using swabs can be useful in identifying a number of clinical disorders. For example, allergies may be identified, e.g., by identifying inflammatory mediators (eicosanoids) such as prostaglandins (PGD2), leukotriends, histamine, etc. Inflammation (such as pharyngitis, angina, etc.) may be identified, e.g., by identifying microbial, e.g., bacterial secondary metabolites, lipids, etc. from bacteria such as *streptococcus* sp., *staphylococcus* sp., *haemophilus* sp., etc. Pre-term delivery may also be identified, e.g. by identifying healthy (e.g. comprising a stable lactobacilli environment including e.g., *L. crispatus* dominant, *L. iners* dominant, and/or *L. gasseri* mix, etc.) or unhealthy mucosa (e.g. comprising an overgrowth of pathogens including, e.g., *Escherchia coli*, *Atopobium vaginae*, *Peptostreptococcus*, and/or *Bacteroides* sp., etc.).

According to various embodiments, mucosal diagnostics enable non-invasive direct sampling of the mucosa from patients at a clinical point of care.

According to various embodiments, analytes may be obtained from mucosal membranes using, e.g., a standard medical swab.

For clinical analysis, the swabs may be wiped over or into an infected area, e.g. to sample microbe rich body fluid, such as, sanies, and/or the mucosa. The swab may then be placed into a sterile tube containing a buffer solution for storage before the tube is sent to a laboratory for analysis. A laboratory receiving the tube may wipe the smear content across a culture medium such as an agar plate. The culture medium may then be incubated to allow organisms present to grow. Microbial identification may then be performed under a microscope. Any organisms present in the sample may also be identified, e.g., by sequence analysis, e.g., 16S gene-sequencing of bacteria, and/or by using matrix-assisted laser desorption ionisation ("MALDI") mass and/or ion mobility spectrometry and then comparing the mass and/or ion mobility spectra with a commercially available database.

Figure 31:
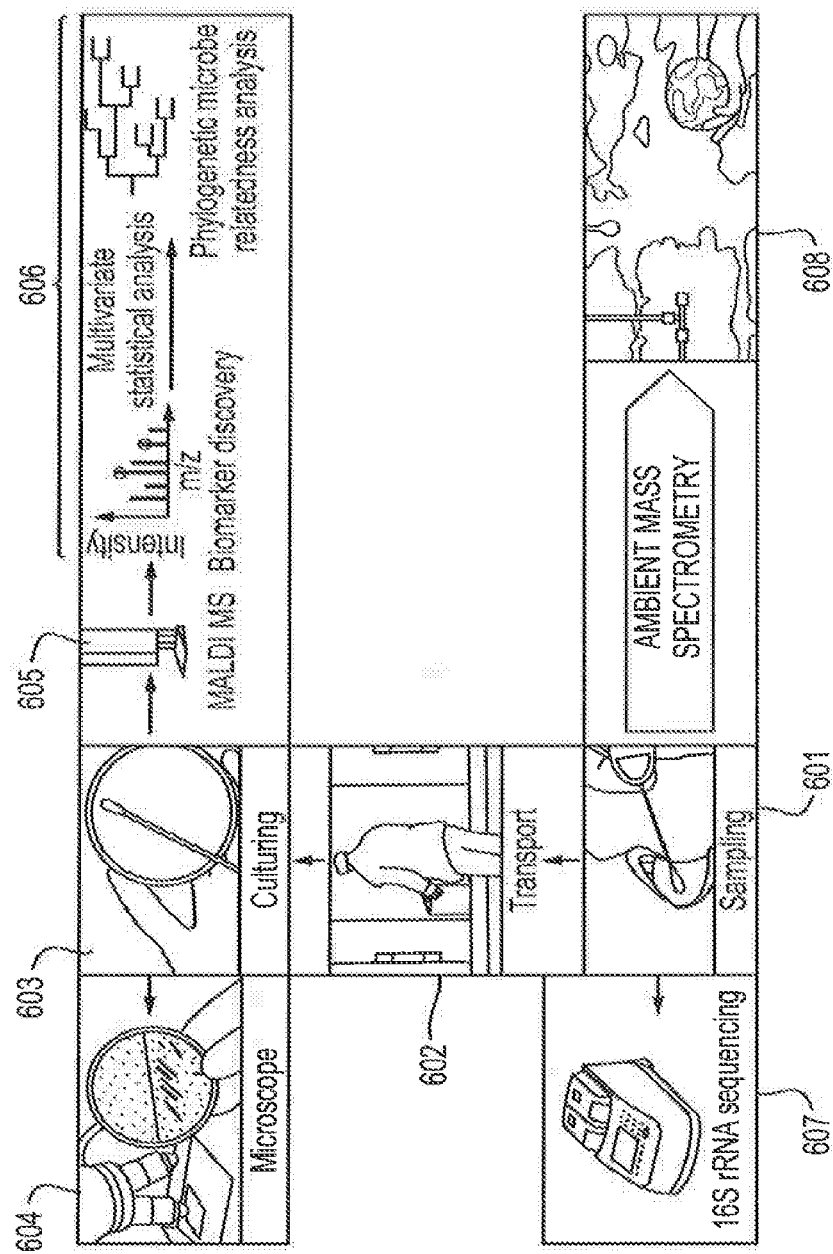
FIG. 31 shows various approaches for microbial analysis together with a real time rapid and direct analysis method using ambient mass spectrometry according to various embodiments.

FIG. 31 illustrates a microbe identification workflow and shows sampling 311 an analyte using a swab and then transporting 312 the swab to a specialist laboratory for microbe culturing 313 and further analysis. As shown in FIG. 31, such culture based analysis may comprise imaging using a microscope 314 and/or Matrix Assisted Laser Desorption Ionisation ("MALDI") Mass Spectrometry ("MS") 315 followed by statistical analysis 316, etc. 16*s* rRNA sequencing 317 is a culture independent analysis method.

Although easy to handle, the current analysis of medical swabs for diagnostic purposes is culture-dependent and involves a relatively time consuming and relatively costly workflow. Diagnosis of pathogen-associated diseases and appropriate treatment is therefore associated with considerable delay. Furthermore, around 95% of bacteria cannot be cultured for analysis.

Various embodiments which are described in more detail below provide a fast and direct way to investigate clinical samples from mucosal membranes, e.g. by identifying microbes and/or biomarkers characteristic of specific clinical disorders in mucosal samples, thereby permitting faster diagnoses and treatment of patients.

Various embodiments are directed to real time rapid and direct analysis of analytes present, e.g., on a swab, using ambient mass and/or ion mobility spectrometry. Ambient ionisation mass and/or ion mobility spectrometry based techniques may be employed for direct analysis of the sample surface. A sample may be analysed in its native state with minimal or no prior sample preparation.

In particular, Desorption Electrospray Ionisation ("DESI") has been found to be a particularly useful and convenient method for the real time rapid and direct analysis of analytes, e.g. those present on a swab. Desorption electrospray ionisation ("DESI") allows direct and fast analysis of surfaces without the need for prior sample preparation. DESI is described elsewhere herein.

The desorption electrospray ionisation ("DESI") technique allows for ambient ionisation of a trace sample at atmospheric pressure with little sample preparation. The desorption electrospray ionisation ("DESI") technique allows, for example, direct analysis of biological compounds such as lipids, metabolites and peptides in their native state without requiring any advance sample preparation.

Some embodiments described herein relate to directly analysing medical swabs using desorption electrospray ionisation ("DESI") mass and/or ion mobility spectrometry. According to various embodiments chemical signature identification of specific microbes, e.g., bacteria and/or biomarkers on the surface of the swabs is possible within a relatively short period of time.

Various specific embodiments relate to the rapid diagnosis of infections and/or dysbiosis, e.g., associated with preterm (premature) delivery (and these results may optionally be compared with standard microbial testing).

Further embodiments relate to a real-time rapid medical swab analysis using desorption electrospray ionisation ("DESI") mass and/or ion mobility spectrometry to reveal pathogenic and/or inflammatory metabolomic markers.

Various embodiments relate to the development of a non-invasive point of care diagnostic technique, directed toward detection of diseases with a particular emphasis on the detection of infections, dysbiosis, cancer and/or inflammatory diseases, and/or any of the other diseases mentioned elsewhere herein.

Clinical studies have shown that vaginal microbial, e.g., bacterial diversity is associated with specific vaginal mucosal metabolites. For example, during healthy pregnancy the vaginal mucosa is colonized mainly by the *Lactobacillus* species. However, importantly, a shift towards vaginal dysbiosis during pregnancy may be a causal trigger for preterm birth.

Using the ambient ionisation mass and/or ion mobility spectrometry based technique disclosed herein allows females, e.g., women, who have had a spontaneous preterm birth to be evaluated and compared to controls in order to identify biomarkers that can be used to predict preterm delivery. Moreover, the vaginal mucosa of pregnant females may be analysed using the ambient ionisation mass and/or ion mobility spectrometry based technique disclosed herein to analyse, e.g., diagnose or predict the risk of, a (spontaneous) preterm birth.

Spectrometric profiling of vaginal mucosa can enable an early identification of females, e.g., women who are at risk of infection during pregnancy based upon microbial, e.g., bacterial diversity in the vaginal mucosa. Furthermore, this enables targeted treatment response strategies.

Various embodiments are contemplated and include: (i) identification of vaginal mucosa metabolite biomarkers that are related to specific microbial, e.g., bacterial communities, optionally as determined using sequencing microbiome analysis; (ii) profiling of vaginal mucosal membrane during healthy pregnancy wherein microbe, e.g., bacteria-specific metabolites and signatures that are excreted during healthy pregnancy may be characterised in detail; and (iii) identification of diagnostic and prognostic metabolic signatures from vaginal mucosa membranes with poor pregnancy outcomes (e.g. preterm delivery).

It will be appreciated that various embodiments provide a new desorption electrospray ionisation ("DESI") mass and/or ion mobility spectrometry setup for non-invasive and fast analysis of the mucosal metabolome profile from the surface of medical swabs. This arrangement has been successfully shown to be capable of differentiating animal, e.g., human mucosal membrane models and to enable microorganism identification.

Since desorption electrospray ionisation ("DESI") mass and/or ion mobility spectrometry allows a less destructive analysis method which preserves the main content of the sample surface material, according to various embodiments the medical swab can optionally be sent directly after desorption electrospray ionisation ("DESI") analysis to a microbiological lab for further cultivation and microbe identification/confirmation.

Various embodiments provide a new point of care mucosal screening diagnostic method which uses standard cotton medical swabs as both the sampling probe for mucosal membrane uptake and ionisation probe for desorption electrospray ionisation ("DESI") mass and/or ion mobility spectrometry analysis. After data acquisition the obtained spectra may be compared with spectra collected in a database to provide a rapid diagnosis to the patient, e.g., within several seconds.

Various embodiments relate to the application of the desorption electrospray ionisation ("DESI") technique for direct metabolomic profiling of specific mucus models (nasal, vaginal, pharyngeal, bronchial, oesophageal) from the surface of standard medical swabs. Various embodiments relate to a rapid point-of-care diagnostic method for diseases, optionally selected from any of the diseases mentioned herein, e.g., inflammatory and pathogen-related diseases such as in immunological disorders, dysbiosis in the microflora (which may, e.g. be indicative of the risk of pre-term delivery during pregnancy), microbial, e.g., bacterial infections, or the detection of cancer or pre-cancerous states. The metabolomic profiling of animal, e.g., human mucosal membrane followed by detailed statistical analysis permits the identification of disease-specific metabolic profiles and/or taxon specific microbial, e.g., bacterial markers in a rapid, robust manner conducive to a point-of-care diagnostic method.

Figure 39:
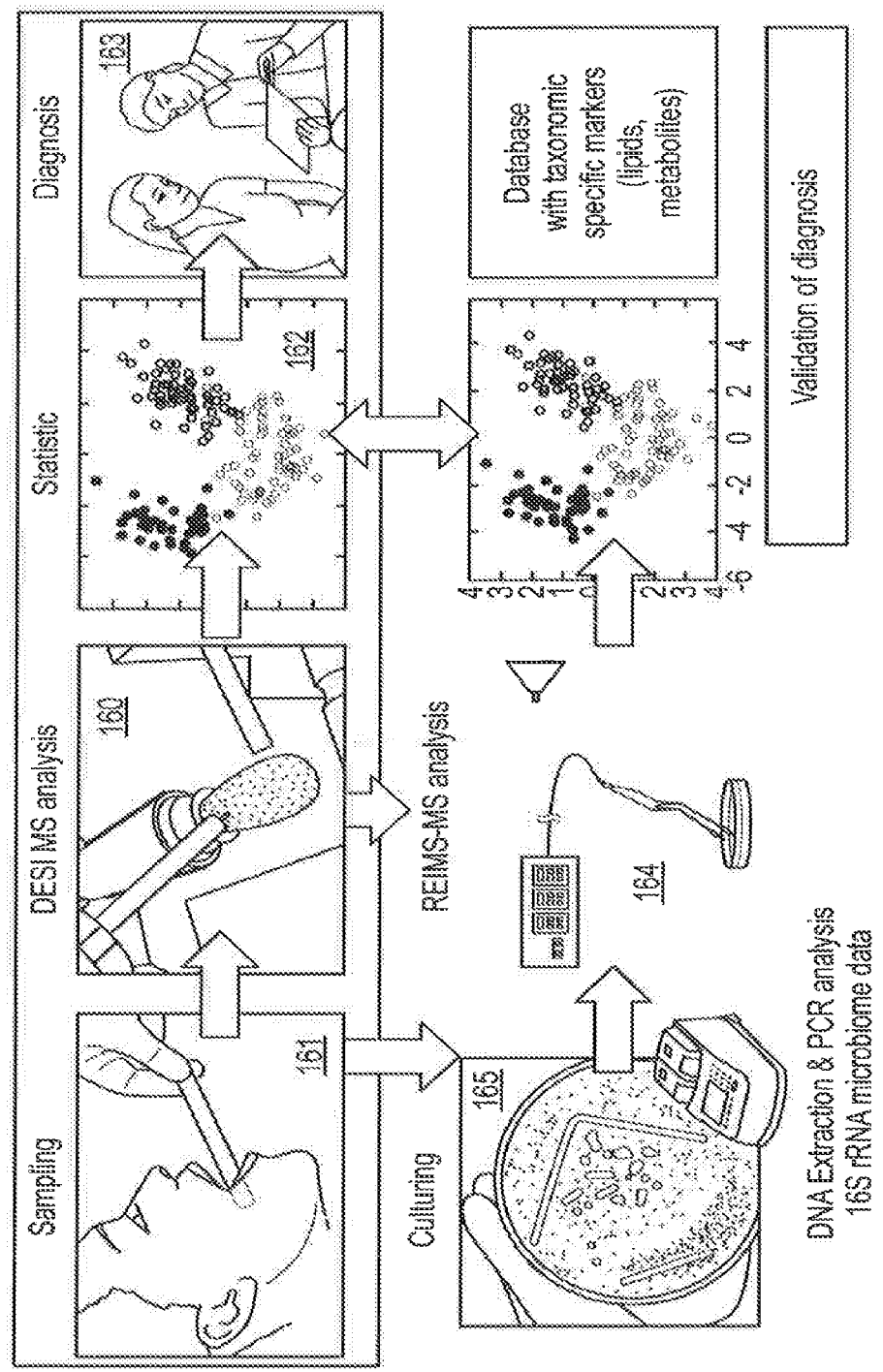
FIG. 39 shows schematically desorption electrospray ionisation ("DESI") mass spectrometry analysis, rapid evaporative ionisation mass spectrometry ("REIMS") mass spectrometry analysis and culturing based analysis of a sample on a swab according to various embodiments.

As shown in FIG. 39, according to various embodiments, desorption electrospray ionisation ("DESI") spectrometric analysis 390 of a sample sampled 391 onto a swab may be subjected to statistical analysis 392 in order to provide a diagnosis 393 (or prognosis).

The sample may be additionally or alternatively be analysed by rapid evaporative ionisation mass spectrometry ("REIMS") 394, or any other ambient ionisation mass and/or ion mobility spectrometry method.

Embodiments are contemplated wherein multiple different analysis techniques may be applied to the same swab (or another swab) so as to additionally perform analyses that rely on culturing 165, such as DNA extraction and PCR analysis, e.g., to produce complementary 16S rRNA microbiome data.

As shown in FIG. 39, any one or more or all of the additional analyses may be used to validate the desorption electrospray ionisation ("DESI") based diagnosis 393.

Various embodiments described herein also relate to methods of rapid evaporative ionisation mass spectrometry ("REIMS") analysis of a swab, wherein a sample on a swab is subjected to rapid evaporative ionisation mass spectrometry ("REIMS") analysis. This approach, however, is destructive for the swab, and in the bipolar mode the contact closure of the electrodes is restricted.

When a swab is analysed by rapid evaporative ionisation mass spectrometry, then the swab may be dipped, soaked or otherwise immersed in a fluid (such as water) prior to be being subjected to rapid evaporative ionisation mass spectrometry ("REIMS") analysis.

As discussed above, a particular benefit of using desorption electrospray ionisation ("DESI") mass and/or ion mobility spectrometry to analyse a sample provided on a medical swab is that multiple different analyses of the same sample, i.e. of the same swab, may be performed.

Performing multiple different analyses of or on the same sample enables multiple different sets of information about the same sample to be obtained in a particularly convenient and efficient manner. This is in particular possible because desorption electrospray ionisation ("DESI") mass and/or ion mobility spectrometry is a relatively non-destructive analysis technique and also because various commercial analysis techniques, such as culturing techniques and nucleic acid sequencing techniques, e.g., 16S rRNA sequencing techniques, are optimised to use samples which are provided on medical swabs.

Accordingly, following a single sample acquisition onto a swab, the sample on the swab may be analysed multiple times using multiple different analysis techniques, where at least one of the techniques (e.g. the first technique used) comprises desorption electrospray ionisation ("DESI") mass and/or ion mobility spectrometry.

Medical swabs were analysed by desorption electrospray ionisation ("DESI") mass and/or ion mobility spectrometry as shown in Example 16.

Figure 55A:
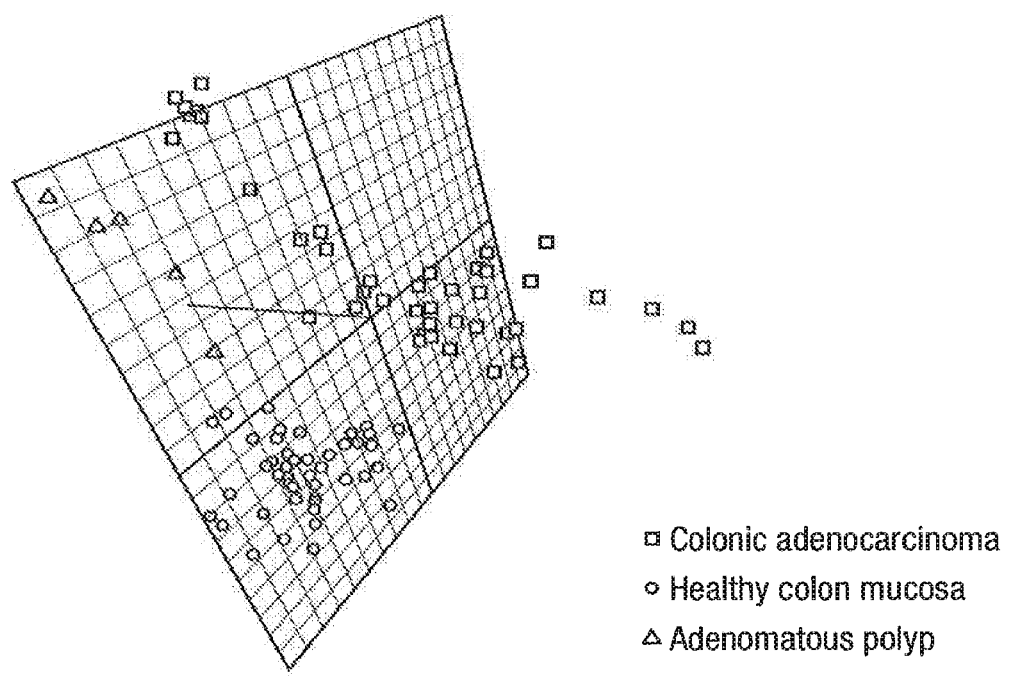
FIG. 55A shows a 3-dimensional PCA plot of human colon adenocarcinoma (n=43) and healthy colon mucosal data (n=45) acquired from seven patients using an LTQ Velos® mass spectrometer wherein the adenomatous polyps (n=5) collected from two patients were sampled ex vivo after their removal and wherein a significant difference can be observed in the PCA space between all three groups and FIG. 55B shows a 3-dimensional PCA plot of healthy gastric mucosa (n=32), gastric submucosa (n=10) and adenocarcinoma of the stomach (n=29) acquired from three patients ex vivo using a Xevo G2-S® Q-Tof mass spectrometer (Waters®) wherein the significant differences between submucosa and the other two layers may be used to provide a perforation risk alert system for interventional endoscopy according to an embodiment.
Figure 55B:
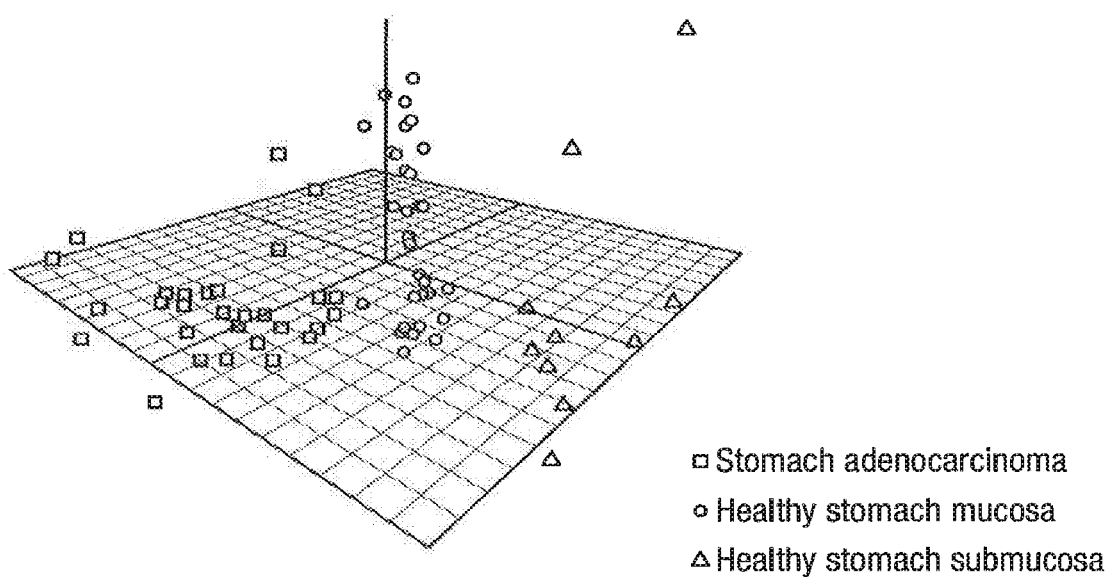
Figure 56B:
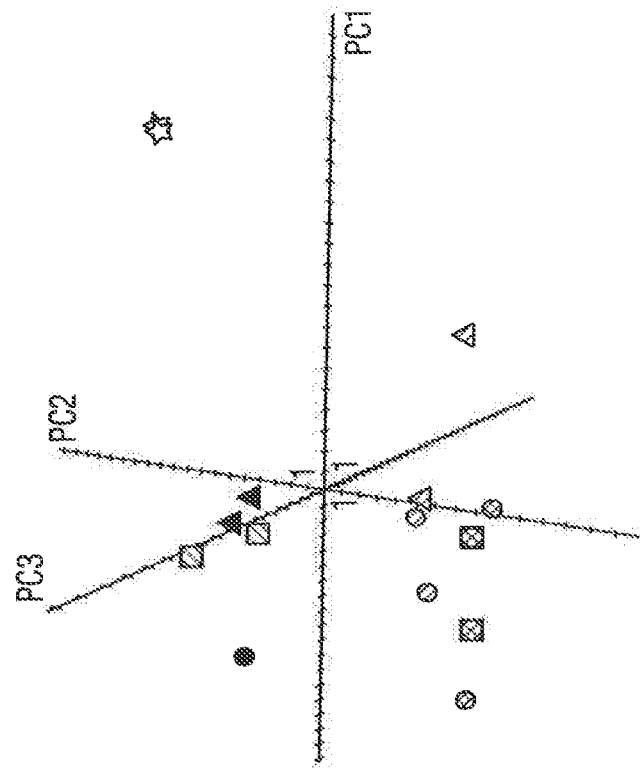
FIG. 56A shows in vivo utilization of a rapid evaporative ionisation mass spectrometry compatible endoscope system and sampling points taken from three patients undergoing colonoscopy and FIG. 56B shows the sampling points depicted on a 3-dimensional PCA plot wherein the spectra acquired in vivo when the polyps were removed localize in a different part of space whilst all other mucosal spectra are quasi uniformly independent from the sampling location.
Figure 56A:
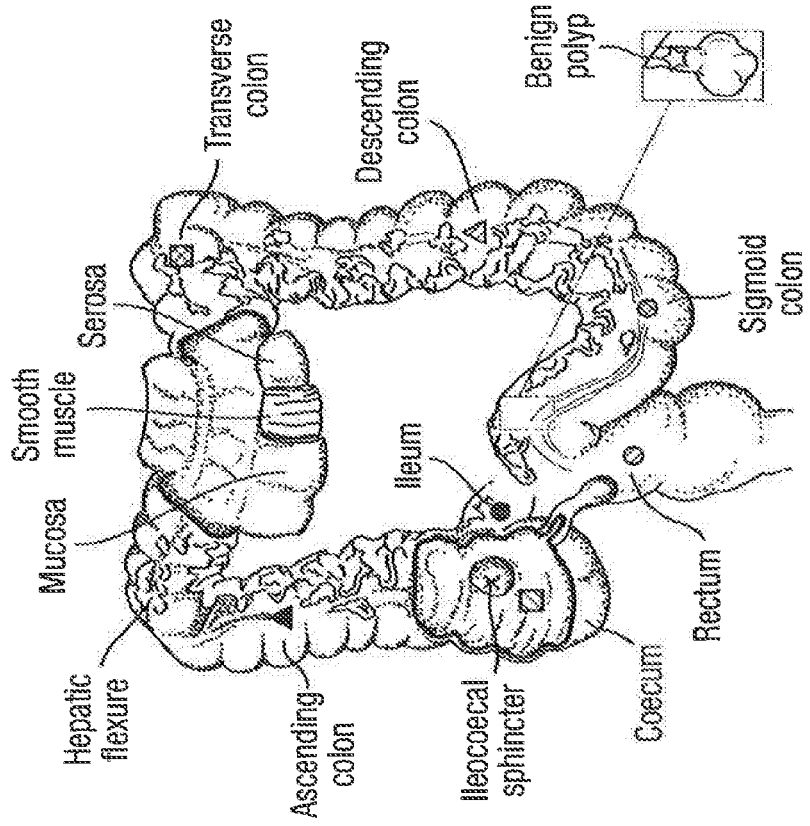

Healthy submucosa and GI polyps were analysed via a method of the invention, as shown in Example 19 and FIGS. 54-56. Clear differences were observed between the rapid evaporative ionisation mass spectrometry fingerprints of the submucosa and mucosal layer. This may optionally be exploited as a potential safety function for interventional surgery, e.g., endoscopy.

Colonoscopic procedures involving electrocautery are associated with a 9× increase in perforation risk compared to a purely diagnostic procedure. It has also been reported that endomucosal resection ("EMR") of ulcerated lesions are at higher risk of perforation. Optionally the method of the invention may use REIMS in GI surgery to analyse whether there is a breach of the submucosal layer during surgery, such as polypectomy or endomucosal resection. Thus, the method of surgery may involve the use of REIMS technology as described herein to analyse whether there is a breach of the submucosal layer during surgery, such as polypectomy or endomucosal resection.

Thus, the method advantageously helps in decreasing perforation rates and the significant morbidity associated with this complication.

Real time and/or delayed information may be provided to a user of an electrosurgical tool that may comprise spectrometric information and/or tissue classification information. A feedback device and/or an alarm and/or an alert may also may be provided to provide a user of the electrosurgical tool with feedback and/or an alarm and/or an alert that analyte from an undesired target region or area is being analysed by the analyser or that the electrosurgical tool is operating in and/or is located in an undesired target region or area.

The method may optionally be used to analyse cancer in the mucosa, as illustrated in Example 20.

Analysis of Microbes and/or the Microbiome

A "microbe", also known as a micro-organism, is an organism which is too small to be visible to the naked eye, i.e. is microscopic. A microbe may be selected from bacteria, fungi, archaea, algae, protozoa and viruses. Although the terms bacteria, fungi, archaea, algae, protozoa and viruses technically denote the plural form, it is common practice to use them also to denote the singular form. Consequently, the terms "bacteria" and "bacterium" are used interchangeably herein; the terms "fungi" and "fungus" are used interchangeably herein; the terms "archaea" and "archaeum" are used interchangeably herein; the terms "protozoa" and "protozoum" are used interchangeably herein; and the terms "viruses" and "virus" are used interchangeably herein.

In the case of a microbe, analysis may optionally be on any taxonomic level, for example, at the Kingdom, Phylum or Division, Class, Order, Family, Genus, Species and/or Strain level.

"Taxonomy" is the classification of organisms, and each level of classification may be referred to as a "taxon" (plural: taxa). Organisms may be classified into the following taxa in increasing order of specificity: Kingdom, Phylum or Division, Class, Order, Family, Genus, Species and Strain. Further subdivisions of each taxon may exist. It must be appreciated that within the vast scientific community there are some discrepancies within some taxonomic classifications. There may also be a lack of consensus with regard to the nomenclature of certain microbes, resulting in a particular microbe having more than one name or in two different microbes having the same name.

As a shorthand, the term "type" of microbe is used to refer to a microbe that differs from another microbe at any taxonomic level.

In some embodiments, the microbe may be selected from bacteria, fungi, archaea, algae and protozoa. In some embodiments, it may be selected from bacteria and fungi. In some embodiments, it may be selected from bacteria.

The microbe may be single-cellular or multi-cellular. If the microbe is a fungus, it may optionally be filamentous or single-cellular, e.g., a yeast.

A fungus may optionally be yeast. It may optionally be selected from the genus *Aspergillus, Arthroascus, Brettanomyces Candida, Cryptococcus, Debaryomyces, Geotrichum, Pichia, Rhodotorula, Saccharomyces, Trichosporon,* and *Zygotorulaspora.*

It may optionally be selected from the species *Arthroascus schoenii, Brettanomyces bruxellensis, Candida albicans, C. ascalaphidarum, C. amphixiae, C. antarctica, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogil, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis, C. zemplinina, Cryptococcus neoformans, Cryptococcus uniguttulatus, Debaryomyces carsonii, Geotrichum capitatum, Trichosporon asahll, Trichosporon mucoides, Trichosporon inkin, Saccharomyces cerevisiae, Pichia acaciae, Pichia anomala, Pichia capsulata, Pichia farinosa, Pichia guilliermondii, Pichia spartinae, Pichia ohmeri, Rhodotorula glutinous, Rhodotorula mucilaginosa, Saccharomyces boulardii, Saccharomyces cerevisiae,* and/or *Zygotorulaspora florentinus.*

The protozoa may be selected from the group of amoebae, flagellates, ciliates or sporozoa. It may be selected from the genus *Acanthamoeba, Babesia, Balantidium, Cryptosporidium, Dientamoeba, Entamoeba, Giardia, Leishmania, Naegleria, Plasmodium Paramecium, Trichomonas, Trypanosoma, Typanosoma, Toxoplasma*

The protozoa may be of the species *Balantidium coli, Entamoeba histolytica, Giardia lamblia* (also known as *Giardia* intestinalis, or *Giardia duodenalis*), *Leishmania donovani, L. tropics, L. brasiliensis, Plasmodium falciparum, P. vivax, P. ovale, P. malariae, P. knowlesi, P. reichenowi, P. gaboni, P. mexicanum, P. floridense Trypanosoma brucei, Typanosoma evansi, Trypanosoma rhodesiense, Trypanosoma cruzi, Toxoplasma*

The bacteria may optionally be selected from the phylum Aquficae, Thermotogae, Thermodesulfobacteria, Deinococcus-*Thermus,* Chrysiogenetes, Chloroflexi, Thermomicrobia, Nitrospira, Deferribacteres, Cyanobacteria, Chlorobi, Proteobacteria, Firm icutes, Actinobacteria, Planctomycetes, Chlamydiae, Spirochaetes, Fibrobacteres, Acidobacteria, Bacteroidetes, Fusobacteria, Verrucomicrobia, Dictyoglomi, Gemmatomonadetes, and Lentisphaerae.

The bacteria may optionally be selected from the class Actinobacteria, Alphaproteobacteria, Bacilli, Betaproteobacteria, Clostridia, Deltaproteobacteria, Epsilonproteobacteria, Flavobacteriaceae, Fusobacteria, Gammaproteobacteria, Mikeiasis, Mollicutes, or Negativicutes.

The bacteria may optionally be of the Order Aeromonadales, Actinomycetales, Bacillales, Bacteroidales, Bifidobacteriales, Burkholderiales, Campylobacterales, Caulobacterales, Cardiobacteriales, Clostridiales, Enterobacteriales, Flavobacteriales, Fusobacteriales, Lactobacillales, Micrococcales, Neisseriales, Pasteurellales, Pseudomonadales, Rhizobiales, Rhodospirillales, Selenomonadales, Vibrionales, Xanthomonadales.

The bacteria may optionally be selected from the Family Acetobacteraceae, Alcaligenaceae, Bacillaceae, Bacteroidaceae, Burkholderiaceae, Caulobacteraceae, Comamonadaceae, Enterobacteriaceae, Flavobacteriaceae, Fusobacteriaceae Nocardiaceae, Prevotellaceae, Porphyromonadaceae, Pseudomonadaceae, Rikenellaceae, Rhizobiaceae, Sutterellaceae.

The bacteria may optionally be of a genus selected from, e.g., *Abiotrophia, Achromobacter, Acidovorax, Acinetobacter, Actinobacillus, Actinomadura, Actinomyces, Aerococcus, Aeromonas, Anaerococcus, Anaplasma, Bacillus, Bacteroides, Bartonella, Bifidobacterium, Bordetella, Borrelia, Brevundimonas, Brucella, Burkholderia Campylobacter, Capnocytophaga, Chlamydia, Citrobacter, Chla-*

*mydophila, Chryseobacterium, Clostridium, Comamonas, Corynebacterium, Coxiella, Cupriavidus, Delftia, Dermabacter, Ehrlichia, Eikenella, Enterobacter, Enterococcus, Escherichia, Erysipelothrix, Facklamia, Finegoldia, Francisella, Fusobacterium, Gemella, Gordonia, Haemophilus, Helicobacter, Klebsiella, Lactobacillus, Legionella, Leptospira, Listeria, Micrococcus, Moraxella, Morganella, Mycobacterium, Mycoplasma, Neisseria, Nocardia, Orientia, Pandoraea, Pasteurella, Peptoniphilus, Peptostreptococcus, Plesiomonas, Porphyromonas, Pseudomonas, Prevotella, Proteus, Propionibacterium, Rhodococcus, Ralstonia, Raoultella, Rickettsia, Rothia, Salmonella, Serratia, Shigella, Staphylococcus, Stenotrophomonas, Streptococcus, Tannerella, Treponema, Ureaplasma, Vibrio* or *Yersinia*.

The bacteria may optionally be of a species selected from, e.g., *Abiotrophia defective, Achromobacter xylosoxidans, Acidovorax avenae, Acidovorax citrulli, Akkermansia muciniphila, Bacillus anthracis, B. cereus, B. subtilis, B. licheniformis, Bacteroides fragilis, Bartonella henselae, Bartonella quintana, Bordetella pertussis, Borrelia burgdorferi, Borrelia Borrelia afzelii, Borrelia recurrentis, Brucella abortus, Brucella canis, Brucella melitensis, Brucella suis, Burkholderia cepacia, Burkholderia genomovars, Campylobacter jejuni, Chlamydia pneumoniae, Chlamydia trachomatis, Chlamydophila psittaci, Citrobacter koseri, Clostridium botulinum, Clostridium difficile, C. perfringens, C. tetani, Corynebacterium diphtheriae, C. striatum, C. minutissimum, C. imitans, C. amycolatum, Delftia acidovorans, Enterobacter aerogenes, E. cloacae Enterococcus faecalis, Enterococcus faecium, Escherichia coli, Francisella tularensis, Fusobacterium nucleatum, Haemophilus influenzae, Helicobacter pylori, Klebsiella oxytoca, K. pneumonia, Legionella pneumophila, Leptospira interrogans, Leptospira santarosai, Leptospira weilii, Leptospira noguchii, Listeria ivanovii, Listeria monocytogenes, Micrococcus luteus, Morganella morganli, Moraxella catarrhalis, Mycobacterium avium, M. fortuitum, M. leprae, M. peregrium, M. tuberculosis, M. ulcerans, Mycoplasma pneumoniae, Neisseria gonorrhoeae, N. lactamica, N. meningitidis, Nocardia asteroids, Proteus mirabilis, Pseudomonas aeruginosa, Rhodococcus equi, Rhodococcus pyridinivorans, Rickettsia rickettsii, Salmonella typhi, Salmonella typhimurium, Serratia marcescens, Shigella sonnei, Staphylococcus aureus, S. capitis, S. epidermidis, S. haemolyticus, S. hominis, S. saprophyticus, Stenotrophomonas maltophilia, Streptococcus agalactiae, S. pyogenes, S. pneumonia, Treponema pallidum, Ureaplasma urealyticum, Vibrio cholerae, Yersinia pestis, Yersinia enterocolitica* and *Yersinia pseudotuberculosis*.

The virus may optionally be a DNA virus, and RNA virus or a retrovirus. It may optionally be a single stranded (ss) or a double stranded (ds) virus. More particularly, it may optionally be a ssDNA, dsDNA, dsRNA, ssRNA (positive strand), ssRNA (negative strand), ssRNA (reverse transcribed) or dsDNA (reverse transcribed) virus.

It may optionally be selected from one or more of the Herpesviridae, optionally selected from Simplexvirus, Varicellovirus, Cytomegalovirus, Roseolovirus, Lymphocryptovirus, and/or Rhadinovirus; the Adenoviridae, optionally selected from Adenovirus and/or Mastadenovirus; Papillomaviridae, optionally selected from Alphapapillomavirus, Betapapillomavirus, Gammapapilloma-virus, Mupapillomavirus, and/or Nupapillomavirus; Polyomaviridae, optionally selected from Polyomavirus; Poxviridae, optionally selected from Molluscipoxvirus, Orthopoxvirus and/or Parapoxvirus; Anelloviridae, optionally selected from Alphatorquevirus, Betatorquevirus, and/or Gammatorquevirus; Mycodnaviridae, optionally selected from Gemycircular-viruses; Parvoviridae, optionally selected from Erythrovirus, Dependovirus, and/or Bocavirus; Reoviridae, optionally selected from Coltivirus, Rotavirus, and/or Seadornavirus; Coronaviridae, optionally selected from Alphacoronavirus, Betacoronavirus, and/or Torovirus; Astroviridae, optionally selected from Mamastrovirus; Caliciviridae, optionally selected from Norovirus, and/or Sapovirus; Flaviviridae, optionally selected from Flavivirus, Hepacivirus, and/or Pegivirus; Picornaviridae, optionally selected from Cardiovirus, Cosavirus, Enterovirus, Hepatovirus, Kobuvirus, Parechovirus, Rosavirus, and/or Salivirus; Togaviridae, optionally selected from Alphavirus and/or Rubivirus; Rhabdoviridae, optionally selected from Lyssavirus, and/or Vesiculovirus; Filoviridae optionally selected from Ebolavirus, and/or Marburgvirus; Paramyxoviridae, optionally selected from Henipavirus, Heffalumpvirus, Morbilivirus, Respirovirus, Rubulavirus, Metapneumovirus, and/or Pneumovirus; Arenaviridae, optionally selected from Arenavirus; Bunyaviridae, optionally selected from Hantavirus, Nairovirus, Orthobunyavirus, and/or Phlebovirus; Orthomyxoviridae, optionally selected from lnfluenzavirus A, lnfluenzavirus B, lnfluenzavirus C and/or Thogotovirus; Retroviridae, optionally selected from Gammaretrovirus, Deltaretrovirus, Lentivirus, Spumavirus; Epadnaviridae, optionally selected from Orthohepadnavirus; Hepevirus; and/or Deltavirus.

The microbes may optionally be pathogenic, or non-pathogenic. A pathogenic microbe, which may also be called a "pathogen", may be defined as a microbe that is able to cause disease in a host, such as a plant or animal. A pathogen may optionally be an obligate pathogen or an opportunistic pathogen.

The ability of a microbe to cause disease depends both on its intrinsic virulence factors and on the ability of the host to fight off the microbe. The distinction between non-pathogens and opportunistic pathogens is therefore not clear-cut, because, for example, immuno-compromised hosts will be susceptible to infection by microbes that may be unable to infect a host with a healthy immune system.

For example, *Neisseria gonorrhoeae* is an obligate pathogen, *Pseudomonas aeruginosa* and *Candida albicans* are typically referred to as opportunistic pathogens, and *Lactobacillus acidophilus* and *Bifidobacterium bifidum* are typically considered to be non-pathogens, and may be referred to as "commensal".

Drugs, such as, an antimicrobial and/or an anti-inflammatory drug, may also create an environment in which a microbe will flourish as an opportunistic pathogen. Thus, the use of drugs may alter a microbiome. The method may therefore optionally involve analysing the microbiome, e.g., the mucosal microbiome, to analyse the response to a drug.

Pathogenic microbes may optionally be characterised by the expression of one or more virulence factors, i.e. factors that allow or facilitate infection of a host. Virulence factors may optionally be selected from factors that mediate cell adherence, cell growth, the ability to bypass or overcome host defence mechanisms, and/or the production of toxins. Toxins may be selected from exotoxins and endotoxins. The method may optionally involve analysing one or more virulence factors.

Commensal microbes are those which are part of the natural flora of a human or animal and which, in a balanced state, do not cause disease.

The community of microbes in a particular environment may be referred to as a "microbiome". Thus, the microbiome comprises the community of microorganisms that inhabit human or non-human animal bodies, e.g., human bodies. Humans and non-human animals have co-evolved with microbes as a symbiotic system. Complex reactions of microbe communities influence health and disease.

A microbiome may be a complex mixture of a vast number and vast variety of different microbes. The GI microbiome is estimated to comprise over 100 trillion microbes that represent at least several hundreds or even over a thousand different species. The healthy human gut microbiota is dominated by the Bacteroidetes and the Firmicutes, whereas, for example, Proteobacteria, Verrucomicrobia, Actinobacteria, Fusobacteria, and Cyanobacteria are typically present in minor proportions.

The microbiome may vary from one environment to another within the same human or animal, so a person's gastrointestinal (GI) microbiome may be different from that person's nasal microbiome. The GI microbiome may further be divided into the different GI regions, such as, stomach, duodenum, jejunum, ileum, and/or colon. The lumen microbiome may also differ from the mucosal microbiome. Each microbiome may also vary from one individual to another. The disturbance of the normal microbiome may be referred to as "dysbiosis". Dysbiosis may cause, or be associated with, a disease, such as, any of the diseases mentioned herein. The method may optionally involve the analysis of a microbiome to analyse dysbiosis. The GI microbiome may also be referred to as the "gut flora".

The microbiome may change during pregnancy, so an analysis of the female (human or animal) microbiome may allow an analysis of pregnancy. Dysbiosis in pregnancy is associated with complications, such as, an increased risk of premature birth.

Dysbiosis may involve the presence of one or more types of microbes that are normally, or were previously, absent from a particular microbiome. However, more commonly, dysbiosis may involve a relative increase in the proportion of one or more particular microbes, and/or a relative decrease in the proportion of one or more particular microbes.

As mentioned above, the mucosa comprises layers of mucus. Microbes, such as bacteria, may adhere to and/or partially or fully infiltrate the mucus layer. The microbial adherence and/or proliferation may be influenced by carbohydrate modifications present on mucins; by antimicrobial agents, such as, host-derived antimicrobial peptides; by drugs; and/or by toxins, such as, toxins produced by (pathogenic) microbes.

The mucosal (epithelial) surface beneath the mucus layer is free of microbes in at least about 80% of healthy humans. The thickness of the mucus layer and its spread may vary, for example, they may decrease with increasing severity of inflammation. Under certain conditions, for example, in a disease, microbes may infiltrate and/or adhere to the mucus layer, the epithelium and/or the LP. For example, bacteria may typically be found within the mucus of biopsy specimens from subjects with ulcerative colitis, SLC, and/or acute appendicitis. The concentration of microbes within the mucus layer may inversely correlate to the numbers of leucocytes.

The term "mucosal microbiome" is used herein to denote the microbiome which is associated with the mucosa, including the microbiome that has infiltrated the mucosa and the microbiome that is associated with (for example, through adhesion or partial or full infiltration) with mucus layer.

The method may optionally involve the analysis of a target to detect, identify and/or characterise a microbe. For example, the method may be used to analyse whether a target is sterile or non-sterile; whether any microbes present are pathogenic or commensal; whether any microbes present are the cause of an infection; and/or whether any microbes present in a target specimen were present in the subject from which the specimen was provided, or whether the microbes represent contamination of the specimen. For example, when taking a blood sample, there is typically a risk of the blood becoming contaminated with microbes that were present at or around the site at which the needle is inserted, which can lead to the presence, and hence detection, of microbes in a blood sample that would otherwise not have contained said microbes. Thus, the method may optionally be used to determine the significance of any microbes present in the target; and or to determine whether the subject from which the specimen was derived should receive an antimicrobial treatment.

The method may optionally involve the analysis of an infection, e.g., the diagnosis of an infection, analysis of the genotype or phenotype of the infection-causing microbe, monitoring of progression of infection, and/or monitoring of treatment response to infection.

The method may optionally involve the analysis of vaccination. This may, e.g., involve analysing a target prior to and after vaccination. Optionally, the subject may be challenged after vaccination with the microbe against which the vaccination is aimed, and a suitable target may then be analysed to determine whether, or at what level, the microbe is present. The presence or level of the microbe may be indicative of the success of vaccination, e.g., the absence or presence at low levels of the microbe may be indicative of successful vaccination, whereas the presence, or presence at high levels of the microbe may be indicative of the vaccine being deficient or ineffective.

Faecal or Body Fluid Specimen Analysis

The analysis of a faecal or body fluid specimen may provide information about a disease and/or microbiome, optionally a mucosal microbiome and/or the microbiome of the GI lumen. Thus, optionally, the method may involve the analysis of a faecal and/or body fluid specimen. For example, a faecal and/or body fluid specimen may be analysed for the presence of a cell, a compound, and/or a microbe.

The method may optionally allow an analysis of metabolic differences between various conditions, which may optionally be selected from any of the conditions listed elsewhere herein, e.g., Irritable Bowel Syndrome, Colorectal cancer and/or Inflammatory Bowel Disease. By identifying taxonomic specific biomarkers the method may optionally allow the analysis, e.g., diagnosis, of microbial infections and/or mixed microbial communities.

The cell may, e.g., be a mammalian cell, a white blood cell, a red blood cell, a foetal cell, and/or a cancer cell.

The compound may, e.g., comprise or consist of a biomolecule, an organic compound, and/or an inorganic compound. Optionally, it may be bile, haemoglobin, or a derivative of any thereof.

Optionally, a faecal and/or body fluid specimen may be analysed for the presence of a microbe and/or to analyse a microbiome. Details of analysis of microbes and/or the microbiome are provided elsewhere herein.

Optionally, a faecal and/or body fluid specimen other than blood may be analysed for the presence of blood. For example, the presence of blood in urine may be indicative of an infection or other disease. For example, the presence of blood in a faecal specimen may optionally be used to analyse a bleed in the GI tract and/or anus. Optionally, the bleed may be indicative of a disease selected, for example, from anal fissure, diverticular disease, an inflammatory disease, angiodysplasia, and/or any of the diseases mentioned elsewhere herein.

Optionally, a faecal and/or body fluid specimen may be analysed for the presence of bile or a derivative thereof, e.g., to analyse a liver and/or kidney disease, and/or any of the diseases mentioned elsewhere herein.

Optionally, a faecal and/or body fluid specimen may be analysed for the presence and/or level of a compound, e.g., a compound comprising or consisting of a lipid, such as, a glycolipid or phospholipid; a carbohydrate; DNA; RNA; a protein; a polypeptide, such as, a ribosomal peptide or a non-ribosomal peptide; an oligopeptide; a lipoprotein; a lipopeptide; an amino acid; and/or a chemical molecule, optionally an organic chemical molecule. Optionally, the compound may be endogenous, i.e. produced by the subject, or exogenous, i.e., administered, ingested or otherwise introduced into the subject.

Optionally, the compound may be a therapeutic drug, an illicit drug, or a metabolite or derivative of a therapeutic or illicit drug.

It may optionally be selected, e.g., from any of the drugs or agents mentioned herein, and/or Mescaline, PCP (Phencyclidine), Psilocybin, LSD, Heroin, Morphine, Codeine, dextroamphetamine, bupropion, cathinone, lisdexamfetamine, Allobarbital, Alphenal (5-allyl-5-phenylbarbituric acid), Amobarbital, Aprobarbital, Brallobarbital, Butobarbital, Butalbital, Cyclobarbital, Methyl phenobarbital, Mephobarbital, Methohexital, Pentobarbital, Phenobarbital, Secobarbital, Talbutal, Thiamylal, and/or Thiopental. Ranitidine, phenylalanine PKU, dimethylamylamine, cocaine, diazepam, androstadienedione, stigmastadienone, androsterone-hemisuccinate, 5α-androstan-3β,17β-diol-16-one, androsterone glucuronide, epitestosterone, 6-dehydrocholestenone, phenylalanine, leucine, valine, tyrosine, methionine, sitamaquine, terfenadine, prazosin, methadone, amitripyline, nortriptyline, pethidine, DOPA, ephedrine, ibuprofen, propranolol, atenolol, acetaminophen, bezethonium, citalopram, dextrorphan, paclitaxel, proguanil, simvastatin, sunitinib, telmisartan, verapamil, amitriptyline, pazopanib, tamoxifen, imatinib, cyclophosphamide, irinotecan, docetaxel, topotecan, acylcarnitines (C2-C18), nicotine, cotinine, trans-3'-hydroxycotinine, anabasine, amphetamine, amphetamine-like stimulants, methamphetamine, MDA, MDMA, MDEA, morphine, $\Delta^9$-THC, tacrolimus, benzethonium, meprobamate, O-desmethyl-cis-tramadol, carisoprodol, tramadol, nordiazepam, EDDP, norhydrocodone, hydromorphone, codeine, temazepam, noroxycodone, alprazolam, oxycodone, buprenorphine, norbuprenorphine, fentanyl, propoxyphene, 6-monoacetylmorphine, caffeine, carbadox, carbamazepine, digoxigenin, diltiazem, diphenhydramine, propanolol, sulfadiazine, sulfamethazine, sulfathiazole, thiabendazole, ketamine, norketamine, BZE, AMP, MAMP, and/or 6-MAM.

The analysis of faecal specimens may optionally involve the use forceps-based REIMS, wherein a sample of the faecal specimen may be taken between the forceps and the probes may then be drawn together.

Imaging

According to the various embodiments herein, ion imaging may be used to generate an image or map of one or more properties of the target. This may be achieved by using the first device to generate aerosol, smoke or vapour from multiple different regions of the target; ionising analytes in the smoke, aerosol or vapour originating from the different regions to produce analyte ions (or ions derived therefrom, e.g., fragment ions); and then analysing the analyte ions (or ions derived therefrom) to obtain spectrometric data for each of the regions of the target. The spectrometric data is correlated to the region of the target to which it relates (i.e. from where the smoke, aerosol or vapour that generated the spectrometric data originated from) so as to generate image or map data. An image or map of the target can then be generated based on the image or map data. For example, one or more properties of each region of the target may be determined from the spectrometric data and this may be included in the image or map data and hence mapped as a function of location within the target. The image or map data may then be displayed to a user.

The first device may be stepped between multiple spaced apart regions of the target so as to generate the aerosol, smoke or vapour from discrete regions of the target. Alternatively, a plurality of devices may be used to generate the aerosol, smoke or vapour from discrete regions of the target, optionally simultaneously. These plurality of devices may not move across the target, although may move into and out of engagement with the target. Spatial profiling of the target may therefore be performed (e.g., which does not perform a continuous map). Alternatively, the first device may be moved across or through the target continuously so as to generate aerosol, smoke or vapour from the different regions of the target. Any movements of the first device, or the plurality of devices, may be automated and controlled by a machine.

The spectrometric data for each region may be analysed and converted into data representative of the type, condition or constituent(s) of the material at that region in the target.

The representative data may then be displayed as an image or map showing the type, condition or constituents of the material as a function of location in the target.

For example, the representative data may indicate the type, level, presence and/or absence of: diseased; cancerous; and/or necrotic material at each of the regions in the target. For example, the spectrometric data may be used to identify and/or display the locations of margins of diseased, cancerous, and/or necrotic tissue in the target. These tissue types, such as tumour tissue, may closely resemble normal tissue and may have indistinct boundaries, making it difficult to determine where the tumour ends and the normal tissue begins. The method of the invention enables the locations of such tissue margins to be identified.

Additionally, or alternatively, the spectrometric data may be used to identify and/or display the location and/or margins of one or more cell or tissue type of interest. For example, the cell or tissue type of interest may comprise diseased and/or cancerous and/or necrotic tissue or cells in the target; and/or the cell or tissue type of interest may comprise healthy tissue or cells.

The representative data may indicate the different type of cells or constituents in the target.

Additionally, or alternatively, the representative data may indicate the presence and/or distribution of one or more types of microbes within the target.

Additionally, or alternatively, the representative data may indicate the presence and/or distribution of one or more types of compounds within the target.

Additionally, or alternatively, the representative data may indicate the type or level of biomarker in the target, and the distribution of the type or level of biomarkers within a target may be identified and/or displayed.

The ion imaging and map data may be generated and/or displayed in real-time. This may be useful, for example, to determine action to be taken during surgical procedures. The position of at least a portion of the first device and/or another tool relative to the target may be displayed on the image or map, e.g., in real time. For example, the position of a surgical tool, such as a tool for resecting or ablating tissue, may be displayed on the map of the target. This enables the surgeon to selectively resect or ablate tissue based on the representative data displayed in the image or map.

Ion imaging mass and/or ion mobility spectrometry technology, such as DESI-MS and/or REIMS technology, may optionally be used to obtain the spectrometric data for the different regions of the target. A REIMS technology device may optionally be used in cutting and/or pointing mode.

Ion imaging is illustrated in Example 18 and exemplary details are also provided in Example 21.

This ion imaging analysis may optionally be combined with a further analysis of the specimen. Details of further analysis methods and tools are provided elsewhere herein. Optionally, the results of mass and/or ion mobility spectrometry imaging may be correlated with the results of a further analysis.

For example, optionally the method may be used for imaging to distinguish between tumour, stroma and/or healthy tissue.

Therapy-Related Methods

The method of the present invention may optionally be used to monitor the progress of disease.

During therapy or subsequent to therapy, the method of the present invention may optionally be used to monitor the progress of disease to assess the effectiveness of therapy, or to monitor the progress of therapy.

Optionally, serial (periodic) analysis of a target for a change may be used to assess whether or not therapy has been effective; the extent to which therapy has been effective; whether or not a disease is re-occurring or progressing in the subject; and/or to assess the likely clinical outcome (prognosis) of the disease, should it re-occur or progress.

Optionally, the method may be used in the active monitoring of subjects which have not been subjected to therapy, e.g. to monitor the progress of the disease in untreated subjects.

Optionally, serial (periodic) analysis of a target for a change may be used to assess whether or not, or the extent to which, the disease is progressing, thus, for example, allowing a more reasoned decision to be made as to whether therapeutic intervention is necessary or advisable.

Such monitoring may optionally be carried out on a healthy individual, e.g., an individual who is thought to be at risk of developing a particular disease, in order to obtain an early and ideally pre-clinical indication of said disease. A particular example is cervical smear testing to analyse the cervix for cancer or pre-cancerous biomarkers.

The skilled person will appreciate that any of the methods provided herein may optionally be combined with one or more of the other methods provided herein and/or with one or more further methods.

For example, provided is a method which is a combination of two or more, e.g. three or more, four or more or five or more of the methods disclosed herein. Two or more of the diagnosis, prognosis, prediction, assessment, monitoring and/or stratification methods disclosed herein may be combined in any combination. When combining the methods, each method may be referred to as a step. The details provided herein regarding the methods of the invention apply mutatis mutandis to these steps.

Thus, provided is a method of assessing the onset and course of a disease, said method including at least two steps selected from a step of diagnosing disease, a step of monitoring the progression of disease, a step of predicting the likelihood of disease response to treatment, a step of stratification, a step of prognosis, and a step of assessing response to treatment. Optionally, said method includes at least 3, 4, 5 or 6 of these steps. Optionally, any of these steps may be carried out more than once. For example, a step of monitoring the progression of disease may optionally be carried out both before and after treatment.

Optionally, any of the methods provided herein may also include a step of determining whether the subject should receive a treatment. Suitable treatments are discussed elsewhere herein. Particularly, if the method involves a determination that the subject has a disease, that a disease has developed, that a disease has progressed, that the prognosis is poor, that a disease is likely to respond to treatment, and/or that a disease has responded to treatment, then the method may include a step of determining that the subject should receive an appropriate treatment.

Optionally, any of the methods provided herein may also include a step of determining, for a subject who is receiving, or has received, treatment, whether the treatment should be altered or ceased. For example, the method may optionally include a step of determining that the treatment dose and/or frequency should be increased or decreased. In particular, if the method involves a determination that one or more biomarkers for a disease are increased, have increased over time, or have not decreased (or not decreased sufficiently) in response to a treatment, then the method may optionally include a step of determining that the treatment dose and/or frequency should be increased; and if the method involves a determination that one or more biomarkers for a disease are not increased, have decreased over time, or have decreased in response to a treatment, then the method may optionally include a step of determining that the treatment dose and/or frequency should be decreased or that the treatment may be ceased; or vice versa.

The method may include a step of determining that a particular treatment should be replaced by another treatment, for example that one drug should be replaced with another drug. In particular, if the method involves a determination that one or more biomarkers for a disease are increased, have increased over time, or have not decreased (or not decreased sufficiently) in response to a treatment, then the method may include a step of determining that the treatment should be replaced by another treatment; and if the method involves a determination that one or more biomarkers for a disease are not increased, have decreased over time, or have decreased in response to a treatment, then the method may include a step of determining that the treatment should not be replaced by another treatment; or, vice versa.

Optionally, any of the methods provided herein may also include a step of administering a treatment to said subject. The method may then, for example, be referred to as a method of diagnosis and treatment; monitoring and treatment; prognosis and treatment; prediction and treatment; or stratification and treatment.

Optionally, any of the methods provided herein may be used in conjunction with any other known methods, particularly a known diagnostic, prognostic, predictive, and/or monitoring method for a disease.

Treatments and Agents

Cancer Treatments and Anti-Cancer Agents

The treatment may optionally be an anti-cancer treatment, for example, if cancer is detected. Reference herein to "anti-cancer treatment" includes any treatment/agent directed at treating cancer. The terms "drug treatment", "drug" and "agent" are used interchangeably herein. The treatment may optionally involve surgery, radiation and/or drugs. Drug treatment may optionally involve chemotherapy. Optionally, the treatment may be a combination treatment in which 2 or more different therapeutic agents are used simultaneously, separately or sequentially.

Surgery may optionally be selected, for example, from lumpectomy and mastectomy.

Drugs may optionally be selected, for example, from hormonal therapy with, e.g., tamoxifen or aromatase inhibitors. Drug treatment may optionally involve, for example, an antibody specific for a receptor expressed by cancer cells, which may optionally be conjugated to a chemotherapy drug or to a radioactive particle.

The antibody may optionally, for example, be selected from a HER-2/neu specific monoclonal antibody, such as, Trastuzumab (Herceptin); Adecatumumab, alemtuzumab, Blinatumomab, Bevacizumab, Catumaxomab, Cixutumumab, Gemtuzumab, Rituximab, Trastuzumab, and/or Ibritumomab.

Drug treatment may optionally involve, for example, an anti-angiogenic agent.

Drug treatment may optionally involve, for example, a cytostatic agent, optionally selected from an alkylating agent, a cross-linking agent, an intercalating agent, a nucleotide analogue, an inhibitor of spindle formation, and/or an inhibitor of topoisomerase I and/or II.

More, particularly, it may optionally be selected from, for example, actinomycin D, BCNU (carmustine), carboplatin, CCNU, Campothecin (CPT), cantharidin, Cisplatin, cyclophosphamide, cytarabine, dacarbazine, daunorubicin, docetaxel, Doxorubicin, DTIC, epirubicin, Etoposide, gefinitib, gemcitabine, ifosamide irinotecan, ionomycin, Melphalan, Methotrexate, Mitomycin C (MMC), mitozantronemercaptopurine, Oxaliplatin, Paclitaxel (taxol), PARP-1 inhibitor, taxotere, temozolomide (TZM), teniposide, topotecane, treosulfane vinorelbine, vincristine, vinblastine, 5-Azacytidine, 5,6-Dihydro-5-azacytidine and 5-fluorouracil.

Antimicrobial Treatments

The treatment may optionally be an antimicrobial treatment, for example, if a microbial infection or imbalance is detected.

The term "antimicrobial" includes any agents that act against any type of microbe. Thus, the antimicrobial may optionally be selected from antibacterial, an antiviral, an antifungal, and an antiprotozoal. More particularly, it may optionally be selected from aminoglycosides, beta-lactam antibiotics, chloramphenicol, fluroquinolones, glycopeptides, lincosamides, macrolides, polymixins, rifampins, streptogramins, sulphonamides, tetracyclines, and/or diaminopyrimidines.

The Aminoglycoside may optionally be selected from gentamicin, tobramycin, amikacin, streptomycin, kanamycin. The beta-lactam antibiotic may optionally be selected from a penicillin such as methicillin, penicillin, amoxicillin, ampicillin, carbenicillin, oxacillin or nafcillin; a cephalosporin, such as, cephalothin, cefamandole, cefotaxime, ceftazidime, cefoperazone, or ceftriaxone; a carbapenem, such as, imipenem, meropenem, ertapenem, ordoripenem; or a monobactam, such as, aztreonam. The fluroquinolone may optionally be selected from Enrofloxacin, ciprofloxacin, Danofloxacin, Difloxacin, Ibafloxacin, Marbofloxacin, Pradofloxacin and Orbifloxacin. The glycopeptide may optionally be selected from vancomycin, teicoplanin and avoparcin. The lincosamide may optionally be selected from Lincomycin, Clindamycin and Pirlimycin. The macrolide may optionally be selected from Erythromycin, Tylosin, Spiramycin, Tilmicosin and Tulathromycin. The polymixin may optionally be selected from Polymixin B and colistin (Polymixin E). The rifampin may optionally be selected from Rifampin, Rifabutin and Rifapentine. The Streptogramin may optionally be selected from Virginiamycin. The sulfonamide may optionally be selected from Sulfadiazine, sulfamethoxazole and sulfadoxine. The tetracycline may optionally be selected from Chlortetracycline, oxytetracycline, demethylchlortetracycline, rolitetracycline, limecycline, clomocycline, methacycline, doxycycline and minocycline. The Diaminopyrimidine may optionally be selected from Trimethoprim, Aditoprim, Baquiloprim and/or Ormetoprim.

Probiotic Treatments

The treatment may optionally be an probiotic treatment, for example, if a microbial imbalance is detected, or in the treatment of a gastrointestinal disorder, such as, any of those mentioned herein.

The probiotic may comprise one or more live bacteria and/or yeasts. Optionally, it may also comprise one or more prebiotics, which are carbohydrates that act as food for probiotics and are non-digestible by humans.

Gastrointestinal and/or Anti-Inflammatory Treatments

The treatment may optionally involve surgery and/or drugs.

Drug treatment may optionally involve, for example, an antibody, selected, for example, from Adalimumab, Certolizumab, Infliximab, and/or Natalizumab.

Drug treatment may optionally involve, for example, an anti-inflammatory drug. Anti-inflammatory drugs may optionally be selected from, e.g., steroids, diclofenac, ibuprofen, naproxen, celecoxib, mefenamic acid, etoricoxib, indomethacin, and/or aspirin.

Analysis of Radio-Tracers

Positron Emission Tomography (PET) is a radiotracer imaging technique, in which tracer compounds labelled with positron-emitting radionuclides are injected into the subject of the study. These radio-tracer compounds can then be used to track biochemical and physiological processes in vivo. One of the prime reasons for the importance of PET in medical research and practice is the existence of positron-emitting isotopes of elements such as carbon, nitrogen, oxygen and fluorine which may be processed to create a range of radio-tracer compounds which are similar to naturally occurring substances in the body.

Optionally, the radio-tracer may be a compound labelled with $^{11}C$, $^{13}N$, $^{15}O$, and/or $^{18}F$. Optionally, it may be selected from the compounds listed in the table below.

| Isotope | Tracer compound | Physiological process or function | Typical application |
| --- | --- | --- | --- |
| $^{11}C$ | methionine | protein synthesis | oncology |
| $^{11}C$ | flumazenil | benzodiazepine receptor antagonist | epilepsy |
| $^{11}C$ | raclopride | D2 receptor agonist | movement disorders |
| $^{13}N$ | ammonia | blood perfusion | myocardial perfusion |
| $^{15}O$ | carbon dioxide | blood perfusion | brain activation studies |
| $^{15}O$ | water | blood perfusion | brain activation studies |
| $^{18}F$ | Fluoro-deoxy-glucose | glucose metabolism | oncology, neurology, cardiology |
| $^{18}F$ | Fluoride ion | bone metabolism | oncology |
| $^{18}F$ | Fluoro-mizonidazole | hypoxia | oncology - response to radiotherapy |

Thus, e.g., if the biologically active molecule chosen is fluorodeoxyglucose (FDG), an analogue of glucose, the concentrations of tracer will indicate tissue metabolic activity as it corresponds to the regional glucose uptake. Use of this tracer to explore the possibility of cancer metastasis (i.e., spreading to other sites) is the most common type of PET scan in standard medical care (90% of current scans).

Optionally, a subject and/or specimen may be exposed to a radio-tracer and the method may be used to analyse the location and/or concentration of a radio-tracer. Thus, the method may optionally be used to analyse the metabolism of a compound labelled with a positron-emitting radionuclide.

Xenografts

Cells and/or tissue may optionally be xenografted into a host organism for a suitable period of time, e.g., at least 1, 2 3, 4, 5, 6, 7, 8, 9, 10, 11, 12, 13, 14, 15, 16, 17, 18, 19, 20, 21, 22, 23, or 24 hours and/or 1, 2 3, 4, 5, 6, 7, 8, 9, 10, 11, 12, 13, 14, 15, 16, 17, 18, 19, 20, 21, 22, 23, or 24 days. For example, cells or tissue obtained from a human tumour may be xenografted into a host animal. Optionally, the method may involve making a xenograft and/or removing a xenograft or sample thereof from a host organism. Optionally, the method may be performed on a provided xenograft.

Optionally, the xenograft may comprise or consist of tumour cells. A xenograft specimen may optionally be analysed, e.g., to analyse the impact of the host environment on the cells of the xenograft. Optionally, a cell population and/or tissue may be analysed prior to and after xenografting, and/or a xenograft specimen may be compared to a cell population or tissue that was not xenografted.

Further Definitions

The term "target entity" is used herein to refer to the entity which it is desired to analyse within the target. Thus, any reference to a "target" should be understood to mean a target comprising one or more different target entities. Thus, the target entity may, e.g., be a cell, microbe and/or compound. For example, the target may be tissue and the target entity may be cancer cells.

The terms "analysis", "analysing" and derivatives of these terms are used herein to encompass any of the following: detection of a target entity; identification of a target entity; characterisation of a target entity; determination of the location of target entity; determination of a status, e.g. a disease status; and/or determination of a margin between two different disease or tissue types and the like.

It should be understood that any reference herein to "analysing" a target is intended to mean that the target is analysed on the basis of the spectrometric data. Thus, for example, by an expression, such as, "analysing spectrometric data in order to identify a cell type" is meant that the identity of a cell type is determined based upon the spectrometric data.

The analysis may be qualitative and/or quantitative. Thus, optionally, any type of analysis may involve determining the concentration, percentage, relative abundance or the like of the target entity. For example, the percentage of cancer cells within a tissue, the relative abundance of microbes in a target, and/or the concentration of a compound may be analysed. Optionally, an increase or decrease in a target entity may be analysed.

The terms "detection", "detecting" and derivatives of these terms are used interchangeably herein to mean that the presence or absence of a target entity or biomarker therefor is determined.

The terms "identify", "identification" and derivations of these terms are used interchangeably herein to mean that information about the identity of a target entity or biomarker therefor is obtained. This may optionally be the determination of the identity, and/or the confirmation of the identity. This may optionally include information about the precise identity of the target entity or biomarker therefor. However, it may alternatively include information that allows the target entity to be identified as falling into a particular classification, as discussed elsewhere herein.

By "identifying" a microbe is meant that at least some information about the identity is obtained, which may, for example, be at any taxonomic level.

By "identifying" a cell is meant that at least some information about the cell type is obtained. By "identifying" a diseased cell is meant that it is determined or confirmed that a cell is diseased.

By "identifying" a compound is meant that at least some information about the structure and/or function of the compound is obtained, e.g., the information may optionally allow a compound to be identified as comprising or consisting of a compound selected from any of the types disclosed herein, and/or as being characterised by one or more of the functional groups disclosed herein.

The terms "diagnosis" or "diagnosing" and derivations of these terms as used herein refer to the determination whether or not a subject is suffering from a disease. Optionally, the method may involve analysing a target and, on the basis of one or more of the following making a diagnosis that a subject is or is not suffering from a particular disease: detecting a target entity; identifying a target entity; detecting an increase in a target entity; detecting a decrease in a target entity.

An increase or decrease may be determined by reference to a suitable reference, comparator or control. For example, it is known how many inflammatory cells or inflammatory molecules are typically present in the tissue of a healthy individual, so an increase in inflammatory cells or inflammatory molecules in a target may easily be determined by comparing it to a healthy control.

The term "monitoring" and derivations of this term as used herein refer to the determination whether any changes take place/have taken place. Typically, it is determined whether any changes have taken place over time, i.e. since a previous time point. The change may, for example, be the development and/or progression of a disease, such as, any of the diseases mentioned. Optionally, the method may involve analysing a target and, on the basis of one or more of the following monitoring a subject or disease: detecting a target entity; identifying a target entity; detecting an increase in a target entity; detecting a decrease in a target entity.

The term "prognosis" and derivations of this term as used herein refer to risk prediction of the severity of disease or of the probable course and clinical outcome associated with a disease. Thus, the term "method of prognosis" as used herein refers to methods by which the skilled person can estimate and/or determine a probability that a given outcome will occur. The outcome to which the prognosis relates may be morbidity and/or mortality. In particular, the prognosis may relate to "progression-free survival" (PFS), which is the length of time that a subject lives with the disease without the disease progressing. Thus, PFS may, for example, be the time from the start of therapy to the date of disease progression, or the time from the end of therapy to the date of disease progression.

Optionally, the method may involve analysing a target and, on the basis of one or more of the following making a prognosis: detecting a target entity; identifying a target entity; detecting an increase in a target entity; detecting a decrease in a target entity.

By "progressing" or "progression" and derivations of these terms is meant that the disease gets worse, i.e. that the severity increases. For example, in the case of cancer, it may mean that the tumour burden increases, for example a tumour increases in size and/or weight; that the cancer becomes malignant or more malignant; and/or that metastasis develops or the incidence and/or rate of metastasis increases.

The prognosis may relate to overall survival. By "overall survival" (OS) is meant the length of time that a subject lives with the disease before death occurs. Overall survival may, for example, be defined as the time from diagnosis of the disease; the time of treatment start; or the time of treatment completion, until death. Overall survival is typically expressed as an "overall survival rate", which is the percentage of people in a study or treatment group who are still alive for a certain period of time after they were diagnosed with, or started treatment for, or completed treatment for, a disease. The overall survival rate may, for example, be stated as a five-year survival rate, which is the percentage of people in a study or treatment group who are alive five years after their diagnosis or the start or completion of treatment.

Statistical information regarding the average (e.g. median, mean or mode) OS and PFS of subjects having a particular type of disease is available to those skilled in the art. A determination whether a subject has, or is likely to have, an increased or decreased OS or PFS compared to such an average may therefore be made.

A determination that the likelihood and/or length of PFS and/or overall survival is decreased means that the prognosis is poor or adverse. The terms "poor" and "adverse" are used interchangeably herein. A "poor" prognosis may be defined as a prognosis that is worse than the reference prognosis for a subject, so it may also be referred to as a "worse" prognosis, and a "good" or "non-adverse" prognosis may be defined as a prognosis that is better than the reference prognosis for a subject so it may also be referred to as a "better" prognosis. The skilled person will appreciate that for the "reference prognosis" subjects having the same type of disease, optionally the same stage of disease, should be used. The "reference prognosis" may be the average prognosis or a typical prognosis determined by any other suitable method.

An adverse or worse prognosis may be defined as a shorter overall survival or an increased likelihood of shorter overall survival and/or shorter PFS or an increased likelihood of shorter PFS.

By "regressing" or "regression" is meant that the disease improves, i.e. that the severity decreases. For example, in the case of cancer or a tumour, it may mean that the tumour burden decreases, for example a tumour decreases in size and/or weight, or becomes undetectable; that the cancer becomes less malignant; and/or that the incidence and/or rate of metastasis decreases.

A response to treatment may include progression, regression, a combination of progressive and regressive elements, or the absence of any progression or regression. Thus, for example, in the case of cancer, a response to treatment may include a change in one or more criteria selected from tumour size, tumour weight, tumour number, malignancy and metastasis.

By "development" is meant the onset of a disease.

The term "prediction" or "predicting" as used herein refers to determining the likelihood of a particular outcome.

The term "stratification" or "stratifying" as used herein refers to the division of a population into subpopulations on the basis of specified criteria. More particularly, it refers to the division of a cohort of subjects into at least two groups on the basis of specific criteria, which in the context of the present invention comprise or consist of the results of the method of analysis. Optionally, subjects may be stratified into those likely to respond to a particular treatment and those unlikely to respond; and/or subjects may be stratified based on their diagnosis, prognosis and/or the response that they have presented to treatment.

Optionally, the method may involve analysing a target and, on the basis of one or more of the following, stratifying subjects: detecting a target entity; identifying a target entity; detecting an increase in a target entity; detecting a decrease in a target entity.

The term "treatment" or "treating" as used herein refers to a course of action which is aimed at bringing about a medical benefit for a subject. The treatment may be prophylactic or therapeutic.

By "prophylactic" is meant that the treatment is preventative, i.e. it is applied before the onset of disease. By "therapeutic" is meant that the treatment is applied after the onset of disease.

Optionally, the method may involve analysing a target and, on the basis of one or more of the following, determining that a subject should or should not receive a particular treatment: detecting a target entity; identifying a target entity; detecting an increase in a target entity; detecting a decrease in a target entity.

Optionally, the method may involve analysing a target and, on the basis of one or more of the following, determining that a subject has or has not responded a particular treatment: detecting a target entity; identifying a target entity; detecting an increase in a target entity; detecting a decrease in a target entity.

Optionally, the method may involve analysing a target and, on the basis of one or more of the following, administering a particular treatment to a subject: detecting a target entity; identifying a target entity; detecting an increase in a target entity; detecting a decrease in a target entity.

Optionally, the method may additionally involve one or more of the following steps, particularly in the context of diagnosis:

a) Determining the presence of one or more symptoms of disease; b) blood test; c) bone marrow test; d) bone scan; e) computerised tomography (CT) scan; f) x-ray; m) MRI; n) positron emission tomography (PET) scan; o) ultrasound scan; p) biopsy analysis; q) Metabolomics, i.e. the study of the entire set of small-molecule metabolites present in a biological specimen.

Analysis of Spectrometric Data

Any of the methods of the invention may optionally involve the analysis of spectrometric data; more particularly, the analysis of spectrometric data from a target, e.g., a first target location. The terms "spectral data" and "spectrometric data" are used interchangeably herein.

The analysis of a target may be based solely on the analysis of spectral data, or it may optionally involve one or more further analytical tools, details of which are discussed elsewhere herein.

In some embodiments, the spectrometric data may optionally provide direct information about the target or target entity.

For example, if a particular cell type has a specific spectrometric signal pattern, then obtaining this signal pattern from a target provides direct information about the presence, identity and/or characteristics of that cell type.

For example, if a particular microbe has a specific spectrometric signal pattern, then obtaining this signal pattern from a target provides direct information about the presence, identity and/or characteristics of that microbe.

For example, if a particular compound has a specific spectrometric signal pattern, then obtaining this signal pattern from a target provides direct information about the presence, identity and/or characteristics of that compound. This may be the case, for example, for a compound which is secreted by a cell and/or by a microbe, or for an agent, such as, a drug or a metabolite thereof.

However, in other embodiments, spectrometric data may optionally provide indirect information about the target or target entity. This may be the case, for example, for a compound which is produced, but not secreted, by a cell and/or by a microbe. The presence of this compound may optionally be detected indirectly by detecting a spectrometric signal pattern which is characteristic of a cell and/or microbe containing said compound.

Spectrometric data obtained from a target, e.g., a first target location, may optionally be compared to one or more other spectrometric data, which may conveniently be referred to herein as "reference", "control" or "comparator" spectrometric data.

As explained elsewhere herein, analysing spectrometric data may optionally comprise analysing one or more sample spectra so as to classify an aerosol, smoke or vapour sample. This may comprise developing a classification model or library using one or more reference sample spectra, or may comprise using an existing library.

Optionally, an analysis may be made to determine whether spectrometric data obtained from a target matches or corresponds sufficiently to the "reference", "control" or "comparator" spectrometric data to make a positive determination. Optionally, a positive determination may be made if the spectrometric data corresponds more closely to one library entry than any other library entry.

The term "reference" spectrometric data is used herein to mean spectrometric data from a known cell type, microbe or compound. Reference spectrometric data may optionally be publicly available, or the skilled person may generate a library of reference spectrometric data. The method may optionally involve comparing the spectrometric data to one or more reference spectrometric data. If the spectrometric data obtained from a target matches or corresponds sufficiently to a reference spectrometric data, then optionally a positive determination may be made. If the spectrometric data obtained from a target does not match or correspond sufficiently to a reference spectrometric data, then optionally a negative determination may be made.

The term "comparator" spectrometric data is used herein to mean spectrometric data obtained from a second target location. The first and second target locations may be located in different targets, or at the different locations of the same target. The method may optionally involve comparing the spectrometric data to one or more comparator spectrometric data. If the spectrometric data obtained from a target matches or corresponds sufficiently to a comparator spectrometric data, then optionally a positive determination may be made. If the spectrometric data obtained from a target does not match or correspond sufficiently to a comparator spectrometric data, then optionally a negative determination may be made.

The term "control" spectrometric data is used herein to mean spectrometric data obtained from the first target at an earlier point in time. Control spectrometric data may, for example, be used when monitoring, e.g., an operation, a disease, a cell culture, a tissue culture, and/or a microbial culture. Any of the methods may optionally involve comparing the spectrometric data to one or more control spectrometric data. If the spectrometric data obtained from a target matches or corresponds sufficiently to a control spectrometric data, then optionally a positive determination may be made. If the spectrometric data obtained from a target does not match or correspond sufficiently to a control spectrometric data, then optionally a negative determination may be made.

By a "positive determination" is meant that the presence, identity and/or characteristics of a particular cell type, microbe and/or compound is determined. For example, a positive determination may involve determining that a target entity of a particular classification is present; that a target entity has a certain characteristic; and/or that a particular compound is present.

For example, in the case of a microbial target entity, a positive determination may, e.g., involve determining that a microbe of a particular taxonomic rank is present; that a particular microbe has a certain characteristic, such as, resistance to a particular drug; and/or that a particular compound is being produced by a microbe.

For example, in the case of a cell target entity, a positive determination may, e.g., involve determining that a cancer cell or lymphocyte is present; and/or that a cell has a certain characteristic, such as, that it expresses a particular cell surface marker.

For example, in the case of a compound target entity, a positive determination may, e.g., involve determining that a particular type of compound is present; and/or that a compound has a certain characteristic, such as, a particular glycosylation pattern.

Thus, for example, if the spectrometric data of a first sample matches or corresponds sufficiently to a reference spectrometric data, then the presence in the first sample of a target entity corresponding to the entity from which the reference spectrometric data was obtained may optionally be confirmed. If the spectrometric data of a first sample matches or corresponds sufficiently to a reference spectrometric data, then the target entity present in the first sample may optionally be identified as corresponding to the identity of the entity from which the reference spectrometric data was obtained. If the spectrometric data of a first sample matches or corresponds sufficiently to a reference spectrometric data, then the target entity present in the first sample may optionally be characterised as having a characteristic corresponding to the characteristic of the entity from which the reference spectrometric data was obtained. If the spectrometric data of a first sample matches or corresponds sufficiently to a reference spectrometric data, then a determination may optionally be made that the target entity present in the first sample produces the compound produced by the entity from which the reference spectrometric data was obtained.

As explained elsewhere herein, by determining or confirming the "identity" of a microbe or cell is meant that at least some information about the identity is obtained, which may, for example, be at any taxonomic level. Thus, for example, if the reference spectrometric data is from *Candida albicans*, then in one embodiment a match or sufficient correspondence may optionally be used to identify the first microbe as belonging to the genus *Candida*, whereas in another embodiment a match or sufficient correspondence may optionally be used to identify the first microbe as belonging to the species *Candida albicans*.

As another example, if the spectrometric data of a first sample matches or corresponds sufficiently to a comparator spectrometric data, then the presence in the first sample of a target entity corresponding to the entity from which the comparator spectrometric data was obtained may optionally be confirmed. If the spectrometric data of a first sample matches or corresponds sufficiently to a comparator spectrometric data, then the target entity present in the first sample may optionally be identified as corresponding to the identity of the entity from which the comparator spectrometric data was obtained. If the spectrometric data of a first sample matches or corresponds sufficiently to a comparator spectrometric data, then the target entity present in the first sample may optionally be characterised as having a characteristic corresponding to the characteristic of the entity from which the comparator spectrometric data was obtained. If the spectrometric data of a first sample matches or corresponds sufficiently to a comparator spectrometric data, then a determination may optionally be made that the target entity present in the first sample produces the compound produced by the entity from which the comparator spectrometric data was obtained.

In other words, a match or sufficient correspondence to a reference or comparator spectrometric data respectively may be used to confirm that the first target entity and the reference or comparator entity respectively have the same identity, whereas the lack of a match or sufficient correspondence to a reference or comparator spectrometric data respectively may be used to confirm that the first target entity and the reference or comparator entity respectively do not have the same identity.

By a "negative determination" is meant that the absence of a particular target entity is determined; and/or that it is determined that a target entity does not have a particular identity and/or characteristic.

For example, a negative determination may involve determining that a particular target entity is not present; that a particular target entity does not have a certain characteristic; and/or that a particular compound is not present.

For example, in the case of a microbial target entity, a negative determination may, e.g., involve determining that a microbe of a particular taxonomic rank is not present; that a particular microbe does not have a certain characteristic such as resistance to a particular drug; and/or that a particular compound is not being produced.

For example, in the case of a cell target entity, a negative determination may, e.g., involve determining that a cancer cell or lymphocyte is not present; and/or that a cell does not have a certain characteristic, such as, that it does not express a particular cell surface marker.

For example, in the case of a compound target entity, a negative determination may, e.g., involve determining that a particular type of compound is not present; and/or that a compound does not have a certain characteristic, such as, a particular glycosylation pattern.

Thus, for example, if the spectrometric data of a first sample does not match or correspond sufficiently to a reference spectrometric data, then the absence or insufficient presence in the first sample of a target entity corresponding to the entity from which the reference spectrometric data was obtained may optionally be confirmed. If the spectrometric data of a first sample does not match or correspond sufficiently to a reference spectrometric data, then the target entity present in the first sample may optionally be identified as not corresponding to the identity of the entity from which the reference spectrometric data was obtained. If the spectrometric data of a first sample does not match or correspond sufficiently to a reference spectrometric data, then the target entity present in the first sample may optionally be characterised as not having a characteristic corresponding to the characteristic of the entity from which the reference spectrometric data was obtained. If the spectrometric data of a first sample does not match or correspond sufficiently to a reference spectrometric data, then a determination may optionally be made that the target entity present in the first sample does not produce, or insufficiently produces, the compound produced by the entity from which the reference spectrometric data was obtained.

As another example, if the spectrometric data of a first sample matches or corresponds sufficiently to a control spectrometric data, then a determination may be made that no, or no significant, change has taken place, whereas if the spectrometric data of a first sample does not match or correspond sufficiently to a control spectrometric data, then a determination may be made that a change, optionally a significant change, has taken place. Examples of a change may, for example, be the presence of a contaminating or infiltrating cell, microbe and/or compound; or a change in the cell or microbe's behaviour or its environment, such as, a change in the cell or microbe's growth rate, respiration rate; rate of production of a compound, such a secreted compound; environmental temperature, pH, nutrient availability and so on.

As mentioned elsewhere herein, the method may optionally involve the analysis of biomarkers.

If a biomarker for a target entity or disease status is known (e.g., from the prior art or from the work disclosed herein), then the method may optionally involve analysing the target for the presence of the spectrometric signal of that biomarker. The spectrometric signal of any biomarker may optionally be looked up in the literature, a database, or, if necessary, it may easily be determined experimentally.

For example, as shown herein, C26:1 sulfatide ($C_{50}H_{94}NO_{11}S$) is a biomarker for normal brain tissue, with a spectrometric signal of m/z about 916.655. When analysing a brain target to try to distinguish between healthy and diseased brain tissue, the method may optionally involve analysing the target for the presence of a spectrometric signal of m/z about 916.655.

As mentioned elsewhere herein, the analyte giving rise to a particular spectrometric signal, e.g., a particular m/z, may optionally be further characterised, e.g., using MS-MS. Thus, ionic species in the mass spectra may optionally be identified based on exact mass measurements, e.g., with a mass deviation <3 ppm, and/or MS/MS fragmentation patterns.

Isobaric lipids with different head groups may optionally be differentiated by ion mobility.

Thus, optionally, the method may involve analysing the target for the presence of a spectrometric signal of one or more biomarkers, optionally selected from any of the biomarkers mentioned herein.

A biomarker for diseased cells may optionally be determined, e.g., by subtracting the spectrometric signals obtained from normal cells from the spectrometric signals obtained from diseased cells, to arrive at spectrometric signals that are specific for the diseased cells.

Optionally, the analyte giving rise to a particular m/z and/or ion mobility spectrometric signal may optionally be further characterised, e.g., using MS/MS. Thus, ionic species in the mass and/or ion mobility spectra may optionally be identified based on techniques such as use of the ion mobility drift time and/or exact mass measurements (e.g., with a mass deviation <3 ppm), and/or MS/MS fragmentation patterns and/or.

Thus, optionally, the method may involve analysing the target for the presence of a spectrometric signal of one or more biomarkers, optionally selected from any of the biomarkers mentioned herein.

The spectrometric data may comprise one or more sample spectra. Obtaining the spectrometric data may comprise obtaining the one or more sample spectra. Analysing the spectrometric data may comprise analysing the one or more spectra. Obtaining the one or more sample spectra may comprise a binning process to derive a set of time-intensity pairs and/or a set of sample intensity values for the one or more sample spectra. The binning process may comprise accumulating or histogramming ion detections and/or intensity values in a set of plural bins. Each bin in the binning process may correspond to particular range of times or time-based values, such as masses, mass to charge ratios, and/or ion mobilities. The bins in the binning process may each have a width equivalent to a width in Da or Th (Da/e) in a range selected from a group consisting of: (i) < or >0.01; (ii) 0.01-0.05; (iii) 0.05-0.25; (iv) 0.25-0.5; (v) 0.5-1.0; (vi) 1.0-2.5; (vii) 2.5-5.0; and (viii) < or >5.0. It has been identified that bins having widths equivalent to widths in the range 0.01-1 Da or Th (Da/e) can provide particularly useful sample spectra for classifying some aerosol, smoke or vapour samples, such as samples obtained from tissues. The bins may or may not all have the same width. The widths of the bin in the binning process may vary according to a bin width function. The bin width function may vary with a time or time-based value, such as mass, mass to charge ratio and/or ion mobility. The bin width function may be non-linear (e.g., logarithmic-based or power-based, such as square or square-root based). The bin width function may take into account the fact that the time of flight of an ion may not be directly proportional to its mass, mass to charge ratio, and/or ion mobility. For example, the time of flight of an ion may be directly proportional to the square-root of its mass and/or mass to charge ratio.

Spectrometric Library

The terms "spectrometric library" and "spectrometric database" are used interchangeably herein.

The skilled person may use any publicly available spectrometric data as reference spectrometric data. Examples of useful databases are: LipidMaps, LipidBlast and LipidXplorer, details of which are provided in the following publications: "LipidBlast—in-silico tandem mass spectrometry database for lipid identification" by Kind et al., Nat Methods. 2013 August; 10(8): 755-758; "LipidXplorer: A Software for Consensual Cross-Platform Lipidomics" by Herzog et al. PLoS ONE 7(1): e29851; and "Lipid classification, structures and tools" by Fahy et al. Biochimica et Biophysica Acta (BBA)—Molecular and Cell Biology of Lipids, Volume 1811, Issue 11, November 2011, Pages 637-647, Lipidomics and Imaging Mass Spectrometry, see also http://www.lipidmaps.org/.

Alternatively or in addition, the skilled person may construct a spectrometric library by obtaining spectrometric data from one or more samples, which may optionally, in the case of microbes, include type culture strains and/or clinical and/or environmental microbial isolates; in the case of cells or tissues, the sample(s) may optionally include a cell line, cell culture, tissue sample and the like; in the case of compound, the sample(s) may optionally be purchased or synthesised.

Type culture strains and cell lines may optionally be obtained from culture collections, such as, the American Type Culture Collection (ATCC) (10801 University Boulevard, Manassas, VA 20110 USA).

The present inventors generated a spectrometric library using over 1500 microbial strains, including clinical isolates and type culture strains from the ATCC, encompassing about 95 genera and about 260 species of bacteria and fungi. To expedite the generation of the spectrometric library, the inventors set up high throughput culturing, automated colony imaging, colony picking and REIMS analysis.

The present inventors have also generated spectrometric libraries using tissues and/or cell lines, details of which are provided elsewhere herein, including in the Examples.

The generation of a spectrometric library from microbes, cell lines and/or tissues may optionally be combined with a further analysis, e.g., taxonomic classification and/or histology, e.g., based on any of the further analytical tools discussed elsewhere herein. For example, the tool may be DNA analysis. This may involve DNA sequencing, optionally preceded by DNA isolation and/or amplification using, e.g., PCR. For bacteria, sequencing of all or part of the 16S rRNA gene is particularly suitable, whereas for fungi, sequencing of all or part of the internal transcribed spacer (ITS) region is particularly suitable.

Analysing Sample Spectra

The step of analysing the spectrometric data may comprise analysing one or more sample spectra so as to classify an aerosol, smoke or vapour sample.

Analysing the one or more sample spectra so as to classify the aerosol, smoke or vapour sample may comprise unsupervised analysis of the one or more sample spectra (e.g., for dimensionality reduction) and/or supervised analysis of the one or more sample spectra (e.g., for classification).

Analysing the one or more sample spectra may comprise unsupervised analysis (e.g., for dimensionality reduction) followed by supervised analysis (e.g., for classification).

Analysing the one or more sample spectra may be performed as discussed elsewhere herein.

A list of analysis techniques which are intended to fall within the scope of the present invention are given in the following table:

| Analysis Techniques |
| --- |
| Univariate Analysis |
| Multivariate Analysis |
| Principal Component Analysis (PCA) |
| Linear Discriminant Analysis (LDA) |
| Maximum Margin Criteria (MMC) |
| Library Based Analysis |
| Soft Independent Modelling Of Class Analogy (SIMCA) |
| Factor Analysis (FA) |
| Recursive Partitioning (Decision Trees) |
| Random Forests |
| Independent Component Analysis (ICA) |
| Partial Least Squares Discriminant Analysis (PLS-DA) |
| Orthogonal (Partial Least Squares) Projections To Latent Structures (OPLS) |
| OPLS Discriminant Analysis (OPLS-DA) |
| Support Vector Machines (SVM) |
| (Artificial) Neural Networks |
| Multilayer Perceptron |
| Radial Basis Function (RBF) Networks |
| Bayesian Analysis |
| Cluster Analysis |
| Kernelized Methods |
| Subspace Discriminant Analysis |
| K-Nearest Neighbours (KNN) |
| Quadratic Discriminant Analysis (QDA) |
| Probabilistic Principal Component Analysis (PPCA) |
| Non negative matrix factorisation |
| K-means factorisation |
| Fuzzy c-means factorisation |
| Discriminant Analysis (DA) |

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 40:
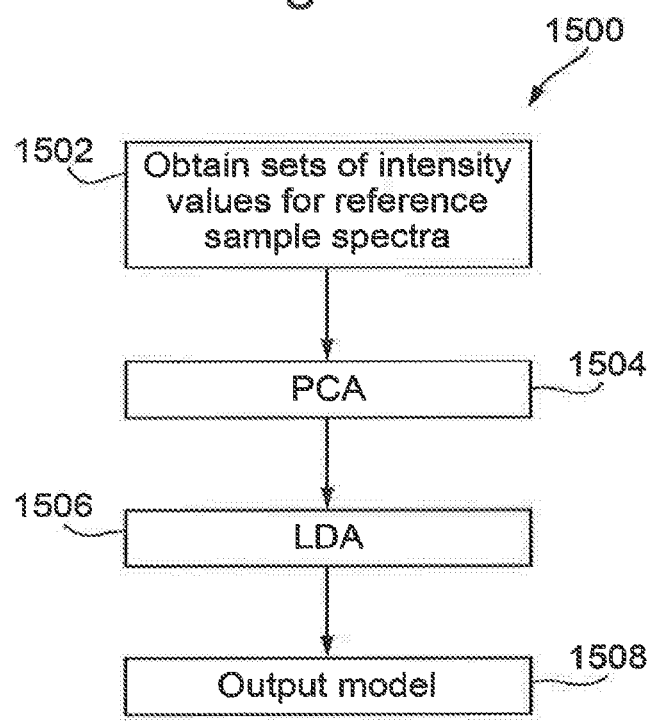
FIG. 40 shows a method of analysis that comprises building a classification model according to various embodiments.

FIG. 40 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 41:
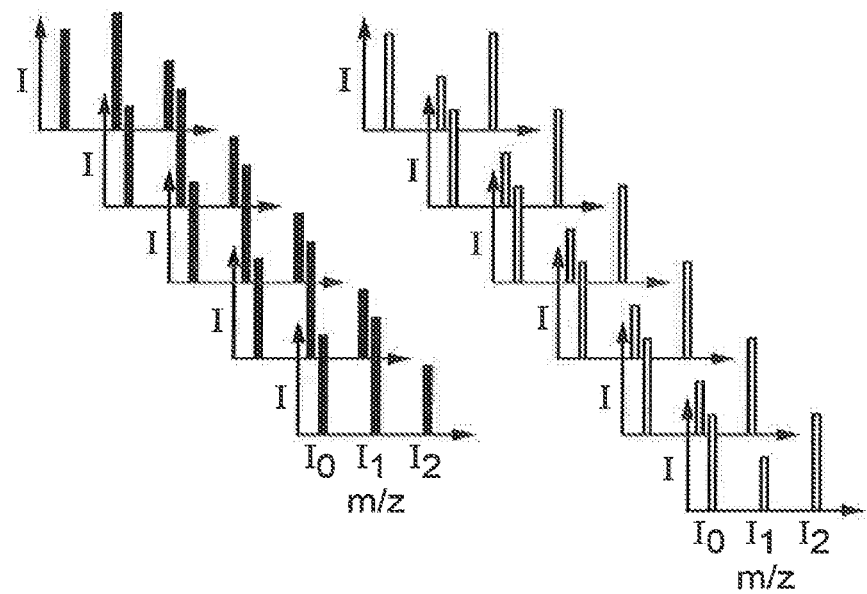
FIG. 41 shows a set of reference sample spectra obtained from two classes of known reference samples.

FIG. 41 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 42:
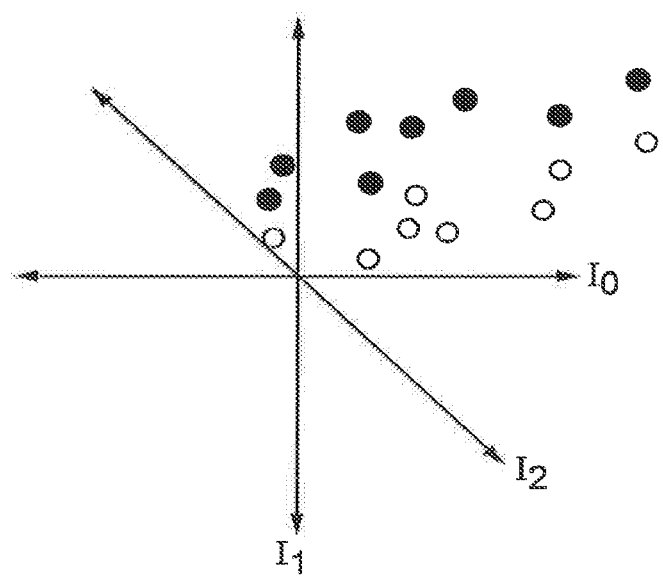
FIG. 42 shows a multivariate space having three dimensions defined by intensity axes, wherein the multivariate space comprises plural reference points, each reference point corresponding to a set of three peak intensity values derived from a reference sample spectrum.

FIG. 42 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 43:
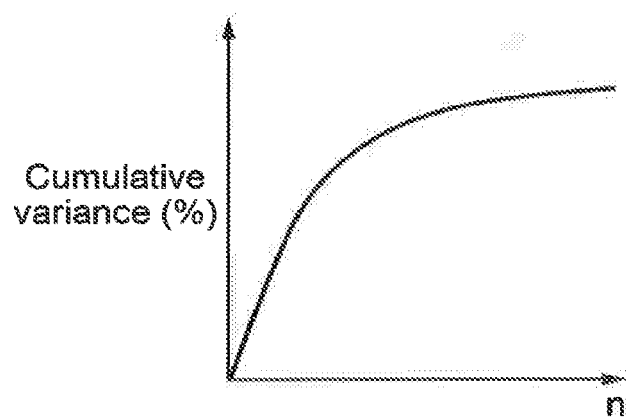
FIG. 43 shows a general relationship between cumulative variance and number of components of a PCA model.

FIG. 43 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \qquad (1)$$

Figure 44:
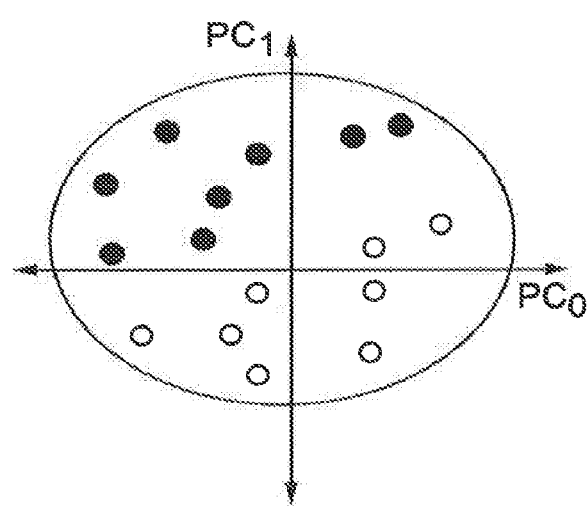
FIG. 44 shows a PCA space having two dimensions defined by principal component axes, wherein the PCA space comprises plural transformed reference points or scores, each transformed reference point or score corresponding to a reference point of FIG. 42.

FIG. 44 shows the resultant PCA space for the reference sample spectra of FIGS. 41 and 42. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 41 and therefore to a reference point of FIG. 42.

As is shown in FIG. 44, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z = SU \qquad (2)$$

where the matrix Z contains the scores transformed into the LDA space.

Figure 45:
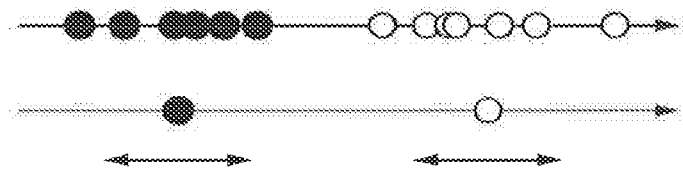
FIG. 45 shows a PCA-LDA space having a single dimension or axis, wherein the LDA is performed based on the PCA space of FIG. 44, the PCA-LDA space comprising plural further transformed reference points or class scores, each further transformed reference point or class score corresponding to a transformed reference point or score of FIG. 44.

FIG. 45 shows a PCA-LDA space having a single dimension or axis, wherein the LDA is performed in the PCA space of FIG. 44. As is shown in FIG. 45, the LDA space comprises plural further transformed reference points or PCA-LDA scores, with each further transformed reference point corresponding to a transformed reference point or PCA score of FIG. 44.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \qquad (3)$$

where $V_g$ are the class covariance matrices in the PCA space.

The transformed class average position $z_g$ for class g may be given by $$s_g U = z_g \qquad (4)$$

where $s_g$ is the class average position in the PCA space.
Multivariate Analysis—Using a Model for Classification By way of example, a method of using a classification model to classify an aerosol, smoke or vapour sample will now be described.

Figure 46:
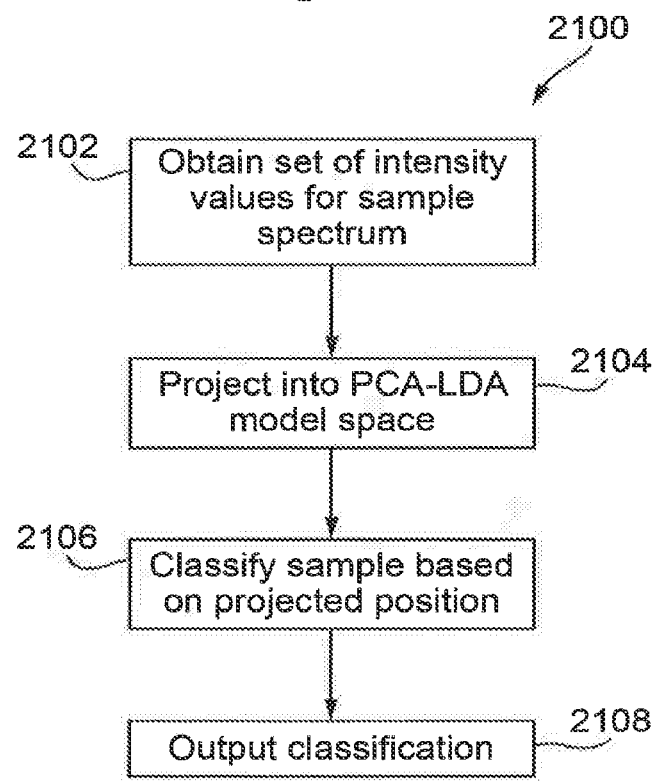
FIG. 46 shows a method of analysis that comprises using a classification model according to various embodiments.

FIG. 46 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 47:
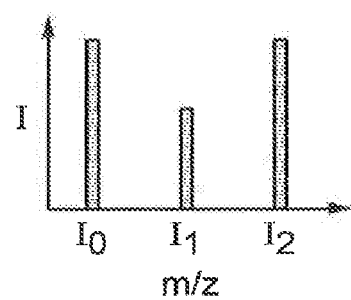
FIG. 47 shows a sample spectrum obtained from an unknown sample.

FIG. 47 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector $s_x$ for the sample spectrum can be obtained as follows:

$$d_x L = s_x \qquad (5)$$

Then, a transformed PCA-LDA vector $z_x$ for the sample spectrum can be obtained as follows:

$$s_x U = z_x \qquad (6)$$

Figure 48:
FIG. 48 shows the PCA-LDA space of FIG. 45, wherein the PCA-LDA space further comprises a PCA-LDA projected sample point derived from the peak intensity values of the sample spectrum of FIG. 47.

FIG. 48 again shows the PCA-LDA space of FIG. 45. However, the PCA-LDA space of FIG. 48 further comprises the projected sample point, corresponding to the transformed PCA-LDA vector $z_x$, derived from the peak intensity values of the sample spectrum of FIG. 47.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \qquad (8)$$

and the data vector $d_x$ may be assigned to the class for which this distance is smallest.

In addition, treating each class as a multivariate Gaussian, a probability of membership of the data vector to each class may be calculated.
Library Based Analysis—Developing a Library for Classification By way of example, a method of building a classification library using plural input reference sample spectra will now be described.

FIG. 49 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} / \log \frac{M_{max}}{M_{min}} \right\rfloor$$

where $N_{chan}$ is a selected value and [x] denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i=1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i \mid \mu_i, D_i) = \frac{1}{D_i} \frac{C^{C-1/2}\Gamma(C)}{\sqrt{\pi}\,\Gamma(C-1/2)} \frac{1}{\left(C + \frac{(y_i - \mu_i)^2}{D_i^2}\right)^C}$$

where $1/2 \le C < \infty$ and where $\Gamma(C)$ is the gamma function.

The above equation is a generalised Cauchy distribution which reduces to a standard Cauchy distribution for C=1 and becomes a Gaussian (normal) distribution as $C \to \infty$. The parameter $D_i$ controls the width of the distribution (in the Gaussian limit $D_i=\sigma_i$ is simply the standard deviation) while the global value C controls the size of the tails.

In one example, C is 3/2, which lies between Cauchy and Gaussian, so that the likelihood becomes:

$$Pr(y_i \mid \mu_i, D_i) = \frac{3}{4}\frac{1}{D_i}\frac{1}{(3/2 + (y_i - \mu_i)^2/D_i^2)^{3/2}}$$

For each library entry, the parameters $\mu_i$ are set to the median of the list of values in the i'th channel of the input reference sample spectra while the deviation $D_i$ is taken to be the interquartile range of these values divided by $\sqrt{2}$. This choice can ensure that the likelihood for the i'th channel has the same interquartile range as the input data, with the use of quantiles providing some protection against outlying data.

Library-Based Analysis—Using a Library for Classification

By way of example, a method of using a classification library to classify an aerosol, smoke or vapour sample will now be described.

FIG. 50 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y \mid \mu, D) = \prod_{i=1}^{N_{chan}} Pr(y_i \mid \mu_i, D_i)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class s is given by:

$$Pr(\tilde{s} \mid y) = \frac{L_{\tilde{s}}^{(1/F)}}{\Sigma_s L_s^{(1/F)}}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}}$$

Again, the scores $R_s$ are normalised over all candidate classes 's'.

The aerosol, smoke or vapour sample may then be classified as belonging to the class having the highest probability and/or highest RMS classification score.

Further Analytical Tools

Any of the methods of the invention may optionally include a step of using one or more additional analytical tools. Such a tool may, for example, be selected from microscopic examination; nucleic acid analysis, for example, using restriction enzymes, hybridisation, polymerase chain reaction (PCR) amplification and/or sequencing; and/or testing for antigens. Such tools are well known in the art, but brief details are provided below.

The specimen may be examined visually, without any additional aids, such as, a microscope.

Microscopic examination may, for example, optionally be light microscopy and/or electron microscopy.

Nucleic acid analysis may optionally involve isolation and purification of DNA and/or RNA.

Nucleic acid analysis via PCR amplification may, for example, optionally involve amplification of all or part of a suitable gene. For example, in the case of a microbe, the gene may be the bacterial 16S rRNA gene, and universal and/or species-specific primers may be used. Other examples of suitable microbial genes which may optionally be analysed alternatively or in addition include, for example, microbial species-specific genes or virulence genes, for example, Shiga toxin (stx), intimin (eae), flagellar H-antigen genes fliC-fliA, hsp65, rpoB and/or recA. For fungi, PCR amplification of all or part of the internal transcribed spacer (ITS) is particularly suitable. When analysing human or animal cells, PCR may, e.g., be used to amplify a disease-specific and/or a tissue-specific gene.

Optionally, the PCR may be Real-time PCR or quantitative PCR. Optionally, Reverse-transcriptase polymerase chain reaction (RT-PCR) may be used to analyse RNA expression.

Nucleic acid analysis with restriction enzymes may, for example, optionally involve restriction-fragment length polymorphism (RFLP) analysis. RFLP, is a technique that exploits variations in the length of homologous DNA sequences. RFLP analysis may involve a restriction digest, i.e. incubating a DNA with a suitable restriction enzyme such as BamHI, HindIII or EcoRI. Each restriction enzyme can recognise and cut a specific short nucleic acid sequence. The resulting DNA fragments may then be separated by length, for example, through agarose gel electrophoresis. The DNA fragments in the gel may optionally be stained, for example, with ethidium bromide, and the pattern of the fragments of different length may be determined.

Optionally, the DNA fragment may be transferred to a membrane via the Southern blot procedure. The membrane may then be exposed to a labelled DNA probe to allow hybrisidation to occur. The label may, for example, be or comprise a radioactive isotope or digoxigenin (DIG). Any unhybridised probe may then be washed off. The label may then be detected and the pattern of the fragments which have hybridised to the labelled probe may be determined.

Sequencing may, for example, optionally involve the dideoxy or chain termination method. In this method, the DNA may be used as a template to generate a set of fragments that differ in length from each other by a single base. The fragments may then be separated by size, and the bases at the end may be identified, recreating the original sequence of the DNA.

Hybridisation analysis may, for example, optionally include DNA-DNA hybridization of one or more selected DNA fragments, genes or whole genomic DNA from a first cell or microbe to a labelled DNA probe to determine the genetic similarity between the first cell or microbe and the known or comparator cell or microbe. Hybridisation analysis may, for example, involve transfer of the DNA to a membrane via the Southern blot procedure, labelling and detection as described above.

Nucleic acid analysis may optionally involve e.g., denaturing gradient gel electrophoresis (DGGE) and/or temperature gradient gel electrophoresis (TGGE).

Fatty acid profiling of cells or microbes may, for example, optionally be carried out using gas-chromatography coupled to a flame ionisation detector (GC-FID), or high performance liquid chromatography (HPLC).

With respect to microbial colony morphology, one or more of the following may, for example, optionally be examined: size; whole colony shape, which may, for example, be circular, irregular, or rhizoid; colony edge, which may, for example, be smooth, filamentous, or undulating; elevation, which may, for example, be flat, raised, convex or crateriform; surface, which may, for example, be wrinkled, rough, waxy, or glistening; opacity, which may, for example, be transparent, translucent, or opaque; pigmentation; colour, which may, for example, be red, yellow, or white; and/or water solubility.

With respect to the morphology of individual microbes, this may, for example, optionally be determined to be a coccus (spherical), *bacillus* (rod-shaped), spiral (twisted), or pleomorphic. Cocci may optionally be a single coccus, diplococcic, streptococci, tetrads, sarcinae or staphylococci. Bacilli may optionally be a single *bacillus*, diplobacilli, streptobacilli or coccobacilli. Spirals may optionally be *vibrio*, spirilla or Spirochetes.

With respect to the morphology of mammalian cells, this may, for example, optionally be determined to be fibroblastic, epithelial-like, lymphoblast-like, and/or neuronal, with or without an axon.

Culture-based screening for nutrient requirements may optionally involve inoculating cells or microbes onto on into one or more different growth media, such as different selective media, and observing in/on which media cell or microbial growth occurs, and to what extent the growth differs between different media.

Culture-based screening for antimicrobial sensitivity may optionally involve inoculating microbes onto one or more different growth media, which may be done, for example, by streaking or plating the microbes onto a petri dish containing a suitable nutrient agar. An antimicrobial agent may then be added, which may be done, for example, by placing a filter paper disk impregnated with the antimicrobial onto the growth medium. Several disks each containing a different antimicrobial agent may be added onto a single petri dish. A determination may then be made as to whether a zone of growth inhibition occurs around any of the disk(s), and, if so, how large this zone is.

Immunohistochemical analysis may involve contacting the tissue sample with one or more labelled agents, such as antibodies. Thus, the presence of specific antigens, particularly on the cell surface of a cell or microbe, may optionally be tested for by using specific antibodies. Testing for antigens may also be referred to as serotyping. The antibodies may be polyclonal or monoclonal. If the antibodies are specific for a particular cell type, then the number of cells of that type may be assessed. The test may optionally involve simply detecting the presence or absence of agglutination, i.e. the formation of complexes of cells/microbes and antibodies. Alternatively or in addition, the antibodies may be labelled and the assay may involve, for example, an enzyme-linked immunosorbent assay ("ELISA") and/or fluorescence activated cell sorting ("FACS").

The antibody may optionally be selected from e.g., a CD3 or CD8 antibody.

Flow cytometry may optionally be used to analyse the properties of cells or microbes in a sample or specimen, e.g., the number of cells/microbes, percentage of live cells/microbes, cell/microbe size, cell/microbe shape, and/or the presence of particular antigens on the cell/microbe surface.

Western blot hybridization may optionally be used to analyse proteins and/or peptides.

Optionally, in situ hybridization of labelled probes to tissues, microbes and/or cells may be performed, optionally using an array format. The method may be Fluorescence in situ hybridization (FISH), which may, e.g., be used to analyse chromosomal abnormalities and/or to map genes.

EXAMPLES

Example 1—DESI-MS Analysis of Human Breast Cancer Biopsies

Manual histological evaluation of the stained biopsy tissue sections has been the gold standard method when it comes to providing a diagnosis for breast cancers. However, the accuracy of this morphology-based tissue diagnosis is often compromised as it is dependent on the pathologists' interpretation, resulting in poor prognosis for a given subject.

DESI-MSI enables the skilled person to visualise spatial distribution of lipid species across tissue sections allowing direct correlation with the histological features. Therefore, breast cancer tissues were analysed with DESI-MSI to obtain lipidomic data. About 45 samples, including Grade II invasive ductal carcinoma (IDC), have been analysed in positive and negative ion mode.

Figure 5A:
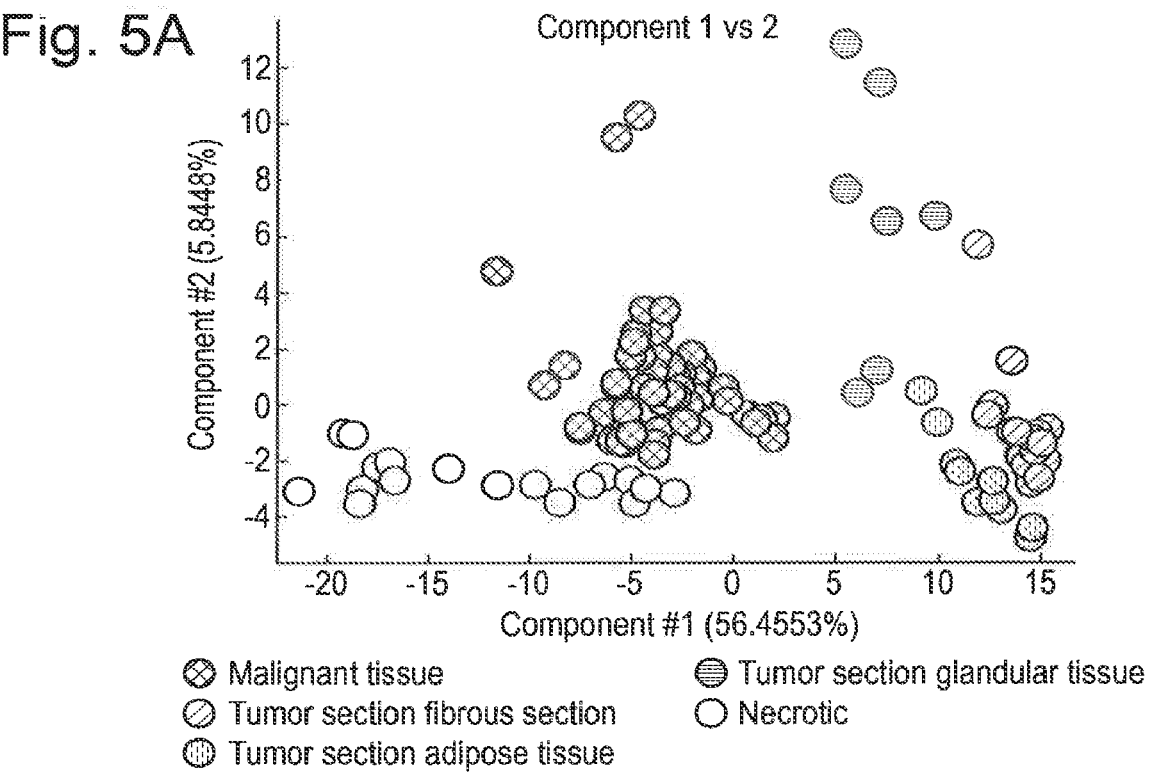
FIG. 5*a* shows results of Example 1: PCA analysis of Grade II invasive ductal carcinoma (IDC) in negative ion mode.
Figure 5B:
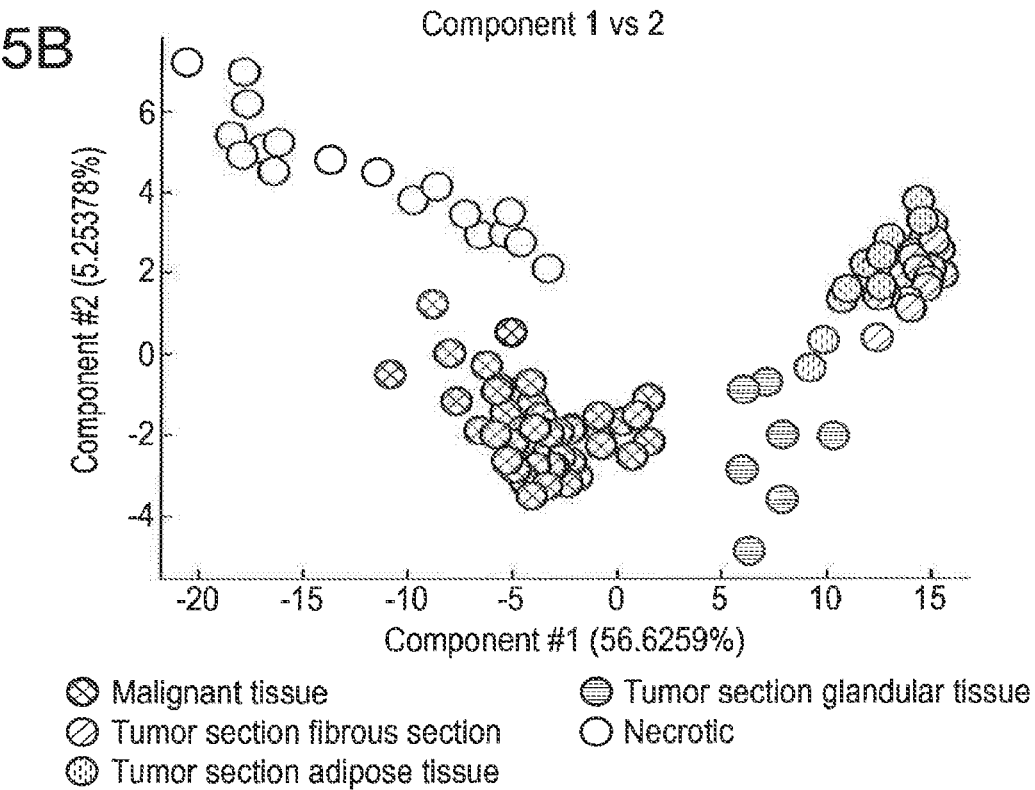
FIG. 5*b* shows results of Example 1: MMC analysis of Grade II IDC negative ion mode.
Figure 6A:
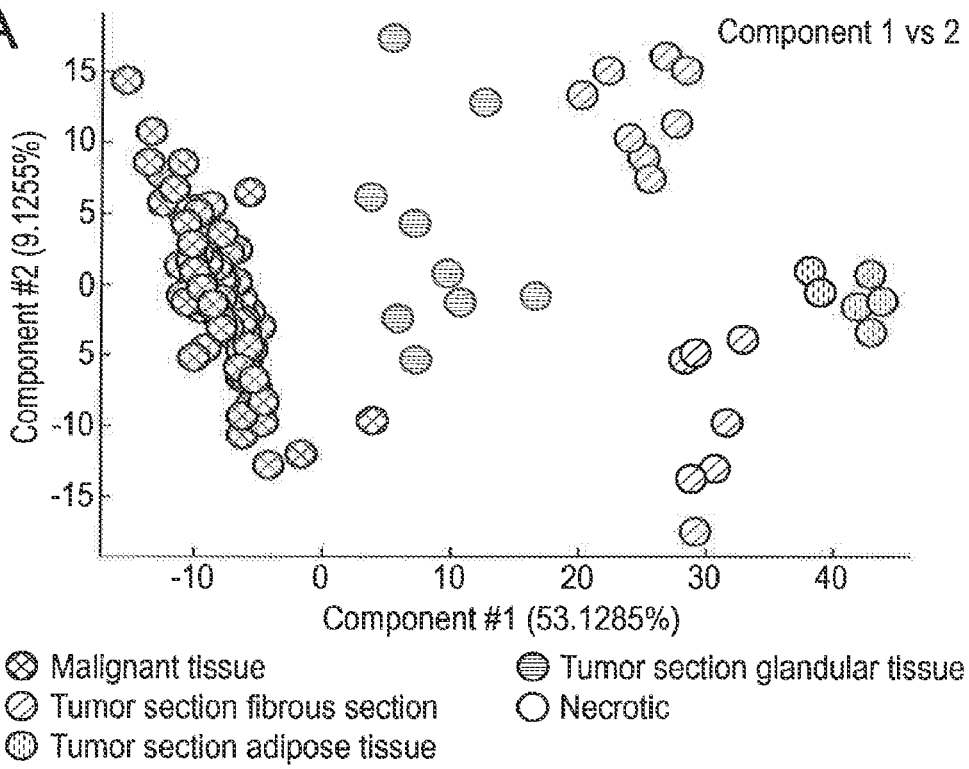
FIG. 6*a* shows results of Example 1: PCA analysis of Grade II IDC in positive ion mode.
Figure 6B:
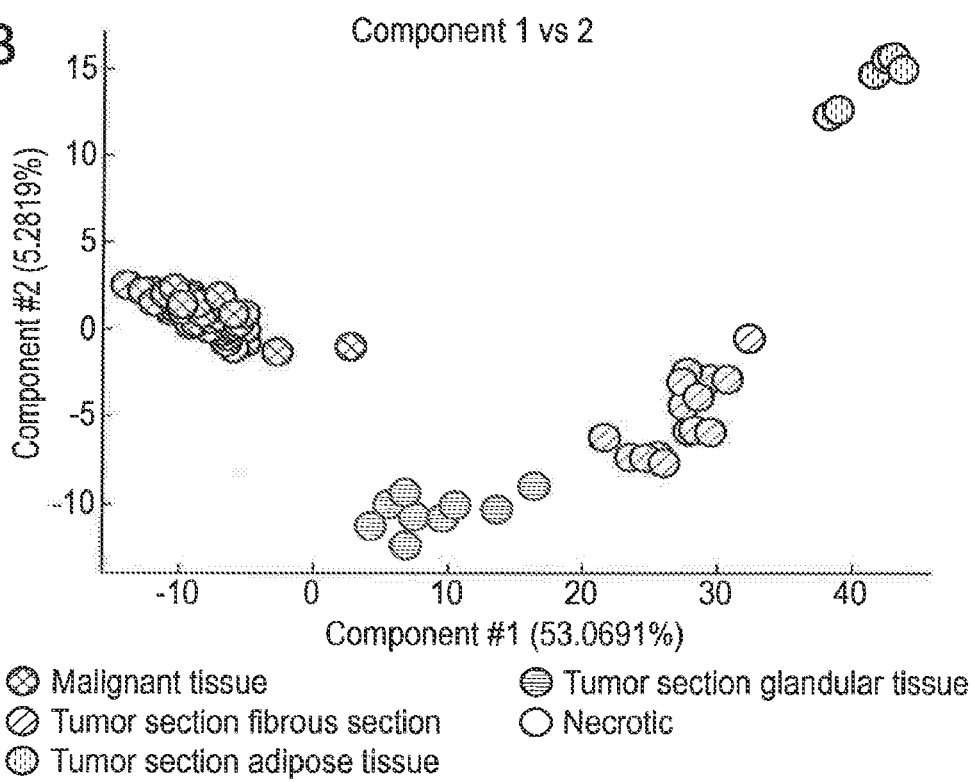
FIG. 6*b* shows results of Example 1: MMC analysis of Grade II IDC positive ion mode.
Figure 7A:
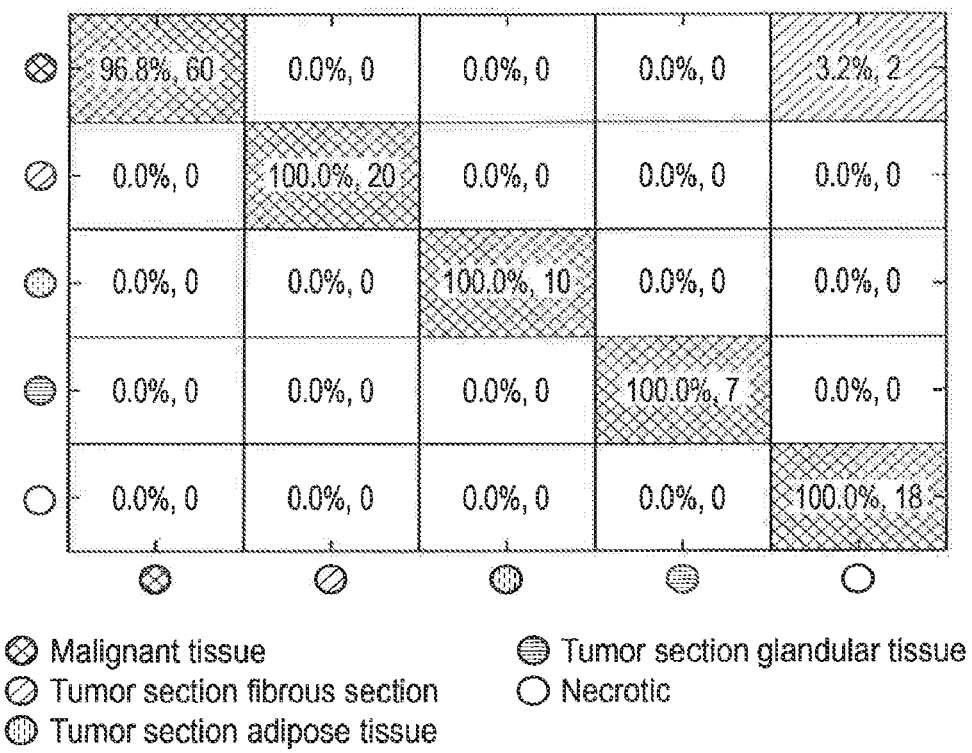
FIGS. 7*a* and *b* shows results of Example 1: Leave one out cross validation of different tissue types in a Grade II IDC in negative ion mode (7*a*) and (7*b*) in positive ion mode.
Figure 7B:
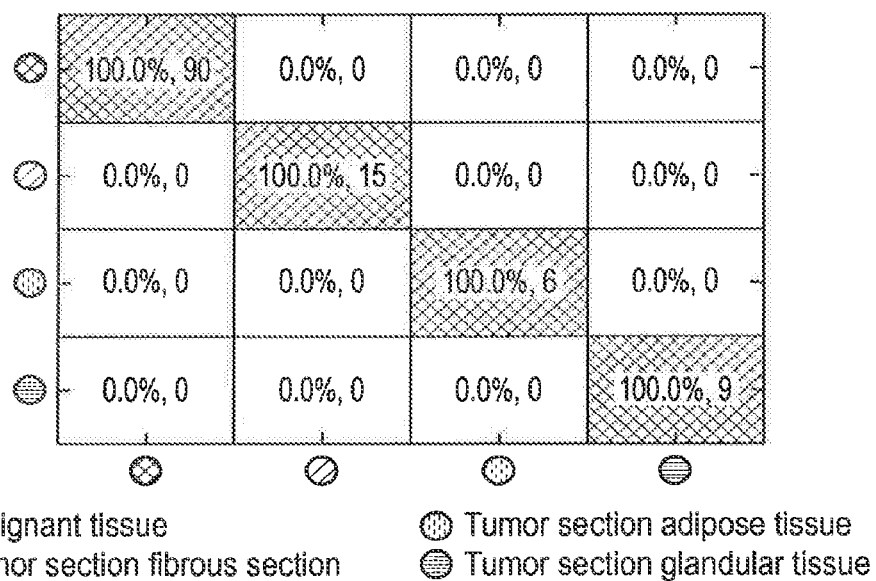
Figure 8A:
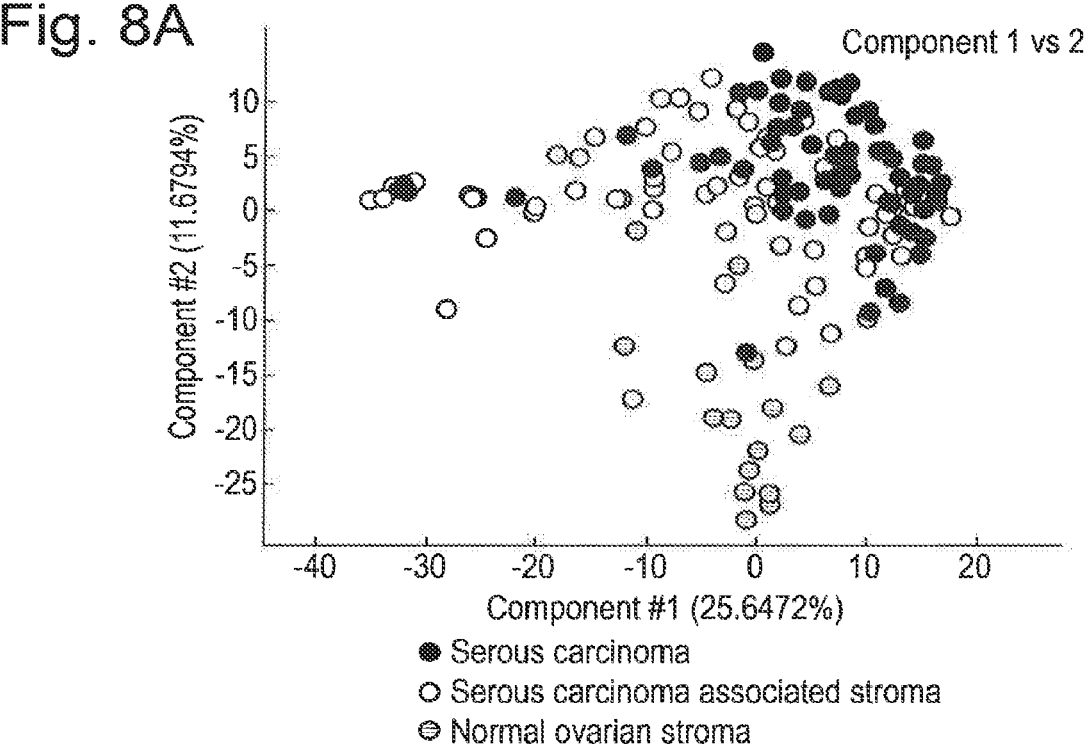
FIG. 8 shows results of Example 2: Analysis of a combined dataset from multiple samples (negative ion mode). a) PCA of identified regions; b) MMC supervised analysis; c) MMC analysis excluding the samples with outliers identified in b); d) respective leave-one-region-per-patient-out cross validation.
Figure 8B:
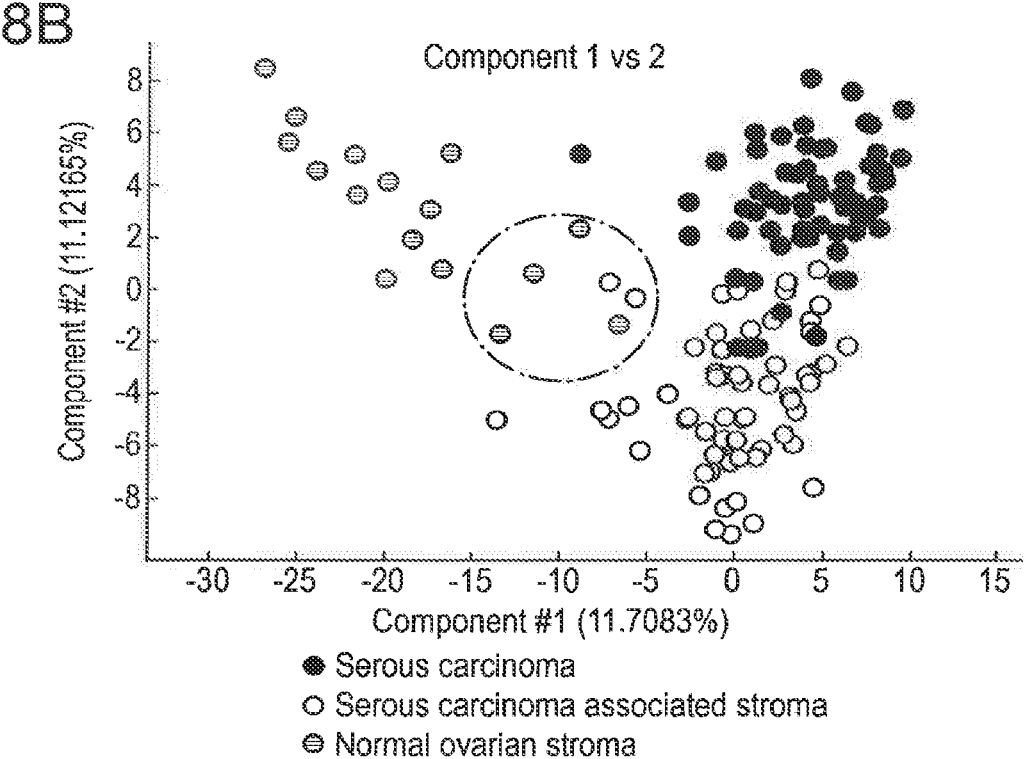
Figure 8C:
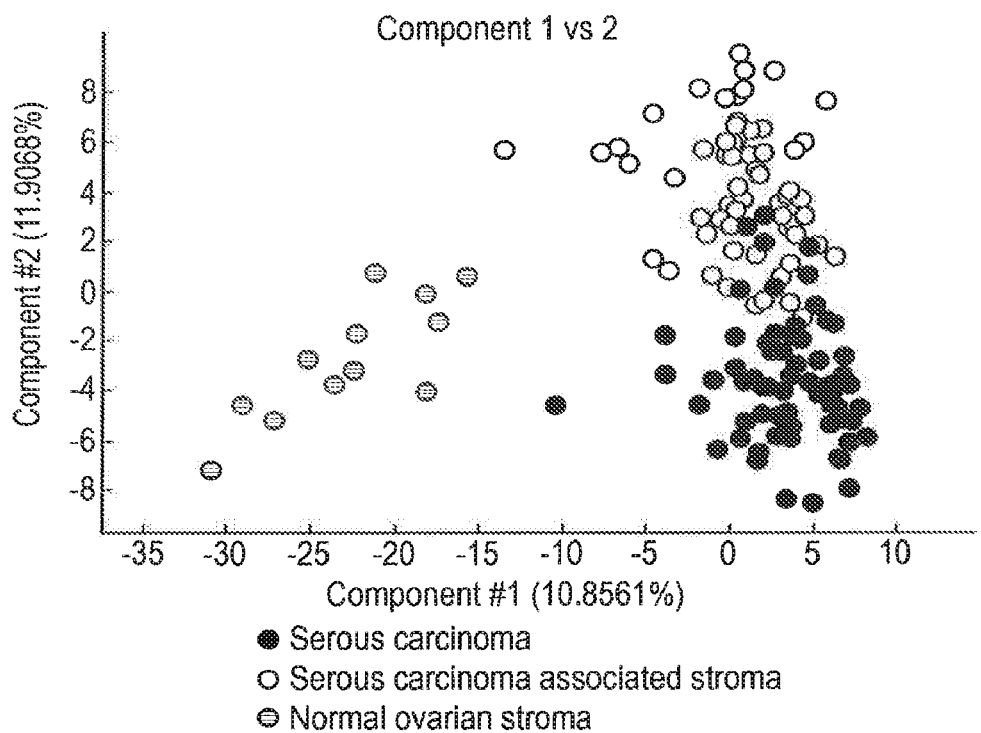
Figure 8D:
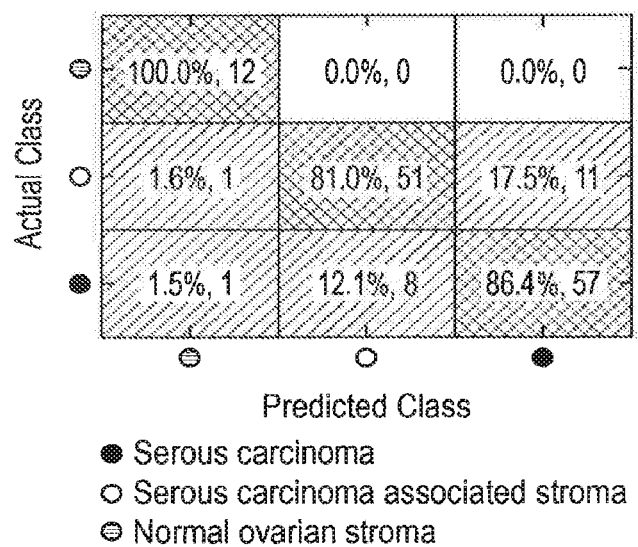

Each individual breast sample was subjected to unsupervised principal component analysis (PCA) to visualize differences between different tissue types (data is in colour and therefore not shown). In both positive and negative ion mode, a clear distinction between the stroma and the tumour tissue was observed in almost all of the samples (FIGS. 5a & 6a). Recursive maximum margin criterion (RMMC) analysis was used for supervised classification (FIGS. 5b & 6b). Tissue types in each sample and their spatial distribution were determined by an independent histopathologist based on the H&E stained optical image. Based on this information, a small number of representative mass spectra per tissue were selected from the integrated MS ion image to build a sample-specific RMMC model which was used to classify all pixels in the different tissue types. This data was submitted to cross validation, which exceeded 95% accuracy generally for all tissue types in all samples in both negative and positive ion mode (FIGS. 7 a&b).

The method distinguished between the following tissue specimens: malignant tissue, tumour section fibrous section, tumour section adipose tissue, tumour section glandular tissue and necrotic tissue. Thus, the method may optionally be used to analyse, e.g. identify or distinguish between one or more tissue types, optionally selected from, e.g., malignant tissue, fibrous tumour tissue, adipose tumour tissue, glandular tumour tissue, and/or necrotic tissue.

Example 2 Development of Spatially—Resolved Shotgun Lipidomic Methods for Histology-Level Cancer Diagnostics An ovarian cancer dataset with different epithelial carcinomas (endometrioid, serous and clear cell carcinomas), borderline tumours, and healthy ovary and fallopian tube has been analysed. A total of 109 human samples were collected and mass spectrometry data was acquired by DESI-MS in positive and negative ion mode.

The dataset was initially pre-processed and multivariate statistical analysis was performed on each individual sample's dataset in order to compile a database of histologically authentic lipidomic profiles. The morphological regions of interest were assigned by a qualified histopathologist and automatically co-registered and aligned with the mass spectrometry imaging (MSI) dataset.

Using principal component analysis (PCA), it was observed that different tissue types within the same sample show different lipid profiles. For example, normal ovary contains corpus and stroma tissue, and these are completely separated in PCA. In the borderline and cancer samples, one can also distinguish 2 different tissue types, the tumour cells and the surrounding stroma cells presenting large differences in their lipidomic profile. When supervised maximum margin criteria (MMC) analysis and colour map according to the MMC components is applied, it is possible to produce tissue maps that reflect the different tissue types identified in the histological image.

This profile database was also used to perform comparative analysis across multiple samples. PCA was used to perform unsupervised tissue segmentation based on the lipidomic profiles, without taking into account histological assignment. A supervised analysis was then performed and a respective leave-one-tissue-per-subject-out cross validation was calculated.

PCA shows some separation between normal ovary, serous carcinoma, and serous carcinoma associated stroma (FIG. 8). The supervised MMC analysis shows good separation between all three tissue types, with six outliers. Interestingly, all four misclassified normal samples were samples which were classified as normal ovary but were taken from an ovary with a tumour distant from the sampling area. This suggests that the biochemistry of this tissue is altered, even though this cannot be detected in a morphological examination. MMC analysis was repeated under exclusion of the outliers and leave-one-region-per-subject-out cross validation was performed, showing a complete separation of normal tissue and an overall accuracy of 85%.

Figure 9A:
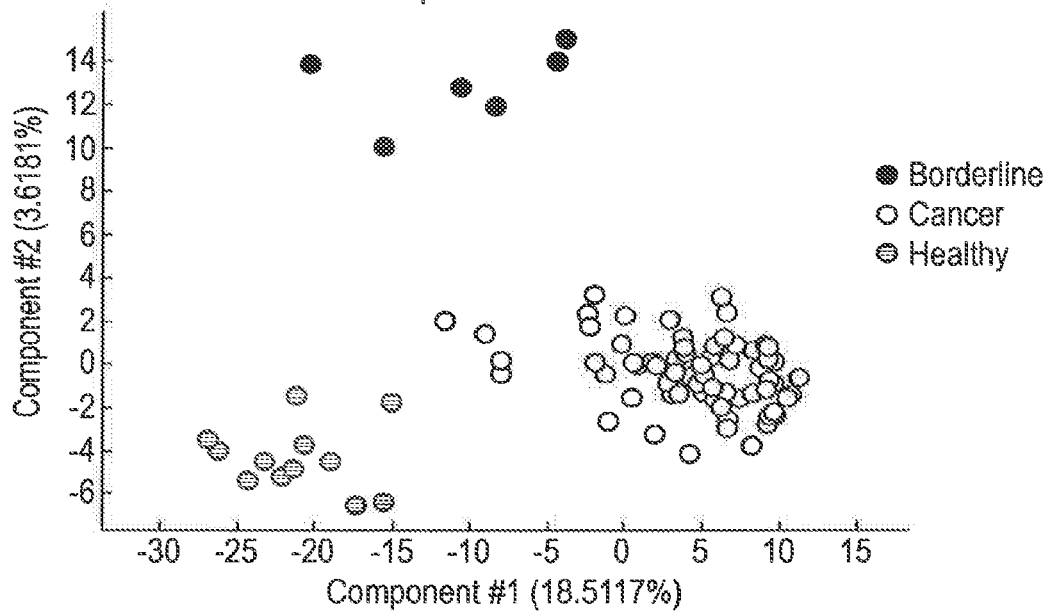
FIG. 9 shows results of Example 2: a) Supervised MMC analysis of healthy ovary, borderline tumours and carcinomas together with b) leave one patient out cross validation.
Figure 9B:
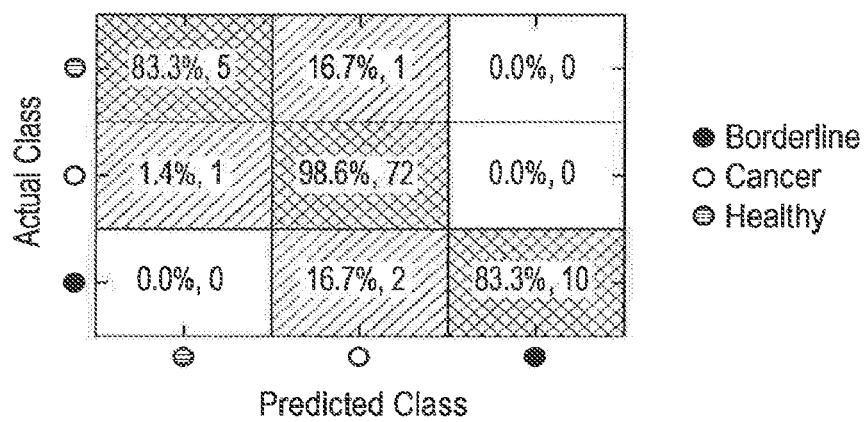

The variances between different types of samples was also examined. For example, it was evaluated how well negative ion mode DESI-MSI can separate cancer tissues, borderline and healthy ovary (FIG. 9). An overall classification accuracy of 95.6% was achieved.

Figure 10A:
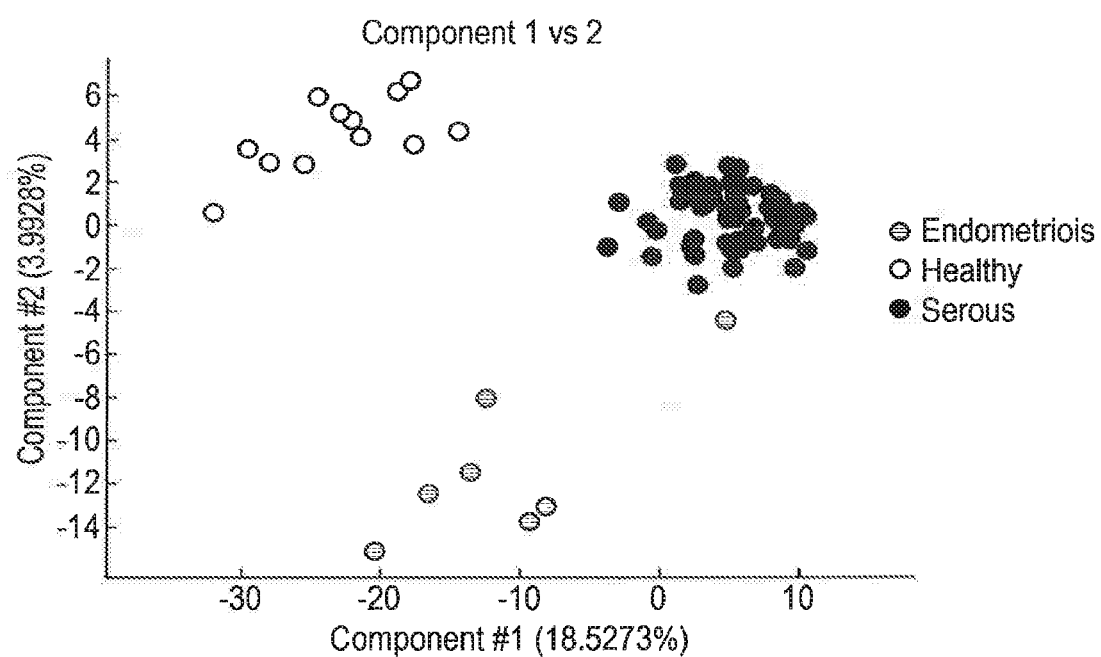
FIG. 10 shows results of Example 2: a) Supervised MMC analysis of healthy ovary and different epithelial carcinomas (endometrioid and serous) with the respective b) leave one patient out cross validation.
Figure 10B:
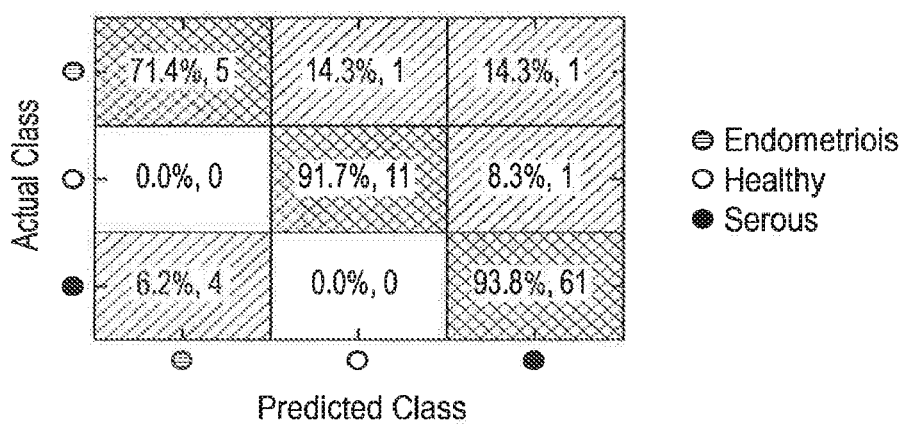

A further analysis performed was the comparison between different types of epithelial carcinomas in the dataset: endometrioid and serous carcinomas. Using the negative ion mode data, healthy ovary, serous carcinoma, and endometrioid carcinoma could be classified with an overall accuracy of 90% (see FIG. 10).

Figure 11A:
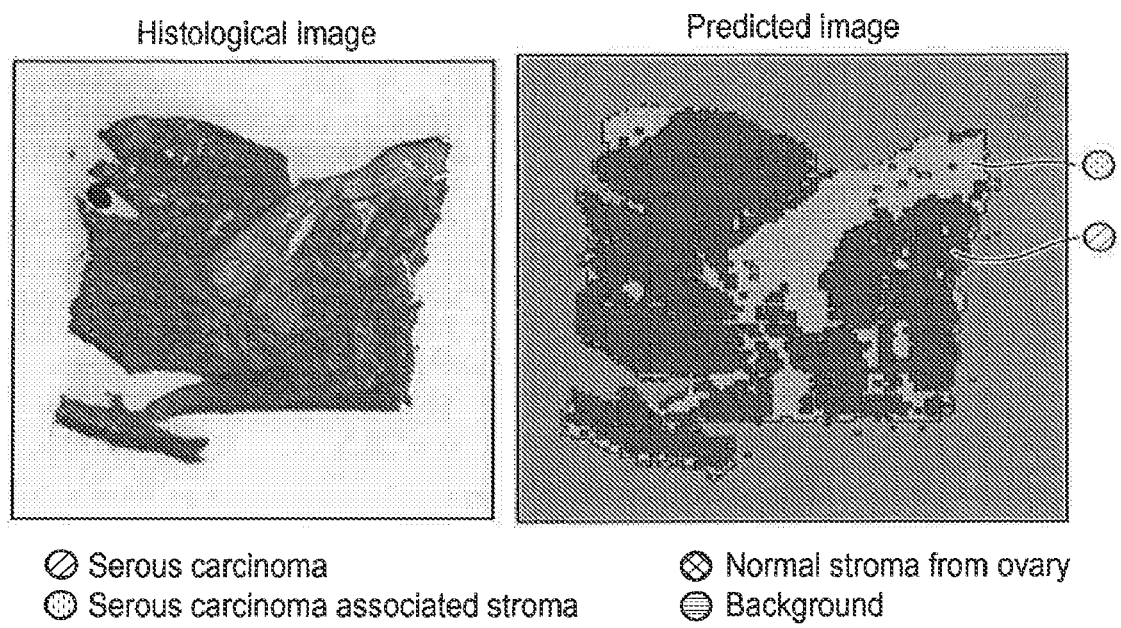
FIG. 11 shows results of Example 2 A sample with unknown histology was used to predict the different tissue types. Serous carcinoma, serous carcinoma associated stroma, normal ovarian stroma and background were correctly predicted. Cross validation of this prediction based on the histological annotation was performed and a classification accuracy of almost 100% was achieved.
Figure 11B:
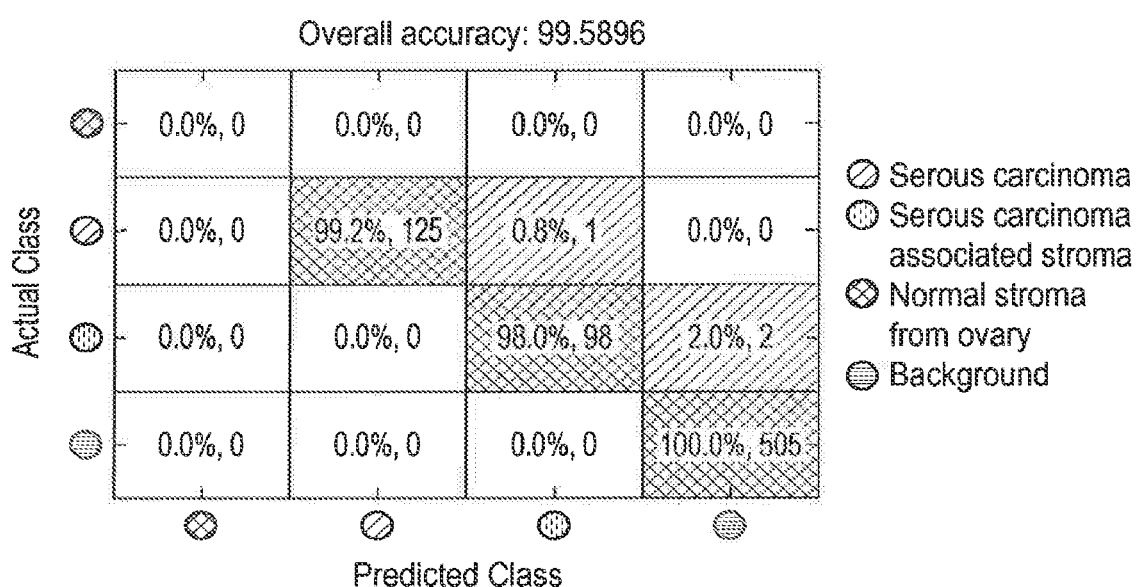

It was also examined whether, based on the models created, it was possible to predict the different tissue types of a blind sample. The number of serous carcinomas analysed provided a robust model to perform this validation using negative ion mode data (See FIG. 11).

The DESI data allowed an excellent prediction of the two tissue types present in the sample, i.e. ovarian stroma and ovarian cancer. Serous carcinoma, serous carcinoma associated stroma, normal ovarian stroma and background were differentiated. A cross validation was performed based on histological annotation performed after this analysis and a classification accuracy of almost 100% was achieved.

Example 3—Breast Cancer Diagnosis Ex Vivo Using REIMS Technology

About 227 samples from tumour, normal and fibroadenoma human tissue were obtained and analysed. The distribution of the samples is shown in Table 3.1. The samples were histologically validated.

TABLE 3.1

| Sample type | Number of subjects |
| --- | --- |
| Normal | 120 |
| Tumour | 73 |
| Fibroadenoma | 34 |

Sampling took place with either diathermy or plasmablade taking measurements in separate files using cut or coagulation modes if the amount of tissue allowed. Diathermy cut mode was the preferred method if the tissue collected was small. Regardless of whether diathermy or plasmablade were used, and regardless of whether cut or coagulation mode were used, each sample was correctly identified as being normal, tumour or fibroadenoma (for an extract of the data, see Table 3.2).

TABLE 3.2

| | | |
|---|---|---|
| IKB349 | IKB349_20150713_DOLORES_FRESH_NORMAL_CUT.raw | Normal |
| | IKB349_20150713_DOLORES_FRESH_NORMAL_COAG.raw | |
| | IKB349_20150713_DOLORES_FRESH_NORMAL_PLASMABLADE_CUT.raw | |
| | IKB349_20150713_DOLORES_FRESH_NORMAL_PLASMABLADE_COAG.raw | |
| IKB352 | IKB352_20150717_DOLORES_FRESH_NORMAL_CUT.raw | Normal |
| | IKB352_20150717_DOLORES_FRESH_NORMAL_COAG.raw | |
| | IKB352_20150717_DOLORES_FRESH_NORMAL_PLASMABLADE_CUT.raw | |
| | IKB352_20150717_DOLORES_FRESH_NORMAL_PLASMABLADE_COAG.raw | |
| IKB353 | IKB353_20150717_DOLORES_FRESH_NORMAL_CUT.raw | Normal |
| | IKB353_20150717_DOLORES_FRESH_NORMAL_COAG.raw | |
| | IKB353_20150717_DOLORES_FRESH_NORMAL_PLASMABLADE_CUT.raw | |
| | IKB353_20150717_DOLORES_FRESH_NORMAL_PLASMABLADE_COAG.raw | |
| | IKB353_20150717_DOLORES_FRESH_TUMOUR_CUT.raw | Tumour |
| | IKB353_20150717_DOLORES_FRESH_TUMOUR_COAG.raw | |
| | IKB353_20150717_DOLORES_FRESH_TUMOUR_PLASMABLADE_CUT.raw | |
| | IKB353_20150717_DOLORES_FRESH_TUMOUR_PLASMABLADE_COAG.raw | |
| IKB357 | IKB357_20150721_DOLORES_FRESH_NORMAL_CUT.raw | Normal |
| | IKB357_20150721_DOLORES_FRESH_NORMAL_COAG.raw | |
| | IKB357_20150721_DOLORES_FRESH_NORMAL_PLASMABLADE_CUT.raw | |
| | IKB357_20150721_DOLORES_FRESH_NORMAL_PLASMABLADE_COAG.raw | |
| | IKB357_20150721_DOLORES_FRESH_TUMOUR_CUT.raw | Tumour |
| | IKB357_20150721_DOLORES_FRESH_TUMOUR_COAG.raw | |
| | IKB357_20150721_DOLORES_FRESH_TUMOUR_PLASMABLADE_CUT.raw | |
| | IKB357_20150721_DOLORES_FRESH_TUMOUR_PLASMABLADE_COAG.raw | |
| IKB362 | IKB362_20150724_DOLORES_FRESH_NORMAL_CUT.raw | Normal |
| | IKB362_20150724_DOLORES_FRESH_NORMAL_COAG.raw | |
| | IKB362_20150724_DOLORES_FRESH_NORMAL_CUT_2.raw | |
| | IKB362_20150724_DOLORES_FRESH_NORMAL_PLASMABLADE_CUT.raw | |
| | IKB362_20150724_DOLORES_FRESH_NORMAL_PLASMABLADE_COAG.raw | |
| | IKB362_20150724_DOLORES_FRESH_TUMOUR_CUT.raw | Tumour |
| | IKB362_20150724_DOLORES_FRESH_TUMOUR_COAG.raw | |
| | IKB362_20150724_DOLORES_FRESH_TUMOUR_PLASMABLADE_CUT.raw | |
| | IKB362_20150724_DOLORES_FRESH_TUMOUR_PLASMABLADE_COAG.raw | |
| IKB363 | IKB363_20150727_DOLORES_FRESH_NORMAL_CUT.raw | Normal |
| | IKB363_20150727_DOLORES_FRESH_NORMAL_COAG.raw | |
| | IKB363_20150727_DOLORES_FRESH_NORMAL_PLASMABLADE_CUT.raw | |
| | IKB363_20150727_DOLORES_FRESH_NORMAL_PLASMABLADE_COAG.raw | |
| | IKB363_20150727_DOLORES_FRESH_TUMOUR_CUT.raw | Tumour |
| | IKB363_20150727_DOLORES_FRESH_TUMOUR_COAG.raw | |
| | IKB363_20150727_DOLORES_FRESH_TUMOUR_PLASMABLADE_CUT.raw | |
| | IKB363_20150727_DOLORES_FRESH_TUMOUR_PLASMABLADE_COAG.raw | |
| IKB367 | IKB367_20150730_DOLORES_FRESH_NORMAL_CUT.raw | Normal |
| | IKB367_20150730_DOLORES_FRESH_NORMAL_COAG.raw | |
| | IKB367_20150730_DOLORES_FRESH_NORMAL_PLASMABLADE_CUT.raw | |
| | IKB367_20150730_DOLORES_FRESH_NORMAL_PLASMABLADE_COAG.raw | |
| | IKB367_20150730_DOLORES_FRESH_TUMOUR_CUT.raw | Tumour |
| | IKB367_20150730_DOLORES_FRESH_TUMOUR_COAG.raw | |
| | IKB367_20150730_DOLORES_FRESH_TUMOUR_PLASMABLADE_CUT.raw | |
| | IKB367_20150730_DOLORES_FRESH_TUMOUR_PLASMABLADE_COAG.raw | |
| IKB369 | IKB369_20150730_DOLORES_FRESH_NORMAL_CUT.raw | Normal |
| | IKB369_20150730_DOLORES_FRESH_NORMAL_COAG.raw | |
| | IKB369_20150730_DOLORES_FRESH_NORMAL_PLASMABLADE_CUT.raw | |
| | IKB369_20150730_DOLORES_FRESH_NORMAL_PLASMABLADE_COAG.raw | |
| | IKB369_20150730_DOLORES_FRESH_TUMOUR_CUT.raw | Tumour |
| | IKB369_20150730_DOLORES_FRESH_TUMOUR_COAG.raw | |
| | IKB369_20150730_DOLORES_FRESH_TUMOUR_PLASMABLADE_CUT.raw | |
| | IKB369_20150730_DOLORES_FRESH_TUMOUR_PLASMABLADE_COAG.raw | |
| IKB370 | IKB370_20150731_DOLORES_FRESH_FIBROADENOMA_CUT.raw | Fibroadenoma |
| | IKB370_20150731_DOLORES_FRESH_FIBROADENOMA_COAG.raw | |
| | IKB370_20150731_DOLORES_FRESH_FIBROADENOMA_PLASMABLADE_CUT.raw | |
| | IKB370_20150731_DOLORES_FRESH_FIBROADENOMA_PLASMABLADE_COAG.raw | |
| IKB371 | IKB371_20150803_DOLORES_FRESH_FIBROADENOMA_CUT.raw | Fibroadenoma |
| | IKB371_20150803_DOLORES_FRESH_FIBROADENOMA_COAG.raw | |
| | IKB371_20150803_DOLORES_FRESH_FIBROADENOMA_PLASMABLADE_CUT.raw | |
| | IKB371_20150803_DOLORES_FRESH_FIBROADENOMA_PLASMABLADE_COAG.raw | |
| IKB373 | IKB373_20150803_DOLORES_FRESH_NORMAL_CUT.raw | Normal |
| | IKB373_20150803_DOLORES_FRESH_NORMAL_COAG.raw | |
| | IKB373_20150803_DOLORES_FRESH_NORMAL_PLASMABLADE_CUT.raw | |
| | IKB373_20150803_DOLORES_FRESH_NORMAL_PLASMABLADE_COAG.raw | |
| | IKB373_20150803_DOLORES_FRESH_TUMOUR_CUT.raw | Tumour |
| | IKB373_20150803_DOLORES_FRESH_TUMOUR_COAG.raw | |
| | IKB373_20150803_DOLORES_FRESH_TUMOUR_PLASMABLADE_CUT.raw | |
| | IKB373_20150803_DOLORES_FRESH_TUMOUR_PLASMABLADE_COAG.raw | |
| IKB374 | IKB374_20150803_DOLORES_FRESH_FIBROADENOMA_CUT.raw | Fibroadenoma |
| | IKB374_20150803_DOLORES_FRESH_FIBROADENOMA_COAG.raw | |
| | IKB374_20150803_DOLORES_FRESH_FIBROADENOMA_PLASMABLADE_CUT.raw | |
| | IKB374_20150803_DOLORES_FRESH_FIBROADENOMA_PLASMABLADE_COAG.raw | |
| IKB367 | IKB367_20150807_DOLORES_FRESH_FIBROADENOMA_CUT.raw | Fibroadenoma |
| | IKB367_20150807_DOLORES_FRESH_FIBROADENOMA_COAG.raw | |
| | IKB367_20150807_DOLORES_FRESH_FIBROADENOMA_PLASMABLADE_CUT.raw | |

TABLE 3.2-continued

| | | |
|---|---|---|
| | IKB367_20150807_DOLORES_FRESH_FIBROADENOMA_PLASMABLADE_CUT_02.raw | |
| | IKB367_20150807_DOLORES_FRESH_FIBROADENOMA_PLASMABLADE_COAG.raw | |
| IKB377 | IKB377_20150810_DOLORES_FRESH_FIBROADENOMA_CUT.raw | Fibroadenoma |
| | IKB377_20150810_DOLORES_FRESH_FIBROADENOMA_COAG.raw | |
| | IKB377_20150810_DOLORES_FRESH_FIBROADENOMA_PLASMABLADE_CUT.raw | |
| | IKB377_20150810_DOLORES_FRESH_FIBROADENOMA_PLASMABLADE_COAG.raw | |
| IKB378 | IKB378_20150810_DOLORES_FRESH_NORMAL_CUT.raw | Normal |
| | IKB378_20150810_DOLORES_FRESH_NORMAL_COAG.raw | |
| | IKB378_20150810_DOLORES_FRESH_NORMAL_PLASMABLADE_CUT.raw | |
| | IKB378_20150810_DOLORES_FRESH_NORMAL_PLASMABLADE_COAG.raw | |
| IKB281 | IKB281_20150813_DOLORES_FRESH_NORMAL_CUT.raw | Normal |
| | IKB281_20150813_DOLORES_FRESH_NORMAL_COAG.raw | |
| | IKB281_20150813_DOLORES_FRESH_NORMAL_PLASMABLADE_CUT.raw | |
| | IKB281_20150813_DOLORES_FRESH_NORMAL_PLASMABLADE_COAG.raw | |
| | IKB281_20150813_DOLORES_FRESH_TUMOUR_CUT.raw | Tumour |
| | IKB281_20150813_DOLORES_FRESH_TUMOUR_COAG.raw | |
| | IKB281_20150813_DOLORES_FRESH_TUMOUR_PLASMABLADE_CUT.raw | |
| | IKB281_20150813_DOLORES_FRESH_TUMOUR_PLASMABLADE_COAG.raw | |
| IKB382 | IKB382_20150817_DOLORES_FRESH_NORMAL_CUT.raw | Normal |
| | IKB382_20150817_DOLORES_FRESH_NORMAL_COAG.raw | |
| | IKB382_20150817_DOLORES_FRESH_NORMAL_PLASMABLADE_CUT.raw | |
| | IKB382_20150817_DOLORES_FRESH_NORMAL_PLASMABLADE_COAG.raw | |
| | IKB382_20150817_DOLORES_FRESH_TUMOUR_CUT.raw | Tumour |
| | IKB382_20150817_DOLORES_FRESH_TUMOUR_COAG.raw | |
| | IKB382_20150817_DOLORES_FRESH_TUMOUR_PLASMABLADE_CUT.raw | |
| | IKB382_20150817_DOLORES_FRESH_TUMOUR_PLASMABLADE_COAG.raw | |
| | IKB382_20150817_DOLORES_FRESH_NORMAL_TO_TUMOUR_TEST_CUT.raw | Margin test |
| | IKB382_20150817_DOLORES_FRESH_NORMAL_TO_TUMOUR_TEST_COAG.raw | |
| | IKB382_20150817_DOLORES_FRESHvNORMAL_TO_TUMOUR_TEST_PLASMABLADE_CUT.raw | |
| | IKB382_20150817_DOLORES_FRESH_NORMAL_TO_TUMOUR_TEST_PLASMABLADE_COAG.raw | |
| | IKB382_20150817_DOLORES_FRESH_RULER_MARGIN_TEST_CUT.raw | Margin test |
| | IKB382_20150817_DOLORES_FRESH_RULER_MARGIN_TEST_COAG.raw | |
| IKB391 | IKB391_20150820_DOLORES_FRESH_FIBROADENOMA_CUT.raw | Fibroadenoma |
| | IKB391_20150820_DOLORES_FRESH_FIBROADENOMA_COAG.raw | |
| | IKB391_20150820_DOLORES_FRESH_FIBROADENOMA_PLASMABLADE_CUT.raw | |
| | IKB391_20150820_DOLORES_FRESH_FIBROADENOMA_PLASMABLADE_COAG.raw | |
| IKB396 | IKB396_20150824_DOLORES_FRESH_FIBROADENOMA_CUT.raw | Fibroadenoma |
| | IKB396_20150824_DOLORES_FRESH_FIBROADENOMA_COAG.raw | |
| | IKB396_20150824_DOLORES_FRESH_FIBROADENOMA_PLASMABLADE_CUT.raw | |
| | IKB396_20150824_DOLORES_FRESH_FIBROADENOMA_PLASMABLADE_COAG.raw | |

Figure 12:
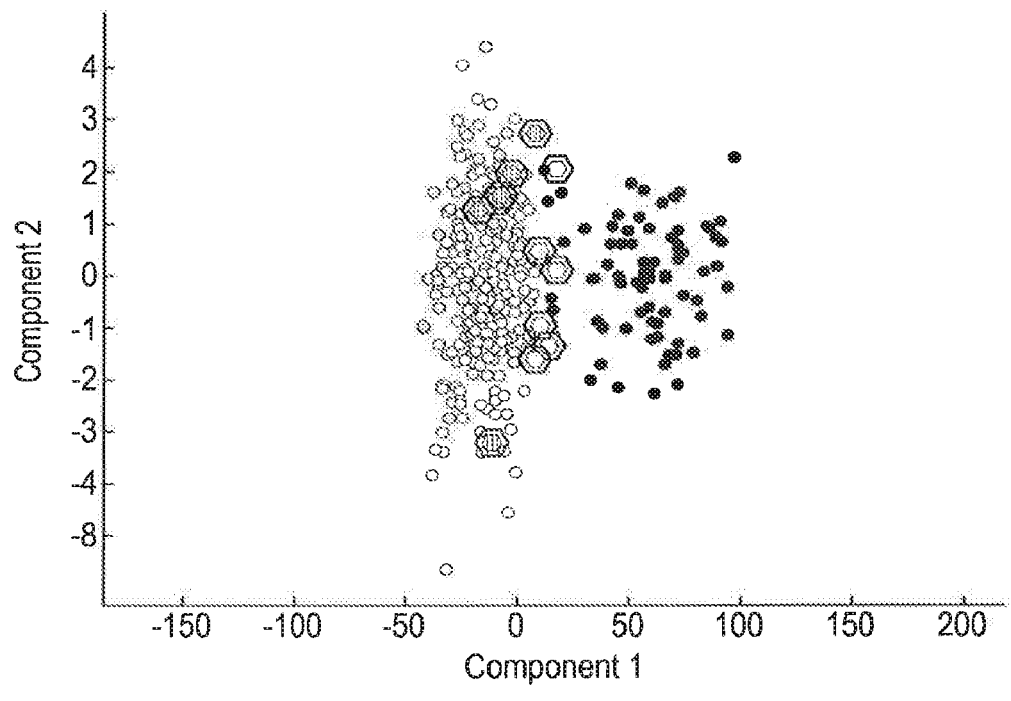
FIG. 12 shows data from Example 3: cut mode (normal tissue from 61 patients, 280 spectra, tumour tissue from 37 patients, 80 spectra)
Figure 13:
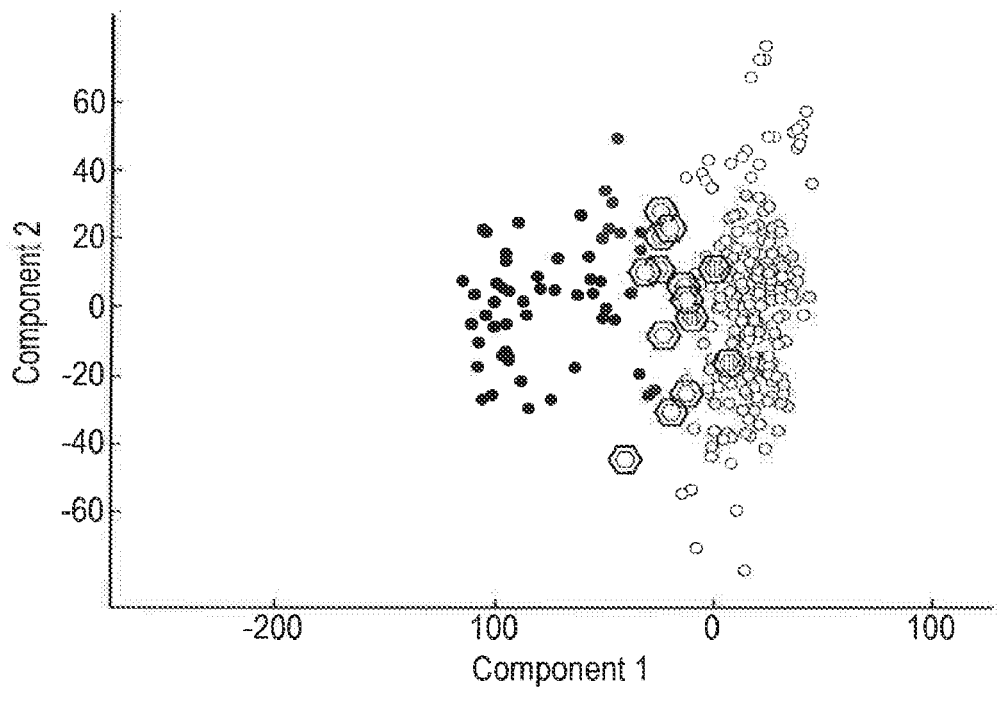
FIG. 13 shows data from Example 3: Coagulation mode (normal tissue from 66 patients, 281 spectra, tumour tissue from 31 patients, 59 spectra)

Principal component analysis and linear discriminant analysis with cross validation have been done separately for samples run in cut and coagulation modes. See FIGS. 12 and 13.

Example 4 Breast Cancer Tumour Margins Ex Vivo Via REIMS Technology

Figure 14:
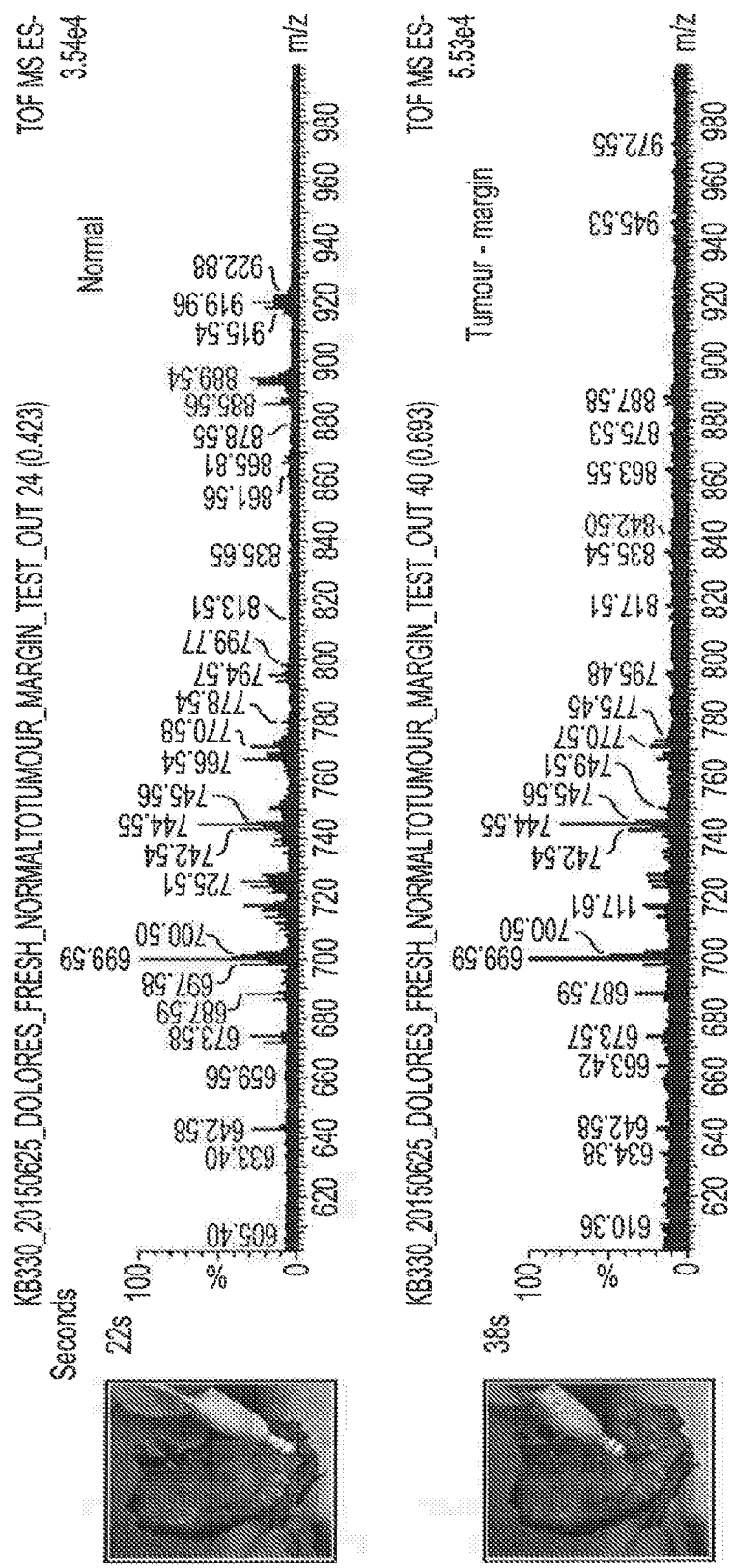
FIG. 14 shows an example of a margin test run across a mastectomy sample (Example 4)
Figure 14:
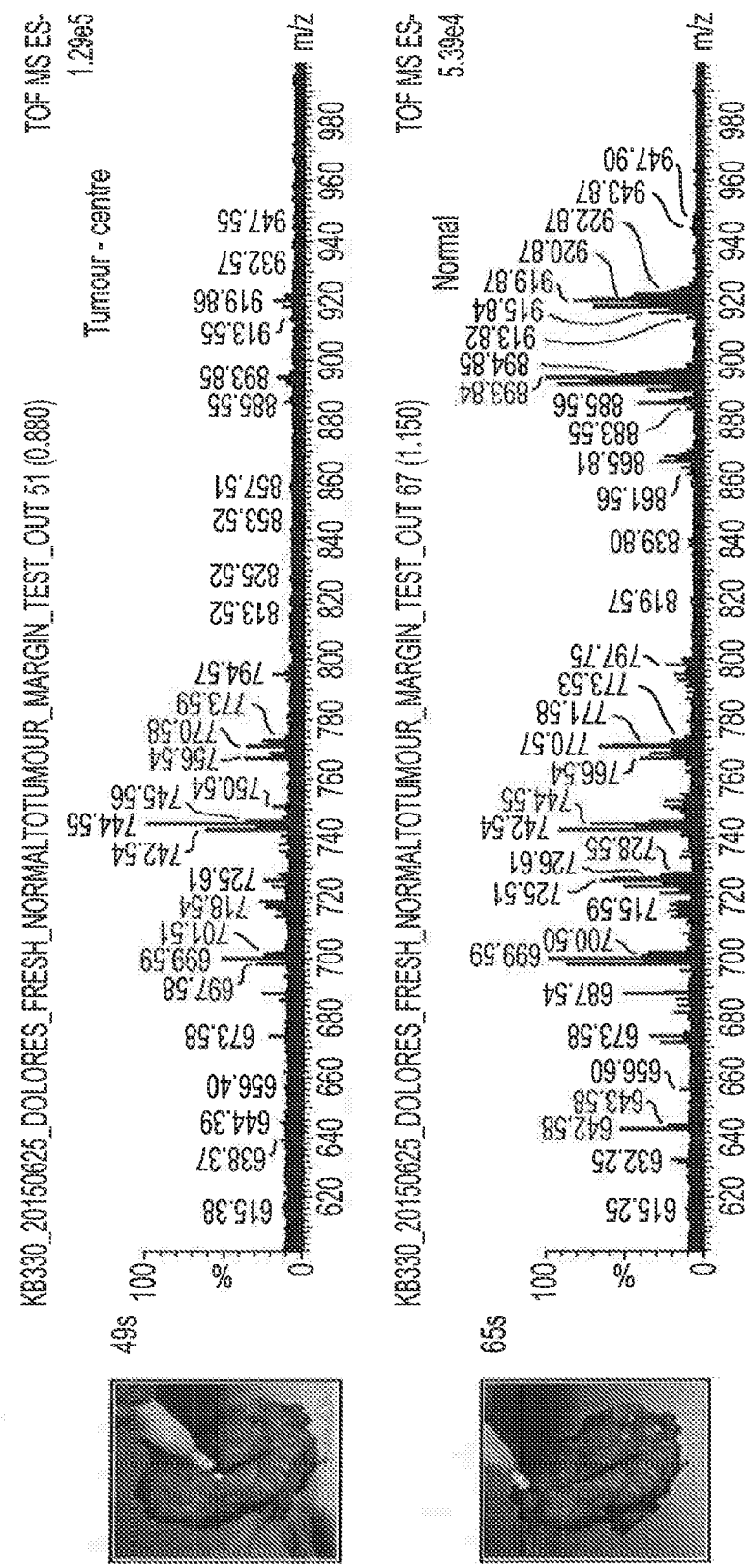

Three margin to tumour tests have been acquired, where a measurement was taken across the sample through normal and tumour human tissue and video was acquired to match the spectra using a GoPro set up. This data provides insight into lipid profiles across the tumour margin. Thus, tumour margins may be analysed ex vivo by analysing tissue samples. Results are shown in FIG. 14.

Example 5 Gastrointestinal Cancer Analysis Via REIMS Technology 242 samples were collected from 102 human subjects, as shown in Table 5.1.

TABLE 5.1

| | |
|---|---|
| Total Subjects | 102 |
| Total Samples | 242 |
| Normal | 90 |
| Tumour | 62 |
| Adenomatous Polyp | 21 |
| Appendix | 26 |
| Muscle | 20 |
| Submucosa | 14 |
| Total Classified Samples | 175 |

The samples were histologically validated and analysed by mass spectrometry (Table 5.2).

TABLE 5.2

| Subject number | Location | Sample identifier | Sample type |
|---|---|---|---|
| JLA079 | SMH | JLA079_20150410_NORMAL_MUCOSA_CUT.raw | NORMAL |
| | SMH | JLA079_20150410_NORMALLAYER_MUCOSA_CUT.raw | NORMAL |
| | SMH | JLA079_20150410_NORMALLAYER_MUSCLE_CUT.raw | MUSCLE |
| | SMH | JLA079_20150410_TUMOUR1_CUT.raw | TUMOUR |
| | SMH | JLA079_20150410_TUMOUR2_CUT.raw | TUMOUR |

TABLE 5.2-continued

| Subject number | Location | Sample identifier | Sample type |
|---|---|---|---|
| JLA077 | SMH | JLA077_20150313_NORMAL.raw | NORMAL |
| | SMH | JLA077_20150313_TUMOUR.raw | TUMOUR |
| | SMH | JLA077_20150313_APPENDIX.raw | APPENDIX |
| JLA082 | CXH | JLA082_20150421_NORMAL.raw | NORMAL |
| | CXH | JLA082_20150421_TUMOUR.raw | TUMOUR |
| JLA083 | CXH | JLA083_20150421_NORMAL.raw | NORMAL |
| | CXH | JLA083_20150421_POLYP.raw | POLYP |
| | CXH | JLA083_20150421_POLYP2.raw | POLYP |
| JLA085 | CXH | JLA085_20150421_NORMAL.raw | NORMAL |
| | CXH | JLA085_20150421_POLYP.raw | POLYP |
| JLA086 | SMH | JLA086_20150422_NORMAL.raw | NORMAL |
| | SMH | JLA086_20150422_TUMOUR.raw | TUMOUR |
| AS13 | SMH | AS13_20150422_APPENDIX.raw | APPENDIX |
| JLA091 | CXH | JLA091_20150428_NORMAL.raw | NORMAL |
| | CXH | JLA091_20150428_POLYP.raw | POLYP |
| | CXH | JLA091_20150428_TUMOUR.raw | TUMOUR |
| JLA096 | SMH | JLA096_20150429_NORMAL.raw | NORMAL |
| | SMH | JLA096_20150429_TUMOUR.raw | TUMOUR |
| AS14 | SMH | AS14_20150501_APPENDIX.raw | APPENDIX |
| AS15 | SMH | AS16_20150502_APPENDIX.raw | APPENDIX |
| AS16 | SMH | AS16_20150503_APPENDIX.raw | APPENDIX |
| | SMH | AS168_20150503_APPENDIX.raw | APPENDIX |
| JLA094M | SMH | JLA094M_20150505_NORMAL.raw | NORMAL |
| | SMH | JLA094M_20150505_TUMOUR.raw | TUMOUR |
| AS17 | SMH | AS18_20150511_APPENDIX.raw | APPENDIX |
| | SMH | AS18_20150512_APPENDIX.raw | APPENDIX |
| JLA095 | SMH | JLA095_20150511_NORMAL.raw | NORMAL |
| | SMH | JLA095_20150511_TUMOUR.raw | TUMOUR |
| AS18 | SMH | AS18_20150512_APPENDIX.raw | APPENDIX |
| AS19 | SMH | AS19_20150512_APPENDIX.raw | APPENDIX |
| JLA096 | SMH | JLA096_20150513_NORMAL.raw | NORMAL |
| | SMH | JLA096_20150513_TUMOUR.raw | TUMOUR |
| | SMH | JLA096_20150513_APPENDIX.raw | APPENDIX |
| JLA097 | SMH | JLA097_20150513_APPENDIX.raw | APPENDIX |
| AS20 | SMH | AS20_20150513_APPENDIX.raw | APPENDIX |
| JLA099 | SMH | JLA099_20150518_NORMAL.raw | NORMAL |
| | SMH | JLA099_20150518_TUMOUR.raw | TUMOUR |
| JLA100M | RMH | JLA100M_20150522_NORMAL.raw | NORMAL |
| | RMH | JLA100M_20150522_SUBMUCOSA_MUSCLE.raw | MUSCLE |
| | RMH | JLA100M_20150522_TUMOUR.raw | TUMOUR |
| JLA101 | SMH | JLA101_20150528_NORMAL.raw | NORMAL |
| | SMH | JLA101_20150528_TUMOUR.raw | TUMOUR |
| | SMH | JLA101_20150528_APPENDIX.raw | APPENDIX |
| JLA104 | SMH | JLA104_20150615_NORMAL | NORMAL |
| | SMH | JLA104_20150615_TUMOUR_POSTCHEMORAD | TUMOUR |
| JLA105 | SMH | JLA105_20150615_NORMAL | NORMAL |
| | SMH | JLA105_20150615_TUMOUR | TUMOUR |
| JLA106 | SMH | JLA106_20150615_NORMAL | NORMAL |
| | SMH | JLA106_20150615_APPENDIX | APPENDIX |
| | SMH | JLA106_20150615_TERMINAL_ILEUM | MUSCLE |
| | SMH | JLA106_20150615_TUMOUR_SITE1 | TUMOUR |
| | SMH | JLA106_20150615_TUMOUR_SITE2 | TUMOUR |
| JLA107 | CXH | JLA107_20150616_NORMAL | NORMAL |
| | CXH | JLA107_20150616_POLYP | POLYP |
| JLA109 | CXH | JLA109_20150618_NORMAL.raw | NORMAL |
| | CXH | JLA109_20150618_TUMOUR.raw | TUMOUR |
| JLA110 | SMH | JLA110_20150625_NORMAL | NORMAL |
| | SMH | JLA110_20150625_NORMAL_02 | NORMAL |
| | SMH | JLA110_20150625_TUMOUR_01 | TUMOUR |
| | SMH | JLA110_20150625_TUMOUR_02 | TUMOUR |
| JLA111 | SMH | JLA111_20150626_NORMAL_01 | NORMAL |
| | SMH | JLA111_20150626_TUMOUR_01 | TUMOUR |
| | SMH | JLA111_20150626_TUMOUR_02 | TUMOUR |
| JLA112 | SMH | JLA112_20150629_NORMAL | NORMAL |
| | SMH | JLA112_20150629_TUMOUR_01 | TUMOUR |
| | SMH | JLA112_20150629_TUMOUR_02 | TUMOUR |
| JLA119 | SMH | JLA119_20150709_NORMAL_01 | NORMAL |
| | SMH | JLA119_20150709_TUMOUR_01 | TUMOUR |
| | SMH | JLA119_20150709_TUMOUR_02 | TUMOUR |
| JLA123M | SMH | JLA123M_20150720_TUMOUR | TUMOUR |
| JLA124M | SMH | JLA124M_20150720_TUMOUR_01 | TUMOUR |
| | SMH | JLA124M_20150720_TUMOUR_02 | TUMOUR |
| JLA125M | SMH | JLA125M_20150720_NORMAL | NORMAL |
| | SMH | JLA125M_20150720_TUMOUR | TUMOUR |
| JLA128 | SMH | JLA128_20150728_NORMAL | NORMAL |
| | SMH | JLA128_20150728_TUMOUR | TUMOUR |

TABLE 5.2-continued

| Subject number | Location | Sample identifier | Sample type |
|---|---|---|---|
| JLA133 | SMH | JLA133_20150729_NORMAL | NORMAL |
|  | SMH | JLA133_20150729_POLYP | POLYP |
| JLA140 | SMH | JLA140_20150730_NORMAL | NORMAL |
|  | SMH | JLA140_20150730_TUMOUR | TUMOUR |

Example 6 Ovarian Cancer Analysis Using REIMS Technology

In this ex vivo data study, a total of 146 samples were analysed (Table 6.1)

TABLE 6.1

| Total Samples | 146 |
|---|---|
| Ovarian Cancer | 67 |
| Normal (15 ovary, 15 peritoneum, 15 fallopian tube) | 45 |
| Borderline tumour of ovary | 15 |
| Benign ovarian lesions | 14 |
| Non-ovarian tumours | 4 |
| Non-ovarian smooth muscle tumour of uncertain malignant potential (STUMP) | 1 |

The samples were histologically validated and analysed by mass spectrometry. Statistical analysis using supervised linear discriminant analysis showed excellent separation of cancer and borderline tissue on the margins of cancer and normal tissue. Good separation was also seen when including benign lesions. See FIG. 15.

Example 7—Neurosurgery

At least 28 intraoperative cases for neurosurgery were analysed, with over with 199 in vivo and over 207 ex vivo samples. An example data set is shown in Table 7.1.

TABLE 7.1

| Subject | Location | Tumour type | No. of in-vivo samples | No. of ex-vivo samples |
|---|---|---|---|---|
| IKBRA16 | CXH | Glioblastoma multiforme | 7 | 8 |
| IKBRA17 | CXH | TBC | 10 | 10 |
| IKBRA18 | CXH | Low grade glioma with high grade parts | 7 | 7 |
| IKBRA19 | CXH | Likely glioblastoma multiforme |  |  |
| IKBRA20 | CXH | Low grade glioma | 14 | 13 |
| IKBRA21 | CXH | Low grade glioma | 6 | 7 |
| IKBRA22 | CXH | Low grade glioma | 8 | 9 |
| IKBRA23 | CXH | Potential glioblastoma | 8 | 10 |
| IKBRA24 | CXH | Potential glioblastoma multiforme | 8 | 10 |

Haemangioblastoma specimens were also analysed. Histology data has been matched to previous cases and specimen measurements.

Example 8—Brain Cancer Analysis Using REIMS Technology

Analysis was carried out on a subject suffering from glioblastoma multiforme ("GBM"), as discussed with reference to FIG. 16.

Figure 16:
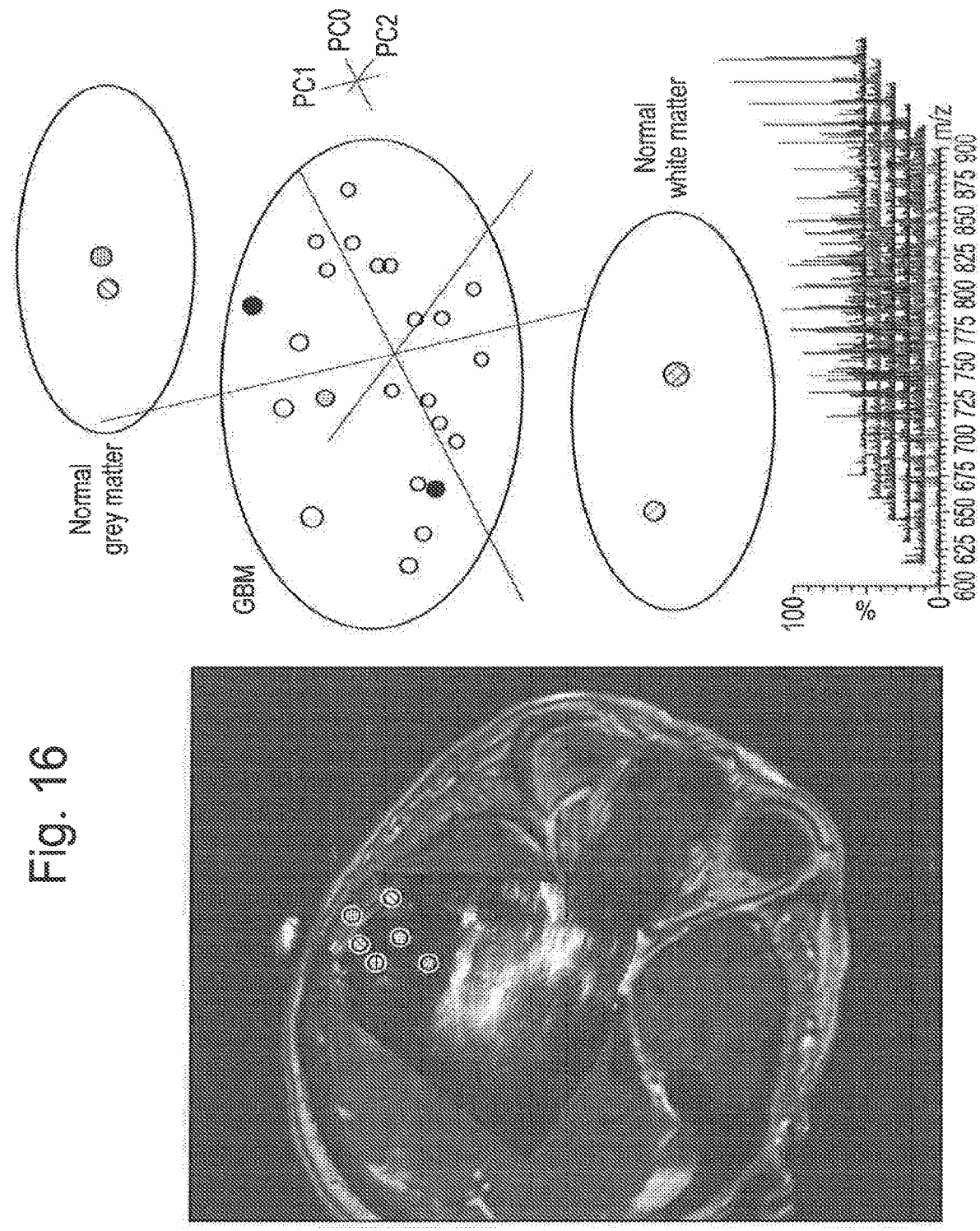
FIG. 16 shows results from Example 8, which provides more detail on this Figure.

The left-hand portion of FIG. 16 shows a 3D image of the brain of the subject which has been overlayed with a real time ultrasonic image. Six sampling points were taken with a REIMS technology probe during surgery and are also depicted on the image shown in FIG. 16.

FIG. 16 also shows six corresponding mass spectra which were recorded which each mass spectrum corresponding to a different sampling point.

FIG. 16 also shows a 3D PCA plot of all sampling point taken during the surgery. The 3D PCA plot was labelled by a neuropathologist.

All in vivo and ex vivo sampling points are shown on the PCA plot shown in FIG. 16. It is apparent from FIG. 16 that normal grey and white matter group separately both from the cancerous samples and from each other.

Thus, the method may optionally be used to analyse, e.g. identify or distinguish between, one or more brain tissue types, e.g. selected from grey matter, white matter, and/or cancer, wherein the cancer may, e.g. be glioblastoma multiforme.

Example 9—Tumour Typing and Grading Using REIMS Probe

Figure 17:
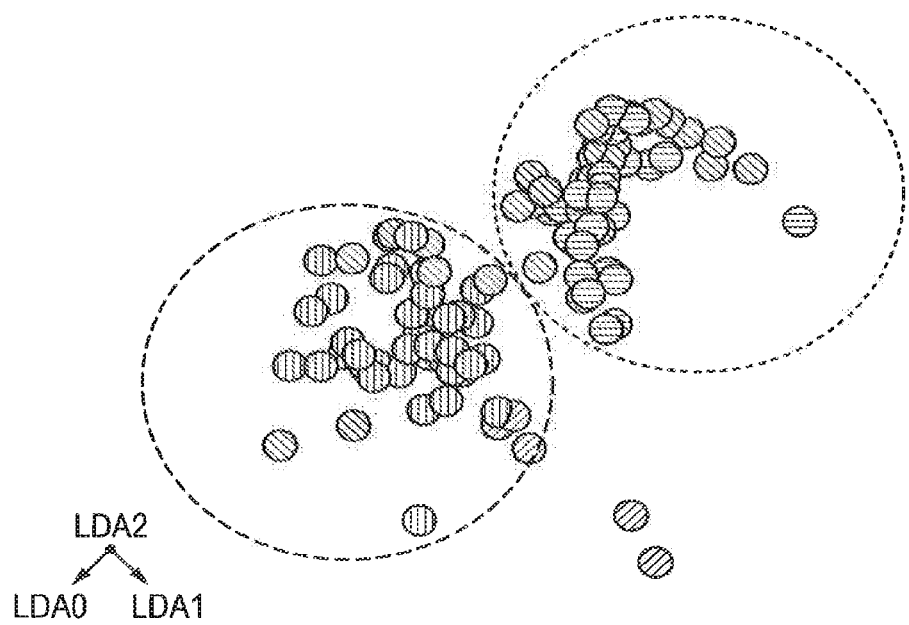
FIG. 17 shows results from Example 9, which provides more detail on this Figure.

FIG. 17 shows the result of comparing subjects with high grade (grade IV) glioblastoma multiforme (e.g., glioblastoma, giant cell glioblastoma and recurrent gliobastoma) and low grade (grade II and III) tumours (e.g. anaplastic astrocytoma, oligodendroglioma and diffuse astrocytoma).

It is apparent from FIG. 17 that high grade (grade IV) and low grade (grade II and III) tumours separated well on the 3D pseudo LDA plot.

Subjects having intermediate grade III tumours grouped either with the high grade area of the space or with the low grade area of the space.

Thus, the method may optionally be used to analyse, e.g. identify or distinguish between, one or more cancer grades, wherein the cancer may, e.g. be grade I, II, III, and/or IV, and/or be selected from, e.g., glioblastoma, giant cell glioblastoma, recurrent gliobastoma, anaplastic astrocytoma, oligodendroglioma, and/or diffuse astrocytoma.

Example 10—Comparison of Healthy and Cancerous Samples with Both Raman Spectroscopy and REIMS Sampling A Subject was suffering from a low grade (grade II) astrocytoma. The subject was subjected to a combination of Raman spectroscopy sampling and REIMS sampling. Raman data from a total of 32 sampling points were recorded. 13 of these 32 sampling points corresponded with normal tissue, 18 of these 32 sampling points corresponded with cancerous tissue and 1 corresponded with background.

REIMS sampling was also performed at 14 of the 32 sampling points.

Figure 18A:
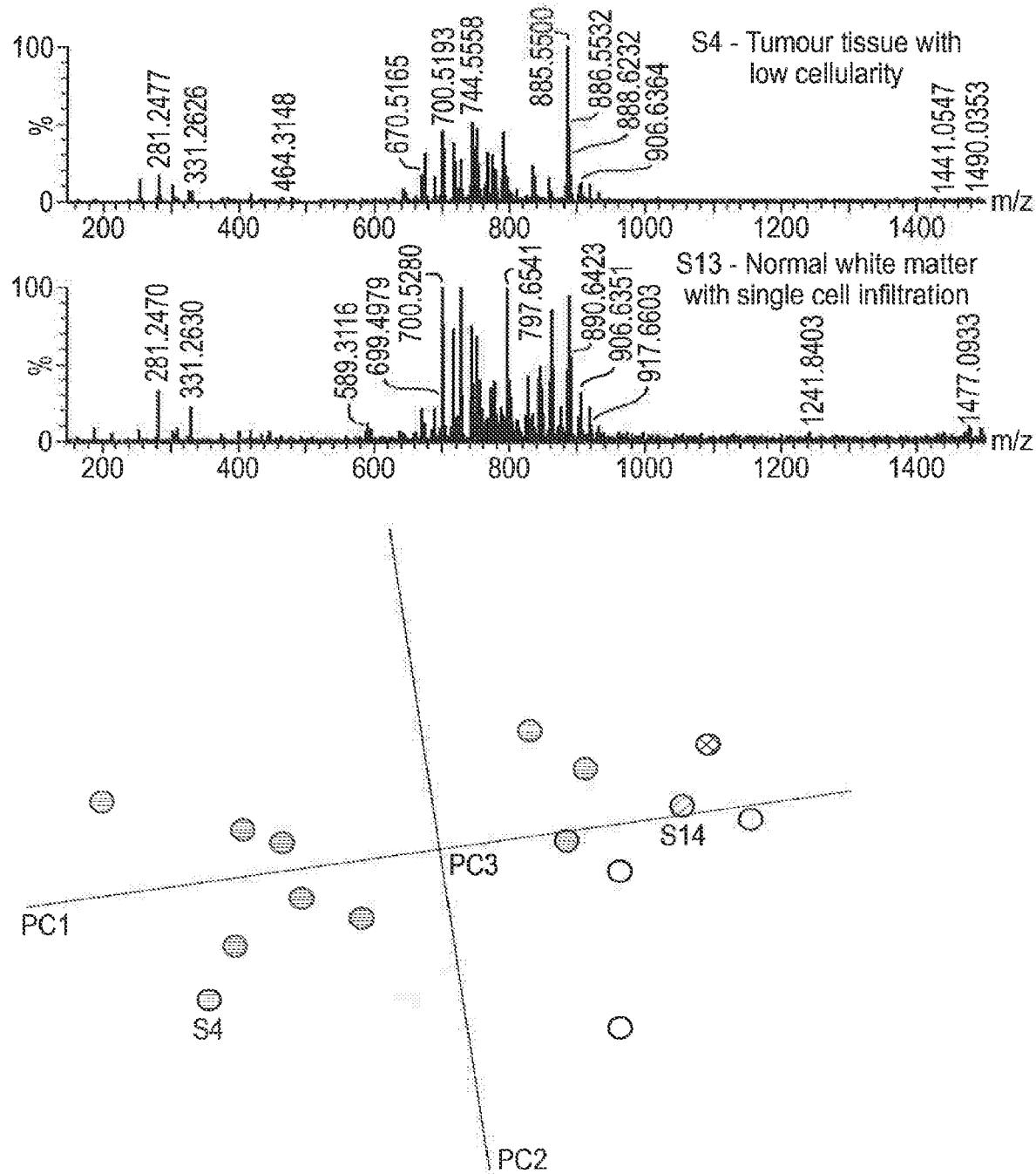
FIG. 18 shows results from Example 10, which provides more detail on this Figure.

FIG. 18a shows REIMS mass spectra from two sampling points. Sampling point S4 corresponded of tumour tissue with low cellularity. In particular, sampling point S4 corresponded with posterior medial superficial tumour. Fragments of the tumour tissue had low cellularity and some degree of reactive gliosis. Sampling point S14 corresponded with normal white matter have single cell infiltration. In particular, sampling point S14 corresponded with posterior base pot. Multiple fragments of white matter with reactive gliosis and single-cell tumour infiltration are present.

FIG. 18a also shows a 3D PCA plot corresponding to all sampling points taken throughout the surgery.

FIG. 18b shows corresponding Raman spectra from sampling points S4 (tumour) and S14 (normal white matter) together with a 3D PCA plot from all sampling points taken throughout the surgery.

Both the Raman spectra and REIMS technology spectra have a tissue specific "fingerprint" in the phospholipid range. The main differences observed on the PCA plot are due to the lipid vibration region.

There are a number of sulfatides which are very specific for normal white matter of brain. For example, the following sulfatides are specific for normal white matter of the brain:

TABLE 10.1

| m/z (calculated) | compound | formula |
| --- | --- | --- |
| 888.624 | C24:1 sulfatide | $C_{48}H_{91}NO_{11}S$ |
| 906.635 | C24-OH sulfatide | $C_{48}H_{92}NO_{12}S$ |
| 916.655 | C26:1 sulfatide | $C_{50}H_{94}NO_{11}S$ |

Example 11 Detection of Bacteria in Human Colorectal Tissue Specimens

The inventors attempted to visualise the presence and distribution of bacteria in human colorectal tissue specimens. Bacteria are known to cover the mucosal membranes in the gut and the gut microbial community is arguably most extensively studied and characterised. The analysis was performed by generating single ion images for the taxonomical markers that are listed in Table 14. Bacteria could be visualised in >90% of analysed colorectal specimens, including healthy and cancerous tissue specimens. Among cancerous specimens, bacteria were largely found localised in areas that were identified as necrotic by histopathological examination of the H&E stained tissue sections. However, bacteria were also frequently detected along healthy mucosa. An example of each will be further discussed below.

11 A) Analysis of Necrotic Tissue

Figure 19A:
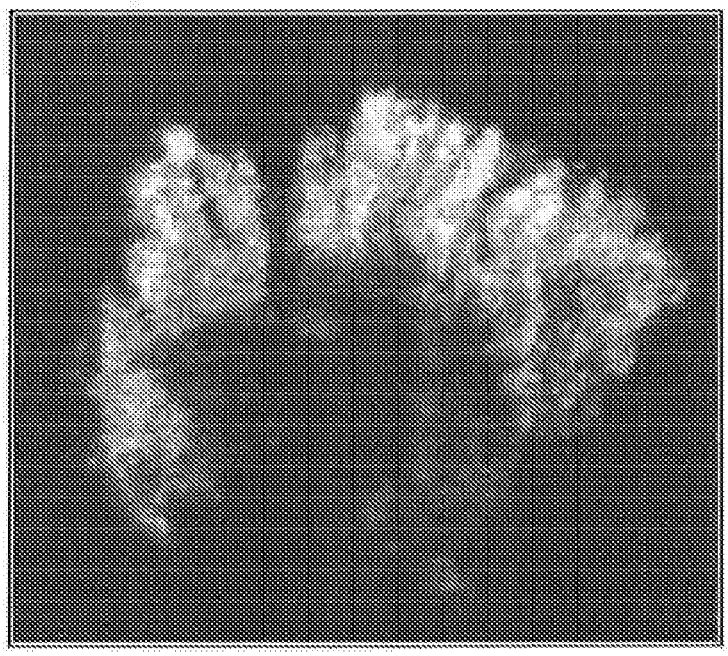
FIG. 19 shows results of Example 11. DESI-MS image displaying tissue type distribution in a colorectal tissue specimen; In the original picture, tumour tissue was shown in green and stroma tissue in red. In the black and white version, tumour tissue is shown in light grey and stroma tissue in darker grey; B) H&E stained and histopathologically annotated section post-DESI.
Figure 19B:
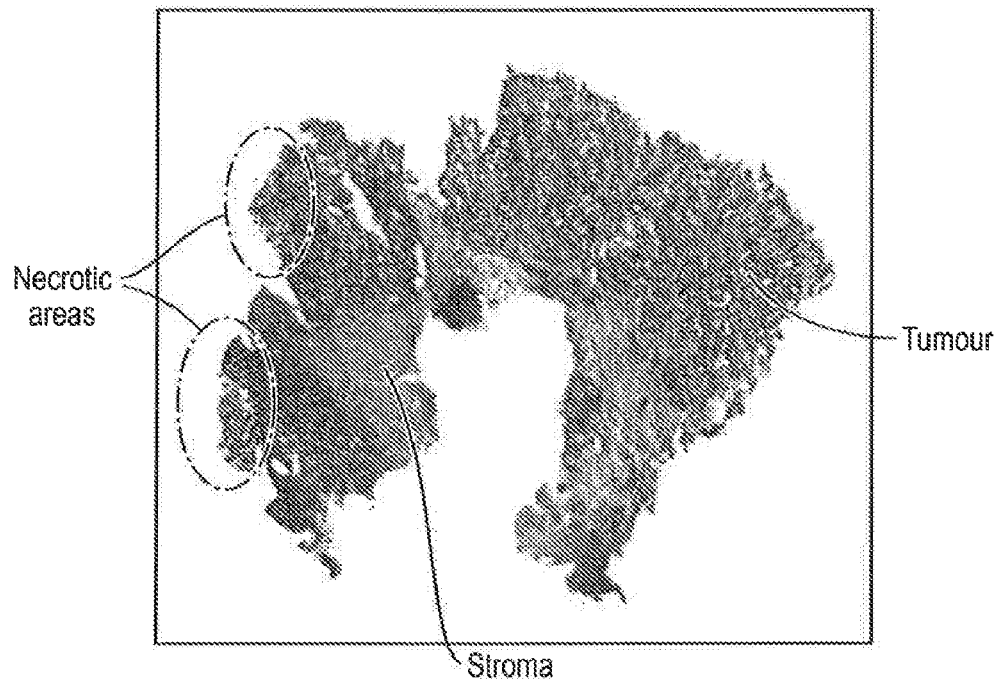

FIG. 19 shows the tissue type-distribution of a cancerous tissue specimen that originated from the centre of tumour dissected during a right hemicolectomy. Histopathological examination revealed the presence of cancerous and stromal tissue.

Mass spectra of the necrotic tissue area as well as surrounding cancerous and stromal tissue are shown in FIG. 19 and display a markedly different phospholipid composition for the necrotic area compared to viable human tissue, namely a significantly reduced glycerophospholipid content and a variety of lower molecular weight sphingolipid-derived taxonomic marker species in the mass range of m/z=500-700.

Figure 20:
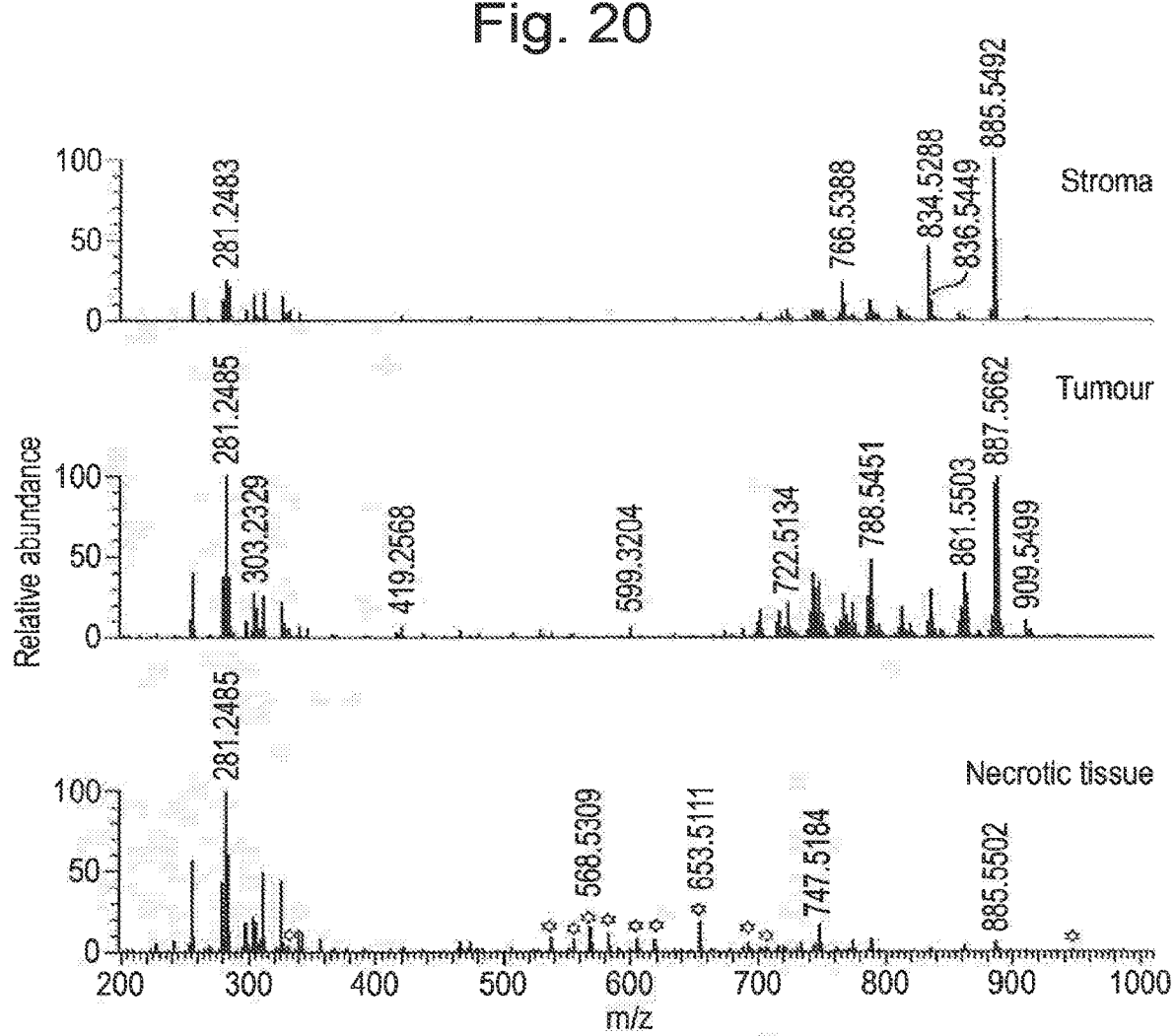
FIG. 20 shows results of Example 11. Full scan mass spectra for colorectal adenocarcinoma, tumour surrounding stroma and necrotic tissue of same tissue section shown in FIG. 19. Stars indicate major taxonomic markers.

When visualising these taxonomical markers, the respective single ion images were found to largely display co-localisation of the taxonomical marker molecules and thus bacterial cells. An array of co-localised single ion images of homologous molecules are displayed in FIG. 20 and could be attributed to the Bacteroidetes phylum. Iso-C15:O-substituted phosphoglycerol dihydroceramides were found to be specific for the Porphyromonadaceae family (part of Bacteroidetes phylum), which in this study were only represented by *Parabacteroides* spp., however, named compounds were reported present in high abundance in *Porphyromonas gingivalis*, suggesting general applicability of this marker for this family. Members of the Bacteroidetes phylum were reported in metagenomic studies to be accountable for up to 50% of the gut microbial community. However, taxon-specific markers for Bacteroidetes *fragilis* were not detected suggesting that the Bacteroidetes bacteria present do not contain a high amount of the opportunistic pathogen *B. fragilis*.

Figure 21:
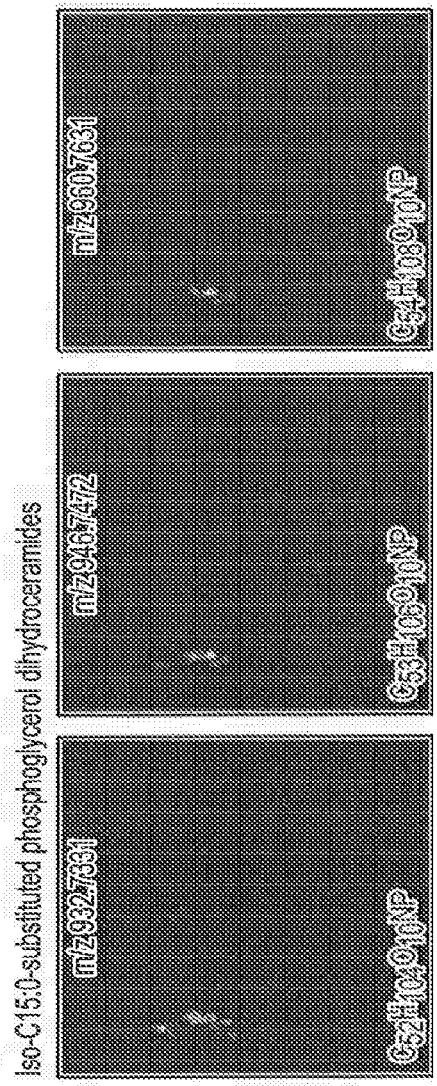
FIG. 21 shows results of Example 11. Single ion images and representative intensity distribution plots for known and confirmed homologous sphingolipid species that showed specificity as taxonomic markers.

FIG. 21 shows single ion images of further taxonomical markers which were found to be specific for the Bacteroidetes phylum, among those dihydroceramide and a related compound with two more double-bonds (or equivalents). The compound at m/z=639.4954 was found to be a homologue of the lipid species at m/z=653.5113 mentioned earlier. A signal at m/z=566.4790 indicates the presence of members of the Flavobacteria class. Specific plasmalogen species for Clostridiales and Fusobacteria were additionally found, as well as an odd numbered PE that shows specificity for the Enterobacteriales order. All of these bacterial classes are capable of living under anaerobic conditions and were reported to be major components of the human gut microbiome.

While members of the Bacteroidetes phylum largely cluster around the left hand side of the tissue section where necrotic areas were identified, Clostridiales and Fusobacteria were additionally detected in at a spot more centred within the tissue section, thus confirming the expectation that not all bacterial species show identical localisation. The large bacterial presence observed in the necrotic tissue areas is tentatively associated with the lack of immunoresponse of the human body, which enables bacteria to multiply largely uncontrolled.

11B Detection of Bacteria in Healthy Mucosa

Figure 22:
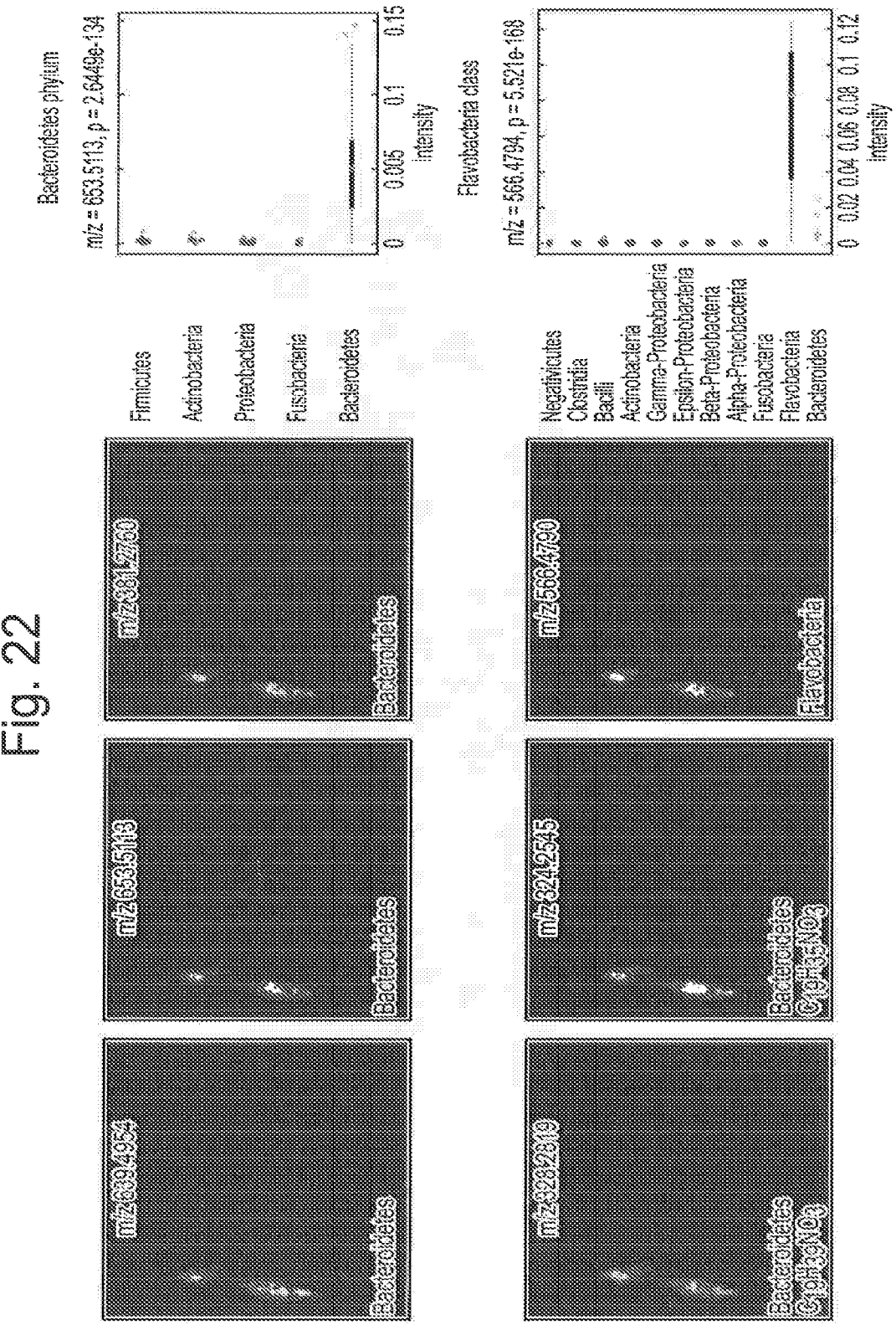
FIG. 22 shows results of Example 11. Single ion images and intensity selected distribution plots for other taxonomical markers.
Figure 22:
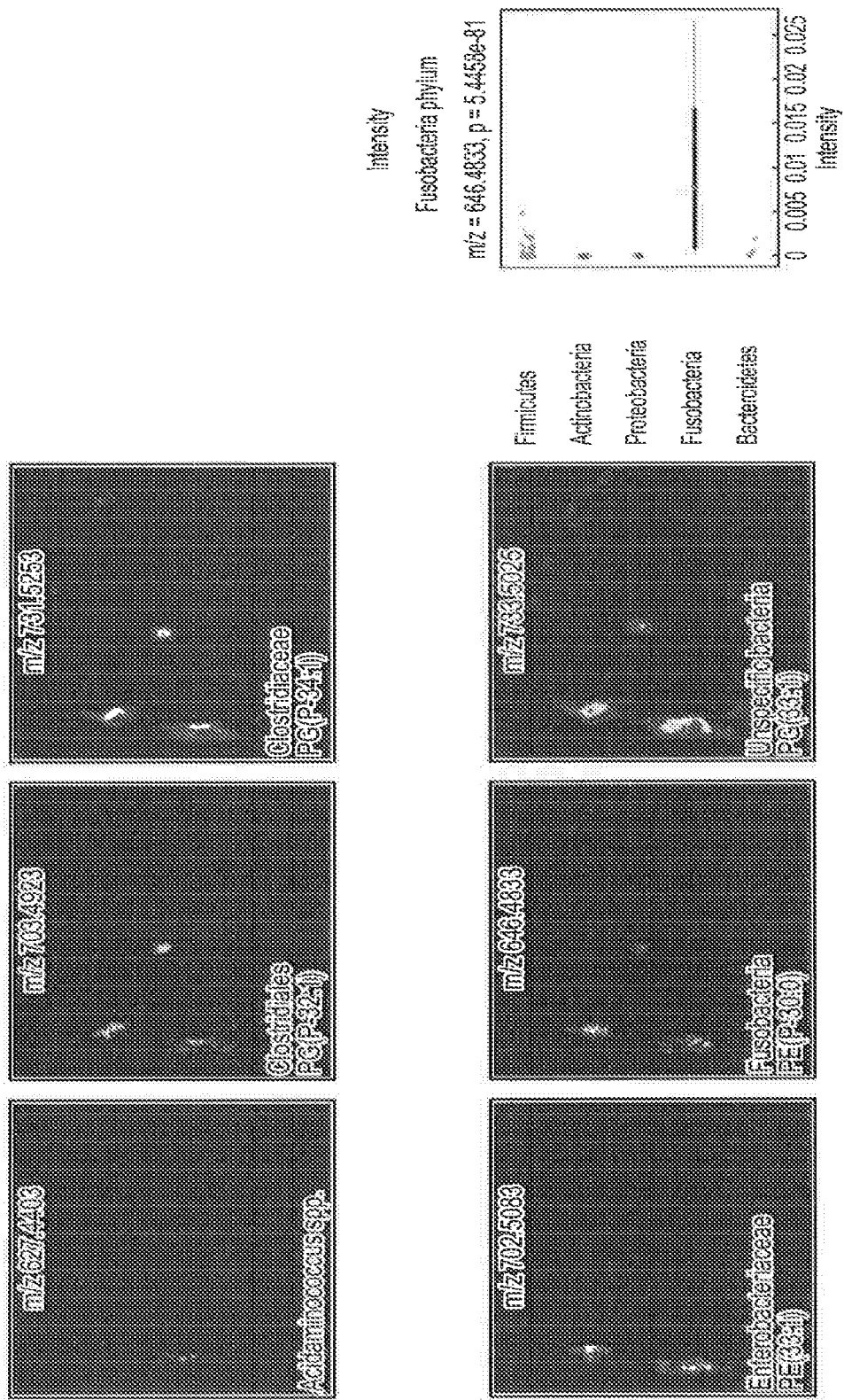

FIG. 22 shows the tissue type-distribution of a healthy tissue specimen that originated from a right hemicolectomy. It originated from healthy colon tissue 5 cm distance from the centre of tumour. Histopathological examination revealed healthy mucosa and submucosa, divided by the muscularis mucosae layer. Additionally, two lymphoid aggregates (inflammation) can be observed.

FIG. 22 shows single ion images for those taxon-specific markers that were detected in this sample. Generally, far fewer and less intense signals were observed than for necrotic tissue. This is tentatively attributed to the healthy immune response that restricts unlimited bacterial growth as was observed in the necrotic tissue specimen. However, the two main bacterial components of the commensal human microbiome could still be detected, namely members of the Bacteroidetes phylum and Clostridiaceae family.

Metagenomic characterisations were performed for this sample and confirmed the presence of large amounts of Bacteroidetes, Proteobacteria and Firmicutes which on class level were largely attributable to Clostridia, Bacteroidia, and Gamma-Proteobacteria, respectively.

This study demonstrates that molecular species differ significantly between microbial lipidomes and the human tissue lipidome. Taxon-specific markers for a variety of bacterial types were shown to be absent in human lipidomes/metabolome and can thus be used to visualize the presence of bacteria in human samples, as shown for human colorectal tissues. It was further demonstrated that taxonomic markers derived by the REIMS technique can be used in conjunction with other mass spectrometric ionization techniques detecting lipid profiles, such as, DESI.

Example 12 Analysis of Necrosis

The method may be used to analyse necrosis, e.g., to detect necrotic tissue. This was exemplified in human lung tissue samples of two different patients. Samples were analysed using histopathology, which identified 100% necrotic cancer tissue. The samples were also analysed using MS and it was possible to distinguish between necrotic and non-necrotic tissue using MS.

Figure 23B:
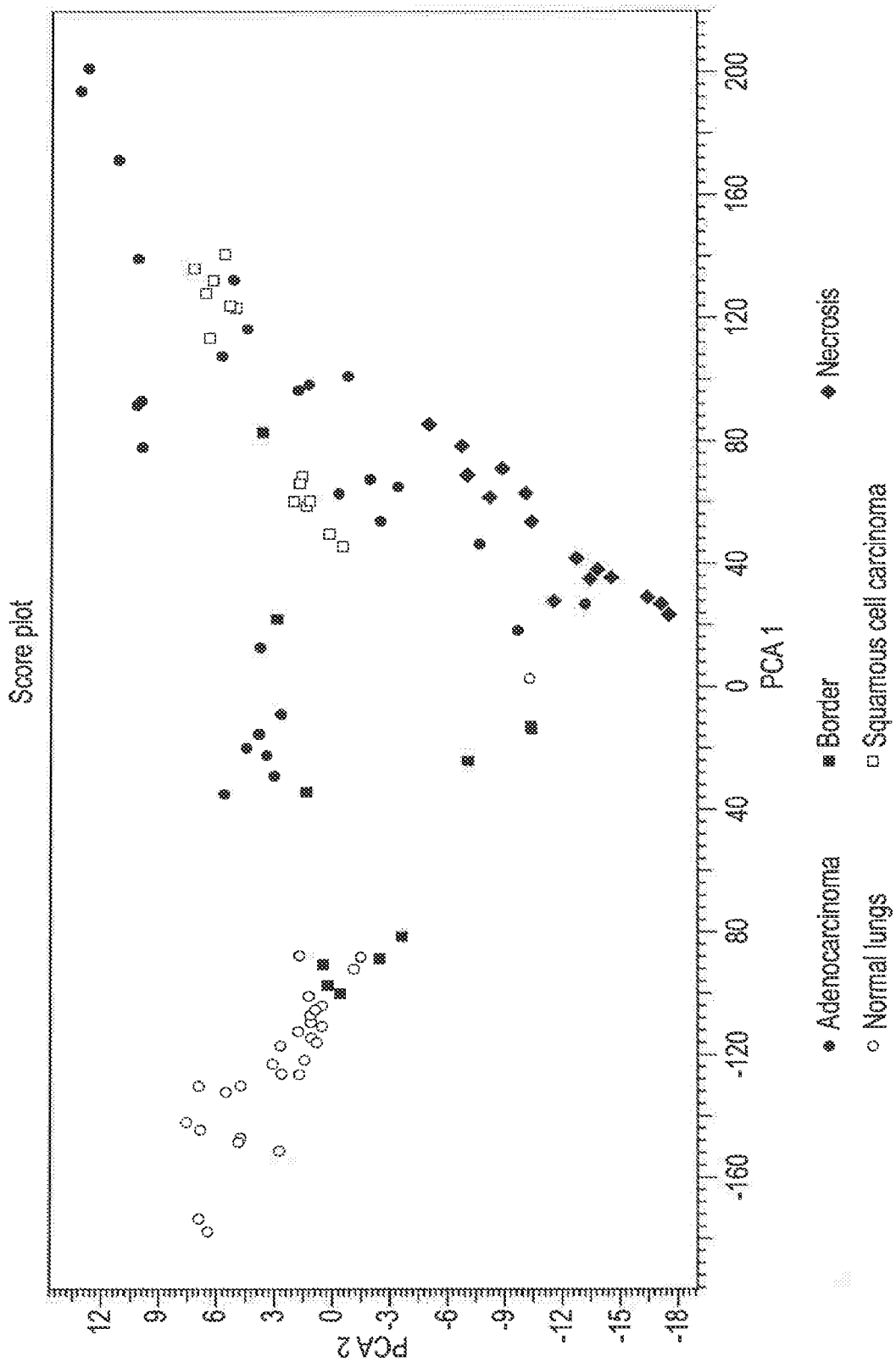
FIGS. 23 (*a*) and (*b*) show results of Example 12.

The second PC component separates necrosis from the other tissue, this can be seen in FIG. 23. Adenocarcinoma, normal lung, cancer border, squamous cell carcinoma and necrotic tissue was analysed and could clearly be distinguished.

Example 13 Analysis of Ovarian Cancer

Background

Ovarian cancer (OC) is common and five-year survival is 21.9% and 5.6% for stage 3 or stage 4 disease respectively, which is when 60% of women first present. Intra-operative tissue identification typically relies on frozen section histopathological analysis, which is time-consuming and expensive. Macroscopic non-descript lesions, which may be cancer, can be difficult to correctly identify intra-operatively, especially after neo-adjuvant chemotherapy.

Methods

Fresh frozen ovarian samples (normal, benign, borderline, OC), plus fallopian tube and peritoneum were cut with the Covidien diathermy hand-piece. Surgical smoke was extracted and ionised in a Water's Xevo G2-S mass spectrometer. Resultant mass spectra underwent pre-processing and background subtraction with lock-mass. Processed tissue samples were re-reported by histopathologists to confirm histology. These data were used to create an authentic spectral database, which was histologically ratified. Data were processed with principal component and linear discriminant analyses and leave one patient out cross-validation.

In total 144 different samples were collected from 130 individual patients (some patients provided more than one tissue type), which is summarised in Table 13.1. Fresh tissue samples had been snap frozen and stored at −80° c. Data including age of sample, International Federation of Gynaecology and Obstetrics (FIGO) stage and grade of disease, histopathology as reported in medical records and sample site was recorded on a National Health Service (NHS) networked computer and only accessed by clinically authorised personnel.

Batches of tissue were issued from the tissue bank and logged to the study accordingly. The samples were thawed and cut with a Covidien ForceTriad™ energy generator coupled with a modified electrosurgical knife. Samples were processed in cut mode using 25 watts and the resultant smoke analysed with a Waters® G2-S TOF mass spectrometer in negative-ion mode.

TABLE 13.1

Tissue types included in study

| Organ group | Tissue type | Sub-type | No of samples | Spectra |
|---|---|---|---|---|
| Ovary | Normal | | 15 | 64 |
| | Benign | | 8 | 32 |
| | Borderline | | 8 | 30 |
| | Cancer | Serous | 32 | 115 |
| | | Endometrioid | 9 | 35 |
| | | Clear cell | 7 | 24 |
| | | Mucinous | 5 | 21 |
| | No tumour seen | | 11 | 37 |
| | Inconclusive | | 15 | 49 |
| | Excluded | | 5 | 18 |
| Fallopian tube | Normal | N/A | 14 | 49 |
| Peritoneum | Normal | N/A | 15 | 55 |
| | | | 144 | 529 |

Figure 24:
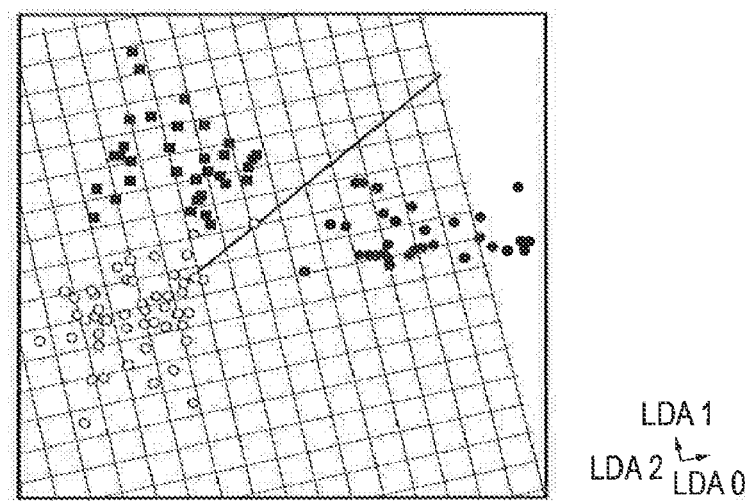
FIG. 24 shows results of Example 13.

Findings 144 tissue samples were processed, producing 529 spectra. Normal ovary and OC could be distinguished in principal component and linear discriminant analyses. Cross-validation resulted in 100% sensitivity and 100% specificity in the separation of normal ovary from viable OC (n=189). A further analysis comparing OC with fallopian tube, normal ovary and peritoneum resulted in 100% sensitivity and 97.8% specificity with cross validation (n=291). Results are shown in FIG. 24.

Interpretation

This study has shown that normal ovarian, peritoneal and fallopian tube tissues have unique spectral signatures, which may be used to accurately determine tissue type. The method may be used intra-operatively (in-vivo). The method's ability to rapidly determine tissue type may shorten operations and reduce morbidity and mortality, potentially improving patient care and survival.

Example 14 Faecal Analysis Using REIMS

1. Take a sample, e.g., a 10 μl loop of fresh or, if frozen, a defrosted sample of stool.
2. If using forceps based REIMS, take a small amount between the forceps and draw the probes together.
3. Perform REIMS analysis, e.g., using previously described parameters for REIMS.

Figure 25:
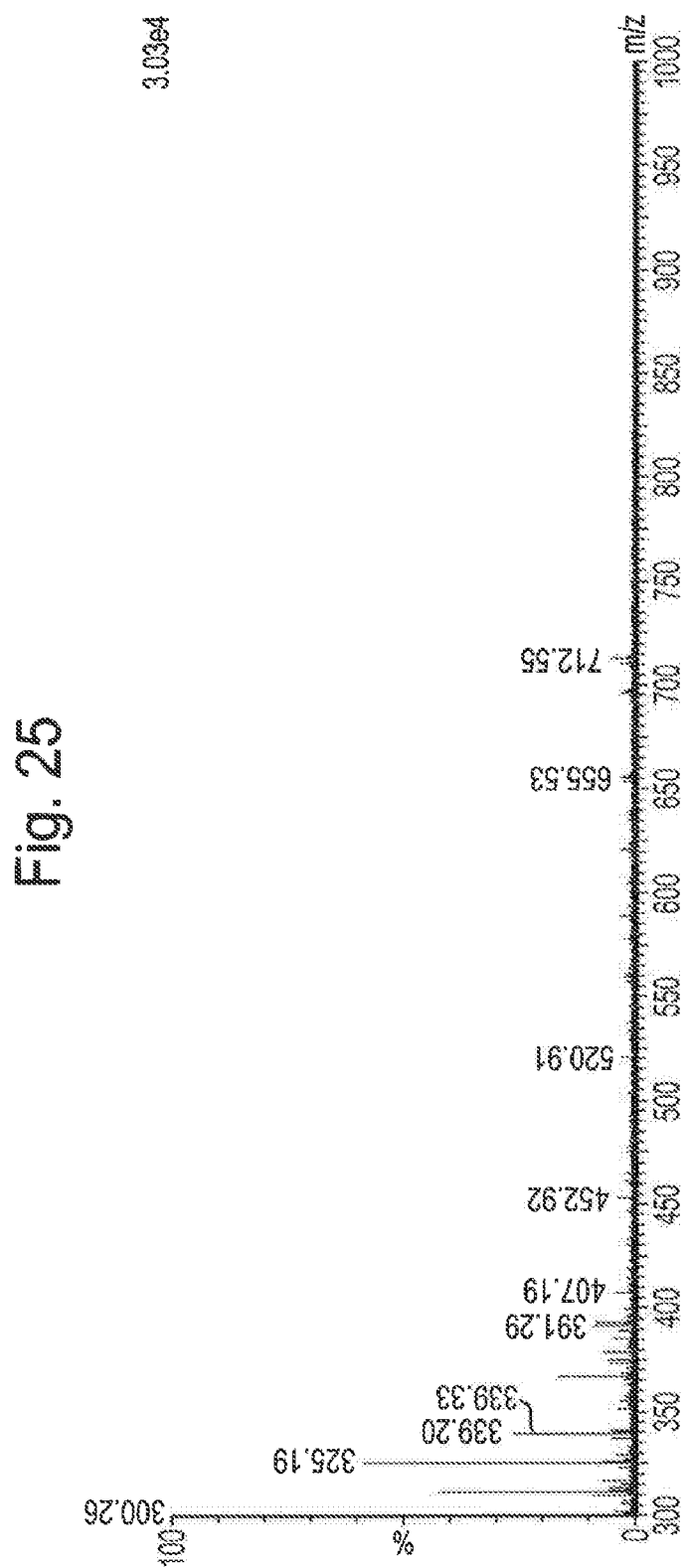
FIG. 25 shows a spectrum observed when analysing stool samples using rapid evaporative ionisation mass spectrometry ("REIMS") analysis.

FIG. 25 shows a spectrum observed when analysing stool samples using REIMS

Example 15 REIMS Analysis of Blood Culture Pellets

Objective: This protocol describes a specific example of a procedure for analysing blood culture samples using REIMS analysis.

Initially, inoculate 10 ml of defibrinated horse blood with a single microbial colony. Grow this aerobically at 37° C. for 24 hours. Next, inoculate 1 l of horse blood with 1 ml of the overnight culture. Grow aerobically at 37° C. and at time 0 and each hour thereafter remove 25 ml to analyse in the following way:

a. Transfer 10 ml into a 50 falcon tube and centrifuge the sample for 10 mins at 3,2000 g. Use REIMS to analyse the pellet as described below.

b. Make a 2.5% Microbiology grade agar solution using HPLC water and heat until the solution reaches 50° C. Leave to stand for 1 minute to remove air bubbles. Next, add 2 ml of this to 8 ml of the blood culture described above and mix gently by pipetting. Pour into a small agar plate and allow to set for 15 minutes. Use this to perform REIMS analysis.

c. With 1 ml of this solution make serial dilutions to 10-6 using molecular grade water, and plate 100 μl of each onto a blood agar plate. Incubate for 24 hours and after count the number of colonies to determine the CFU.

d. Use a further 2 ml of the blood culture and freeze at −80° C. for LC-MS analysis.

REIMS analysis may be performed on the centrifuged pellet and/or the agarose block.

Example 16 Analysis of Mucosal Specimens Using DESI Mass Spectrometry

Medical swabs were analysed by desorption electrospray ionisation ("DESI") mass spectrometry with the intention of extracting chemical information relevant to patient care in a non-invasive procedure. In this context, desorption electrospray ionisation ("DESI") mass spectrometry represents a fast and direct method for metabolomic profiling of different mucosal membrane models or membranes (e.g. nasal, vaginal, oral) by desorbing and analysing molecules from the surface of standard medical cotton swabs.

A study was performed in which vaginal mucosa (n=25 pregnant, n=25 non-pregnant), nasal mucosa (n=20) and oral mucosa (n=15) were sampled with medical ryon swabs from patients. Medical cotton swabs sold as Transwab® Amies (MWE medical wire, Wiltshire, UK) were used for sampling mucosal membranes which were then transferred to a sterile tube without buffer or storage medium solution and were stored at −80° C. in a freezer.

Figure 32:
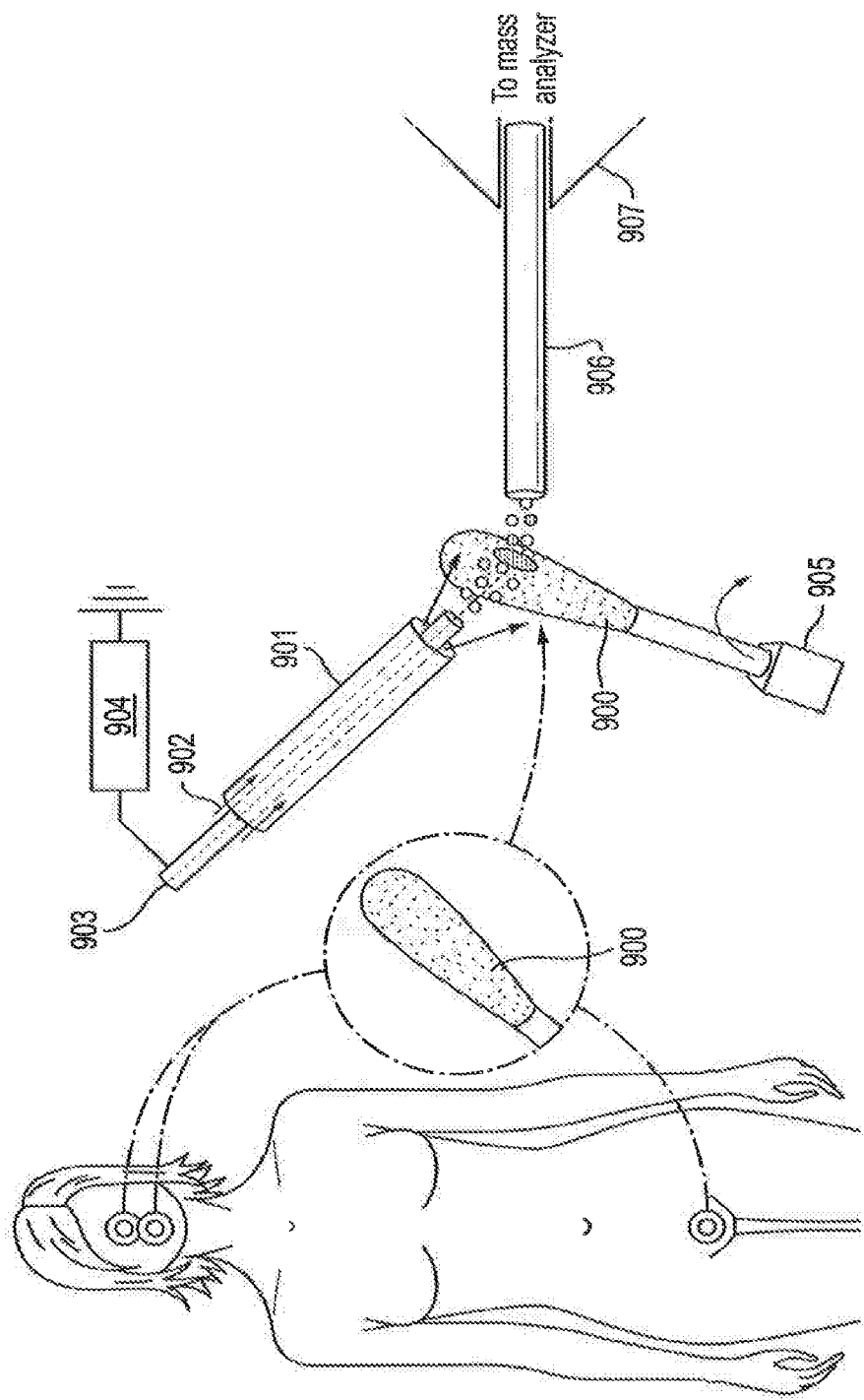
FIG. 32 shows schematically mucosal membrane sampling from selected parts of the human body (e.g., urogenital tract, oral or nose cavity) using medical cotton swabs as a sampling device wherein the surface of the medical swab may then be directly analysed by desorption electrospray ionisation ("DESI") mass spectrometry without prior sample preparation procedures according to various embodiments.

FIG. 32 highlights the sampling points of analysed mucosal membranes collected from the urogenital tract, oral and nasal cavity with a medical cotton swab 320. As illustrated by FIG. 32, the surface of the medical swab 320 was directly analysed by desorption electrospray ionisation ("DESI") mass spectrometry without prior sample preparation procedures.

Desorption electrospray ionisation ("DESI") mass spectrometry experiments were performed using a Xevo G2-S Q-TOF® mass spectrometer (Waters®, Manchester, UK). The desorption electrospray ionisation ("DESI") source comprises an electronic spray emitter 321 connected with a gas 322, solvent 323 and power supply 324 and an automatic rotatable swab holder device 325 with adjustable rotation speed.

For the desorption electrospray ionisation ("DESI") mass spectrometry analysis the medical swab 320 was positioned orthogonally to and in front of an inlet capillary 326 connected to the mass spectrometer atmospheric pressure interface 327. A mixed methanol:water solution (95:5) spray solvent was used at a flow rate of around 10 μL/min for desorption of the sample material. Nitrogen gas at around 7 bar and a voltage of around 3.4 kV were also provided to the sprayer 320.

The mucosa was absorbed from the surface of the rotated swabs by gently desorbing molecules with charged droplets of the organic solvent, and desorbed ions (e.g. lipids) were subsequently transferred to the mass spectrometer.

Full scan mass spectra (m/z 150-1000) were recorded in negative ion mode. Spectrometric data were then imported into a statistical analysis toolbox and processed. For data analysis and extraction of specific molecular ion patterns, an unsupervised principal component analysis ("PCA") as well as a recursive maximum margin criterion ("RMMC") approach were applied to improve supervised feature extraction and class information with leave one out cross validation ("CV") to determine classification accuracy within the data set.

Figure 33A:
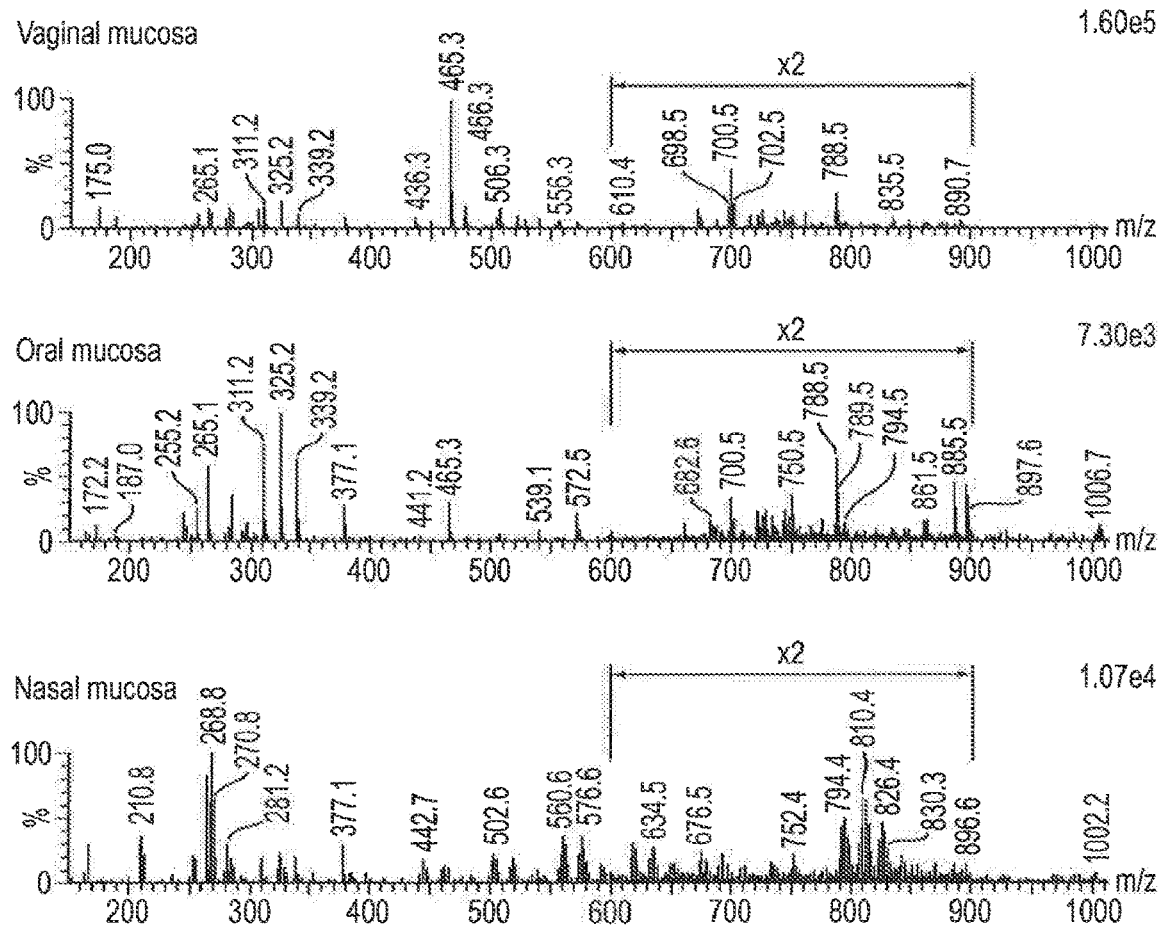
FIG. 33A shows averaged negative-ion desorption electrospray ionisation ("DESI") mass spectra from vaginal, oral and nasal mucosa recorded using a Xevo G2-S Q-Tof® mass spectrometer.
Figure 33B:
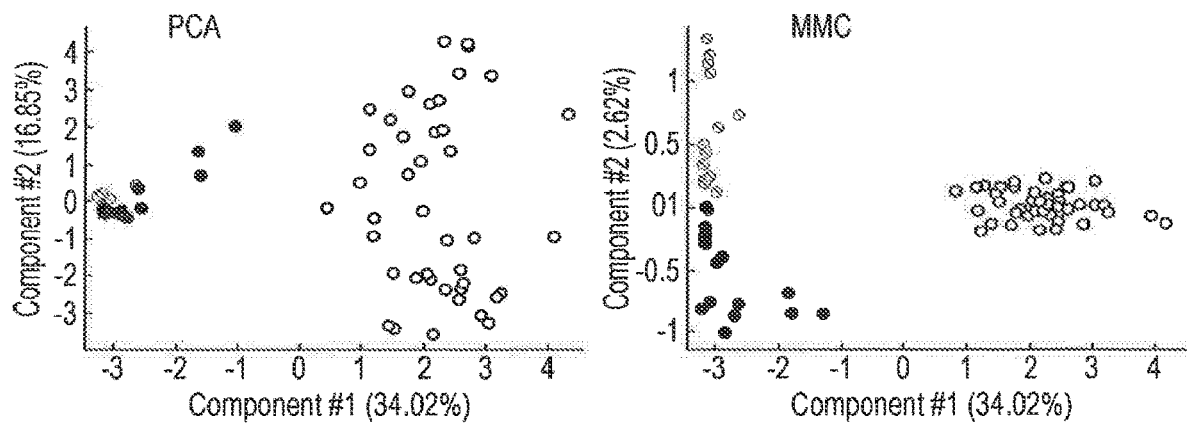
FIG. 33B shows a PCA and MMC score plot for vaginal (n=68, shown as shaded circles), oral (n=15, shown as white-filled circles) and nasal (n=20, shown as black-filled circles) mucosa acquired with desorption electrospray ionisation ("DESI") mass spectrometry.

FIGS. 33A and 33B show the results of desorption electrospray ionisation ("DESI") mass spectrometry analysis of swabs, and multivariate statistical analysis including principal component analysis (PCA) and recursive maximum margin criterion (RMMC) in an investigation of metabolic signatures in different mucosal membrane models.

FIG. 33A shows averaged negative-ion mode desorption electrospray ionisation ("DESI") mass spectra from vaginal, oral and nasal mucosa recorded using a Xevo G2-S Q-Tof® mass spectrometer.

FIG. 33B shows a principal component analysis ("PCA") and a maximum margin criterion ("MMC") score plots for vaginal (n=68), oral (n=15) and nasal (n=20) mucosa acquired with desorption electrospray ionisation ("DESI") mass spectrometry.

As shown in FIG. 33A, unique lipid patterns were observed between different mucosal membrane models. The spectra for vaginal mucosa and oral mucosa featured predominately glycerophospholipids, e.g., [PS(34:1)-H]$^-$ having a mass to charge ratio ("m/z") of 760.4, [PS(36:2)-H]$^-$ having a m/z of 788.5 and [PI (36:1)-H]$^-$ having a m/z of 863.4.

As shown in FIG. 33A, nasal mucosa featured mainly [PC(36:2)-Cl]$^-$ m/z 820.5, [PC(34:2)+Cl]$^-$ and [PI(36:2)-H]$^-$ m/z 826.4 in the m/z 700-900 range.

An interesting feature was observed predominantly in the vaginal mucosal membrane where the deprotonated cholesterol sulphate peak at a m/z of 465.3 is the most dominant peak in the spectrum. Chemical assignment of this peak was confirmed by tandem mass spectrometry experiments. This compound is an important component of cell membranes with regulatory functions including a stabilizing role, e.g., protecting erythrocytes from osmotic lysis and regulating sperm capacitation.

Leave-one-patient-out cross validation of the multivariate model containing spectra obtained by the analyses of three mucosal models resulted in a high classification accuracy. This show that MS based profiling of different mucosal membranes allows stratification of patients based upon bacterial diversity.

Figure 34:
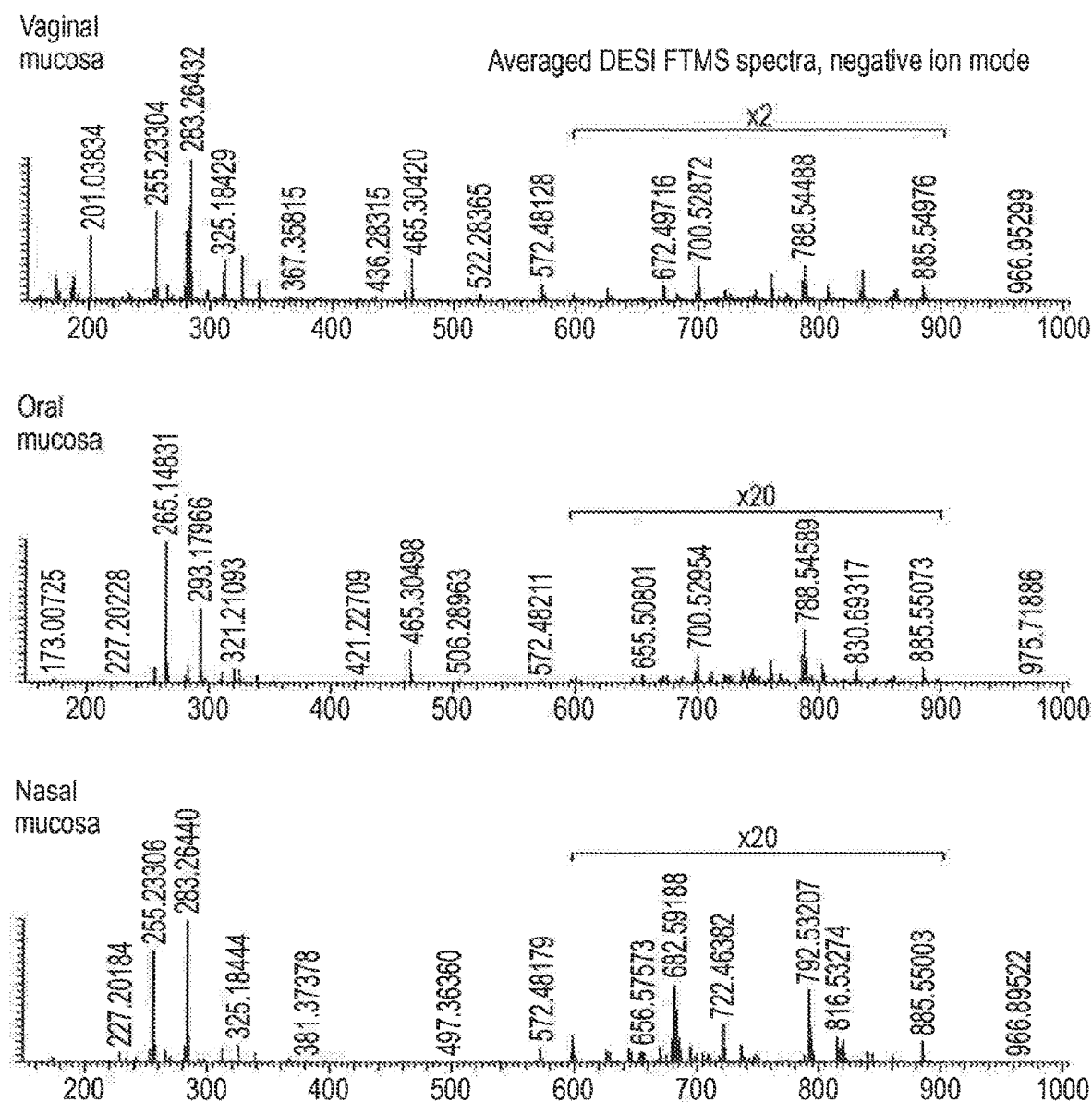
FIG. 34 shows desorption electrospray ionisation ("DESI") mass spectrometry spectra of vaginal, oral and nasal mucosal membranes in a negative ion mode obtained from medical cotton swabs, together with principal component analysis (PCA) and maximum margin criterion analysis providing a separation between different mucosal classes (nasal, oral, vaginal) with a prediction accuracy ranging from 92-100% obtained by leave one out cross validation.

Similarly, FIG. 34 shows Fourier transform mass spectrometry ("FTMS") spectrometric data obtained from vaginal, oral and nasal mucosa on medical cotton swabs in negative ion mode in the mass range of m/z 150-1000. Again, different metabolic signatures were observed in each mucosal membrane model.

In total, 300 to 1000 spectral features found without isotopes and adducts including small human primary metabolites such as cholesterol sulphate, bacterial secondary metabolites including lactate as well as glycerophospholipids were tentatively identified by exact mass, isotope cluster distribution and tandem mass spectrometry experiments in the mucosal membrane.

Figure 35:
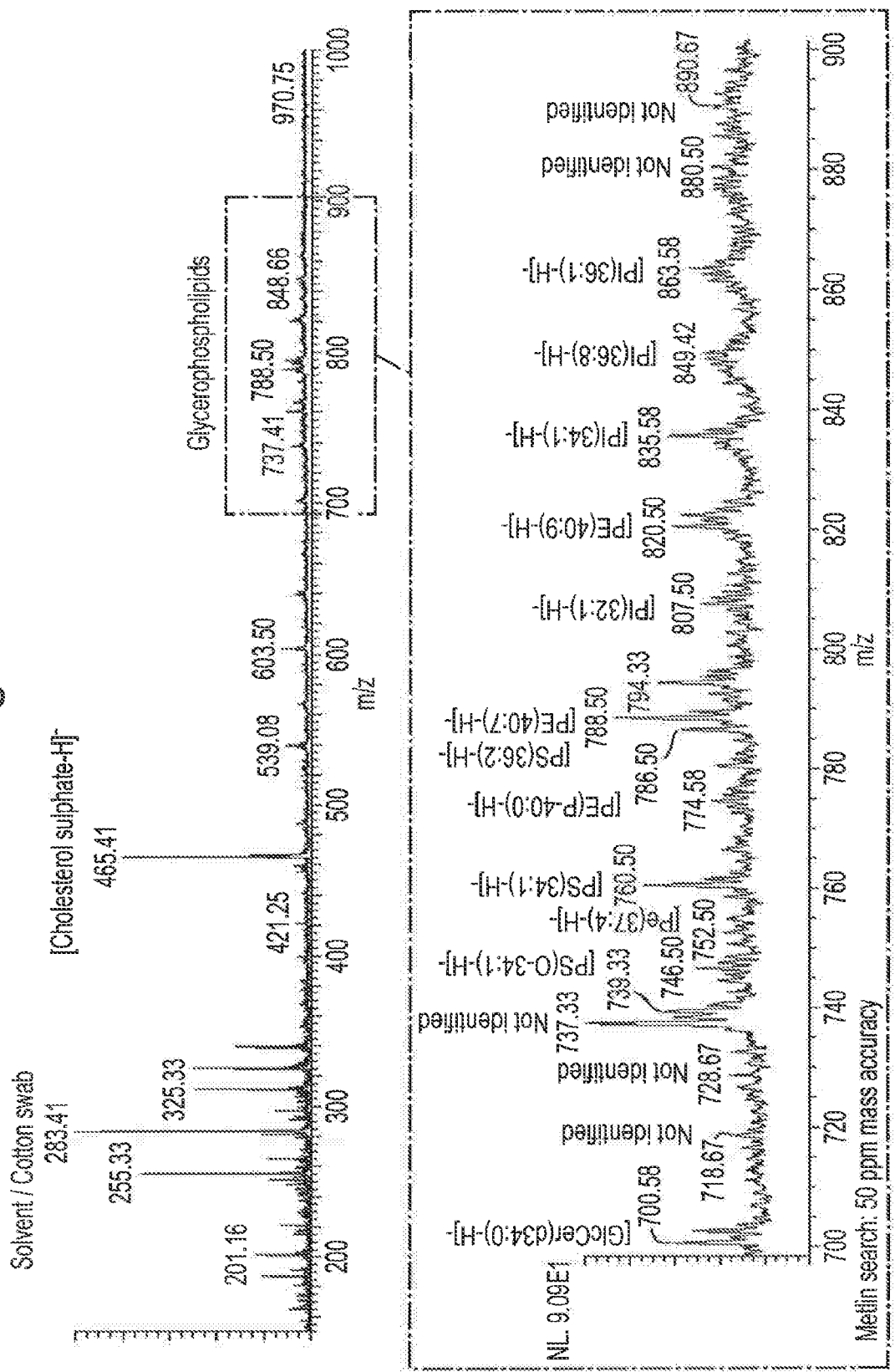
FIG. 35 shows a desorption electrospray ionisation ("DESI") mass spectrum of pregnant vaginal mucosal membrane obtained in negative ion mode from a medical cotton swab, wherein the urogenital mucosa was found to produce cholesterol sulphate [M-H]$^-$ having a mass to charge ratio of 465.41 as the most abundant lipid species as well as a different glycerophosholipids species such as glycerophosphoethanolamine (PE) [PE(40:7)-H]$^-$ having a mass to charge ratio of 788.50, glycerophosphoserine (PS) [PS(34:1)-H]$^-$ having a mass to charge ratio of 760.50 and glycerophosphoinositol (P1) [P1(36:1)-H]$^-$ having a mass to charge ratio of 863.58.
Figure 35:
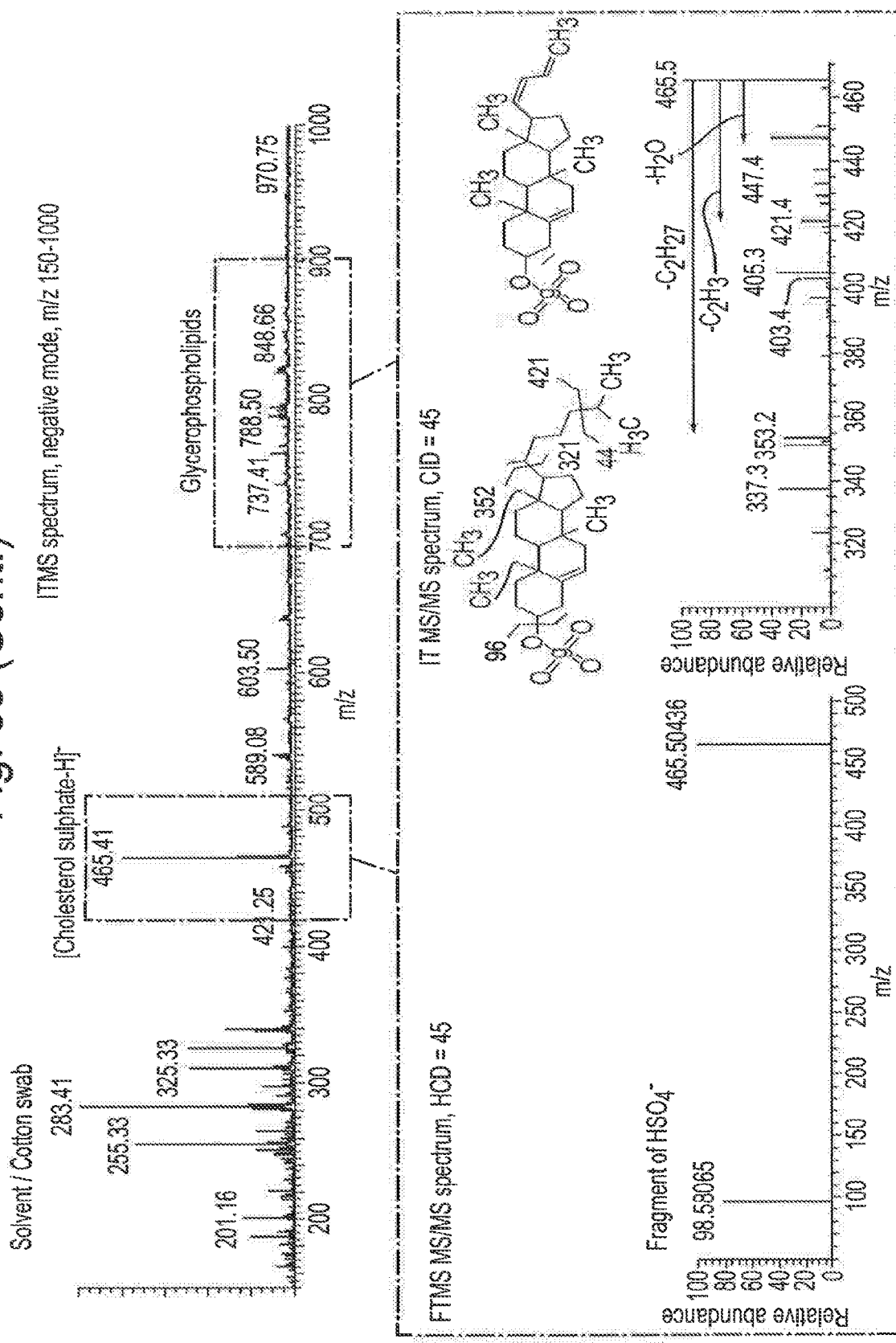

FIG. 35 shows a desorption electrospray ionisation ("DESI") mass spectrum relating to a pregnant vaginal mucosal membrane in more detail which was obtained in negative ion mode using a medical cotton swab. The urogenital mucosa was found to produce cholesterol sulphate [M-H]$^-$ at a m/z of 465.41 as the most abundant lipid species as well as a different glycerophosholipids species such as glycerophosphoethanolamine (PE) [PE(40:7)-H]$^-$ at a m/z of 788.50, glycerophosphoserine (PS) [PS(34:1)-H]$^-$ at a m/z of 760.50 and glycerophoshoinositol (PI) [PI(36:1)-H]$^-$ at a m/z of 863.58. As shown in FIG. 35, chemical assignment of the cholesterol sulphate peak was confirmed by tandem mass spectrometry experiments.

The spectrometric data of FIG. 34 were further processed using median normalization, background subtraction, Savitzky-Golay peak detection, peak alignment and log-transformation. Following data processing, multivariate statistical analysis was applied on the data set to characterise distinct mucosa models based on their metabolic profile. Multivariate statistical analysis tools including principal component analysis (PCA) and maximum margin criterion (MMC) were used to analyse the data set.

As shown in FIG. 34, the PCA score plot as well as the MMC score plot reveal a separation of the different mucosal membrane types within the first two components with a prediction accuracy between 92-100% obtained by leave one out cross validation.

It will be appreciated that analysis according to various embodiments results in characteristic profiles for the various sample types that can be clearly distinguished e.g., by using PCA, MMC and/or leave one out cross validation analyses. These results show the use of desorption electrospray ionisation ("DESI") mass spectrometry to characterise human mucosal membrane models, e.g. based on their metabolic signatures excreted by characteristic bacteria, as a fast bacterial identification method, e.g., compared to 16S rRNA sequencing.

Further embodiments are contemplated wherein chemical biomarkers in human mucosal membranes may be measured, which are reliable predictors e.g. in the cases of dysbiotic, inflammatory, cancerous and/or infectious diseases.

In the case of vaginal mucosa, a clinical set of pregnant (n=22, in a gestational age between 26 and 40 weeks) and non-pregnant mucosal membrane (n=22) were evaluated in more detail in order to reveal metabolic signature differences caused by a change in the vaginal microbiome during pregnancy. Desorption electrospray ionisation ("DESI") mass spectrometry spectra were acquired from both groups in negative ion mode in the mass range of m/z 150-1000. A number of different metabolites were detected in the vaginal mucosal membrane.

FIG. 36A shows averaged desorption electrospray ionisation ("DESI") mass spectra from pregnant and non-pregnant group acquired in the negative ion mode in the mass range m/z 150-1000. A comparison of the averaged spectra shown in FIG. 36A shows spectral differences between non-pregnant and pregnant mucosa metabolic profiles, especially in the lipid mass range from m/z 550-900.

Further data analysis comprising unsupervised PCA and RMMC analysis were utilised to visualize differences between both groups.

FIGS. 36B and 36C show the results of multivariate statistical analysis of pregnant (n=22) and non-pregnant (n=22) vaginal mucosal membrane using desorption electrospray ionisation ("DESI") mass spectrometry.

FIG. 36B shows principal component analysis and discriminatory analysis using RMMC and FIG. 36C shows analysis with leave-one-out cross-validation.

Figure 36D:
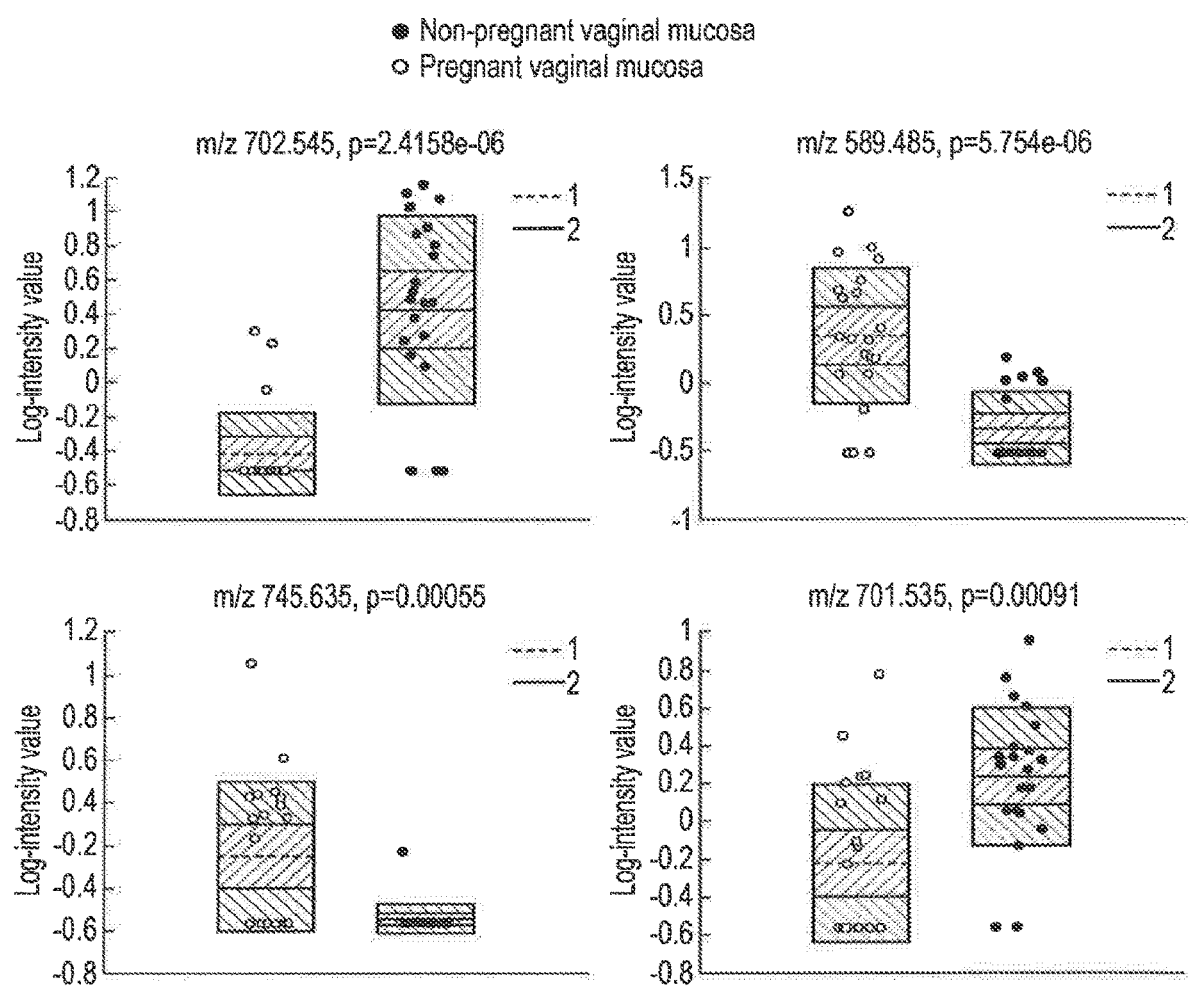
FIG. 36D shows box plots indicating significant differences of the abundance for selected peaks between non-pregnant and pregnant vaginal mucosal membranes mainly in the mass to charge ratio ("m/z") range 550-1000.

FIG. 36D shows box plots which indicate significant differences in the abundance of selected peaks between non-pregnant and pregnant vaginal mucosal membrane mainly in the range from m/z 550-1000 obtained by Kruskal-Wallis ANOVA, p<0.005.

Figure 36E:
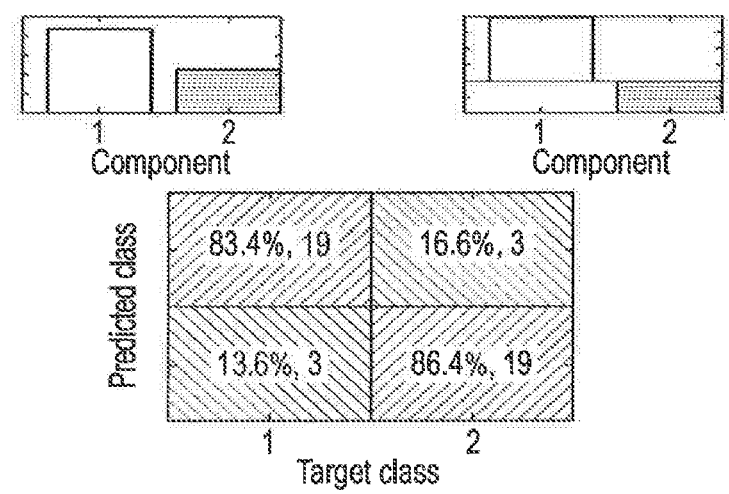
FIG. 36E shows the leave-one-out cross-validation.

As shown in FIG. 36E, using RMMC both groups separate well in the RMMC space with a high (>80%) classification accuracy according to distinct metabolic signatures obtained by leave-one-patient-out cross validation.

FIG. 37A shows desorption electrospray ionisation ("DESI") mass spectrometry analysis of a bacteria (*Klebsiella pneumonia*) sample on a swab in accordance with an embodiment. The data illustrated in FIG. 37A shows that bacterial samples can be detected using desorption electrospray ionisation ("DESI") mass spectrometry on swabs, according to various embodiments. FIG. 37B shows for comparison rapid evaporative ionisation mass spectrometry ("REIMS") time of flight ("TOF") mass spectrometry data of a corresponding bacterial sample measured directly from an agar plate. The peaks highlighted by stars were detected with both ionisation techniques.

Desorption electrospray ionisation ("DESI") swab analysis for microorganism detection was further tested on six cultivated species including *Candida albicans, Pseudomonas montelli, Staphylococcus epidermis, Moraxella catarrhalis, Klebsiella pneumonia* and *Lactobacillus* sp. These are all important bacteria and fungi species that were isolated from vaginal mucosal membranes of pregnant patients and which were identified by sequence analysis such as 16S rRNA gene sequencing.

A swab was quickly dipped into a solution of diluted biomass from each species in 10 µL methanol, followed by desorption electrospray ionisation ("DESI") mass spectrometry analysis of the swab surface.

Figure 38A:
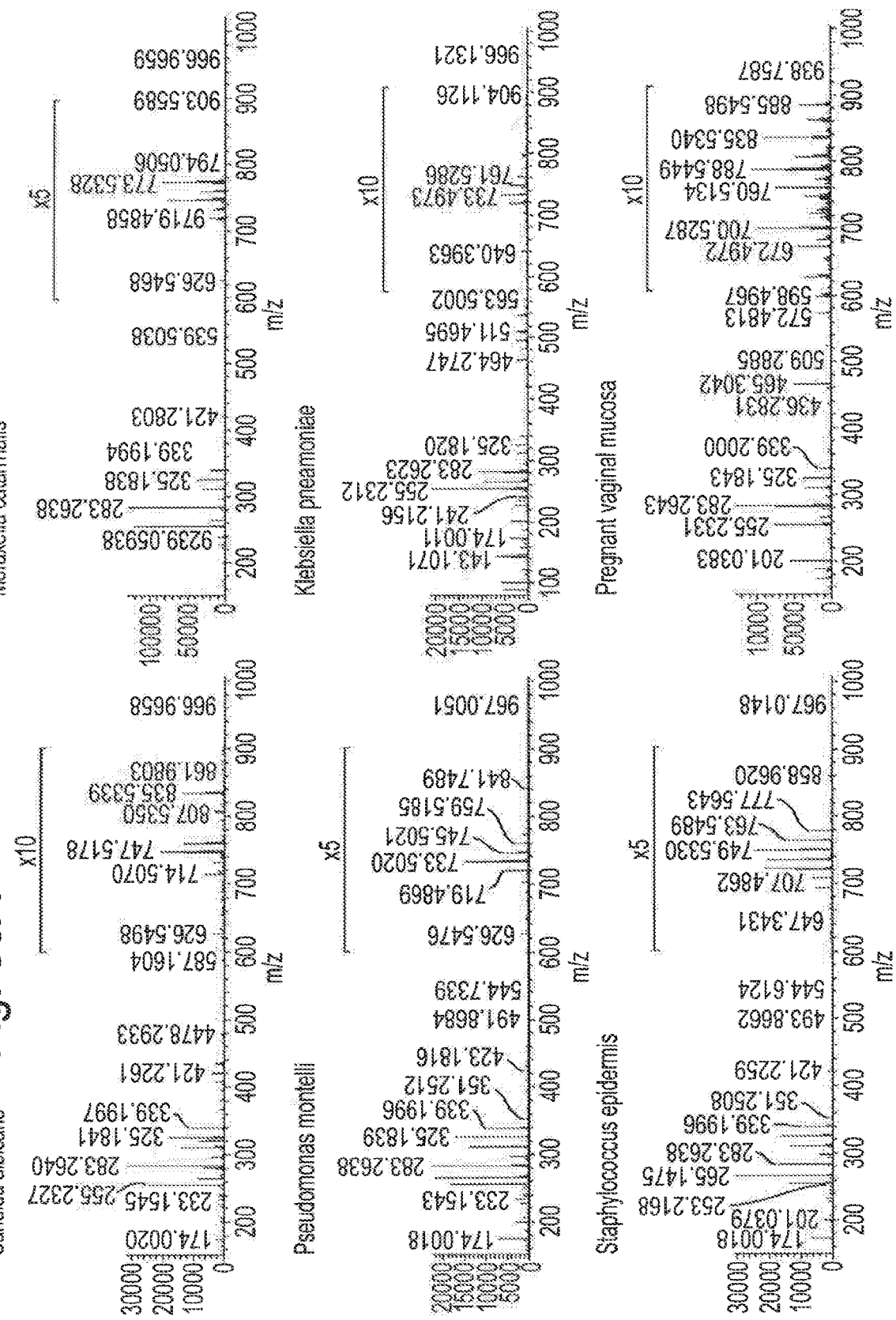
FIG. 38A shows averaged desorption electrospray ionisation ("DESI") mass spectra of diverse analysed microorganism species including *Candida albicans, Pseudomonas montelli, Staphylococcus epidermis, Moraxella catarrhalis, Klebsiella pneumonia* and *Lactobacillus* sp as well as pregnant vaginal mucosa.
Figure 38C:
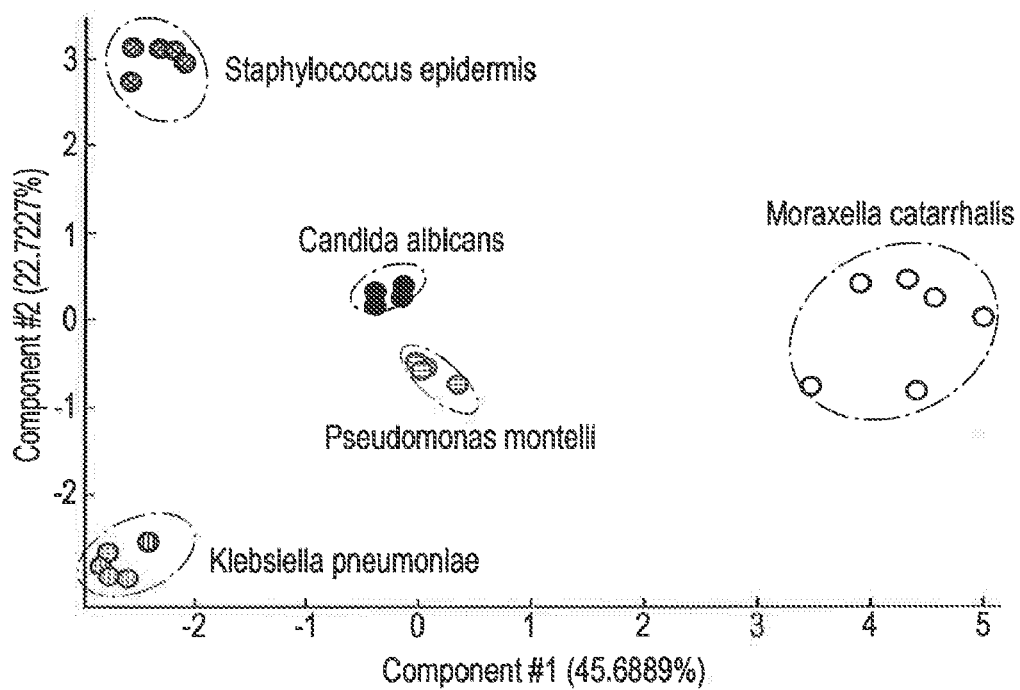

FIGS. 38A-C show microorganism analysis using desorption electrospray ionisation ("DESI") mass spectrometry on swabs.

FIG. 38A shows averaged desorption electrospray ionisation ("DESI") mass spectra of diverse analysed microorganism species including *Candida albicans, Pseudomonas montelli, Staphylococcus epidermis, Moraxella catarrhalis, Klebsiella pneumonia* and *Lactobacillus* sp.

FIGS. 38B and 38C show PCA plots showing a separation between the vaginal mucosa (pregnant and non-pregnant group) and the microorganism species within the first two components. In addition, a separation can be observed between the different bacteria and fungi species.

Unique spectral features were observed in the mass spectra as shown in FIG. 38A resulting in the ability to separate between different microorganism classes as well as from the vaginal mucosa in the PCA score plots (FIGS. 38B and 38C) within the first two components.

This result shows the potential to characterise microbe, e.g., bacteria-specific and host-response metabolite biomarkers and signatures from specific microbial, e.g., bacterial communities from the animal, e.g., human mucosal membrane using desorption electrospray ionisation ("DESI") mass spectrometry on medical swabs.

Example 17 Example of Data Analysis

Raw mass spectrometric files were converted into mzML format and subsequently imported as imzML format (REF) into MATLAB (Mathworks, Natick, MA; http://www.mathworks.co.uk/) for data pre-processing. All REIMS spectra were linearly interpolated to a common sampling interval of 0.01 Da. Recursive segment wise peak alignment was then used to remove small mass shifts in peak positions across spectral profiles. The aligned data were subjected to total ion count (TIC) data normalization and log-based transformation. Pattern recognition analysis and visualization were performed either in Matlab or in RStudio (Boston, MA, USA, see also www.r-project.com). Only the mass range of m/z 150-1000 was used for data analysis. For self-identity experiments, the data set was filtered to keep a reduced set of m/z values: a m/z value was kept, if the difference between the available samples were significantly different at alpha=0.01 threshold level based on the Kruskal-Wallis test.

Ionic species in the mass spectra were identified based on exact mass measurements (mass deviation <3 ppm) and MS/MS fragmentation patterns.

Example 18 Imaging Liver with Metastatic Tumour

Figure 51:
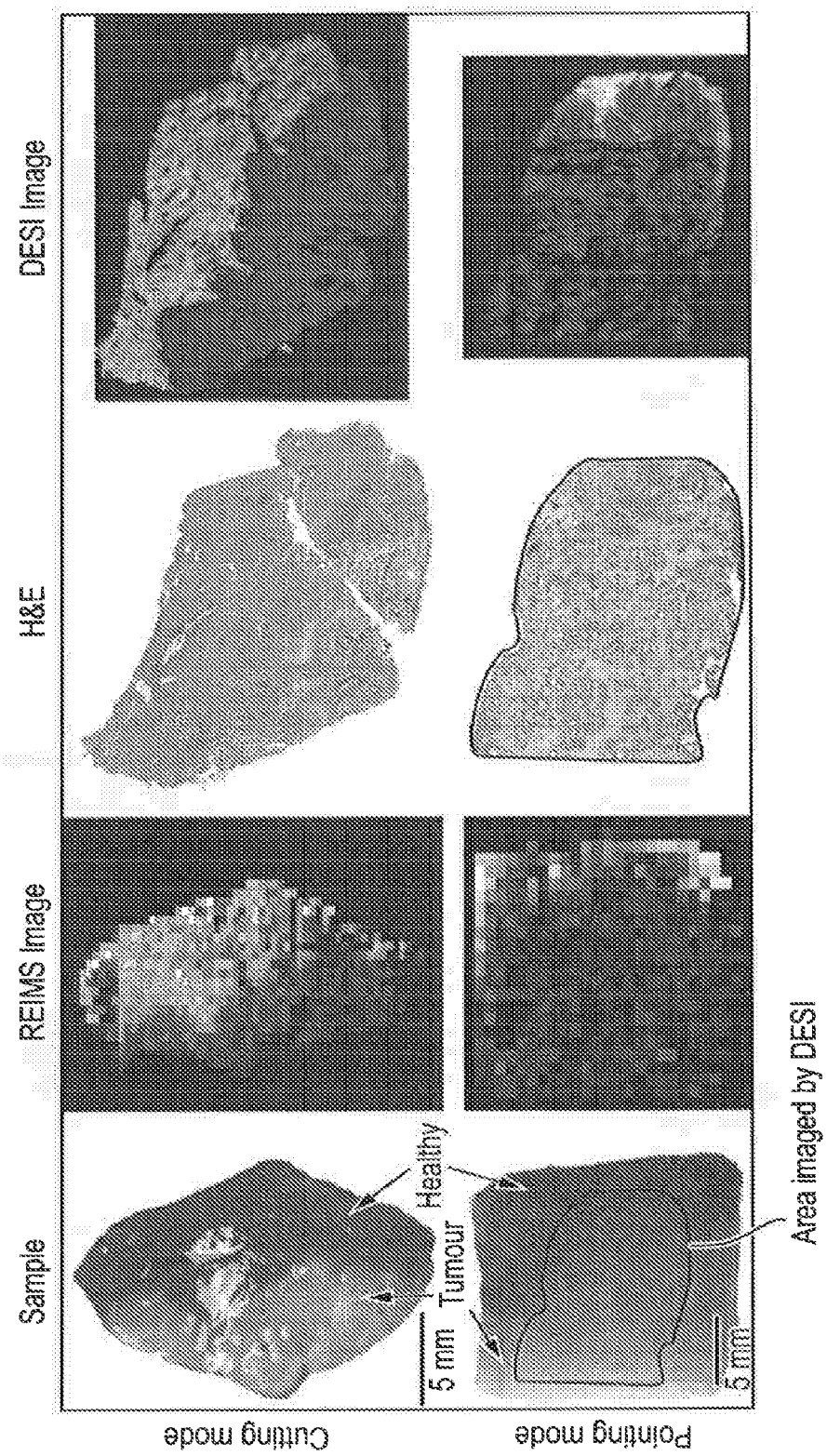
FIG. 51 shows a sample, H&E and mass spectrometric multivariate images of liver samples with metastatic tumour analysed by rapid evaporative ionization mass spectrometry and DESI wherein it is apparent that both techniques clearly differentiate the tissue types.

Human liver tumour samples were analysed by ion imaging using REIMS imaging technology or DESI imaging mass spectrometry (as illustrated in FIG. 51). A cutting mode rapid evaporative ionization mass spectrometry image was obtained on a first instrument whilst a pointing mode image was obtained on a Time of Flight mass spectrometer. Spatially resolved mass spectrometric information was co-registered with H&E images to locate mass spectra with the desired histological identity. Supervised multivariate analysis of the tissues revealed clear distinction between healthy and cancerous tissue for both rapid evaporative ionization mass spectrometry imaging and DESI imaging data.

The DESI images show a sharp border between the two tissue types as a result of the high spatial resolution and small pixel size of 100 μm. The upper half of the cutting mode rapid evaporative ionization mass spectrometry image contains pixels of mixed healthy and tumour pattern influences causing a blurred border. A possible explanation is due to the direction of the rapid evaporative ionization mass spectrometry cut that was performed which started at healthy tissue and continued towards the tumour region. This might have caused transport of tumour tissue pieces into the healthy area. Another reason may be inhomogeneous tissue below the surface of the seemingly cancerous area.

Assuming that the mass spectra are to be used as reference data for the iKnife technology, then only pixels with a high class-membership probability should be used for training the multivariate models (i.e. the sample classification model).

Figure 52:
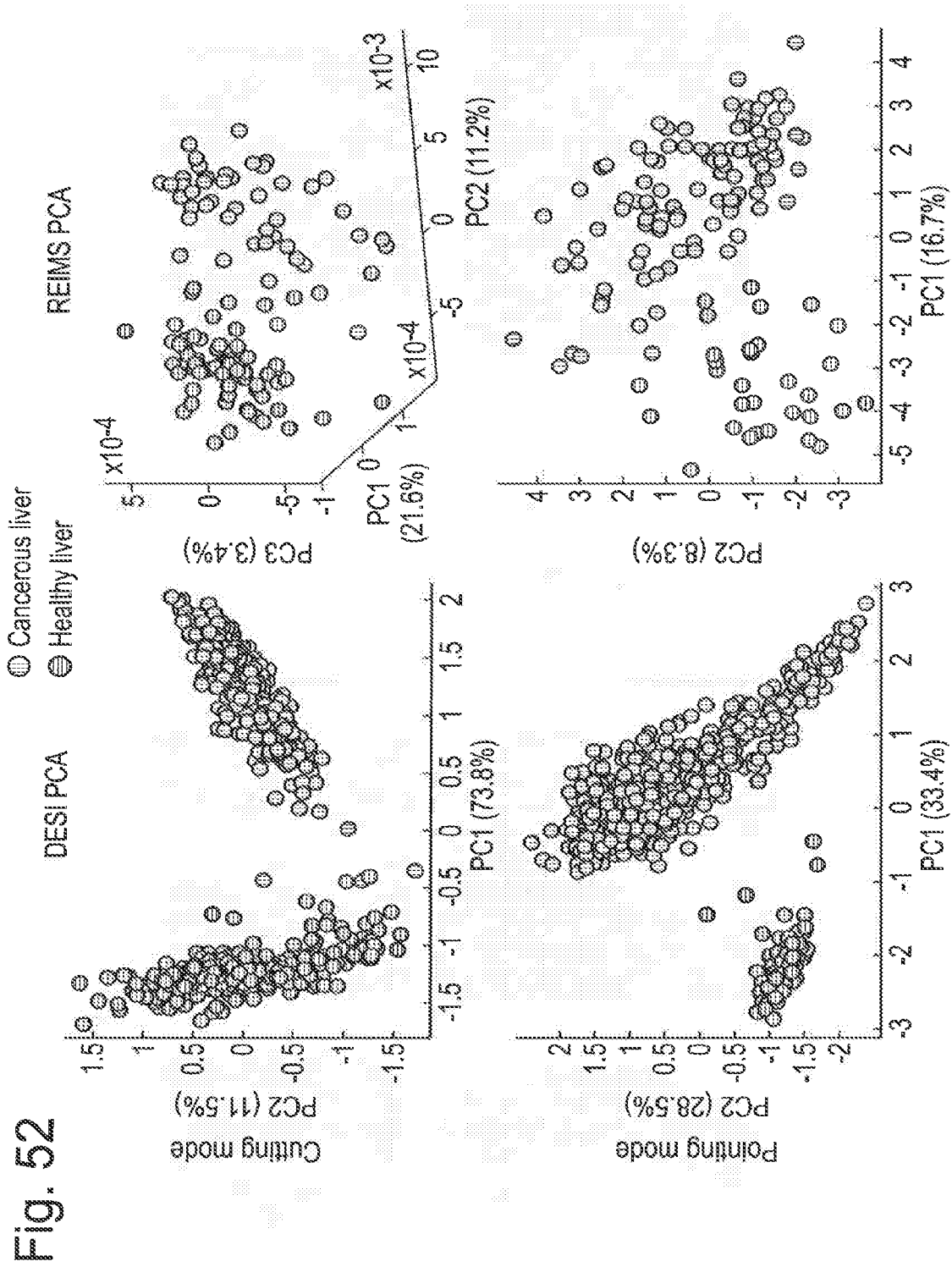
FIG. 52 shows principal component analysis plots of healthy and cancerous liver tissues for rapid evaporative ionization mass spectrometry imaging cutting and pointing modes as well as for DESI data wherein PC is the principal component and percentage values are explained variance.

Unsupervised principal component analysis (PCA) demonstrates high intra-tissue-type spectral similarity together with spatially distinct clustering of healthy and cancerous data points in PCA space (see FIG. 52).

DESI imaging data acquired at high spatial resolution can also be used to locate histological fine structures and their corresponding mass spectra which can then be co-registered with the rapid evaporative ionization mass spectrometry data. A limiting factor for co-registration of DESI and rapid evaporative ionization mass spectrometry data is the spatial resolution currently achievable with the rapid evaporative ionization mass spectrometry platform. While the cutting mode image was recorded at 500 μm pixel size, the pointing mode image features 750 μm sized pixels. In the case of this liver metastasis sample, the resolution is sufficient. However, in case of tissues with higher heterogeneity, higher spatial resolution images may be advantageous. The spatial resolution may be increased to decrease the diameter of the electrosurgical tip of the sampling probe which would also be accompanied by lower spectral intensities. However, by connecting the sampling probe directly to the mass spectrometer inlet capillary (as is also done in the bipolar forceps approach described above) ion yield improves, thus overcoming the possible sensitivity issue. This also allows less penetration in z-direction, decreasing the probability of ionizing unanticipated tissue types. A resolutions of, for example, 250 μm sized pixels may be achieved.

Multivariate analysis of the liver metastasis samples shows a clear distinction of tissue types based on their molecular ion patterns. While rapid evaporative ionization mass spectrometry and DESI exhibit different ionization mechanisms resulting in mass spectrometric patterns that are not directly comparable to each other, univariate biochemical comparison of single ions provides a comparable measure for DESI and rapid evaporative ionization mass spectrometry co-registration. For certain compounds, the relative intensity difference between two tissue types is similar across all tissue types, ionization techniques and rapid evaporative ionization mass spectrometry analysis modes (cutting and pointing modes). This enables DESI to be used as a fold-change intensity-predictor for rapid evaporative ionization mass spectrometry based on up- and down-regulated compounds, which ultimately represents additional information for unknown tissue type identification. The higher spatial resolution of DESI allows the up- and down-regulated ions to be registered with certain histological features which may not be resolvable by rapid evaporative ionization mass spectrometry. This gives insight to the underlying histological composition of a tissue if certain changes in single ion intensities are observed in low resolution rapid evaporative ionization mass spectrometry.

Figure 53:
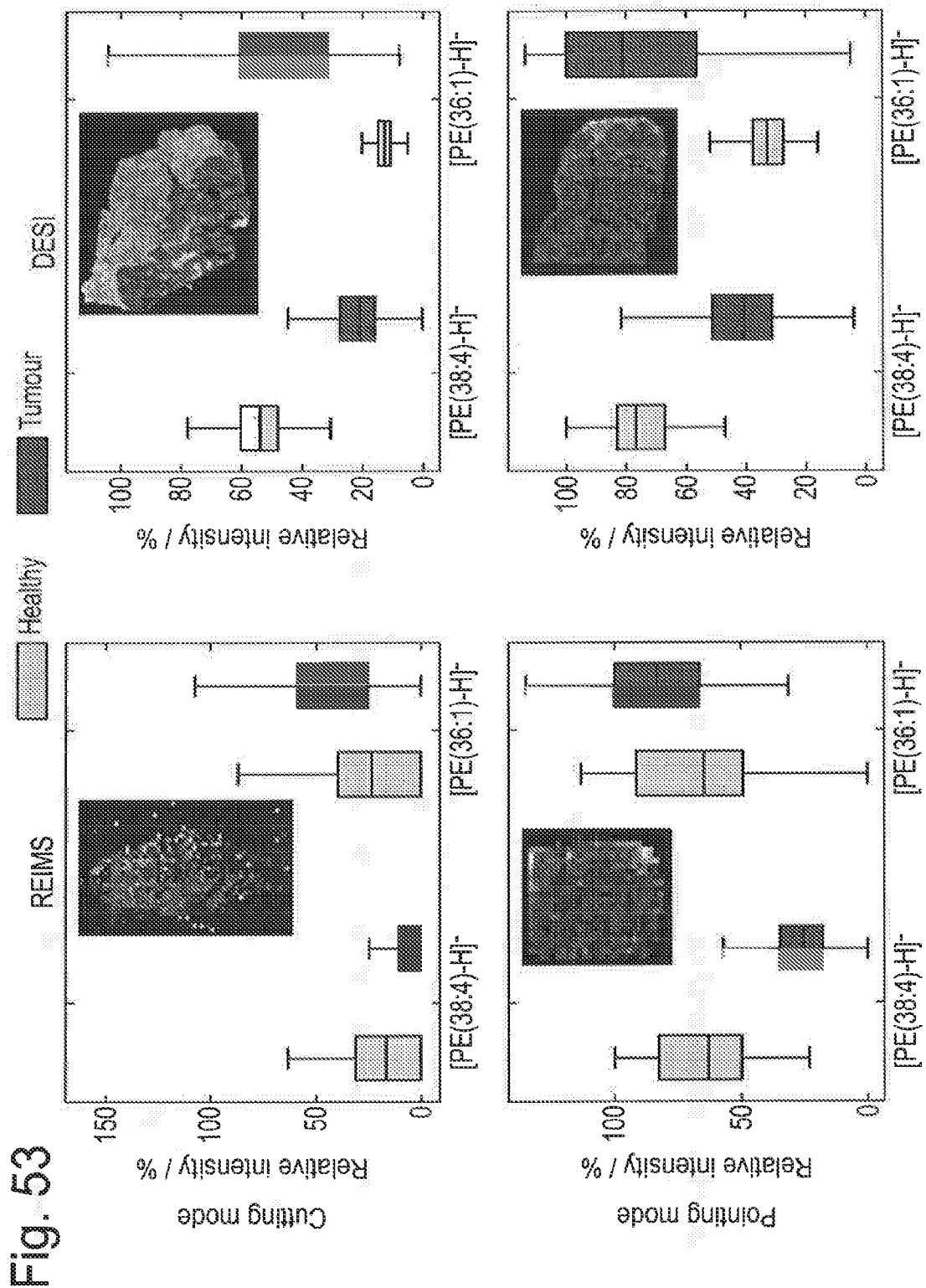
FIG. 53 shows an univariate intensity comparison of single phospholipid ion species wherein the depicted images of samples are ion-images of the respective ions and DESI and rapid evaporative ionization mass spectrometry show similar relative intensity values for the same ions wherein PE is phosphatidyl-ethanolamine.

In the case of metastatic liver comparison, two different phosphatidyl-ethanolamine (PE) species were found to possess opposite relative intensities between healthy and metastatic tissue types as shown in FIG. 53. The represented images are ion images of the two PE ion species. PE(38:4) has a higher abundance in healthy tissue in all four cases, with the rapid evaporative ionization mass spectrometry cutting mode image showing barely any presence of this ion in tumour tissue. However, compared to the DESI images where this lipid is well abundant even in tumour tissue, the absence of intensity has to be associated with the lower sensitivity achieved by rapid evaporative ionization mass spectrometry cutting. Opposite behaviour is seen by the ion [PE(36:1)-H]⁻ showing elevated intensities in tumour tissue.

Example 19 Analysis of Healthy Submucosa and GI Polyps

Figure 54A:
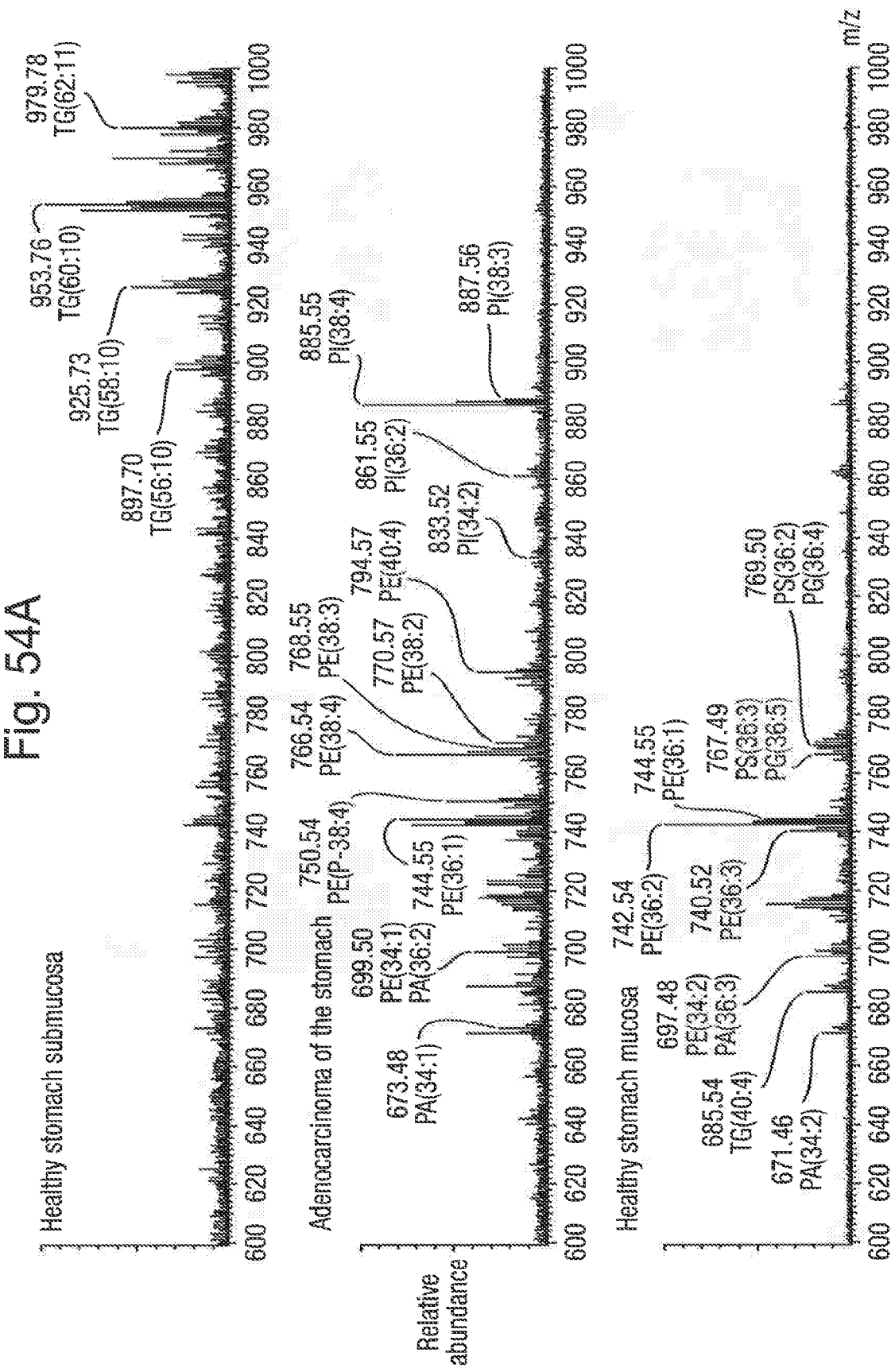
FIG. 54A shows mass spectra of gastric mucosa, gastric submucosa and adenocarcinoma tissue which was recorded using a modified Xevo G2-S® Q-Tof mass spectrometer (Waters®), wherein cancerous and healthy mucosa tissue feature mainly phospholipids in the 600-900 m/z range whilst submucosa feature triglyceride and phosphatidyl-inositol species in the 800-1000 m/z range

Significant spectral differences were observed between healthy gastric mucosa, healthy gastric submucosa and gastric cancer tissue. Spectra of healthy gastric mucosa (n=32) and gastric adenocarcinoma (n=29) featured phospholipids in the range m/z 600-900 while the gastric submucosa (n=10) featured intensive triglyceride ("TG") and phosphatidyl-inositol ("PI") species in the m/z 900-1000 range as shown in FIG. 54A.

The submucosa in the GI tract represents a connective tissue layer containing arterioles, venules and lymphatic vessels. It is made up of mostly collagenous and elastic fibres with varying amounts of adipose elements. It is hypothesised that the PI and triglycerides species observed in the m/z 900-1000 mass range are associated with these histological features present within the submucosa.

An interesting feature was observed regarding the abundance of phosphatidyl-ethanolamines and corresponding plasmalogen species. While the PEs show higher abundance, the plasmalogens are depleted in the tumour tissue, probably due to the impaired peroxisomal function of the cancer cells.

FIG. 54B shows a number of selected peaks which are significantly different between the healthy tissue layers and cancer tissue in the mass range 600-900. All peaks between m/z 900 to 1000 show significant differences when comparing the gastric submucosa to either adenocarcinoma or gastric mucosa.

Example 20 Analysis of Cancer in Mucosa

Analysis of ex vivo human colonic adenocarcinoma (n=43) and healthy colonic mucosa (n=45) acquired from seven patients was conducted using a LTQ Velos® mass spectrometer at the University of Debrecen, Hungary.

Adenomatous polyps (n=5) from two patients were also sampled ex vivo and the resulting rapid evaporative ionisation mass spectrometry data was analysed using multivariate statistical tools as shown in FIGS. 55A and 55B. The spectra acquired from healthy mucosa and adenocarcinoma of both the stomach and colon were discovered to separate well in 3 dimensional PCA space as can be seen from FIGS. 55A and 55B. The sampled adenomatous polyps also demonstrate good separation from both healthy mucosa and malignant tissue from the colon as shown in FIG. 55A.

Following the proof of concept analysis of ex vivo samples, the rapid evaporative ionisation mass spectrometry endoscopic method was also tested in vivo on three consecutive patients referred for colonoscopy. Different regions of the colon and rectum were sampled during the colonoscopy procedures. The first and third patients had evidence of colonic polyps and these were confirmed to be benign. The second patient had evidence of a normal colon with no visible polyps. The mucosal layer showed uniform spectral pattern independently from anatomical location. However, colonic polyps showed marked differences from the healthy mucosal layer as shown in FIG. 56B.

The data presented herewith demonstrates the significant advantages in using the rapid evaporative ionisation mass spectrometry technique as a real-time diagnostic tool in endoscopy.

For the experiments described in Examples 19 and 20, a commercially available polypectomy snare (Olympus® Model No. SD-210U-15) having a working length of about 2300 mm, minimum channel size about 2.8 mm, opening diameter about 15 mm and wire thickness about 0.47 mm was equipped with an additional T-piece in order to establish connection with a ⅛" OD 2 mm ID PFTE tubing between the tissue evaporation point and the atmospheric inlet of a mass spectrometer (Xevo G2-S® Q-TOF, Waters®, Manchester, UK, and a LTQ Velos® linear ion trap mass spectrometer, Thermo Fischer Scientific®, Bremen, Germany).

The snare was used with a commercially available endoscope (Olympus®, Tokyo, Japan) and the associated endoscopic stack which was coupled with an electrosurgical generator (Valleylab Surgistat II®).

The endoscopic plume generated during the removal of polyps was captured through the fenestrations on the rapid evaporative ionisation mass spectrometry snare. The endoscopic plume was then transferred to the mass spectrometer through the endoscope housing and via PFTE tubing which was coupled directly to the inlet capillary of a mass spectrometer using the internal vacuum of the mass spectrometer for plume capturing.

High resolution mass spectrometry was performed in negative ion mode between m/z 150-1500 range.

The data analysis workflow for the separation of healthy, cancerous and adenomatous polyps of the gastrointestinal tract included the construction of a tissue specific spectral database followed by multivariate classification and spectral identification algorithms in a known manner.

Example 21 DESI-MS Imaging

Specimens, such as tissue sections or microbes smeared onto the surface of a standard glass microscope slide, were subjected to DESI-MS imaging analysis using an Exactive mass spectrometer (Thermo Fisher Scientific Inc., Bremen, Germany). Exactive instrument parameters are listed in the Table below.

Thermo Exactive instrumental parameters used for DESI-MS imaging.

| Parameter | Setting. |
|---|---|
| Polarity | negative |
| Resolution | 100,000 |
| Mass range | 200-1050 |
| Spray voltage | −4.5 kV |
| Capillary temperature | 250° C. |
| Capillary voltage | −50 V |
| Tube lens voltage | −150 V |
| Skimmer Voltage | −24 V |
| Max. injection time | 1000 ms |
| Microscans | 1 |
| AGC target | 5e6 |

Methanol/water (95:5 v/v) was used as the electrospray solvent at a flow-rate of 1.5 μL/min. Nitrogen N4.8 was used as nebulising gas at a pressure of 7 bars. All solvents used were of LC-MS grade (Chromasolv, Sigma Aldrich, St Louis, MO, USA). The height distance between the DESI sprayer and the sample surface was set to 2 mm with the distance between the sprayer and sniffer set to 14 mm. The distance between the sample surface and the inlet capillary of the mass spectrometer was <<1 mm. The angle between the sprayer tip and the sample surface was set at 80°. The collection angle between inlet capillary and sample was set to 10°.

The general principle underlying imaging processes using DESI MS is that rather than point-by-point sampling, horizontal line scans are performed over the specimen surface by moving the automated sampling platform at a speed that covers the area determined as a pixel (spatial resolution) in the time the mass spectrometer requires to complete one scan (acquire one mass spectrum). This results in each one file per row of the resulting image (number of rows determined by sample height divided by spatial resolution).

For image analysis, individual horizontal line scans were converted into .imzML files using the imzML Converter Version 1.1.4.5 (www.maldi-msi.org). Single ion images and RGB images were generated using MSiReader Version 0.05(146) with linear interpolation (order 1) and 0.005 Da bin size.

TABLE 1

Table of biomarkers: phospholipids and their spectrometric signals
Identified phospholipids detected in the mass range m/z = 600-900 for all analysed microbial species. Only phospholipids with relative abundances >5% and only the most abundant acyl chain combination were included. Solid growth media on which bacteria were grown is given in parentheses. ID based solely on exact mass when lipid composition given as sum carbon number rather than individual acyl chains.

| Nominal mass m/z | C. koseri (CBA) | E. coli (CBA) | K. pneumoniae (LB) | P. mirbilis (MCC) | P. aeruginosa (LB) | S. marascans (MCC) | S. aureus (CBA) | S. agalactiae (CBA) | S. pyogenes (CBA) |
|---|---|---|---|---|---|---|---|---|---|
| 645 | | | | | | | | | PA(32:1)* |
| 659 | | | PA(16:0/ 17:1) | PA(16:0/ 17:1) | | PA(16:0/ 17:1) | | | |

TABLE 1-continued

Table of biomarkers: phospholipids and their spectrometric signals
Identified phospholipids detected in the mass range m/z = 600-900 for all analysed microbial species. Only phospholipids with relative abundances >5% and only the most abundant acyl chain combination were included. Solid growth media on which bacteria were grown is given in parentheses. ID based solely on exact mass when lipid composition given as sum carbon number rather than individual acyl chains.

| Nominal mass m/z | C. koseri (CBA) | E. coli (CBA) | K. pneumoniae (LB) | P. mirbilis (MCC) | P. aeruginosa (LB) | S. marascans (MCC) | S. aureus (CBA) | S. agalactiae (CBA) | S. pyogenes (CBA) |
|---|---|---|---|---|---|---|---|---|---|
| 661 | | | | | | | PA(33:0)* | | |
| 665 | | | | | | | | | PG(12:0/16:0) |
| 671 | | | | | | | | | PA(34:2)* |
| 673 | | | | PA(16:0/18:1) | PA(16:0/18:1) | | | | PA(16:0/18:1)* |
| 675 | | | | | | | PG(15:0/15:0-H$_2$O) | | PG(30:0-H$_2$O)* |
| 688 | PE(16:1/16:0) | | | PE(16:1/16:0) | | | | | |
| 691 | | | | | | | | | PG(14:0/16:1) |
| 693 | PG(16:0/14:0) | | PG(16:0/14:0) | | | | PG(15:0/15:0) | PG(15:0/15:0) | PG(14:0/16:0) |
| 697 | | | | | | | | | PA(36:3)* |
| 699 | | | | | | | | | PA(18:1/18:1)* |
| 701 | | | | | | | | PG(32:1)-H$_2$O* | PG(32:1)-H$_2$O* |
| 702 | PE(16:0/17:1) | PE(16:0/17:1) | PE(16:0/17:1) | PE(16:0/17:1) | | PE(16:0/17.:1) | | | |
| 707 | | | | | | | PG(15:0/16:0) | | |
| 716 | PE(18:1/16:0) | | | PE(18:1/16:0) | PE(18:1/16:0) | PE(17:0/17:1) | | | |
| 717 | | | | | | | | PG(32:2)* | PG(16:1-16:1) |
| 719 | PG(16:1/16:0) | PG(16:1/16:0) | PG(16:1/16:0) | PG(16:1/16:0) | PG(16:1/16:0) | PG(16:1/16:0) | | PG(16:1/16:0) | PG(16:1/16:0) |
| 721 | | | | | | | PG(15:0/17:0) | PG(15:0/17:0) | PG(16:0/16:0) |
| 725 | | | | | | | | | PA(16:1/18:2) |
| 727 | | | | | | | | | PG(16:1/18:1)-H$_2$O |
| 729 | | | | | | | | PG(16:0/18:1)-H$_2$O | PG(16:0/18:1)-H$_2$O |
| 730 | | | | PE(16:0/19:1) | | | | | |
| 733 | PG(16:0/17:1) | PG(16:0/17:1) | PG(16:0/17:1) | PG(16:0/17:1) | PG(16:0/17:1) | PG(16:0/17:1) | | | |
| 735 | | | | | | | PG(15:0/18:0) | | |
| 743 | | | | | | | | PG(16:0/18:3) | PG(16:0/18:2) |
| 745 | PG(16:1/18:1) | PG(16:1/18:1) | PG(16:1/18:1) | | PG(16:1/18:1) | PG(16:1/18:1) | | PG(16:0/18:2) | PG(16:0/18:1) |
| 747 | PG(16:0/18:1) | PG(16:0/18:1) | PG(16:0/18:1) | PG(16:0/18:1) | PG(16:0/18:1) | PG(16:0/18:1) | | PG(16:0/18:1) | PG(16:0/18:1) |
| 749 | | | | | | | PG(15:0/19:0) | PG(15:0/19:0) | PG(16:0/18:1)* |
| 752 | | | | | | | | | |
| 759 | | PG(17:1/18:1) | PG(17:1/18:1) | | PG(17:1/18:1) | PG(17:1/18:1) | | | |
| 761 | | PG(16:0/19:1) | PG(16:0/19:1) | PG(16:0/19:1) | PG(16:0/19:1) | PG(16:0/19:1) | | | |
| 763 | | | | | | | PG(15:0/20:0) | | |
| 770 | | | | | | | | | PE(38.2)* |
| 771 | | | | | | | | PG(36:3)* | PG(18:1/18:1)* |
| 773 | PG(18:1/18:1) | PG(18:1/18:1) | PG(17:1/19:1) | | PG(17:1/19:1) | PG(18:1/18:1) | | PG(36:2)* | PG(18:1/18:1) |
| 775 | | | | | | | | PG(36:1)* | PG(18:0/18:1) |
| 787 | | PG(18:1/19:1) | | | | | | | |

TABLE 1-continued

Table of biomarkers: phospholipids and their spectrometric signals
Identified phospholipids detected in the mass range m/z = 600-900 for all analysed microbial species. Only phospholipids with relative abundances >5% and only the most abundant acyl chain combination were included. Solid growth media on which bacteria were grown is given in parentheses. ID based solely on exact mass when lipid composition given as sum carbon number rather than individual acyl chains.

| Nominal mass m/z | C. koseri (CBA) | E. coli (CBA) | K. pneumoniae (LB) | P. mirbilis (MCC) | P. aeruginosa (LB) | S. marascans (MCC) | S. aureus (CBA) | S. agalactiae (CBA) | S. pyogenes (CBA) |
|---|---|---|---|---|---|---|---|---|---|
| 801 | | PG(19:1/19:1) | | | | | | | |

*Signal intensity not sufficient to obtain meaningful MS/MS data;
Abbreviations: PG = phosphatidylglycerol, PE = phosphatidylethanolamine, CBA = Columbia blood agar, LB = lysogenb broth agar, MCC = McConkey agar.

TABLE 2

Table of biomarkers: cardiolipins and their mass spectral signals
Cardiolipin species that were identified for *Staphylococcus epidermidis* ATCC 12228.

| Compound | Sum formula | Exact mass [M − H]− | Exp. mass | Mass Deviation |
|---|---|---|---|---|
| CL(62:0) | $C_{71}H_{138}O_{17}P_2$ | 1323.9335 | 1323.9268 | 5.0 ppm |
| CL(63:0) | $C_{72}H_{140}O_{17}P_2$ | 1337.9492 | 1337.9426 | 4.9 ppm |
| CL(64:0) | $C_{73}H_{142}O_{17}P_2$ | 1351.9649 | 1351.9601 | 3.6 ppm |
| CL(65:0) | $C_{74}H_{144}O_{17}P_2$ | 1365.9806 | 1365.9758 | 3.5 ppm |
| CL(66:0) | $C_{75}H_{146}O_{17}P_2$ | 1379.9962 | 1379.9913 | 3.5 Ppm |
| CL(67:0) | $C_{76}H_{148}O_{17}P_2$ | 1394.0119 | 1394.0070 | 3.5 ppm |
| CL(68:0) | $C_{77}H_{150}O_{17}P_2$ | 1408.0275 | 1408.0238 | 2.6 ppm |
| CL(69:0) | $C_{78}H_{152}O_{17}P_2$ | 1422.0432 | 1422.0400 | 2.3 ppm |
| CL(70:0) | $C_{79}H_{154}O_{17}P_2$ | 1436.0588 | 1436.0561 | 1.9 ppm |
| CL(71:0) | $C_{80}H_{156}O_{17}P_2$ | 1450.0745 | 1450.0748 | 0.2 ppm |
| CL(72:0) | $C_{81}H_{158}O_{17}P_2$ | 1464.0900 | 1464.0970 | 4.8 ppm |

TABLE 3

Table of biomarkers: mycolic acids and their mass spectral signals
Identified mycolic acids as detected in different Corynebacterium species.

| Compound | Sum formula | Exact mass [M-H]- | Exp. mass | Mass Deviation | MS/MS fragments |
|---|---|---|---|---|---|
| alpha-Mycolic acid C28:0 | $C_{28}H_{55}O_3$ | 439.415669 | 439.4159 | 0.5 ppm | — |
| alpha-Mycolic acid C30:0 | $C_{30}H_{59}O_3$ | 467.446969 | 467.4473 | 0.7 ppm | 227 (C14:0), 255 (C16:0) |
| alpha-Mycolic acid C32:1 | $C_{32}H_{61}O_3$ | 493.462619 | 493.4634 | 1.6 ppm | — |
| alpha-Mycolic acid C32:0 | $C_{32}H_{63}O_3$ | 495.478269 | 495.4786 | 0.7 ppm | 255 (C16:0) |
| alpha-Mycolic acid C34:2 | $C_{34}H_{63}O_3$ | 519.478269 | 519.4788 | 1.0 ppm | — |
| alpha-Mycolic acid C34:1 | $C_{34}H_{65}O_3$ | 521.493919 | 521.4942 | 0.5 ppm | 255 (C16:0), 281 (C18:1) |
| alpha-Mycolic acid C36:2 | $C_{36}H_{67}O_3$ | 547.509569 | 547.5102 | 1.2 ppm | 281 (C18:1) |

TABLE 4

Table of biomarkers: mycolic acids and their mass spectral signals
Identified mycolic acids as detected in Rhodococcus species.

| Compound | Sum formula | Exact mass [M-H]- | Exp. mass | Mass Deviation |
|---|---|---|---|---|
| alpha-Mycolic acid C28:0 | $C_{28}H_{56}O_3$ | 439.4157 | 439.4159 | 0.5 ppm |
| alpha-Mycolic acid C30:1 | $C_{30}H_{58}O_3$ | 465.4313 | 465.4315 | 0.4 ppm |
| alpha-Mycolic acid C30:0 | $C_{30}H_{60}O_3$ | 467.4470 | 467.4472 | 0.4 ppm |
| alpha-Mycolic acid C31:1 | $C_{31}H_{60}O_3$ | 479.4470 | 479.4473 | 0.6 ppm |
| alpha-Mycolic acid C31:0 | $C_{31}H_{62}O_3$ | 481.4626 | 481.4630 | 0.8 ppm |
| alpha-Mycolic acid C32:2 | $C_{32}H_{60}O_3$ | 491.4470 | 491.4475 | 1.0 ppm |
| alpha-Mycolic acid C32:1 | $C_{32}H_{62}O_3$ | 493.4626 | 493.4634 | 1.6 ppm |
| alpha-Mycolic acid C32:0 | $C_{32}H_{64}O_3$ | 495.4783 | 495.4786 | 0.6 ppm |
| alpha-Mycolic acid C33:2 | $C_{33}H_{62}O_3$ | 505.4626 | 505.4630 | 0.8 ppm |
| alpha-Mycolic acid C33:1 | $C_{33}H_{64}O_3$ | 507.4783 | 507.4785 | 0.4 ppm |
| alpha-Mycolic acid C33:0 | $C_{33}H_{66}O_3$ | 509.4939 | 509.4943 | 0.8 ppm |
| alpha-Mycolic acid C34:3 | $C_{34}H_{62}O_3$ | 517.4626 | 517.4632 | 1.2 ppm |
| alpha-Mycolic acid C34:2 | $C_{34}H_{64}O_3$ | 519.4783 | 519.4788 | 1.0 ppm |
| alpha-Mycolic acid C34:1 | $C_{34}H_{66}O_3$ | 521.4939 | 521.4944 | 1.0 ppm |
| alpha-Mycolic acid C34:0 | $C_{34}H_{68}O_3$ | 523.5096 | 523.5100 | 0.8 ppm |
| alpha-Mycolic acid C35:3 | $C_{35}H_{64}O_3$ | 531.4783 | 531.4784 | 0.2 ppm |
| alpha-Mycolic acid C35:2 | $C_{35}H_{66}O_3$ | 533.4939 | 533.4946 | 1.3 ppm |

TABLE 4-continued

Table of biomarkers: mycolic acids and their mass spectral signals
Identified mycolic acids as detected in Rhodococcus species.

| Compound | Sum formula | Exact mass [M-H]- | Exp. mass | Mass Deviation |
|---|---|---|---|---|
| alpha-Mycolic acid C35:1 | $C_{35}H_{68}O_3$ | 535.5096 | 535.5100 | 0.7 ppm |
| alpha-Mycolic acid C35:0 | $C_{35}H_{70}O_3$ | 537.5252 | 537.5259 | 1.3 ppm |
| alpha-Mycolic acid C36:3 | $C_{36}H_{66}O_3$ | 545.4939 | 545.4944 | 0.9 ppm |
| alpha-Mycolic acid C36:2 | $C_{36}H_{68}O_3$ | 547.5096 | 547.5102 | 1.1 ppm |
| alpha-Mycolic acid C36:1 | $C_{36}H_{70}O_3$ | 549.5252 | 549.5260 | 1.5 ppm |
| alpha-Mycolic acid C36:0 | $C_{36}H_{72}O_3$ | 551.5409 | 551.5424 | 2.7 ppm |
| alpha-Mycolic acid C37:3 | $C_{37}H_{68}O_3$ | 559.5096 | 559.5102 | 1.1 ppm |
| alpha-Mycolic acid C37:2 | $C_{37}H_{70}O_3$ | 561.5252 | 561.5257 | 0.9 ppm |
| alpha-Mycolic acid C37:1 | $C_{37}H_{72}O_3$ | 563.5409 | 563.5418 | 1.6 ppm |
| alpha-Mycolic acid C37:0 | $C_{37}H_{74}O_3$ | 565.5565 | 565.5573 | 1.4 ppm |
| alpha-Mycolic acid C38:4 | $C_{38}H_{74}O_3$ | 571.5096 | 571.5098 | 0.3 ppm |
| alpha-Mycolic acid C38:3 | $C_{38}H_{74}O_3$ | 573.5252 | 573.5261 | 1.6 ppm |
| alpha-Mycolic acid C38:2 | $C_{38}H_{74}O_3$ | 575.5409 | 575.5415 | 1.0 ppm |
| alpha-Mycolic acid C38:1 | $C_{38}H_{74}O_3$ | 577.5565 | 577.5579 | 2.4 ppm |
| alpha-Mycolic acid C39:2 | $C_{38}H_{76}O_3$ | 589.5565 | 589.5578 | 2.2 ppm |

TABLE 5

Table of biomarkers: mycolic acids and their mass spectral signals
Identified mycolic acids as detected in Nocardia species.

| Compound | Sum formula | Exact mass [M – H]– | Exp. mass | Mass Deviation |
|---|---|---|---|---|
| alpha-Mycolic acid C48:3 | $C_{48}H_{90}O_3$ | 713.6817 | 713.6797 | 2.8 ppm |
| alpha-Mycolic acid C48:2 | $C_{48}H_{92}O_3$ | 715.6974 | 715.6959 | 2.1 ppm |
| alpha-Mycolic acid C50:3 | $C_{50}H_{94}O_3$ | 741.7130 | 741.7114 | 2.2 ppm |
| alpha-Mycolic acid C50:2 | $C_{50}H_{96}O_3$ | 743.7287 | 743.7285 | 0.3 ppm |
| alpha-Mycolic acid C52:3 | $C_{52}H_{94}O_3$ | 769.7443 | 769.7430 | 1.7 ppm |
| alpha-Mycolic acid C52:2 | $C_{52}H_{96}O_3$ | 771.7600 | 771.7588 | 1.6 ppm |
| alpha-Mycolic acid C53:3 | $C_{53}H_{96}O_3$ | 783.7600 | 783.7596 | 0.5 ppm |
| alpha-Mycolic acid C53:2 | $C_{53}H_{94}O_3$ | 785.7756 | 785.7754 | 0.3 ppm |
| alpha-Mycolic acid C54:4 | $C_{54}H_{96}O_3$ | 795.7600 | 795.7594 | 0.8 ppm |
| alpha-Mycolic acid C54:3 | $C_{54}H_{98}O_3$ | 797.7756 | 797.7739 | 2.1 ppm |
| alpha-Mycolic acid C54:2 | $C_{54}H_{100}O_3$ | 799.7913 | 799.7902 | 1.4 ppm |
| alpha-Mycolic acid C55:4 | $C_{54}H_{102}O_3$ | 809.7756 | 809.7748 | 1.0 ppm |
| alpha-Mycolic acid C55:3 | $C_{54}H_{104}O_3$ | 811.7913 | 811.7907 | 0.7 ppm |
| alpha-Mycolic acid C55:2 | $C_{54}H_{106}O_3$ | 813.8069 | 813.8061 | 1.0 ppm |
| alpha-Mycolic acid C56:5 | $C_{56}H_{102}O_3$ | 821.7756 | 821.7748 | 1.0 ppm |
| alpha-Mycolic acid C56:4 | $C_{56}H_{104}O_3$ | 823.7913 | 823.7907 | 0.7 ppm |
| alpha-Mycolic acid C56:3 | $C_{58}H_{106}O_3$ | 825.8069 | 825.8053 | 1.9 ppm |
| alpha-Mycolic acid C56:2 | $C_{56}H_{108}O_3$ | 827.8226 | 827.8213 | 1.6 Ppm |
| alpha-Mycolic acid C57:4 | $C_{57}H_{106}O_3$ | 837.8069 | 837.8050 | 2.3 ppm |
| alpha-Mycolic acid C57:3 | $C_{57}H_{108}O_3$ | 839.8226 | 839.8215 | 1.3 ppm |
| alpha-Mycolic acid C58:5 | $C_{58}H_{106}O_3$ | 849.8069 | 849.8068 | 0.1 ppm |
| alpha-Mycolic acid C58:4 | $C_{58}H_{108}O_3$ | 851.8226 | 851.8218 | 0.9 ppm |
| alpha-Mycolic acid C58:3 | $C_{58}H_{110}O_3$ | 853.8382 | 853.8375 | 0.8 ppm |
| alpha-Mycolic acid C59:3 | $C_{59}H_{112}O_3$ | 867.8539 | 867.8537 | 0.2 ppm |
| alpha-Mycolic acid C60:4 | $C_{60}H_{112}O_3$ | 879.8539 | 879.8537 | 0.2 ppm |
| alpha-Mycolic acid C60:3 | $C_{60}H_{114}O_3$ | 881.8695 | 881.8683 | 1.4 ppm |

TABLE 6

Table of biomarkers: mycolic acids and their mass spectral signals
Identified mycolic acids as detected in different *Mycobacterium* species.

| Compound | Sum formula | Exact mass [M-H]- | Exp. mass | Mass Deviation |
|---|---|---|---|---|
| alpha-Mycolic acid C77:2 | $C_{77}H_{150}O_3$ | 1122.1512 | 1122.1525 | 1.2 ppm |
| alpha-Mycolic acid C78:2 | $C_{78}H_{152}O_3$ | 1136.1669 | 1136.1684 | 1.3 ppm |
| alpha-Mycolic acid C79:2 | $C_{79}H_{154}O_3$ | 1150.1825 | 1150.1833 | 0.7 ppm |
| Epoxy/keto-Mycolic acid C79:1 or Methoxy-Mycolic acid C79:2 | $C_{79}H_{154}O_4$ | 1166.1774 | 1166.1769 | 0.4 ppm |
| Epoxy/keto-Mycolic acid C80:1 or Methoxy-Mycolic acid C80:2 | $C_{80}H_{156}O_4$ | 1180.1931 | 1180.1897 | 2.9 ppm |
| Epoxy/keto-Mycolic acid C81:1 or Methoxy-Mycolic acid C81:2 | $C_{81}H_{158}O_3$ | 1194.2087 | 1194.2102 | 1.3 ppm |

TABLE 7

Table of biomarkers: sphindolipids and their mass spectral signals.
Identified sphingolipid species in members of the Bacteroidetes phylum

| Formula | Experimental mass | Exact mass | Mass Deviation | Observed in |
|---|---|---|---|---|
| Ceramide Phosphorylethanolamine/Phosphoethanolamine Dihydroceramides (PE-DHC) | | | | |
| $C_{36}H_{74}N2O7P$ | 677.5253 | 677.5239 | 2.0 | *B. fragilis, B. ovatus, B. thetaiotaomicron,* |
| $C_{37}H_{76}N2O7P$ | 691.5411 | 691.5396 | 2.2 | *B. uniformis, B. vulgatus, P. bivia, P.* |
| $C_{38}H_{78}N2O7P$ | 705.5569 | 705.5552 | 2.4 | *distonasis* |
| Ceramides | | | | |
| $C_{34}H_{69}NO4Cl$ | 590.4934[a] | 590.4921 | 2.2 | *B. fragilis, B. ovatus, B. thetaiotaomicron,* |
| $C_{35}H_{71}NO4Cl$ | 604.5090 | 604.5077 | 2.1 | *B. uniformis, B. vulgatus, P. bivia, P.* |
| $C_{36}H_{73}NO4Cl$ | 618.5246 | 618.5234 | 1.9 | *distonasis* |

TABLE 7-continued

Table of biomarkers: sphindolipids and their mass spectral signals.
Identified sphingolipid species in members of the Bacteroidetes phylum

| Formula | Experimental mass | Exact mass | Mass Deviation | Observed in |
|---|---|---|---|---|
| Bacteroides fragilis a-Galactosylceramides | | | | |
| $C_{40}H_{79}NO9Cl$ | 752.5465 | 752.5449 | 2.1 | B. fragilis |
| $C_{41}H_{81}NO9Cl$ | 766.5623 | 766.5605 | 2.3 | |
| $C_{42}H_{83}NO9Cl$ | 780.5781 | 780.5762 | 2.4 | |
| C15:0 substituted Phosphoglycerol Dihydroceramides (subPG-DHC) | | | | |
| $C_{50}H_{100}O10NP$ | 904.7007 | 904.7028 | 2.3 | B. fragilis, B. ovatus, B. thetaiotaomicron, |
| $C_{51}H_{102}O10NP$ | 918.7163 | 918.7185 | 2.4 | B. uniformis, B. vulgatus, P. distonasis |
| $C_{52}H_{104}O10NP$ | 932.7324[b] | 932.7337 | 1.4 | |
| $C_{53}H_{106}O10NP$ | 946.7481[b] | 946.7484 | 0.3 | |
| $C_{54}H_{108}O10NP$ | 960.7637[b] | 960.7624 | 1.3 | |
| Unsubstituted Phosphoglycerol Dihydroceramides (unPG-DHC) | | | | |
| $C_{37}H76O9NP$ | 708.5184 | 708.5199 | 2.1 | P. distonasis |
| $C_{39}H80O9NP$ | 736.5497 | 736.5484 | 1.8 | |

TABLE 8

Table of biomarkers: quorum-sensing molecules and their mass spectral signals
Identified quorum-sensing molecules in Psuedomonas aeruginosa.

| Compound | Sum formula | Exact mass | Exp. mass | Mass Deviation |
|---|---|---|---|---|
| 2-Heptylquinoline-4(1H)-one | $C_{16}H_{21}NO$ | [M-H]⁻ = 242.1550 | 242.1552 | −0.8 ppm |
| 2-Heptyl-3-hydroxy-4(1H)-quinolone (PQS) | $C_{16}H_{21}NO_2$ | [M-H]⁻ = 258.1499 | 258.1502 | −1.2 ppm |
| Hydroxynonenylquinoline | $C_{18}H_{23}NO$ | [M-H]⁻ = 268.1707 | 268.1711 | −1.5 ppm |
| Hydroxynonylquinoline | $C_{18}H_{23}NO$ | [M-H]⁻ = 270.1863 | 270.1868 | −1.9 ppm |
| Hydroxyundecenylquinoline | $C_{20}H_{26}NO$ | [M-H]⁻ = 296.2020 | 296.2023 | −1.0 ppm |

TABLE 9

Table of biomarkers: Rhamnolipids and their mass spectral signals.
Rhamnolipid species commonly produced by P. aeruginosa strains.

| Compound | Sum formula | Exact mass [M-H]- | Exp. mass | Mass Deviation |
|---|---|---|---|---|
| Rha-$C_{20}$ | $C_{26}H_{48}O_9$ | 503.3225 | 503.3224 | 0.2 ppm |
| Rha-$C_{22:1}$ | $C_{28}H_{50}O_9$ | 529.3382 | 529.3384 | −0.4 ppm |
| Rha-$C_{22}$ | $C_{28}H_{52}O_9$ | 531.3539 | 531.3538 | 0.2 ppm |
| Rha-Rha-$C_{20}$ | $C_{32}H_{58}O_{13}$ | 649.3805 | 649.3804 | 0.2 ppm |
| Rha-Rha-$C_{22}$ | $C_{34}H_{62}O_{13}$ | 677.4118 | 677.4116 | −0.3 ppm |
| Rha-Rha-$C_{22:1}$ | $C_{34}H_{60}O_{13}$ | 675.3961 | 675.3965 | −0.6 ppm |

TABLE 10

Table of biomarkers: Surfactins and their mass spectral signals.
Surfactin species detected in positive and negative ion mode for Bacillus subtilis.

| | Negative ion mode | | | Positive ion mode | | |
|---|---|---|---|---|---|---|
| Compound | Exp. mass | Exact mass [M − H]⁻ | Δppm | Exp. mass | Exact mass [M + Na]⁺ | Δppm |
| Surfactin (C13) | 1006.6453 | 1006.6440 | 1.3 | 1030.6389 | 1030.6416 | 2.6 |
| Surfactin (C14) | 1020.6604 | 1020.6597 | 0.7 | 1044.6545 | 1044.6573 | 2.7 |
| Surfactin (C15) | 1034.6754 | 1034.6753 | 0.1 | 1058.6702 | 1058.6729 | 2.6 |

TABLE 11

Table of biomarkers: Lichenysins and their mass spectral signals
Lichenysin compounds detected in Bacillus licheniformis.

| Compound | Exp. mass | Exact mass [M-H]⁻ | Δppm |
|---|---|---|---|
| Lichenysin (C13) | 1005.6594 | 1005.6600 | 0.6 |
| Lichenysin (C14) | 1019.6748 | 1019.6756 | 0.8 |
| Lichenysin (C15) | 1033.6906 | 1033.6913 | 0.7 |
| Lichenysin (C16) | 1047.7055 | 1047.7070 | 1.4 |

TABLE 12

Table of biomarkers
Mass spectrometric signals that show strong positive correlation with the ugcg
gene expression for a cell line (NCI60) dataset.

| Exp. mass | Exact mass | Δppm | Tentative ID | Formula | Adduct | Correlation coefficient |
|---|---|---|---|---|---|---|
| 734.5355 | 734.5343 | 0.2 | GlyCer(d18:1/16:0) | $C_{40}H_{77}NO_8$ | $[M + Cl]^-$ | 0.552 |
| 818.6295 | 818.6282 | 0.2 | GlyCer(d18:1/22:0) | $C_{46}H_{89}NO_8$ | $[M + Cl]^-$ | 0.662 |
| 842.6312 | 842.6332 | −0.2 | GlyCer(d18:1/24:2) | $C_{48}H_{89}NO_8$ | $[M + Cl]^-$ | 0.602 |
| 844.6451 | 844.6439 | 0.1 | GlyCer(d18:1/24:1) | $C_{48}H_{91}NO_8$ | $[M + Cl]^-$ | 0.668 |
| 846.6627 | 846.6595 | 0.4 | GlyCer(d18:1/24:0) | $C_{48}H_{93}NO_8$ | $[M + Cl]^-$ | 0.688 |
| 872.6733 | 872.6752 | −0.2 | GlyCer(d18:1/26:1) | $C_{50}H_{95}NO_8$ | $[M + Cl]^-$ | 0.707 |

TABLE 13

Table of biomarkers for Mycoplasma

| significantly different binned m/z | corresponding m/z signal | Annotation |
|---|---|---|
| 687.54 | 687.5468 | |
| 722.51 | 722.5156 | PE(P-36:4) |
| 733.53 | 733.5231 | PE(P-38:4) |
| 747.52 | 747.5193 | PG(34:1) |
| 748.53 | 748.5243 | Isotope of m/z = 747.52 |
| 753.51 | 753.5090 | PG(P-36:4) |
| 764.52 | 764.5264 | PE(38:5) |
| 764.53 | 764.5262 | PE(38:5) |
| 766.53 | 766.5412 | PE(38:4) |
| 773.54 | 773.5359 | PG(36:2) |
| 774.54 | 774.5391 | PG(36:2), Isotope of m/z = 773.54 |
| 774.55 | 774.5391 | PG(36:2), Isotope of m/z = 773.54 |
| 775.56 | 775.5520 | PG(36:1) |
| 776.56 | 776.5564 | PG(36:1), Isotope of m/z = 775.56 |
| 776.57 | 776.5564 | PG(36:1), Isotope of m/z = 775.56 |
| 819.52 | 819.5189 | PG(40:7) |
| 820.53 | 820.5268 | PG(40:7), Isotope of m/z = 819.52 |
| 820.54 | 820.5268 | PG(40:7), Isotope of m/z = 819.52 |

List of m/z peak that are significantly higher in Mycoplasma infected samples compared to Mycoplasma free samples in both HEK and HeLa cell lines. Column 2 displays the corresponding binned peak, column 2 highlights putative isotope peaks, while column 4 shows the tentative annotation of the binned peak. Phosphatidylglycerol and sphingomyelin species, that are main Mycoplasma constituents are written in bold.

TABLE 14

Table of biomarkers: microbial taxon-specific biomarkers
Taxon-specific markers obtained for various microbes. No markers were calculated where the size of sample set was insufficient.

| Gram-negative | Bacteroidetes | Bacteroidetes | Bacteroidales | Bacteroidaceae | *Bacteroides* | *Bacteroides acidifaciens* | 2 |
|---|---|---|---|---|---|---|---|
| | 381.2765 | 616.5094 | | 576.4764 | | *Bacteroides caccae* | 2 |
| | 393.2764 | 617.5124 | | 820.7522 | | *Bacteroides eggerthii* | 2 |
| | 590.4923 | 618.5233 | | | | *Bacteroides fragilis* | 5 |
| | 591.4963 | 619.5273 | | | | *Bacteroides helcogenes* | 1 |
| | 592.4883 | 620.5184 | | | | *Bacteroides ovatus* | 3 |
| | 604.5083 | 627.4883 | | | | *Bacteroides pyogenes* | 1 |
| | 605.5113 | 628.4913 | | | | *Bacteroides thetaiotaomicron* | 3 |
| | 606.5033 | 635.5004 | | | | *Bacteroides uniformis* | 3 |
| | 616.4724 | 636.5044 | | | | *Bacteroides vulgatus* | 3 |
| | | 637.5044 | | | | | |
| | 623.5024 | 644.5033 | | Porphyromonadaceae | *Parabacteroides* | *Parabacteroides distasonis* | 5 |
| | 624.5054 | 648.5003 | | 814.7063 | | *Parabacteroides johnsonii* | 2 |
| | 637.5044 | 697.5743 | | 815.7112 | | | |
| | 639.4954 | 698.5763 | | 828.7232 | | | |
| | 640.4993 | 711.5902 | | 829.7262 | | | |
| | 653.5113 | 712.5933 | | 840.6842 | | | |
| | 654.5143 | | | 841.6942 | | | |
| | 677.5238 | | | 843.7432 | | | |
| | 691.5395 | | | 854.7022 | | | |
| | 705.5562 | | | 858.6972 | | | |
| | | | | 872.7072 | | | |
| | | | | 908.7401 | | | |
| | | | | 909.7431 | | | |
| | | | | 910.7471 | | | |
| | | | | 918.7191 | | | |
| | | | | 921.7912 | | | |
| | | | | 932.7332 | | | |
| | | | | 933.7362 | | | |
| | | | | 934.7422 | | | |
| | | | | 944.7342 | | | |
| | | | | 945.7372 | | | |

TABLE 14-continued

Table of biomarkers: microbial taxon-specific biomarkers
Taxon-specific markers obtained for various microbes. No markers were calculated where the size of sample set was insufficient.

| Phylum | Class | Order | Family | Genus | Species | Count |
|---|---|---|---|---|---|---|
| | | | 946.7472 | | | |
| | | | 947.7502 | | | |
| | | | 948.7562 | | | |
| | | | 949.7592 | | | |
| | | | 958.7461 | | | |
| | | | 959.7501 | | | |
| | | | 960.7611 | | | |
| | | | 961.7661 | | | |
| | | | 962.7691 | | | |
| | | | Prevotellaceae | *Prevotella* | *Prevotella bivia* | 7 |
| | | | 661.5283 | | | |
| | | | 675.5453 | | | |
| | | | 676.5503 | | | |
| | | | 870.8002 | | | |
| | | | 908.7401 | | | |
| | | | 922.7552 | | | |
| | | | 923.7612 | | | |
| | | | 953.5113 | | | |
| | | | Rikenellaceae | *Alistipes* | *Alistipes onderdonkii* | 1 |
| | Flavobacteria | Flavobacteriales | Flavobacteriaceae | *Chryseobacterium* | *Chryseobacterium indologenes* | 3 |
| | 324.2545 | | | | | 1 |
| | 333.2084 | | | | *Chryseobacterium* sp | |
| | 390.2324 | | | *Elizabethkingia* | *Elizabethkingia meningoseptica* | 4 |
| | 392.2484 | | | | | |
| | 393.2504 | | | *Myroides* | *Myroides odoratimimus* | 2 |
| | 552.4643 | | | | | |
| | 553.4674 | | | | | |
| | 553.4674 | | | | | |
| | 554.4714 | | | | | |
| | 556.4034 | | | | | |
| | 565.4654 | | | | | |
| | 566.4794 | | | | | |
| | 567.4834 | | | | | |
| | 568.4864 | | | | | |
| | 600.4664 | | | | | |
| | 601.4723 | | | | | |
| | 618.4773 | | | | | |
| | 619.4813 | | | | | |
| | 620.4883 | | | | | |
| | 651.4953 | | | | | |
| | 651.4953 | | | | | |
| | 891.7411 | | | | | |
| Fusobacteria | Fusobacteria | Fusobacteriales | Fusobacteriaceae | *Fusobacterium* | *Fusobacterium gonidiaformans* | 3 |
| 227.2015 | | | | | | 7 |
| 644.4652 | | | | | *Fusobacterium necrophorum* | 4 |
| 645.4633 | | | | | | 1 |
| 646.4833 | | | | | *Fusobacterium peridontiam* | |
| 647.4812 | | | | | | |
| 648.4832 | | | | | *Fusobacterium* sp | |
| 673.4443 | | | | | | |
| 696.4953 | | | | | | |
| 714.5492 | | | | | | |
| 856.6782 | | | | | | |
| 865.6632 | | | | | | |
| 884.7083 | | | | | | |
| Proteobacteria | Alpha-Proteobacteria | Caulobacterales | Caulobacteraceae | *Brevundimonas* | *Brevundimonas diminuta* | 2 |
| 768.5182 | | 769.5502 | | | | |
| 782.5342 | | 770.5562 | | | | |
| 783.5293 | | 771.5582 | | | | |
| | | 795.5572 | | | | |
| | | 797.5723 | | | | |
| | | 818.5673 | | | | |
| | | 957.6261 | | | | |
| | | Rhizobiales | Rhizobiaceae | *Rhizobium* | *Rhizobium radiobacter* | 5 |
| | | 439.4155 | | | | |
| | | 440.4195 | | | | |
| | | 739.5313 | | | | |
| | | 784.5902 | | | | |
| | | 785.5932 | | | | |
| | | 799.5132 | | | | |
| | | Rhodospirillales | Acetobacteraceae | *Roseomonas* | *Roseomonas mucosa* | 6 |
| | | 662.5393 | | | *Roseomonas* sp | 1 |
| | | 722.5753 | | | | |
| | | 729.5813 | | | | |
| | | 733.5752 | | | | |
| | | 733.6173 | | | | |

TABLE 14-continued

Table of biomarkers: microbial taxon-specific biomarkers
Taxon-specific markers obtained for various microbes. No markers were calculated where the size of sample set was insufficient.

| Class | Order | Family | Genus | Species | Count |
|---|---|---|---|---|---|
| | | 734.5753 | | | |
| | | 747.6283 | | | |
| | | 757.6173 | | | |
| Beta-Proteobacteria | Burkholderiales | Alcaligenaceae | Achromobacter | Achromobacter sp | 3 |
| | | | | Achromobacter xylosoxidans | 3 |
| | | | Alcaligenes | Alcaligenes faecalis | 3 |
| | | Burkholderiaceae | Burkholderia | Burkholderia cepacia complex | 7 |
| | | 589.4013 | | | |
| | | 590.4083 | | | |
| | | 591.4184 | | | |
| | | 592.4214 | | | |
| | | Comamonadaceae | Acidovorax | Acidovorax temperans | 2 |
| | | 520.3044 | Comamonas | Comamonas kerstersii | 2 |
| | | | | Comamonas sp | 1 |
| | | | Delftia | Delftia acidovorans | 4 |
| | | | | Delftia dentocariosa | 1 |
| | | | | Delftia sp | 2 |
| | | Sutterellaceae | Sutterella | Sutterella wadsworthensis | 2 |
| | Neisseriales | Neisseriaceae | Eikenella | Eikenella corrodens | 1 |
| | 494.3855 | | Kingella | Kingella kingae | 3 |
| | 502.3674 | | | Kingella sp | 1 |
| | 526.3673 | | Neisseria | Neisseria cineria | 1 |
| | 527.3704 | | | Neisseria elongata | 2 |
| | 528.3653 | | | Neisseria flavescens | 3 |
| | 544.3774 | | | Neisseria gonorrhoea | 4 |
| | | | | Neisseria lactamica | 3 |
| | | | | Neisseria meningitidis | 4 |
| | | | | Neisseria mucosa | 2 |
| Epsilon-Proteobacteria | Campylobacterales | Campylobacteraceae | Campylobacter | Campylobacter coli | 1 |
| 730.5422 | | 867.6582 | | Campylobacter fetus | 3 |
| 731.5452 | | 993.8381 | | Campylobacter jejuni | 3 |
| 867.6582 | | | | Campylobacter sp | 6 |
| 993.8381 | | Helicobacteraceae | Helicobacter | Helicobacter pylori | 3 |
| | | 271.2284 | | | |
| | | 272.2305 | | | |
| | | 299.2595 | | | |
| | | 300.2625 | | | |
| | | 400.2644 | | | |
| | | 543.4623 | | | |
| | | 544.4634 | | | |
| Gamma-Proteobacteria | Aeromonadales | Aeromonadaceae | Aeromonas | Aeromonas hydrophila | 1 |
| | Cardiobacteriales | Cardiobacteriaceae | Cardiobacterium | Cardiobacterium hominis | 4 |
| | 648.4603 | | | | |
| | 649.4623 | | | | |
| | 650.4653 | | | | |
| | 793.4792 | | | | |
| | 794.4802 | | | | |
| | Enterobacteriales | Enterobacteriaceae | Citrobacter | Citrobacter amalonaticus | 1 |
| | 702.5083 | | | Citrobacter braakii | 3 |
| | 703.5092 | | | Citrobacter freundii | 4 |
| | 993.7282 | | | Citrobacter koseri | 4 |
| | 994.7272 | | Enterobacter | Enterobacter absuriae | 2 |
| | | | | Enterobacter aerogenes | 3 |
| | | | | Enterobacter amnigenus | 1 |
| | | | | Enterobacter cloacae | 3 |
| | | | | Enterobacter gergoviae | 1 |
| | | | Escherichia | Escherichia coli | 7 |
| | | | Hafnia | Hafnia alvei | 3 |
| | | | | Hafnia paralvei | 2 |
| | | | | Hafnia sp | 1 |
| | | | Klebsiella | Klebsiella oxytoca | 5 |
| | | | | Klebsiella pneumoniae | 5 |
| | | | Morganella | Morganella morganii | 7 |
| | | | Panthoea | Panthoea sp | 1 |
| | | | Proteus | Proteus mirabilis | 5 |
| | | | | Proteus vulgaris | 5 |
| | | | Providencia | Providencia rettgeri | 2 |
| | | | | Providencia stuartii | 2 |
| | | | Raoultella | Raoultella ornithololytica | 1 |
| | | | | Raoultella planticola | 1 |
| | | | Salmonella | Salmonella poona | 1 |
| | | | Serratia | Serratia liquifaciens | 3 |

TABLE 14-continued

Table of biomarkers: microbial taxon-specific biomarkers
Taxon-specific markers obtained for various microbes. No markers were calculated where the size of sample set was insufficient.

| | | | | | | | | |
|---|---|---|---|---|---|---|---|---|
| | | | | | | | Serratia marcescens | 5 |
| | | | | | | Shigella | Shigella sonnei | 1 |
| | | | | Pasteurellales | Pasteurellaceae | Aggregatibacter | Aggregatibacter aphrophilus | 5 |
| | | | | 690.4983 | | | | |
| | | | | 746.4503 | | Haemophilus | Haemophilus influenzae | 5 |
| | | | | 823.5453 | | | Haemophilus parahaemolyticus | 2 |
| | | | | 898.6921 | | | | 1 |
| | | | | 915.6902 | | | Haemophilus parainfluenzae | |
| | | | | 977.7282 | | | | |
| | | | | | | Pasteurella | Pasteurella multocida | 2 |
| | | | | Pseudomonadales | Moraxellaceae | Acinetobacter | Acinetobacter baumanii | 5 |
| | | | | | | | Acinetobacter iwoffii | 5 |
| | | | | | | | Acinetobacter johnsonii | 2 |
| | | | | | | | Acinetobacter junii | 1 |
| | | | | | | Moraxella | Moraxella catarrhalis | 5 |
| | | | | | | | Moraxella osloensis | 2 |
| | | | | | Pseudomonadaceae | Pseudomonas | Pseudomonas aearuginosa | 7 |
| | | | | | 286.1805 | | | 1 |
| | | | | | 490.3304 | | Pseudomonas luteola | 2 |
| | | | | | 514.3294 | | Pseudomonas monteilii | 2 |
| | | | | | | | Pseudomonas oryzihabitans | 1 |
| | | | | | | | Pseudomonas putida | 5 |
| | | | | | | | Pseudomonas stutzeri | |
| | | | | Vibrionales | Vibrionaceae | Vibrio | Vibrio alginolyticus | 1 |
| | | | | 605.3823 | | | Vibrio cholerae | 1 |
| | | | | 607.3983 | | | Vibrio furnissii | 1 |
| | | | | 608.4013 | | | | |
| | | | | 633.4134 | | | | |
| | | | | Xanthomonadales | Xanthomonadaceae | Stenotrophomonas | Stenotrophomonas maltophilia | 7 |
| | | | | 377.2105 | | | | |
| | | | | 562.3504 | | | | |
| | | | | 619.4353 | | | | |
| | | | | 620.4384 | | | | |
| | | | | 705.4713 | | | | |
| | | | | 706.4743 | | | | |
| | | | | 929.6852 | | | | |
| | | | | 930.6892 | | | | |
| | | | | 942.6912 | | | | |
| | | | | 943.7012 | | | | |
| | | | | 944.7052 | | | | |
| Gram-positive | Actinobacteria | Actinobacteria | Actinomycetales | Actinomycetaceae | Actinobaculum | Actinobaculum schaalii | 2 |
| | | | | 757.5403 | | Actinomyces | Actinomyces graevenitzii | 1 |
| | | | | 879.6112 | | | Actinomyces israelii | 1 |
| | | | | | | | Actinomyces odontolyticus | 2 |
| | | | | | | | Actinomyces oris | 5 |
| | | | | | | | Actinomyces sp | 1 |
| | | | | | | | Actinomyces turicensis | 1 |
| | | | | | | | Actinomyces viscosis | 2 |
| | | | | Corynebacteriaceae | Corynebacterium | Corynebacterium afermentans | 2 |
| | | | | 493.4624 | | | | 3 |
| | | | | 495.4784 | | | Corynebacterium amycolatum | 2 |
| | | | | 497.4845 | | | | 3 |
| | | | | 521.4934 | | | Corynebacterium diphtheriae | 1 |
| | | | | 535.4734 | | | | 5 |
| | | | | 537.4904 | | | Corynebacterium imitans | 3 |
| | | | | 538.4934 | | | Corynebacterium minutissimum | |
| | | | | | | | Corynebacterium sp | |
| | | | | | | | Corynebacterium striatum | |
| | | | | Microbacteriaceae | Microbacterium | Microbacterium sp | 1 |
| | | | | Mycobacteriaceae | Mycobacterium | Mycobacterium avium | 2 |
| | | | | 391.3684 | | | Mycobacterium fortuitum | 1 |
| | | | | 427.0965 | | | Mycobacterium peregrium | 1 |
| | | | | 724.8873 | | | | |
| | | | | 817.4152 | | | | |
| | | | | 850.5592 | | | | |
| | | | | 851.5662 | | | | |
| | | | | 852.5672 | | | | |
| | | | | Nocardiaceae | Nocardia | Nocardia sp | 1 |
| | | | | 321.2915 | Rhodococcus | Rhodococcus equi | 1 |
| | | | | 743.7273 | | Rhodococcus sp | 2 |
| | | | | 771.7592 | | | |
| | | | | 797.7762 | | | |

TABLE 14-continued

Table of biomarkers: microbial taxon-specific biomarkers
Taxon-specific markers obtained for various microbes. No markers were calculated where the size of sample set was insufficient.

| Phylum | Class | Order | Family | Genus | Species | |
|---|---|---|---|---|---|---|
| | | | 798.7762 | | | |
| | | | 800.7962 | | | |
| | | | 827.8162 | | | |
| | | | 828.8222 | | | |
| | | | 970.7871 | | | |
| | | | Propionibacteriaceae | *Propionibacterium* | *Propionibacterium acnes* | 7 |
| | | | 361.2155 | | | |
| | | | 617.4564 | | | |
| | | | 713.4752 | | | |
| | | | 714.4812 | | | |
| | | | 779.5072 | | | |
| | | | 877.5592 | | | |
| | | | 906.5872 | | | |
| | | Bifidobacteriales | Bifidobacteriaceae | *Bifidobacterium* | *Bifidobacterium adolescentis* | 1 |
| | | 789.5293 | | | | 2 |
| | | 792.5502 | | | *Bifidobacterium bifidum* | 3 |
| | | 819.5783 | | | *Bifidobacterium breve* | 1 |
| | | 830.5622 | | | *Bifidobacterium infantis* | 3 |
| | | 855.5272 | | | *Bifidobacterium longum* | 2 |
| | | 884.6092 | | | *Bifidobacterium pseudocatenulatum* | |
| | | 885.6142 | | | | |
| | | | | *Gardnerella* | *Gardnerella vaginalis* | 2 |
| | | Micrococcales | Micrococcaceae | *Arthrobacter* | *Arthrobacter* | 1 |
| | | 913.5682 | 913.5682 | | *creatinolyticus* | 1 |
| | | | 914.5711 | | *Arthrobacter* sp | |
| | | | 915.5671 | *Kokuria* | *Kokuria kristina* | 2 |
| | | | | | *Kokuria rhizophila* | 2 |
| | | | | | *Kokuria varians* | 1 |
| | | | | *Micrococcus* | *Micrococcus luteus* | 5 |
| | | | | | *Micrococcus lylae* | 2 |
| | | | | *Rothia* | *Rothia aeria* | 3 |
| | | | | | *Rothia amarne* | 1 |
| | | | | | *Rothia dentocariosa* | 5 |
| | | | | | *Rothia mucilaginosa* | 5 |
| | | | | | *Rothia* sp | 1 |
| | | | Micrococcineae | *Brevibacterium* | *Brevibacterium paucivorans* | 1 |
| | | | | | | 3 |
| | | | | | *Brevibacterium* sp | |
| | | | | *Dermabacter* | *Dermabacter hominis* | 2 |
| | | | | | *Dermobacter* sp | 1 |
| Firmicutes | Bacilli | Bacillales | Bacillaceae | *Bacillus* | *Bacillus cereus* | 3 |
| | | | | | *Bacillus clausii* | 3 |
| | | | | | *Bacillus lichenformis* | 3 |
| | | | | | *Bacillus pumilus* | 1 |
| | | | | | *Bacillus sonorensis* | 1 |
| | | | | | *Bacillus* sp | 3 |
| | | | | | *Bacillus subtilis* | 3 |
| | | | Listeriaceae | *Listeria* | *Listeria monocytogenes* | 7 |
| | | | 675.9793 | | | |
| | | | 832.5352 | | | |
| | | | Paenibacillaceae | *Paenibacillus* | *Paenibacillus* sp | 5 |
| | | | 871.5892 | | *Paenibacillus unalis* | 1 |
| | | | 903.7221 | | | |
| | | | 914.7282 | | | |
| | | | 915.7282 | | | |
| | | | 916.7282 | | | |
| | | | Staphylococcaceae | *Staphylococcus* | *Staphylococcus aureus* | 3 |
| | | | 763.5512 | | *Staphylococcus capitis* | 3 |
| | | | 765.5482 | | *Staphylococcus caprae* | 1 |
| | | | | | *Staphylococcus cohnii* | 4 |
| | | | | | *Staphylococcus epidermis* | 3 |
| | | | | | *Staphylococcus haemolyticus* | 3 |
| | | | | | *Staphylococcus hominis* | 3 |
| | | | | | *Staphylococcus lugdunensis* | 3 |
| | | | | | *Staphylococcus pasteuri* | 3 |
| | | | | | *Staphylococcus pettenkoferi* | 3 |
| | | | | | *Staphylococcus saprophyticus* | |
| | | | | | *Staphylococcus warneri* | |
| | | Lactobacillales | Aerococcaceae | *Abiotrophia* | *Abiotrophia defectiva* | 1 |
| | | 898.5391 | 163.0506 | | | |
| | | 923.5512 | | | | |
| | | 925.5671 | | | | |

TABLE 14-continued

Table of biomarkers: microbial taxon-specific biomarkers
Taxon-specific markers obtained for various microbes. No markers were calculated where the size of sample set was insufficient.

| | | | Family | Genus | Species | # |
|---|---|---|---|---|---|---|
| 926.5701 | | | | | | |
| 928.5952 | | | | | | |
| 949.5672 | | | | | | |
| 950.5692 | | | | | | |
| 951.5832 | | | | | | |
| 952.5861 | | | | | | |
| 953.5981 | | | | | | |
| 954.6011 | | | | | | |
| 955.5971 | | | | | | |
| 956.5971 | | | | | | |
| 979.6111 | | | | | | |
| 990.6001 | | | | | | |
| | | | | Aerococcus | Aerococcus sp | 1 |
| | | | | | Aerococcus viridans | 2 |
| | | | Carnobacteriaceae | Granulicatella | Granulicatella adiacens | 1 |
| | | | Enterococcaceae | Enterococcus | Enterococcus avium | 3 |
| | | | | | Enterococcus casseliflavus | 2 |
| | | | | | | 1 |
| | | | | | Enterococcus cecorum | 3 |
| | | | | | Enterococcus faecalis | 3 |
| | | | | | Enterococcus faecium | 3 |
| | | | | | Enterococcus gallinarum | 3 |
| | | | | | Enterococcus raffinosus | |
| | | | Lactobacillaceae | Lactococcus | Lactococcus lactis | 1 |
| | | | | | Lactococcus spp | 2 |
| | | | Leuconostocaceae | Leuconostoc | Leuconostoc sp | 1 |
| | | | Streptococcaceae | Lactobacillus | Lactobacillus gasseri | 2 |
| | | | | | Lactobacillus rhamnosus | 3 |
| | | | 897.5351 | Streptococcus | Streptococcus agalactiae | 3 |
| | | | | | Streptococcus anginosus | 3 |
| | | | | | Streptococcus bovis | 3 |
| | | | | | Streptococcus canis | 1 |
| | | | | | Streptococcus constellatus | 2 |
| | | | | | | 2 |
| | | | | | Streptococcus cristatus | 3 |
| | | | | | Streptococcus dysagalactiae | 3 |
| | | | | | | 3 |
| | | | | | Streptococcus gallolyticus | 3 |
| | | | | | Streptococcus gordonii | 3 |
| | | | | | Streptococcus intermedius | 3 |
| | | | | | | 3 |
| | | | | | Streptococcus lutetiensis | 3 |
| | | | | | Streptococcus milleri | 3 |
| | | | | | Streptococcus mitis | 3 |
| | | | | | Streptococcus mutans | 3 |
| | | | | | Streptococcus oralis | 1 |
| | | | | | Streptococcus parasanguinus | 2 |
| | | | | | | 3 |
| | | | | | Streptococcus pneumoniae | 3 |
| | | | | | | 3 |
| | | | | | Streptococcus povas | 1 |
| | | | | | Streptococcus pseudoporcinus | 3 |
| | | | | | Streptococcus pyogenes | |
| | | | | | Streptococcus salivarius | |
| | | | | | Streptococcus sanguinis | |
| | | | | | Streptococcus vestibularis | |
| | | | | | Streptococcus viridans | |
| Clostridia | Clostridiales | Clostridiaceae | Clostridium | | Clostridium celerecrescens | 1 |
| 449.2685 | | 649.4453 | | | | 4 |
| 703.4923 | | 731.5253 | | | Clostridium difficile | 2 |
| 704.4953 | | 897.6951 | | | Clostridium histolyticum | 3 |
| 731.5253 | | 925.7262 | | | Clostridium innocuum | 2 |
| 732.5283 | | 969.7481 | | | Clostridium paraputrificum | 3 |
| 925.7262 | | 970.7541 | | | | 3 |
| | | | | | Clostridium perfringens | 2 |
| | | | | | Clostridium ramosum | 2 |
| | | | | | Clostridium septicum | 3 |
| | | | | | Clostridium sporogenes | |
| | | | | | Clostridium tertium | |
| | | | Peptostreptococcaceae | Parvinomas | Parvinomas micro | 1 |
| | | | 496.4124 | Peptoniphilus | Peptoniphilus harei | 5 |
| | | | 497.4214 | | | |
| | | | 498.4244 | | | |
| | | | 635.3944 | | | |
| | | | 645.4133 | | | |

TABLE 14-continued

Table of biomarkers: microbial taxon-specific biomarkers
Taxon-specific markers obtained for various microbes. No markers were calculated where the size of sample set was insufficient.

|  |  |  | 646.4173 |  |  |  |
|---|---|---|---|---|---|---|
|  |  |  | 681.3923 |  |  |  |
|  | Negativicutes | Selenomonadales | Acidaminococcaceae | *Acidaminococcus* | *Acidaminococcus* | 2 |
| 423.3505 |  |  | 627.4403 |  | *fermentans* |  |
| 425.3644 |  |  | 643.4343 |  |  |  |
| 426.3674 |  |  | 644.4383 |  |  |  |
| 461.3394 |  |  | 730.4652 |  |  |  |
| 560.4194 |  |  | 734.5933 |  |  |  |
| 851.7352 |  |  | 831.5902 |  |  |  |
|  |  |  | 977.6971 |  |  |  |
|  |  |  | 978.6931 |  |  |  |
|  |  |  | Veillonellaceae | *Dialister* | *Dialister* sp | 1 |
|  |  |  | 218.1855 | *Veillonella* | *Veillonella atypica* | 1 |
|  |  |  | 229.1815 |  | *Veillonella dispar* | 1 |
|  |  |  | 358.2145 |  | *Veillonella parvula* | 1 |
|  |  |  | 364.2495 |  | *Veillonella ratti* | 1 |
|  |  |  | 655.4713 |  |  |  |

TABLE 16

Taxon-specific markers as determined on phylum-level.

| Phylogenetic information | Taxonomic level | m/z value | Compound ID |
|---|---|---|---|
| Gram-negatives | Bacteroidetes (Phylum) | 381.2765 | spingolipid |
|  |  | 653.5113 | Isotope m/z = 653 |
|  |  | 654.5143 | CerP(d34:1)) |
|  |  | 623.5024 | isotope m/z = 623 |
|  |  | 640.4993 | isotope m/z = 635 |
|  |  | 639.4954 | isotope m/z = 590 |
|  |  | 393.2764 | Cer(d18:0/h17:0) |
|  |  | 616.4724 | isotope m/z = 604 |
|  |  | 624.5054 | isotope m/z = 604 |
|  |  | 637.5044 | Cer(d34:0(2OH) |
|  |  | 592.4883 | isotope m/z = 590 |
|  |  | 604.5083 | PE-DHC |
|  |  | 605.5113 | PE-DHC |
|  |  | 606.5033 | PE-DHC |
|  |  | 590.4923 |  |
|  |  | 591.4963 |  |
|  |  | 705.5562 |  |
|  |  | 691.5395 |  |
|  |  | 677.5238 |  |
|  | Fusobacteria (Phylum) | 646.4833 | PE plasmalogen |
|  |  | 227.2015 | PE plasmalogen |
|  |  | 648.4832 | combinatorial marker |
|  |  | 856.6782 | with m/z = 227 |
|  |  | 865.6632 |  |
|  |  | 696.4953 |  |
|  |  | 714.5492 |  |
|  |  | 673.4443 |  |
|  |  | 644.4652 |  |
|  |  | 884.7083 |  |
|  |  | 645.4633 |  |
|  |  | 647.4812 |  |
|  | Proteobacteria | 768.5182 |  |
|  |  | 782.5342 |  |
|  |  | 783.5293 |  |
| Gram-positives | Actinobacteria Firmicutes | — |  |
|  |  | — |  |

TABLE 17

Taxon-specific markers as determined on class-level.

| Phylogenetic information | Taxonomic level | m/z value | Compound ID |
|---|---|---|---|
| Gram-negatives $^L$Bacteroidetes | Bacteroidetes (Phylum) | 635.5004 | sphingolipid |
|  |  | 616.5094 | Cer(d36:1(2OH)) |
|  |  | 628.4913 |  |
|  |  | 636.5044 |  |
|  |  | 627.4883 | PE-Cer(33:1) |
|  |  | 644.5033 |  |
|  |  | 711.5902 | CerP(d36:1) |
|  |  | 618.5233 | Cer(d36:0(2OH)) |
|  |  | 712.5933 |  |
|  |  | 619.5273 | isotope 618 |
|  |  | 697.5743 | DG(42:5) |
|  |  | 620.5184 |  |
|  |  | 698.5763 |  |
|  |  | 648.5003 |  |
|  |  | 637.5044 |  |
|  |  | 617.5124 | isotope m/z = 616 |
|  | Flavobacteria | 333.2084 |  |
|  |  | 390.2324 |  |
|  |  | 566.4794 |  |
|  |  | 567.4834 |  |
|  |  | 568A864 |  |
|  |  | 556.4034 |  |
|  |  | 600.4664 |  |
|  |  | 565.4654 |  |
|  |  | 553.4674 |  |
|  |  | 392.2484 |  |
|  |  | 651.4953 |  |
|  |  | 618.4773 |  |
|  |  | 619.4813 |  |
|  |  | 324.2545 |  |
|  |  | 620.4883 |  |
|  |  | 393.2504 |  |
|  |  | 891.7411 |  |
|  |  | 554.4714 |  |
|  |  | 552.4643 |  |
|  |  | 553.4674 |  |
|  |  | 651.4953 |  |
|  |  | 601.4723 |  |
| Gram-negatives $^L$Fusobacteria | Fusobacteria (class) |  |  |
| Gram-negatives $^L$Proteobacteria | Alpha-Proteobacteria |  |  |
|  | Beta-Proteobacteria | — |  |
|  | Epsilon-Proteobacteria | 993.8381 |  |
|  |  | 867.6582 |  |
|  |  | 731.5452 |  |
|  |  | 730.5422 |  |
|  | Gamma-Proteobacteria | — |  |
| Gram-positives $^L$Actinobacteria | Actinobacteria (class) | — |  |

TABLE 17-continued

Taxon-specific markers as determined on class-level.

| Phylogenetic information | Taxonomic level | m/z value | Compound ID |
|---|---|---|---|
| Gram-positives [L]Firmicutes | Bacilli | — | |
| | Clostridia | 731.5253 | PG plasmalogen |
| | | 732.5283 | Isotope m/z = 731 |
| | | 449.2685 | |
| | | 703.4923 | PG plasmalogen |
| | | 925.7262 | |
| | | 704.4953 | Isotope m/z = 703 |
| | Negativicutes | 660.4194 | Isotope m/z = 425 |
| | | 428.3674 | |
| | | 425.3644 | |
| | | 423.3505 | |
| | | 461.3394 | |
| | | 851.7352 | |

TABLE 18

Taxon-specific markers as determined on order-level.

| Phylogenetic information | Taxonomic level | m/z value | Compound ID |
|---|---|---|---|
| Gram-negatives [L]Bacteroidetes [L]Bacteroidetes | Bacteroidales | | |
| Gram-negatives [L]Bacteroidetes [L]Flavobacteria | Flavobacteriales | | |
| Gram-negatives [L]Fusobacteria [L]Fusobacteria | Fusobacteriales | | |
| Gram-negatives [L]Proteobacteria [L]Alpha-Proteobacteria | Caulobacterales | 795.5572 | |
| | | 797.5723 | |
| | | 769.5502 | |
| | | 770.5562 | |
| | | 957.6261 | |
| | | 771.5582 | |
| | | 818.5673 | |
| | Rhizobiales | 739.5313 | Isotope m/z = 784 |
| | | 784.5902 | Isotope m/z = 439 |
| | | 785.5932 | |
| | | 439.4155 | |
| | | 440.4195 | |
| | | 799.5132 | |
| | Rhodospiralles | 733.5752 | |
| | | 734.5753 | |
| | | 729.5813 | |
| | | 733.6173 | |
| | | 722.5753 | |
| | | 662.5393 | |
| | | 747.6283 | |
| | | 757.6173 | |
| Gram-negatives [L]Proteobacteria [L]Beta-Proteobacteria | Burkholderiales | — | |
| | Neisseriales | 526.3673 | Isotope m/z = 526 |
| | | 527.3704 | |
| | | 502.3674 | |
| | | 544.3774 | |
| | | 494.3855 | |
| | | 528.3653 | |
| Gram-negatives [L]Proteobacteria [L]Epsilon-Proteobacteria | Campylobacterales | — | |
| Gram-negatives [L]Proteobacteria [L]Gamma-Proteobacteria | Aeromonadales | | |
| | Cardiobacterales | 648.4603 | Isotope m/z = 648 |
| | | 649.4623 | |
| | | 793.4792 | |
| | | 650.4653 | |
| | | 794.4802 | |
| | Enterobacteriales | 703.5092 | Isotope m/z = 702 |
| | | 702.5083 | |
| | | 993.7282 | |
| | | 994.7272 | |
| | Pasteurellales | 746.4503 | |
| | | 915.6902 | |
| | | 823.5453 | |
| | | 898.6921 | |
| | | 690.4983 | |
| | | 977.7282 | |

TABLE 18-continued

Taxon-specific markers as determined on order-level.

| Phylogenetic information | Taxonomic level | m/z value | Compound ID |
|---|---|---|---|
| | Pseudomonadales | — | |
| | Vibrionales | 607.3983 | Isotope m/z = 607 |
| | | 608.4013 | |
| | | 633.4134 | |
| | | 605.3823 | |
| | Xanthomonadales | 562.3504 | Isotope m/z = 619 |
| | | 377.2105 | Isotope m/z = 629 |
| | | 619.4353 | Isotope m/z = 705 |
| | | 620.4384 | PG(31:1) |
| | | 930.6892 | |
| | | 929.6852 | |
| | | 944.7052 | |
| | | 943.7012 | |
| | | 942.6912 | |
| | | 706.4743 | |
| | | 705.4713 | |
| Gram-positives | Actinomycetales | — | |
| $^L$Actinobacteria | Bifidobacteriales | 792.5502 | |
| $^L$Actinobacteria | | 819.5783 | |
| | | 884.6092 | |
| | | 885.6142 | |
| | | 789.5293 | |
| | | 830.5622 | |
| | | 855.5272 | |
| | Micrococcales | 913.5682 | |
| Gram-positives | Bacillales | 951.5832 | |
| $^L$Firmicutes | Lactobacillales | 954.6011 | |
| $^L$Bacilli | | 952.5861 | |
| | | 953.5981 | |
| | | 925.5671 | |
| | | 956.5971 | |
| | | 955.5971 | |
| | | 926.5701 | |
| | | 950.5692 | |
| | | 949.5672 | |
| | | 928.5952 | |
| | | 990.6001 | |
| | | 923.5512 | |
| | | 898.5391 | |
| | | 979.6111 | |
| | Clostridiales | | |
| | Selemonadales | | |

TABLE 19

Taxon-specific markers as determined on family-level

| Phylogenetic information | Taxonomic level | m/z value | Compound ID |
|---|---|---|---|
| Gram-negatives | Bacteroidaceae | 820.7522 | |
| $^L$Bacteroidetes | Porphyromonadazeae | 841.6942 | isotope m/z = 840 |
| $^L$Bacteroidetes | | 840.6842 | isotope m/z = 946 |
| $^L$Bacteroidales | | 948.7562 | isotope m/z = 946 |
| | | 949.7592 | isotope m/z = 946 |
| | | 947.7502 | SubPG DHC |
| | | 946.7472 | isotope m/z = 944 |
| | | 945.7372 | SubPG DHC |
| | | 944.7342 | isotope m/z = 932 |
| | | 933.7362 | SubPG DHC |
| | | 932.7332 | isotope m/z = 814 |
| | | 872.7072 | isotope m/z = 960 |
| | | 815.7112 | SubPG DHC |
| | | 814.7063 | isotope m/z = 960 |
| | | 858.6972 | isotope m/z = 828 |
| | | 934.7422 | isotope m/z = 958 |
| | | 962.7691 | |
| | | 960.7611 | |
| | | 961.7661 | |
| | | 828.7232 | |
| | | 829.7262 | |
| | | 854.7022 | |
| | | 959.7501 | |

TABLE 19-continued

Taxon-specific markers as determined on family-level

| Phylogenetic information | Taxonomic level | m/z value | Compound ID |
|---|---|---|---|
| | | 958.7461 | |
| | | 921.7912 | |
| | | 918.7191 | |
| | | 843.7432 | |
| | | 910.7471 | |
| | | 908.7401 | |
| | | 909.7431 | |
| | Prevotellaceae | 661.5283 | |
| | | 908.7401 | |
| | | 675.5453 | |
| | | 922.7552 | |
| | | 923.7612 | |
| | | 676.5503 | |
| | | 870.8002 | |
| | Rikenellaceae | | |
| Gram-negatives<br>$^L$Bacteroidetes<br>$^L$Flavobacteria<br>$^L$Flavobacteriales | Flavobacteriaceae | | |
| Gram-negatives<br>$^L$Fusobacteria<br>$^L$Fusobacteria<br>$^L$Fusobacteriales | Fusobacteriaceae | | |
| Gram-negatives<br>$^L$Proteobacteria<br>$^L$Alpha-Proteobacteria<br>$^L$Caulobacterales | Caulobacteraceae | | |
| Gram-negatives<br>$^L$Proteobacteria<br>$^L$Alpha-Proteobacteria<br>$^L$Rhizobiales | Rhizobiaceae | | |
| Gram-negatives<br>$^L$Proteobacteria<br>$^L$Alpha-Proteobacteria<br>$^L$Rhodospiralles | Acetobacteraceae | | |
| Gram-negatives<br>$^L$Proteobacteria<br>$^L$Beta-Proteobacteria<br>$^L$Burkholderiales | Alcaligenaceae<br>Burkholderiaceae | —<br>589.4013<br>591.4184<br>590.4083<br>592.4214 | Isotope m/z = 589<br>Isotope m/z = 591 |
| | Comamonadaceae<br>Sutterellaceae | 520.3044<br>— | |
| Gram-negatives<br>$^L$Proteobacteria<br>$^L$Beta-Proteobacteria<br>$^L$Neisseriales | Neisseriaceae | | |
| Gram-negatives<br>$^L$Proteobacteria<br>$^L$Epsilon-Proteobacteria<br>$^L$Campylobacterales | Campylobacteraceae<br>Helicobacteriaceae | 993.8381<br>867.6582<br>299.2595<br>300.2625<br>272.2305<br>271.2284<br>543.4623<br>400.2644<br>544.4634 | C18:0(+O)<br>Isotope m/z = 299<br>Isotope m/z = 271<br>C16:0(+O) |
| Gram-negatives<br>$^L$Proteobacteria<br>$^L$Gamma-Proteobacteria<br>$^L$Cardiobacterales | Cardiobacteriaceae | | |
| Gram-negatives<br>$^L$Proteobacteria<br>$^L$Gamma-Proteobacteria<br>$^L$Enterobacterales | Enterobacteriaceae | | |
| Gram-negatives<br>$^L$Proteobacteria<br>$^L$Gamma-Proteobacteria<br>$^L$Pasteurellales | Pasteurellaceae | | |
| Gram-negatives<br>$^L$Proteobacteria<br>$^L$Gamma-Proteobacteria<br>$^L$Pseudomonadales | Moraxellaceae<br>Pseudomonadaceae | —<br>514.3294<br>490.3304<br>286.1805 | |
| Gram-negatives<br>$^L$Proteobacteria<br>$^L$Gamma-Proteobacteria | Vibrionaceae | | |

TABLE 19-continued

Taxon-specific markers as determined on family-level

| Phylogenetic information | Taxonomic level | m/z value | Compound ID |
|---|---|---|---|
| [L]Vibrionales Gram-negatives [L]Proteobacteria [L]Gamma-Proteobacteria [L]Xanthomonadales | Xanthomonadaceae | | |
| Gram-positives [L]Actinobacteria [L]Actinobacteria [L]Actinomycetales | Actinomyceteae | 757.5403 | Combiratorial markers |
| | Corynebacteriaceae | 879.6112 | |
| | | 537.4904 | Mycolic acid C35:0 |
| | | 538.4934 | Isotope m/z = 537 |
| | | 535.4734 | Mycolic acid C35:1 |
| | | 493.4624 | Mycolic acid C32:1 |
| | | 495.4784 | Mycolic acid C32:0 |
| | | 497.4845 | Isotope m/z = 495 |
| | | 521.4934 | Mycolic acid C34:1 |
| | Microbacteriaceae | | |
| | Mycobacteriaceae | 851.5662 | PI(35:0) |
| | | 852.5672 | Isotope m/z = 851 |
| | | 850.5592 | |
| | | 391.3684 | |
| | | 724.8873 | |
| | | 427.0965 | |
| | | 817.4152 | |
| | Nocardiaceae | 798.7762 | Isotope m/z = 797 |
| | | 797.7762 | Mycolic acid C54:3 |
| | | 828.8222 | Isotope m/z = 827 |
| | | 970.7871 | combinatorial |
| | | 321.2915 | Mycolic acid C56:2 |
| | | 827.8162 | Isotope Mycolic |
| | | 800.7962 | acid C54:2 |
| | | 743.7273 | Mycolic acid C50:2 |
| | | 771.7592 | Mycolic acid C52:2 |
| | Propionibacteriaceae | 617.4564 | |
| | | 906.5872 | |
| | | 779.5072 | |
| | | 714.4812 | |
| | | 361.2155 | |
| | | 713.4752 | |
| | | 877.5592 | |
| Gram-positives [L]Actinobacteria [L]Actinobacteria [L]Bifidobacteriales | Bifidobacteriaceae | 792.5502 819.5783 | |
| Gram-positives [L]Actinobacteria [L]Actinobacteria [L]Micrococcales | Micrococcaceae Micrococcineae | 913.5682 914.5711 915.5571 | Isotope m/z = 913 |
| Gram-positives [L]Firmicutes [L]Bacilli [L]Bacillales | Bacillaceae Listeriaceae | 675.9793 832.5352 | |
| | Paenibacillaceae | 915.7282 | |
| | | 916.7282 | |
| | | 914.7282 | |
| | | 871.5892 | |
| | | 903.7221 | |
| | Staphylococcaceae | 765.5482 | Isotope m/z = 763 |
| | | 763.5512 | PG(35:0) |
| Gram-positives [L]Firmicutes [L]Bacilli [L]Lactoacillales | Aerocccaceae Carnobacteriaceae Enterococcaceae Lactobacillaceae Leuconostocaceae | 163.0506 — — | |
| | Streptococcaceae | 897.5351 | |
| Gram-positives [L]Firmicutes [L]Clostridia [L]Clostridiales | Clostridiaceae | 731.5253 | |
| | | 970.7541 | |
| | | 649.4453 | |
| | | 897.6951 | |
| | | 969.7481 | |
| | | 925.7262 | |
| | Peptostreptococcaceae | 497.4214 | Isotope m/z = 497 |
| | | 498.4244 | Isotope m/z = 645 |
| | | 681.3923 | |
| | | 635.3944 | |
| | | 496.4124 | |
| | | 645.4133 | |
| | | 646.4173 | |

TABLE 19-continued

Taxon-specific markers as determined on family-level

| Phylogenetic information | Taxonomic level | m/z value | Compound ID |
|---|---|---|---|
| Gram-positives | Acidaminococcaceae | 730.4652 | |
| [L]Firmicutes | | 627.4403 | |
| [L]Negativicutes | | 831.5902 | |
| [L]Selemonadales | | 977.6971 | |
| | | 978.6931 | |
| | | 643.4343 | |
| | | 644.4383 | |
| | | 734.5933 | |
| | Veillonellaceae | 229.1815 | |
| | | 218.1855 | |
| | | 364.2495 | |
| | | 655.4713 | |
| | | 358.2145 | |

TABLE 20

| m/z | IDs | CD | ANOVA pVal | ANOVA qVal | Healthy EC (Mean) | HO (Mean) | SC (Mean) | SA (Mean) | MedFC-HO-SC | MeanFC-HO-SA |
|---|---|---|---|---|---|---|---|---|---|---|
| 756.5955 | PE(P-38:1) | SC | 0.03335362 | 1 | 0 | 0.001 | 2.9186 | 0.6746 | 11.51106078 | 9.397888508 |
| 865.5746 | PI(36:0) | SC | 8.99775E-06 | 0.000181998 | 4.2331 | 0.2857 | 16.469 | 3.3348 | 5.849108111 | 3.545027299 |
| 747.4995 | PA(40:6) | SC | 0.000029587 | 0.000487705 | 0 | 0.8051 | 33.1513 | 23.0009 | 5.363753646 | 4.836378514 |
| 882.5255 | PS(44:10) | SC | 2.06342E-06 | 4.63105E-05 | 1.2377 | 0.7999 | 17.5562 | 3.0372 | 4.456017148 | 1.924850356 |
| 729.5466 | PA(38:1) | SC | 0.000187847 | 0.00232043 | 0 | 0.6001 | 7.3836 | 2.2515 | 3.621049563 | 1.907611643 |
| 836.5385 | PS(40:5) | SC | 0.000227757 | 0.002766326 | 11.8159 | 4.1195 | 50.29 | 12.0226 | 3.609730406 | 1.545207779 |
| 907.5386 | PI(40:7) | SC | 0.001565923 | 0.01540735 | 0 | 0.2976 | 3.3043 | 0.5694 | 3.472098245 | 0.936067967 |
| 721.5045 | PG(32:0) | SC | 2.591E-07 | 7.14918E-06 | 6.4138 | 1.2772 | 13.6359 | 2.3595 | 3.416353561 | 0.885496713 |
| 725.5165 | PA(38:3) | SC | 0.001014647 | 0.01044902 | 8.9208 | 5.875 | 53.9985 | 45.8083 | 3.200258575 | 2.962948267 |
| 890.5915 | PS(44:6) | SC | 8.93408E-05 | 0.001229222 | 0.7119 | 1.1554 | 10.2085 | 1.4504 | 3.143306593 | 0.32805843 |
| 889.5745 | TG(P-58:20)/PI(38:2) | SC | 2.89892E-07 | 7.87048E06 | 5.4933 | 5.5739 | 48.3826 | 17.6337 | 3.117729275 | 1.661576196 |
| 720.5005 | PE(P-36:5) | SC | 3.9936E-05 | 0.000627725 | 9.821 | 3.4014 | 27.6954 | 6.804 | 3.025445795 | 1.000254466 |
| 798.6055 | PE(40:2) | SC | 4.95954E-07 | 1.28467E-05 | 0 | 0.9016 | 7.193 | 1.6266 | 2.996034183 | 0.851300090 |
| 864.5816 | PS(42:5) | SC | 8.48139E-07 | 2.07019E-05 | 52.7448 | 11.6176 | 91.8789 | 28.7887 | 2.983421521 | 1.30919058 |
| 816.5585 | PE(42:7) | SC | 1.52034E-10 | 7.71875E-09 | 0 | 1.6337 | 12.8847 | 4.1834 | 2.979443959 | 1.356532867 |
| 881.5234 | PI(38:8) | SC | 3.06222E-07 | 8.22587E-06 | 20.1924 | 5.8436 | 44.2926 | 10.5851 | 2.922136354 | 0.857105566 |
| 909.5536 | PI(40:6) | SC | 2.24965E-12 | 1.70469E-10 | 49.0519 | 15.9328 | 114.7333 | 36.869 | 2.848212447 | 1.210408461 |
| 762.5125 | PE(38:6) | SC | 8.97872E-05 | 0.001232026 | 52.1501 | 10.1699 | 70.944 | 40.8521 | 2.802375182 | 2.006104749 |
| 796.5915 | PE(40:3) | SC | 3.79122E-06 | 8.22564E-05 | 5.1935 | 4.9805 | 33.6477 | 20.3448 | 2.756145403 | 2.030297609 |
| 818.5755 | PE(42:6) | SC | 0.000301686 | 0.003521058 | 0.3887 | 2.2777 | 14.9853 | 7.765 | 2.717898322 | 1.769408185 |
| 688.4956 | PE(32:1) | SC | 0.004342958 | 0.03875079 | 0 | 1.5169 | 9.7615 | 1.7478 | 2.685976876 | 0.204414127 |
| 698.5165 | PE(P-34:2) | SC | 2.68247E-05 | 0.000443613 | 15.976 | 10.0868 | 60.439 | 12.0642 | 2.583011233 | 0.258263694 |
| 730.5425 | PE(35:1) | SC | 9.22832E-07 | 2.22048E-05 | 3.0568 | 3.4431 | 18.7517 | 6.1662 | 2.445241406 | 0.840673601 |
| 863.5705 | PI(36:1) | SC | 7.6787E-07 | 1.89247E-05 | 176.9816 | 37.4807 | 200.7699 | 75.9336 | 2.422093229 | 1.019350549 |
| 671.4685 | PA(34:2) | SC | 0.005222022 | 0.04586887 | 1.5406 | 1.0287 | 5.4109 | 2.2209 | 2.395046269 | 1.110322124 |
| 860.5435 | P6(42:7) | SC | 1.01514E-08 | 3.60405E-07 | 11.4123 | 9.893 | 48.7253 | 18.1579 | 2.300191086 | 0.876117379 |
| 862.5576 | PS(42:6) | SC | 2.93214E-09 | 1.20052E-07 | 65.6885 | 24.024 | 111.5443 | 49.95 | 2.215068508 | 1.056008298 |
| 888.5745 | PS(44:7) | SC | 2.70063E-09 | 1.12386E-07 | 135.8857 | 64.5795 | 280.929 | 113.4454 | 2.121057384 | 0.812849935 |
| 859.5395 | PI(36:3) | SC | 1.31586E-08 | 4.51393E-07 | 77.7761 | 26.7501 | 109.2902 | 47.0364 | 2.030547851 | 0.814233361 |
| 752.5645 | PE(P-38:3) | SC | 0.000105486 | 0.001401967 | 9.7931 | 17.5824 | 70.3579 | 40.0642 | 2.000580411 | 1.188181657 |
| 699.5004 | PA(36:2) | SC | 2.16751E-06 | 4.93473E-05 | 21.1742 | 21.3245 | 83.9542 | 57.5307 | 1.977090586 | 1.431820109 |
| 697.4845 | PA(36:3) | SC | 0.003052866 | 0.02802785 | 2.6456 | 1.9677 | 7.6299 | 2.813 | 1.955153868 | 0.515599272 |
| 807.5076 | PI(32:1) | SC | 0.0016283 | 0.01506637 | 1.2143 | 3.5478 | 13.544 | 2.8181 | 1.93265729 | -0.332201876 |
| 724.5235 | PE(P-36:3) | SC | 3.34117E-08 | 1.07361E-06 | 13.3679 | 24.4632 | 90.6672 | 36.2425 | 1.889967599 | 0.567069342 |
| 728.5635 | PE(P-36:1) | SC | 5.35704E-08 | 1.6893E-06 | 75.1233 | 24.7786 | 90.3378 | 34.6904 | 1.866235103 | 0.485441799 |
| 772.5898 | PE(38:1) | SC | 6.81536E-05 | 0.001008793 | 79.1078 | 42.7078 | 147.5674 | 109.7266 | 1.788802554 | 1.36134182 |
| 861.5535 | PI(36:2) | SC | 1.11286E-08 | 3.86985E-07 | 116.1195 | 72.7123 | 249.9238 | 138.848 | 1.781216958 | 0.93323506 |
| 788.5254 | PE(40:7) | SC | 2.13379E-06 | 4.87984E-05 | 19.5351 | 17.2225 | 52.4945 | 26.0242 | 1.607871697 | 0.595559237 |
| 820.5906 | PE(42:5) | SC | 0.000846836 | 0.008846474 | 0 | 4.7141 | 13.8708 | 7.9687 | 1.55699673 | 0.757362022 |
| 720.5476 | PE(P-36:2) | SC | 2.57574E-07 | 7.14592E-06 | 85.965 | 33.5787 | 95.8155 | 34.6192 | 1.515202662 | 0.04660619 |
| 770.5735 | PE(38:2) | SA | 2.30565E-06 | 5.20258E-05 | 152.3456 | 128.0562 | 325.133 | 327.1652 | 1.344252888 | 1.353242195 |
| 690.5105 | PE(32:0) | SC | 0.004089558 | 0.03681327 | 1.8308 | 9.2329 | 23.0854 | 13.957 | 1.322124964 | 0.596133107 |
| 740.5284 | PE(36:3) | SC | 9.15878E-07 | 2.21424E-05 | 56.0117 | 58.7099 | 143.5809 | 71.9384 | 1.290188141 | 0.293158273 |

TABLE 20-continued

| m/z | IDs | CD | ANOVA pVal | ANOVA qVal | Healthy EC (Mean) | HO (Mean) | SC (Mean) | SA (Mean) | MedFC-HO-SC | MeanFC-HO-SA |
|---|---|---|---|---|---|---|---|---|---|---|
| 768.5685 | PE(38:3) | SC | 1.58943E−05 | 0.000287172 | 191.6569 | 129.141 | 290.4791 | 253.9433 | 1.169487262 | 0.975559307 |
| 911.5704 | PI(40:5) | SC | 7.21238E−08 | 2.24646E−06 | 52.6973 | 40.8993 | 85.8625 | 42.5665 | 1.069952028 | 0.057642319 |
| 723.4995 | PA(38:4) | SA | 0.00037395 | 0.004275998 | 7.4888 | 20.0312 | 41.4992 | 62.2382 | 1.050834675 | 1.635551486 |
| 742.5424 | PE(36:2) | SC | 2.87707E−06 | 6.29608E−05 | 395.1418 | 345.5038 | 692.7696 | 581.6404 | 1.003674045 | 0.751425902 |
| 701.5155 | PA(36:1) | SA | 1.406E−05 | 0.000272453 | 104.0595 | 173.6574 | 343.5916 | 393.7826 | 0.984450877 | 1.181155475 |
| 714.6105 | PE(34:2) | SC | 2.38041E−06 | 5.3475E−05 | 21.3764 | 38.1989 | 75.3044 | 29.4042 | 0.979203069 | −0.377508854 |
| 744.5575 | PE(36:1) | SC | 0.000434216 | 0.004834464 | 782.4336 | 603.4562 | 1019.6619 | 1009.0828 | 0.756769896 | 0.741723593 |
| 872.6425 | PS(42:1) | SC | 0.001341361 | 0.01337935 | 2.6642 | 9.756 | 16.3726 | 4.596 | 0.746921779 | −1.08591096 |
| 746.5755 | PE(36:0) | SC | 0.000407838 | 0.004601323 | 37.397 | 47.869 | 79.349 | 55.9679 | 0.729120374 | 0.225507949 |
| 819.5536 | PG(P-41:6) | HO | 3.34792E−05 | 0.000543048 | 41.2026 | 48.6631 | 23.5767 | 17.1004 | −1.045466427 | −1.508798156 |
| 816.5805 | PE(38:2)/PS(38:1) | HO | 1.26476E−08 | 4.36814E−07 | 71.9373 | 73.9657 | 35.4711 | 22.4157 | −1.060212336 | −1.722346854 |
| 788.5475 | PS(36:1) | HO | 1.24345E−14 | 1.34319E−12 | 1310.7695 | 1946.6457 | 887.8471 | 1068.1457 | −1.132607179 | −0.865881879 |
| 749.5355 | PG(34:0) | HO | 2.26439E−11 | 1.40199E−09 | 246.3929 | 344.2116 | 150.2673 | 151.2288 | −1.195764622 | −1.186562805 |
| 748.5325 | PE(P-38:5) | HO | 3.12547E−11 | 1.84571E−09 | 511.038 | 745.9556 | 301.8235 | 364.2202 | −1.305384624 | −1.034278825 |
| 868.6124 | PS(42:3) | HO | 0.000341653 | 0.003960214 | 0 | 4.6648 | 1.713 | 0.4246 | −1.445290076 | −3.457638952 |
| 814.5655 | PE(38:3)/PS(38:2) | HO | 3.33067E−16 | 4.57022E−14 | 45.6966 | 106.7905 | 25.2074 | 25.4809 | −2.082864087 | −2.067295171 |
| 847.5665 | PI(P-36:1) | HO | 1.09395E−07 | 3.30593E−06 | 6.2006 | 13.3224 | 3.044 | 2.4174 | −2.12981374 | −2.462325888 |
| 846.5635 | PS(P-42:6) | HO | 5.18541E−12 | 3.60634E−10 | 24.6104 | 30.5856 | 4.4186 | 7.6053 | −2.791191338 | −2.007775515 |
| 724.5325 | PE(P-36:3) | HO | 9.14935E−13 | 7.25801E−11 | 32.8176 | 65.1551 | 7.4891 | 8.0302 | −3.121013851 | −3.020370285 |
| 818.5316 | PS(P-40.8) | HO | 2.22045E−16 | 3.22092E−14 | 37.1244 | 38.13126 | 4.0168 | 5.1328 | −3.272408545 | −2.918707128 |

SC = Serous carcinoma; HO = Healthy ovary; SA = StromaA; CD = Class Diff

| | Number of lipids | Class Diff | class where the p value is significant |
|---|---|---|---|
| PA | 4 | HealthyEC (Mean) | mean intensity of epithelial cells from Fallopian tube |
| PE | 14 | HealthyOv (Mean) | mean intensity of healthy stroma |
| PI | 4 | Serousearcinoma (Mean) | mean intensity of cancer cells from Serous adenocarcinomas |
| PS | 9 | StromaA (Mean) | mean intensity of cancer associated stroma |
| PG | 3 | MeanFC-HealthyOv-SerousCarcinoma | fold change of mean-log(SerousCarcinoma/HealthyOv) |
| | | MeanFC-HealthyOv-StromaA | fold change of mean-log(StromaNHealthyOv) |

The invention claimed is:

1. A method of analysis using mass spectrometry and/or ion mobility spectrometry comprising:
using a first device to generate aerosol or vapour from one or more regions of a first target of biological material;
mass analysing and/or ion mobility analysing said aerosol or vapour, or ions derived therefrom so as to obtain spectrometric data; and
determining the presence or absence of one or more microbe in said target and identifying said microbe at the species or strain level based upon said spectrometric data;
wherein said first device comprises a desorption electrospray ionisation ("DESI") ion source or a desorption electro-flow focusing ("DEFFI") ion source;
wherein said biological material is a sample of a mucosal membrane of a human or non-human animal subject.

2. A method as claimed in claim 1, wherein said method comprises directing a spray of electrically charged droplets onto said target to generate analyte ions.

3. A method as claimed in claim 1, further comprising analysing said spectrometric data in order to analyse or determine one or more of the following in relation to the one or more regions of the target biological material: (i) determine the grade, severity, stage, presence or absence of a disease; (ii) determine the phenotype and/or genotype of one or more cells; (iii) detect the level, type, presence or absence of necrosis; (iv) determine the genotype and/or phenotype of one or more microbe; (v) analyse a microbial interaction with a tissue; (vi) analyse dysbiosis; (vii) determine the type, level, presence or absence of a compound and/or biomarker.

4. A method as claimed in claim 1, further comprising determining the severity, grade, stage, presence or absence of a disease in said one of more regions of the target based upon said spectrometric data.

5. A method as claimed in claim 4, wherein the severity, grade, stage, presence or absence of the disease is determined by analysing said spectrometric data to determine the type, level, presence or absence of a biomarker for said disease.

6. A method as claimed in claim 1, wherein the microbe is optionally selected from bacteria, fungi, Achaea, algae, protozoa and viruses.

7. A method as claimed in claim 1, further comprising detecting an infection based on said spectrometric data.

8. A method as claimed in claim 7, further comprising determining a genotype or phenotype of an infection-causing microbe based on said spectrometric data.

9. A method as claimed in claim 1, wherein said method comprises analysing said spectrometric data in order to analyse the type, level, presence or absence of a biomarker, wherein the biomarker is a direct biomarker or an indirect biomarker.

10. A method as claimed in claim 9, wherein:
said biomarker is a lipid biomarker; and/or
said biomarker is selected from the group consisting of: fatty acids, glycerolipids, sterol lipids, sphingolipids, prenol lipids, saccharolipids and/or phospholipids; and/or said biomarker is a metabolite, a primary metabolite, a secondary metabolite, an antibiotic, a quorum sensing molecule, a fatty acid synthase product, a pheromone; and/or
said biomarker is a biopolymer; and/or
said biomarker is a biomarker for a bacteria; and/or
said biomarker is an exogenous compound or an endogenous compound.

11. A method as claimed in claim 1, wherein said target comprises a swab, or a smear.

12. A method as claimed in claim 1, wherein the biological material is native or unmodified biological material.

13. A method as claimed in claim 1, wherein said mucosal membrane comprises a endometrium, intestinal, gastric, oral, vaginal, esophageal, gingival, nasal, buccal or bronchial membrane.

14. A method as claimed in claim 13, wherein said mucosal membrane is the vaginal mucosa of a pregnant female, and wherein said method further comprises analysing said spectrometric data in order to analyse pregnancy or to diagnose or predict the risk of spontaneous preterm birth.

15. A method as claimed in claim 11, wherein said swab is a standard medical swab.

16. Apparatus comprising:
a first device arranged and adapted to direct a spray of charged droplets onto a first target of biological material in order to generate a plurality of analyte ions, wherein said first device comprises a Desorption Electrospray Ionisation ("DESI") ion source or a desorption electroflow focusing ionisation ("DEFFI") ion source; and
a mass analyser and/or ion mobility analyser for mass analysing and/or ion mobility analysing said analyte ions or ions derived from said analyte ions in order to obtain mass spectrometric and/or ion mobility data;
wherein said apparatus is further arranged to determine the presence or absence of one or more microbe in said target and identify said microbe at the species or strain level based upon said spectrometric data; and
wherein said biological material is a sample of a mucosal membrane of a human or non-human animal subject.

17. A method of analysis using mass spectrometry and/or ion mobility spectrometry comprising:
using a first device to generate aerosol or vapour from one or more regions of a swab comprising a first target of biological material;
mass analysing and/or ion mobility analysing said aerosol or vapour, or ions derived therefrom so as to obtain spectrometric data; and
determining the presence or absence of one or more microbe in said target and identifying said microbe at the species or strain level based upon said spectrometric data;
wherein said first device comprises a desorption electrospray ionisation ("DESI") ion source or a desorption electro-flow focusing ("DEFFI") ion source;
wherein said microbe is a bacterium;
wherein said biological material is a sample of a vaginal muscosal membrane derived from a human or non-human animal subject.

* * * * *